(12) United States Patent
Shailubhai et al.

(10) Patent No.: US 12,146,003 B2
(45) Date of Patent: *Nov. 19, 2024

(54) ULTRA-PURE AGONISTS OF GUANYLATE CYCLASE C, METHOD OF MAKING AND USING SAME

(71) Applicant: Bausch Health Ireland Limited, Dublin (IE)

(72) Inventors: Kunwar Shailubhai, Audubon, PA (US); Stephen Comiskey, Doylestown, PA (US); Rong Feng, Langhorne, PA (US); Juncai Bai, North Augusta, SC (US); Ruoping Zhang, North Augusta, SC (US); Jun Jia, Shanghai (CN); Junfeng Zhou, Shanghai (CN); Qiao Zhao, Shanghai (CN); Guoqing Zhang, Shanghai (CN)

(73) Assignee: Bausch Health Ireland Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/511,852

(22) Filed: Nov. 16, 2023

(65) Prior Publication Data

US 2024/0287137 A1    Aug. 29, 2024

Related U.S. Application Data

(63) Continuation of application No. 18/193,144, filed on Mar. 30, 2023, now Pat. No. 11,834,521, which is a continuation of application No. 17/397,796, filed on Aug. 9, 2021, now abandoned, which is a continuation of application No. 17/207,215, filed on Mar. 19, 2021, now abandoned, which is a continuation of application No. 16/921,450, filed on Jul. 6, 2020, now Pat. No. 11,142,549, which is a continuation of application No. 16/000,251, filed on Jun. 5, 2018, now Pat. No. 10,745,441, which is a continuation of application No. 14/896,019, filed as application No. PCT/US2014/041143 on Jun. 5, 2014, now Pat. No. 10,011,637.

(60) Provisional application No. 61/831,402, filed on Jun. 5, 2013.

(51) Int. Cl.
| | | |
|---|---|---|
| A61K 38/10 | (2006.01) | |
| B01D 15/42 | (2006.01) | |
| C07K 1/14 | (2006.01) | |
| C07K 7/08 | (2006.01) | |
| C12N 9/88 | (2006.01) | |

(52) U.S. Cl.
CPC ............... *C07K 7/08* (2013.01); *A61K 38/10* (2013.01); *B01D 15/424* (2013.01); *C07K 1/14* (2013.01); *C12N 9/88* (2013.01); *C12Y 406/01002* (2013.01)

(58) Field of Classification Search
CPC .................................. A61K 38/10; C07K 7/08
See application file for complete search history.

(56) References Cited

U.S. PATENT DOCUMENTS

| | | | |
|---|---|---|---|
| 5,359,030 A | 10/1994 | Ekwuribe | |
| 7,041,786 B2 | 5/2006 | Shailubhai et al. | |
| 7,638,299 B2 | 12/2009 | Cho et al. | |
| 7,799,897 B2 | 9/2010 | Jacob et al. | |
| 7,879,802 B2 | 2/2011 | Shailubhai et al. | |
| 8,034,782 B2 | 10/2011 | Shailubhai | |
| 8,114,831 B2 | 2/2012 | Shailubhai et al. | |
| 8,207,295 B2 | 6/2012 | Shailubhai et al. | |
| 8,357,775 B2 | 1/2013 | Shailubhai et al. | |
| 8,367,800 B2 | 2/2013 | Shailubhai | |
| 8,497,348 B2 | 7/2013 | Shailubhai et al. | |
| 8,569,246 B2 | 10/2013 | Shailubhai | |
| 8,637,451 B2 | 1/2014 | Shailubhai et al. | |
| 8,716,224 B2 | 5/2014 | Shailubhai et al. | |
| 8,969,514 B2 | 3/2015 | Shailubhai | |
| 9,089,612 B2 | 7/2015 | Shailubhai | |
| 10,011,637 B2* | 7/2018 | Shailubhai | C07K 1/14 |
| 10,421,787 B2* | 9/2019 | Bai | C07K 7/08 |
| 10,745,441 B2* | 8/2020 | Shailubhai | C12N 9/88 |
| 11,142,549 B2* | 10/2021 | Shailubhai | C07K 1/14 |
| 11,319,346 B2* | 5/2022 | Shailubhai | C07K 1/14 |
| 11,834,521 B2* | 12/2023 | Shailubhai | B01D 15/424 |
| 2010/0120694 A1 | 5/2010 | Shailubhai et al. | |
| 2010/0152118 A1 | 6/2010 | Shailubhai | |
| 2010/0221329 A1* | 9/2010 | Shailubhai | A61P 1/10 |
| | | | 424/463 |

(Continued)

FOREIGN PATENT DOCUMENTS

| | | |
|---|---|---|
| CN | 101772513 A | 7/2010 |
| JP | S5896052 A | 6/1983 |
| JP | 2012520676 A | 9/2012 |

(Continued)

OTHER PUBLICATIONS

PCT Application No. PCT/US2014/041143, International Preliminary Report on Patentability dated Dec. 8, 2015.
PCT Application No. PCT/US2014/041143, International Search Report and Written Opinion dated Jan. 12, 2015.
"Avicel(R) PH-112 microcrystalline cellulose NF, Ph. Eur., JP", FMC Product Overview: Avicel(R) PH-112, 2003.
"Callisto Pharmaceuticals Announces Presentation on SP-304 at the 3rd International Congress on Natural Peptides to Drugs", Obtained from the internet, Apr. 15, 2008.

(Continued)

*Primary Examiner* — Jeffrey E. Russel
(74) *Attorney, Agent, or Firm* — Saul Ewing LLP; Domingos J. Silva; Dennis Ostrovsky

(57) ABSTRACT

The invention provides processes of purifying a peptide including a GCC agonist sequence selected from the group consisting of SEQ ID NOs: 1-251 described herein. The processes include a solvent exchange step before a freeze-drying (lyophilization) step.

12 Claims, 16 Drawing Sheets

Specification includes a Sequence Listing.

(56) References Cited

U.S. PATENT DOCUMENTS

| | | | |
|---|---|---|---|
| 2012/0237593 A1 | 9/2012 | Comiskey et al. | |
| 2016/0145307 A1 | 5/2016 | Shailubhai et al. | |

FOREIGN PATENT DOCUMENTS

| | | | | |
|---|---|---|---|---|
| WO | 02078683 A1 | 10/2002 | | |
| WO | 2010065751 A2 | 6/2010 | | |
| WO | 2010107709 A1 | 9/2010 | | |
| WO | WO-2012037380 A2 * | 3/2012 | ........... | A61K 31/192 |
| WO | WO-2012118972 A2 * | 9/2012 | ............... | C07K 1/22 |
| WO | 2014197720 A2 | 12/2014 | | |

OTHER PUBLICATIONS

"Chapter 4: Reversed Phase Chromatography of Peptides", Techniques and Instrumentation in Analytical Chemistry Book Series, vol. 6, Analysis of Neuropeptides by Liquid Chromatography and Mass Spectrometry, Desiderio, et al., Editors, 1984, pp. 51-73.
"Guidance for Industry for the Submission of Chemistry, Manufacturing, and Controls Information for Synthetic Peptide Substances", Food and Drug Administration, Center for Drug Evaluation and Research (CDER), Nov. 1994, pp. 1-16.
"Guidance for Industry: Content and Format of Investigational New Drug Applications (INDs) for Phase 1 Studies of Drugs, Including Well-Characterized, Therapeutic, Biotechnology-derived Products", Food and Drug Administration, Center for Drug Evaluation and Research (CDER) and Center for Biologics Evaluation and Research (CBER), Nov. 1995, pp. 1-17.
"Handbook of Pharmaceutical Excipients, Sixth Edition", Rowe, et al. (editors), Cellulose, Microcrystalline and Magnesium Stearate, Revision date Feb. 3, 2009, 2009, pp. 129-133 and 404-407.
"Highlights of Prescribing Information", Trulance (Plecanatide) Tablets, for Oral Use, 2017, 13 pgs.
"Impurities: Guideline For Residual Solvents Q3C(R5)", a memo published by the International Conference On Harmonisation Of Technical Requirements For Registration Of Pharmaceuticals For Human Use, ICH Harmonised Tripartite Guideline, Feb. 4, 2011, pp. 1-29.
"SP-304 Dose Ranging Study in Patients with Chronic Idiopathic Constipation (CIC)", Trial Record NCT01053962, Obtained online: https://clinicaltrials.gov/ct2/show/NCT01053962?term=01053962 &draw=2&rank=1, Jan. 22, 2010.
Andersson, et al., "Large-scale synthesis of peptides", Biopolymers (Peptide Science), 55, 2000, pp. 227-250.
Andrews, et al., "Effects of Grinding in Pharmaceutical Table Production", Pharmaceutical Manufacturing Handbook: Production and Processes (S.C. Gad ed.), Chapter 6.7, John Wiley & Sons, Inc. publication, 2008, pp. 1165-1190.
Andrushchenko, et al., "Optimization of the hydrochloric acid concentration used for trifluoroacetate removal from synthetic peptides", J Peptide Sci, 13, 2007, pp. 37-43.
Bakre, et al., "Dual regulation of heat-stable enterotoxin-mediated cGMP accumulation in T84 cells by receptor desensitization and increased phosphodiesterase activity", FEBS Lett, 408, 1997, pp. 345-349.
Baldrick, et al., "Pharmaceutical Excipient Development: The Need for Preclinical Guidance", Regul Toxicol Pharmacol, 32, 2000, pp. 210-218.
Ball, et al., "Investigation into the Alternatives to Acetonitrile for the Analysis of Peptides on a SepTech ST150 10-C18", Agilent Technologies, Inc., May 17, 2011, pp. 1-4.
Ball, et al., "Investigation into the Alternatives to Acetonitrile for the Analysis of Peptides on a VariTide RPC", Agilent Technologies, May 17, 2011, pp. 1-3.
Bastos, et al., "Effects of filler-binders and lubricants on physioichemical properties of tablets obtained by direct compression: a 2 2 factorial design", Latin American Journal of Pharmacy, 27.4, 2008, pp. 578-583.

Bennett, et al., "The use of perfluorinated carboxylic acids in the reversed-phase HPLC of peptides", J Liquid Chromatography, 3(9), 1980, pp. 1353-1365.
Brettschneider, et al., "Replacement of acetonitrile by ethanol as solvent in reversed phase chromatography of biomolecules", J Chromotogr B Analyt Technol Biomed Life Sci, 878(9-10), 2010, pp. 763-768.
Busby, et al., "Pharmacologic properties, metabolism, and disposition of linaclotide, a novel therapeutic peptide approved for the treatment of irritable bowel syndrome with constipation and chronic idiopathic constipation", Journal of Pharmacology Experimental Therapeutics, 344, 2013, pp. 196-206.
Campieri, et al., "Oral budesonide is as effective as oral prednisolone in active Crohn's disease", Gut, 41, 1997, pp. 209-214.
Carr, D., "A Guide to the Analysis and Purification of Proteins and Peptides by Reversed-Phase HPLC", ACE HPLC Columns, 2005, pp. 1-64.
Chipens, et al., "Recognition of Peptide Hormones and Kinins: Molecular Aspects of the Problem", Frontiers of Bioorganic Chemistry and Molecular Biology, Ananchenko, Editor, Pergamon Press, 1980, pp. 99-103.
Cornish, "Trifluoroacetate, a contaminant in purified proteins, inhibits proliferation of osteoblasts and chondrocytes", Am J Physiol (Endocrinol Metab 40), 277(5), 1999, pp. E779-E783.
Cournoyer, "Deamidation: Differentiation of aspartyl from isoaspartyl products in peptides by electron capture dissociation", Protein Science, 14, 2005, pp. 452-463.
Desai, et al., "Acetonitrile shortage: use of isopropanol as an alternative elution system for ultrahigh performance liquid chromatography", Analytical Methods, vol. 3, No. 1, 2011, pp. 56-58.
Duncan, et al., "Comparative analysis of oral delivery systes for live rotavirus vaccines", J Control Rel, 41, 1996, pp. 237-247.
Fan, et al., "Uroguanylin: cloning of preprouroguanylin cDNA, mRNA expression in intestine and heart and isolation of uroguanylin and prouroguanylin from plasma", Biochemical & Biophysical Research Communications, 219, 1996, pp. 457-462.
Forte, et al., "*Escherichia coli* enterotoxin receptors: localizatino in opossum kidney, intestine, and testis", Am J Physiol, 257(2), 1989, pp. F874-F-881.
Forte, et al., "Guanylin peptides: cyclic GMP signaling mechanisms", Braz J Med Biol Res, 32, 1999, pp. 1329-1336.
Forte, L., "Lymphoguanylin: Cloning and Characterization of a Unique Member of the Guanylin Peptide Family", Endocrinology, vol. 140, No. 4, 1999, pp. 1800-1806.
Franks, F., "Freeze-drying of bioproducts: putting principles into practice", Eur J Pharm Biopharm, vol. 45, 1998, pp. 221-229.
French, et al., "What is a Conservative Substitution?", J Mol Evol, 19, 1983, pp. 171-175.
Galloway, J.A., "New Directions in Drug Development: Mixtures, Analogues, and Modeling", Diabetes Care, 16 (Supp 3), 1993, pp. 16-23.
Gerogiannis, et al., "Floating and swelling characteristics of various excipients used in controlled release technology", Drug Dev Ind Pharm, 19(9), 1993, pp. 1061-1081.
Guarino, et al., "T84 cell receptor binding and guanyl cyclase activation by *Escherichia coli* heat-stable toxin", Am J Physiol, 253, 1987, pp. G775-G780.
Guzzetta, et al., "Reverse phase HPLC basics for LC/MS: an IonSource tutorial", https://web.archive.org/web/20120423000557/ https://ionsource.com/tutorial/chromatographyrphplc.htm, archived website captured Apr. 23, 2012, 2012.
Hamra, et al., "Opossum colonic mucosa contains uroguanylin and guanylin peptides", Am J Physiol Gastrointest Liver Physiol, 270, 1996, pp. G708-G716.
Helbock, et al., "The mechanism of calcium transport by rat intestine", Biochim Biophys Acta, 126, 1966, pp. 81-93.
Hewitson, "Alternative solvents for the reversed-phase separation of proteins", Waters Corporation, Jun. 2009.
Hyun, et al., "Interaction of cholera toxin and *Escherichia coli* enterotoxin with isolated intestinal epithelial cells", Am Physiol Soc, 247(6:1), 1984, pp. G623-G631.
Jalan, et al., "Faecal stasis and diverticular disease in ulcerative colitis", Gut, 11, 1970, pp. 688-696.

(56) References Cited

OTHER PUBLICATIONS

Kaiser, et al., "Determination of residual trifluoroacetate in protein purification buffers and peptide preparations by ion chromatography", J Chromatography A, 1039, 2004, pp. 113-117.
Karten, et al., "Gonadotropin-Releasing Hormone Analog Design. Structure-Function Studies Toward the Development of Agonists and Antagonists: Rationale and Perspective", Endocrine Rev, 7(1), 1986, pp. 44-66.
King, R.E., "Chapter 89: Tablets, Capsules, and Pills", Remington's Pharmaceutical Sciences, 16th Edition (Ed. Oslo), Mack Publishing Company, 1980, pp. 1553-1584.
Krause, et al., "Distribution of *Escherichia coli* Heat-Stable Enterotoxin/Guanylin/Uroguanylin Receptors in the Avian Intestinal Tract", Acta Anat, 153, 1995, pp. 210-219.
Lai, et al., "Solid-State Chemical Stability of Proteins and Peptides", J Pharm Sci, 88(5), May 1999, pp. 489-500.
Lauer, et al., "Sequence dependence of aspartimide formation during 9-fluoroenylmethoxycarbonyl solid-phase peptide synthesis", Lett Pept Sci, 1, 1994, pp. 197-205.
Li, et al., "Purification, cDNA Sequence and Tissue Distribution of Rat Uroguanylin", Reg Pep, vol. 68, 1997, pp. 45-56.
Lin, et al., "Heat-Stable Toxin from *Escherichia coli* Activates Chloride Current via cGMP-Dependent Protein Kinase", Cell Physiol Biochem, 5, 1995, pp. 23-32.
Manning, et al., "Stability of Protein Pharmaceuticals: An Update", Pharm Res, 27(4) (epub Feb. 9, 2010), Apr. 2010, pp. 544-575.
Mergler, et al., "Systematic Investigation of the Aspartimide Problem", Peptides: The Wave of the Future (Eds. Lebl, M., et al., American Peptide Society), 2001, pp. 63-64.
Mishra, et al., "Interactions of Synthetic Peptide Analogs of the Class A Amphipathic Helix with Lipids: Evidence for the Snorkel Hypothesis", J Biol Chem, 269(10), 1994, pp. 7185-7191.
Moss, et al., "The Natriuretic Peptide Uroguanylin Elicits Physiologic Actions Through 2 Distinct Topoisomers", Hypertension, vol. 53, 2009, pp. 867-876.
Muflih, et al., "Sugars and sugar derivatives which inhibit the shortcircuit current of the everted small intestine of the rat", J Physiol, 263, 1976, pp. 101-114.
Murphy, et al., "Molecular phylogenetics and the origins of placental mammals", Nature, 409, 2001, pp. 614-618.
Mynott, et al., "Efficacy of Enteric-Coated Protease in Preventing Attachment of Enterotoxigenic *Escherichia coli* and Diarrheal Disease in the RITARD Model", Infect Immun, 59(10), 1991, pp. 3708-3714.
Mynott, et al., "Oral administration of protease inhibits enterotoxigenic *Escherichia coli* receptor activity in piglet small intestine", Gut, 38, 1996, pp. 28-32.
Narayani, et al., "Polymer-coated gelatin capsules as oral delivery devices and their gastointestinal tract behaviour in humans", J Biomater Sci Polymer Edn, 7(1), 1995, pp. 39-48.
Nelson, et al., "Chapters 4-5, 7", Lehninger Principles of Biochemistry, 3rd Edition, (Eds. Ryan, M., et al., Worth Publishers), 2000.
Nguyen, et al., "Stimulation of Secretion by the T84 Colonic Epithelial Cell Line with Dietary Flavonols", Biochem Pharmacol, 41(12), 1991, pp. 1879-1886.
Noble, et al., "Insulin Lispro: A Fast-Acting Insulin Analog", Am Fam Physician, 57(2), 1998, pp. 279-286.
Palladino, et al., "New TFA-free cleavage and final deprotection in Fmoc solid-phase peptide synthesis: dilute HCI in fluoro alcohol", Organic Lett, 14, 2012, pp. 6346-6349.
Pitari, et al., "Pharmacology and clinical potential of guanylyl cyclase C agonists in the treatment of ulcerative colitis", Drug Design Development and Therapy, vol. 7, 2013, pp. 351-360.
Rao, et al., "Symptoms and stool patterns in patients with ulcerative colitis", Gut, 29, 1988, pp. 342-345.
Rehfield, J.F., "The New Biology of Gastrointestinal Hormones", Physiol Rev, 78(4), 1998, pp. 1087-1108.
Roux, et al., "Elimination and exchange of trifluoroacetate counter-ion from cationic peptides: a critical evaluation of different approaches", J Peptide Sci, 14, 2008, pp. 354-359.
Sani, et al., "Pro-apoptotic bax-alpha1 synthesis and evidence for beta-sheet to alpha-helix conformational change as triggered by negatively charged lipid membranes", J Pept Sci, vol. 13, 2007, pp. 100-106.
Santos-Neto, et al., "Guanylin and its lysine-containing analogue in the isolated perfused rat kidney: interaction with chymotrypsin inhibitor", Pharmacology & Toxicology, 92, 2003, pp. 114-120.
Schule, et al., "Monitoring and Control of Genotoxic Impurity Acetamide in the Synthesis of Zaurategrast Sulfate", Org Process Res Dev, 14(4), 2010, pp. 1008-1014.
Schulz, et al., "Side chain contributions to the interconversion of the topological isomers of guanylin-like peptides", J Peptide Sci, 11, 2005, pp. 319-330.
Segaloff, et al., "Chapter 9: Internalization of Peptide Hormones and Hormone Receptors", Hormones and Their Actions, Part I, Cooke, et al. Editors, Elsevier, 1988, pp. 133-149.
Shailubhai, et al., "A Randomized, Double-blind, Placebo-Controlled, Single-, Ascending-, Oral-Dose Safety, Tolerability and Pharmacokinetic Study of SP-304 in Healthy Adult Human Male and Female Volunteers", Digestive Disease Week, San Diego, 2008, 1 page poster.
Shibue, et al., "Effect of anionic ion-pairing reagent concentration (1-60 mM) on reversed-phase liquid chromatography elution behaviour of peptides", J Chromatogr A, 1080(1), 2005, pp. 58-67.
Silverman, R.B., "Chapter 3: Receptors", The Organic Chemistry of Drug Design and Drug Action (Academic Press, Inc.), 1992, pp. 52-97.
Solinga, et al., "A comparison of the physical and pharmacological properties of plecanatide (SP-304) and the human hormone uroguanylin", J American College of Gastroenterology, 106, Abstract, 2011, pp. S513.
Supelco, "Eliminate TFA and improve sensitivity of peptide analyses by LC/MS", Application Note 168, sales brochure, 2002.
Swietlow, et al., "Quality control in peptide manufacturing: specifications for GMP peptides", Peptide Chemistry, 2004, pp. 22-24.
Székely, et al., "Removal of potentially genotoxic acetamide and arylsulfonate impurities from crude drugs by molecular imprinting", J Chromatogr A, 1240, 2012, pp. 52-58.
Tager, et al., "Peptide Hormones", Ann Rev Biochem, 43, 1974, pp. 509-538.
Thomson, "Small bowel review: Part I", Can J Gastroenterol, 14(9), 2000, pp. 791-816.
Tien, et al., "Neurokinin A increases short-circuit current across rat colonic mucosa: A role for vasoacrtive intestinal polypeptide", J Physiol, 437, 1991, pp. 341-350.
Unson, et al., "Positively Charged Residues at Positions 12, 17, and 18 of Glucagon Ensure Maximum Biological Potency", J Biol Chem, 273(17), 1998, pp. 10308-10312.
Vergote, et al., "Quality specifications for peptide drugs: a regulatory-pharmaceutical approach", J Pept Sci, 15, 2009, pp. 697-710.
Visweswariah, et al., "Characterization and partial purification of the human receptor for the heat-stable enterotoxin", Eur J Biochem, 219, 1994, pp. 727-736.
Wade, et al., "Base-induced side reactions in Fmoc-solid phase peptide synthesis: Minimization by use of piperazine as Nalpha-deprotection reagent", Lett Pept Sci, 7, 2000, pp. 107-112.
Wakankar, et al., "Formulation Considerations for Proteins Susceptible to Asparagine Deamidation and Aspartate Isomerization", J Pharm Sci, 95(11), 2006, pp. 2321-2336.
Whitaker, et al., "Uroguanylin and Guanylin: Distinct but Overlapping Patterns of Messenger RNA Expression in Mouse Intestine", Gastroenterol, 113, 1997, pp. 1000-1006.
Zhang, et al., "Cysteine Racemization on IgG Heavy and Light Chains", J Biol Chem, 288(48), Nov. 29, 2013, pp. 34325-34335.
Zhang, J., "Rates of Conservative and Radical Nonsynonymous Nucleotide Substitutions in Mammalian Nuclear Genes", J Mol Evol, 50, 2000, pp. 56-68.

\* cited by examiner

|    | RT     | Area     | % Area | Height |
|----|--------|----------|--------|--------|
| 1  | 35.395 | 25544    | 0.21   | 570    |
| 2  | 40.323 | 4201     | 0.03   | 122    |
| 3  | 41.530 | 6027     | 0.05   | 166    |
| 4  | 42.331 | 17626    | 0.14   | 323    |
| 5  | 44.118 | 12069650 | 97.95  | 158103 |
| 6  | 50.014 | 64915    | 0.53   | 903    |
| 7  | 51.255 | 49338    | 0.40   | 714    |
| 8  | 54.354 | 18505    | 0.15   | 227    |
| 9  | 58.933 | 5886     | 0.05   | 101    |
| 10 | 69.057 | 45061    | 0.37   | 565    |
| 11 | 77.793 | 15160    | 0.12   | 183    |

Scheme 1

Boc-Asn(Trt)-Asp(OtBu)-Glu(OtBu)-Cys(Trt)-Glu(OtBu)-Leu-OH,(Fragment A or BocAA1-6OH)

(SEQ ID NO: 263)

i) Peptide Chain assembly using Fmoc chemistry
ii) 1%TFA/DCM

Fmoc-Cys(Acm)-Val-Asn(Trt)-Val-Ala-Cys(Trt)-Thr(tBu)-Gly-OH,(Fragment B or FmocAA7-14OH)

(SEQ ID NO: 264)

Scheme 2

SEQ ID NO: 266

Scheme 5

Scheme 6

Boc-D-Asn(Trt)-Asp(OtBu)-Glu(OtBu)-Cys(Trt)-Glu(OtBu)-Leu-OH,(Fragment A or BocAA1-6OH)

(SEQ ID NO: 270)

Fmoc-Cys(Acm)-Val-Asn(Trt)-Val-Ala-Cys(Trt)-Thr(tBu)-Gly-OH,(Fragment B or FmocAA7-14OH)

(SEQ ID NO: 264)

Scheme 8

Scheme 9

H-D-Asn-Asp-Glu-Cys-Glu-Leu-Cys(Acm)-Val-Asn-Val-Ala-Cys-Thr-Gly-Cys(Acm)-D-Leu-OH (SEQ ID NO: 272)

ULTRA-PURE AGONISTS OF GUANYLATE CYCLASE C, METHOD OF MAKING AND USING SAME

CROSS-REFERENCE TO RELATED APPLICATIONS

This application is a continuation of, and claims priority to, U.S. application Ser. No. 18/193,144, filed Mar. 30, 2023, now issued as U.S. Pat. No. 11,834,521, which is a continuation of, and claims priority to, U.S. application Ser. No. 17/397,796, filed Aug. 9, 2021, now abandoned, which is a continuation of, and claims priority to, U.S. application Ser. No. 17/207,215, filed Mar. 19, 2021, now abandoned, which is a continuation of, and claims priority to, U.S. application Ser. No. 16/921,450, filed Jul. 6, 2020, now issued as U.S. Pat. No. 11,142,549, which is a continuation of, and claims priority to, U.S. application Ser. No. 16/000,251, filed Jun. 5, 2018, now issued as U.S. Pat. No. 10,745,441, which is a continuation of, and claims priority to, U.S. application Ser. No. 14/896,019, filed Dec. 4, 2015, now issued as U.S. Pat. No. 10,011,637, which is a U.S. national stage application of, and claims priority to, International Application No. PCT/US2014/041143, filed Jun. 5, 2014, which claims priority to U.S. provisional application No. 61/831,402, filed Jun. 5, 2013, the contents of which are herein incorporated by reference in their entireties.

INCORPORATION-BY-REFERENCE OF MATERIAL SUBMITTED AS AN XML FILE VIA THE OFFICE ELECTRONIC FILING SYSTEM

The Sequence Listing concurrently submitted herewith as an xml file named "376464-2011US8.xml" created on Aug. 19, 2024 and having a size of 454,700 bytes, the entire content of which is herein incorporated by reference in its entirety.

FIELD OF THE INVENTION

The present invention relates to processes of purifying guanylate cyclase C peptide agonists useful for preparing formulations for the treatment and prevention of various diseases and disorders.

BACKGROUND OF THE INVENTION

Guanylate cyclase C is a transmembrane form of guanylate cyclase that is expressed on various cells, including gastrointestinal epithelial cells (reviewed in Vaandrager 2002 *Mol. Cell. Biochem.* 230:73-83). It was originally discovered as the intestinal receptor for the heat-stable toxin (ST) peptides secreted by enteric bacteria and which cause diarrhea. The ST peptides share a similar primary amino acid structure with two peptides isolated from intestinal mucosa and urine, guanylin and uroguanylin (Currie, et al., *Proc. Nat'l Acad. Sci. USA* 89:947-951 (1992); Hamra, et al., *Proc. Nat'l Acad. Sci. USA* 90:10464-10468 (1993); Forte, L, *Reg. Pept.* 81:25-39 (1999); Schulz, et al., Cell 63:941-948 (1990); Guba, et al., *Gastroenterology* 111:1558-1568 (1996); Joo, et al., *Am. J. Physiol.* 274: G633-G644 (1998)).

In the intestines, guanylin and uroguanylin act as regulators of fluid and electrolyte balance. In response to high oral salt intake, these peptides are released into the intestinal lumen where they bind to guanylate cyclase C localized on the luminal membrane of enterocytes (simple columnar epithelial cells of the small intestines and colon). The binding of the guanylin peptides to guanylate cyclase C induces electrolyte and water excretion into the intestinal lumen via a complex intracellular signaling cascade that is initiated by an increase in cyclic guanosine monophosphate (cGMP).

The cGMP-mediated signaling that is initiated by the guanylin peptides is critical for the normal functioning of the gut. Any abnormality in this process could lead to gastrointestinal disorders such as irritable bowel syndrome (IBS) and inflammatory bowel diseases. Inflammatory bowel disease is a general name given to a group of disorders that cause the intestines to become inflamed, characterized by red and swollen tissue. Examples include ulcerative colitis and Crohn's disease. Crohn's disease is a serious inflammatory disease that predominantly affects the ileum and colon, but can also occur in other sections of the gastrointestinal tract. Ulcerative colitis is exclusively an inflammatory disease of the colon, the large intestine. Unlike Crohn's disease, in which all layers of the intestine are involved, and in which there can be normal healthy bowel in between patches of diseased bowel, ulcerative colitis affects only the innermost lining (mucosa) of the colon in a continuous manner. Depending on which portion of the gastrointestinal tract is involved, Crohn's disease may be referred to as ileitis, regional enteritis, colitis, etc. Crohn's disease and ulcerative colitis differ from spastic colon or irritable bowel syndrome, which are motility disorders of the gastrointestinal tract. Gastrointestinal inflammation can be a chronic condition. It is estimated that as many as 1,000,000 Americans are afflicted with inflammatory bowel disease, with male and female patients appearing to be equally affected. Most cases are diagnosed before age 30, but the disease can occur in the sixth, seventh, and later decades of life.

IBS and chronic idiopathic constipation are pathological conditions that can cause a great deal of intestinal discomfort and distress but unlike the inflammatory bowel diseases, IBS does not cause the serious inflammation or changes in bowel tissue and it is not thought to increase the risk of colorectal cancer. In the past, inflammatory bowel disease, celiac disease, and IBS were regarded as completely separate disorders. Now, with the description of inflammation, albeit low-grade, in IBS, and of symptom overlap between IBS and celiac disease, this contention has come under question. Acute bacterial gastroenteritis is the strongest risk factor identified to date for the subsequent development of postinfective irritable bowel syndrome. Clinical risk factors include prolonged acute illness and the absence of vomiting. A genetically determined susceptibility to inflammatory stimuli may also be a risk factor for irritable bowel syndrome. The underlying pathophysiology indicates increased intestinal permeability and low-grade inflammation, as well as altered motility and visceral sensitivity. Serotonin (5-hydroxytryptamine [5-HT]) is a key modulator of gut function and is known to play a major role in pathophysiology of IBS. The activity of 5-HT is regulated by cGMP.

While the precise causes of IBS and inflammatory bowel diseases (IBD) are not known, a disruption in the process of continual renewal of the gastrointestinal mucosa may contribute to disease pathology in IBD and aggravate IBS. The renewal process of the gastrointestinal lining is an efficient and dynamic process involving the continual proliferation and replenishment of unwanted damaged cells. Proliferation rates of cells lining the gastrointestinal mucosa are very high, second only to the hematopoietic system. Gastrointestinal homeostasis depends on both the proliferation and programmed cellular death (apoptosis) of epithelial cells lining the gut mucosa. Cells are continually lost from the villus into the lumen of the gut and are replenished at a substantially equal rate by the proliferation of cells in the crypts, followed by their upward movement to the villus. The rates of cell proliferation and apoptosis in the gut epithelium can be increased or decreased in a variety of circumstances, e.g., in response to physiological stimuli such as aging, inflammatory signals, hormones, peptides, growth factors, chemicals and dietary habits. In addition, an enhanced proliferation rate is frequently associated with a reduction in turnover time and an expansion of the proliferative zone. The proliferation index is much higher in pathological states such as ulcerative colitis and other gastrointestinal disorders. Intestinal hyperplasia is a major promoter of gastrointestinal inflammation. Apoptosis and cell proliferation together regulate cell number and determine the proliferation index. Reduced rates of apoptosis are often associated with abnormal growth, inflammation, and neoplastic transformation. Thus, both increased proliferation and/or reduced cell death may increase the proliferation index of intestinal tissue, which may in turn lead to gastrointestinal inflammatory diseases.

In addition to a role for uroguanylin and guanylin as modulators of intestinal fluid and ion secretion, these peptides may also be involved in the continual renewal of gastrointestinal mucosa by maintaining the balance between proliferation and apoptosis. For example, uroguanylin and guanylin peptides appear to promote apoptosis by controlling cellular ion flux. Given the prevalence of inflammatory conditions in Western societies a need exists to improve the treatment options for inflammatory conditions, particularly of the gastrointestinal tract.

Peptide agonists of guanylate cyclase C agonists ("GCC agonists") are described in U.S. Pat. Nos. 7,041,786, 7,799, 897, and U.S. Patent Application Publication Nos. US2009/0048175, US 2010/0069306, US 2010/0120694, US 2010/0093635, and US 2010/0221329, and WO2012/118972. However, the previous syntheses of peptides for pharmaceutical application present a number of special problems such as an overall low yield (e.g., less than 10%), and/or high levels of impurities (e.g., contaminants resulted from organic solvents used during syntheses or purification, and degradation products or topoisomers created, e.g., during purification).

BRIEF SUMMARY OF THE INVENTION

In one aspect, the present invention is derived from the effort to solve various unexpected problems encountered during the purification processes of peptide GCC agonists for pharmaceutical application, such as the lyophilization process and precipitation process described in WO2012/118972. The methods described herein provide a solution to those problems.

In one aspect, the present invention provides a purified peptide comprising the GCC agonist sequence selected from the group consisting of SEQ ID NOs: 1, 9, and 104, wherein the purified peptide has the following characteristics:
 a) has a bulk density of not greater than 0.1 g/mL;
 b) contains less than 50 ppm acetamide;
 c) less than 0.3% alpha-Asp-9-plecanatide.

The purified peptide can have one or more of the following features.

For, example, the peptide is stable at 25° C. for at least three months.

For example, the peptide has a particle size distribution having a D10 value of between about 2 tp 15 µm; a D50 value of between about 15-50 µm; and a D90 value of between about 40-80 µm when measured by light scattering with liquid dispersant.

For example, the purified peptide contains no more than 35 ppm acetamide (e.g., ≤18 ppm).

For example, the purified peptide contains less than 0.15% alpha-Asp-9-plecanatide (which has a Relative Retention Time (RRT) of ~1.33 from the ultra-performance liquid chromatography (UPLC) analysis described herein).

For example, the purified peptide has a bulk density of not greater than 0.09 g/mL, not greater than 0.08 g/mL, not greater than 0.07 g/mL, not greater than 0.06 g/mL, not greater than 0.05 g/mL, not greater than 0.04 g/mL, or not greater than 0.03 g/mL.

For example, the purified peptide is substantially free of water (e.g., water content not exceeding 10%, 9%, 8%, 7%, 6%, 5%, 4%, 3.5%, 3%, 2.5%, 2%, 1.5%, 1%, 0.5%, 0.25%, or 0.1%, of the total weight of the peptide).

For example, the purified peptide has a chromatographic purity of no less than 95%, no less than 96%, or no less than 97%.

For example, the total content of impurities in the purified peptide is less than 3% (e.g., <2% or <1%).

For example, the purified peptide is further substantially free of one or more impurities selected from acetonitrile, alcohols, ammonium, acetates, and TFA.

For example, the purified peptide contains less than 300 ppm acetonitrile (e.g., <250 ppm).

For example, the purified peptide contains less than 0.2% TFA (e.g., <0.15%, <0.1%, <400 ppm, <300 ppm, <200 ppm, <100 ppm, or <50 ppm).

For example, the purified peptide contains less than 0.2% isopropanol, i.e., IPA (e.g., <0.15%, <0.1%, <1000 ppm, <900 ppm<800 ppm, <700 ppm, <600 ppm, <500 ppm, <400 ppm, <300 ppm, <200 ppm, <100 ppm, <50 ppm, or <20 ppm).

For example, the purified peptide contains less than 0.25% acetate (e.g., <0.2% or <0.1%).

For example, the purified peptide is substantially free of topoisomers (e.g., <0.4%, <0.3%, <0.2% or <0.1%).

For example, the purified peptide is substantially free of iso-Asp2-plecanatide (RRT 0.96-0.97) (e.g., <0.4%, <0.3%, <0.2% or <0.1%).

In another aspect, the invention also provides a process of purifying/isolating the peptide comprising the GCC agonist sequence selected from the group consisting of SEQ ID NOs: 1-251. The process includes:
 providing a first peptide solution comprising a peptide comprising the GCC agonist sequence selected from the group consisting of SEQ ID NOs: 1-251, water, and acetonitrile;
 loading a C18 or polymeric adsorbent column with the first peptide solution to adsorb the peptide onto the polymeric adsorbent column,
 eluting the peptide off the C18 or polymeric adsorbent column with an alcohol aqueous solution to form a second peptide solution,
 reducing the amount of alcohol in the second peptide solution, and
 lyophilizing the second peptide solution such that a dry peptide is obtained.

The process can include one or more of the following features.

For example, the alcohol aqueous solution comprises isopropanol (e.g., with isopropanol content in the alcohol aqueous solution being about 40%).

In another embodiment, the alcohol aqueous solution comprises propanol, tert-butanol, 2-butanol, or ethanol.

For example, the first peptide solution further comprises acetamide.

For example, the first peptide solution further comprises acetic acid (e.g., 0.2%) or triethylamine phosphate (e.g., 1%).

For example, the amount of alcohol (e.g., isopropanol) in the second peptide solution is reduced e.g. by rotoevaporation to less than 5%.

For example, the process further comprises dissolving the dry peptide in water to form a third peptide solution after lyophilization. For example, the third peptide solution further comprises ammonium acetate or ammonium hydroxide (e.g., such that the third solution has a pH value of about 5).

For example, the process further comprises lyophilizing the third peptide solution such that a purified peptide is obtained.

For example, the peptide in the first peptide solution is prepared by the fragment condensation process (i.e., hybrid solution- and solid-phase process) as described in WO2012/118972. In one embodiment, the first peptide solution is obtained from a salt exchanging step in which the peptide is washed with an aqueous acetonitrile solution comprising triethylamine phosphate or acetic acid.

For example, the polymeric adsorbent column is a preparative $C_{18}$ RP-HPLC column. In one embodiment, the polymeric adsorbent column comprises a polystyrene resin. In particular, the resin is selected so that the purified peptide eluted or desorbed is not less than 80% of the peptide amount adsorbed on the resin, e.g., not less than 85%, not less than 90%, or not less than 95%. In one embodiment, the resin is formed of crosslinked polystyrene with an average pore diameter greater than 5 nm, e.g., about 6-8 nm, 10-15 nm, 15-20 nm, or 25-30 nm.

In yet another aspect, the invention also provides a purified peptide prepared by the purification process of the invention. The purified peptides may have one or more of the following features.

For example, the purified peptide comprises the GCC agonist sequence selected from the group consisting of SEQ ID NOs: 1, 9, and 104.

For example, the purified peptide has a chromatographic purity of no less than 96%, no less than 97%, or no less than 98%. For example, the GCC agonist peptide has chromatographic impurity content of no greater than 4%, no greater than 3.5%, no greater than 3%, no greater than 2.5%, no greater than 2%, no greater than 1.5%, or no greater than 1%. The chromatographic impurity content is determined as total area percentages of impurities by HPLC. The chromatographic impurity content includes topoisomer content. The impurities do not include any pharmaceutically acceptable excipient used for drug formulation.

For example, the purified peptide is substantially free of contaminants resulted from the peptide preparation process such as organic solvents used in the process, e.g., ammonium, acetonitrile, acetamide, alcohol (e.g., methanol, ethanol, or isopropanol), TFA, ether or other contaminants. In this context "substantially" free of contaminants means that the contaminant content of the peptide at the end of the purification process is preferably less than 0.5%, less than 0.3%, less than 0.25%, less than 0.1%, less than 0.05%, less than 0.04%, less than 0.03%, less than 0.02%, less than 0.01%, less than 0.005%, less than 0.003%, or less than 0.001% of the total weight of the peptide. For example, the purified peptide contains <50 ppm acetamide (e.g., ≤35 ppm or ≤18 ppm), <300 ppm acetonitrile (e.g., <250 ppm), <1000 ppm TFA (e.g., <400 ppm, <300 ppm, <200 ppm, <100 ppm, or <50 ppm), <2000 ppm isopropanol (e.g., <1500 ppm, <1000 ppm, <500 ppm, <400 ppm, <300 ppm, <200 ppm, <100 ppm, <50 ppm, or <20 ppm), and/or <0.25% acetate (e.g., <0.2% or <0.1%). The content of contaminants can be determined by conventional methods such as gas chromatography. Preferably, the residual solvents in the purified peptide of the invention are less than the limits set in the ICH guidelines, e.g., IMPURITIES: GUIDELINE FOR RESIDUAL SOLVENTS Q3C (R5) (available at www.ich.org/fileadmin/Public_Web_Site/ICH_Products/Guidelines/Quality/Q3C/Step4/Q 3C_R5_Step4.pdf).

For example, the purified peptide contains less than 0.3% (e.g., <0.15%) alpha-Asp-9-plecanatide (RRT 1.33).

For example, the purified peptide has a bulk density of not greater than 0.09 g/mL, not greater than 0.08 g/mL, not greater than 0.07 g/mL, not greater than 0.06 g/mL, not greater than 0.05 g/mL, not greater than 0.04 g/mL, or not greater than 0.03 g/mL.

For example, the purified peptide is substantially free of iso-Asp2-plecanatide (RRT ~ 0.96-0.97). In this context "substantially" free of iso-Asp2-plecanatide means that the iso-Asp2-plecanatide content of the peptide at the end of the purification process is preferably less than 2%, less than 1.5%, less than 1.25%, less than 1%, less than 0.9%, less than 0.8%, less than 0.7%, less than 0.6%, less than 0.5%, less than 0.4%, less than 0.3%, less than 0.2%, or less than 0.1%, of the total weight of the peptide.

For example, the purified peptide is substantially free of topoisomers. In this context "substantially" free of topoisomers means that the topoisomer content of the peptide at the end of the purification process is preferably less than 2%, less than 1.5%, less than 1.25%, less than 1%, less than 0.9%, less than 0.8%, less than 0.7%, less than 0.6%, less than 0.5%, less than 0.4%, less than 0.3%, less than 0.2%, or less than 0.1%, of the total weight of the peptide.

For example, the purified peptide is substantially free of water. In this context "substantially" free of water means that the water content of the peptide at the end of the purification process is preferably less than 10%, 9%, 8%, 7%, less than 6%, less than 5%, less than 4.5%, less than 4.25%, less than 4%, less than 3.5%, less than 3%, less than 2.5%, less than 2%, less than 1.5%, less than 1%, less than 0.5%, less than 0.25%, or less than 0.1%, of the total weight of the peptide.

For example, the peptide has a particle size distribution having a D10 value of between about 2 tp 15 μm; a D50 value of between about 15-50 μm; and a D90 value of between about 40-80 μm when measured by light scattering with liquid dispersant.

For example, the purified peptide has a particle size distribution characterized by a D50 value of about 600 μm when measured by light scattering with air dispersant. In comparison, the peptides purified from the lyophilization and precipitation processes described in WO2012/118972 have D50 values of about 180-250 μm and about 300 μm, respectively.

For example, the purified peptide prepared by the processes of the invention has a suitable size distribution for pharmaceutical formulation. In one embodiment, the peptide (e.g., SP-304) has a size distribution (e.g., an average size of 80-120 μm) comparable to that of the pharmaceutical excipient (e.g., microcrystalline cellulose) used in the formulation, for example, in the 3 mg/day unit dose form. The size distribution of the purified peptide may vary based on the unit dose. For example, when unit dose is lower than 3 mg/day, the purified peptide in the pharmaceutical formulation has a smaller average size than that in the 3 mg/day dose. For example, the purified peptide prepared by the processes of the invention is milled to reach the suitable size distribution.

The size distribution of the peptide of the invention can be determined by traditional methods, such as sieve analysis, light obscuration or dynamic light scattering analyses.

The invention also relates to a formulation (e.g., an oral formulation) containing the peptides prepared and/or purified by the methods described herein and in particular, a low dose formulation containing 0.05-10 mg (e.g., 0.1 mg, 0.3 mg or 0.5 mg) of the purified peptides. The low-dose formulation can further have one or more additional features as described in WO2012/037380 and US 2012-0237593 and can be prepared by the methods disclosed therein, such as dry blending.

Other features and advantages of the invention will be apparent from and are encompassed by the following detailed description and claims.

DETAILED DESCRIPTION

Figure 1:
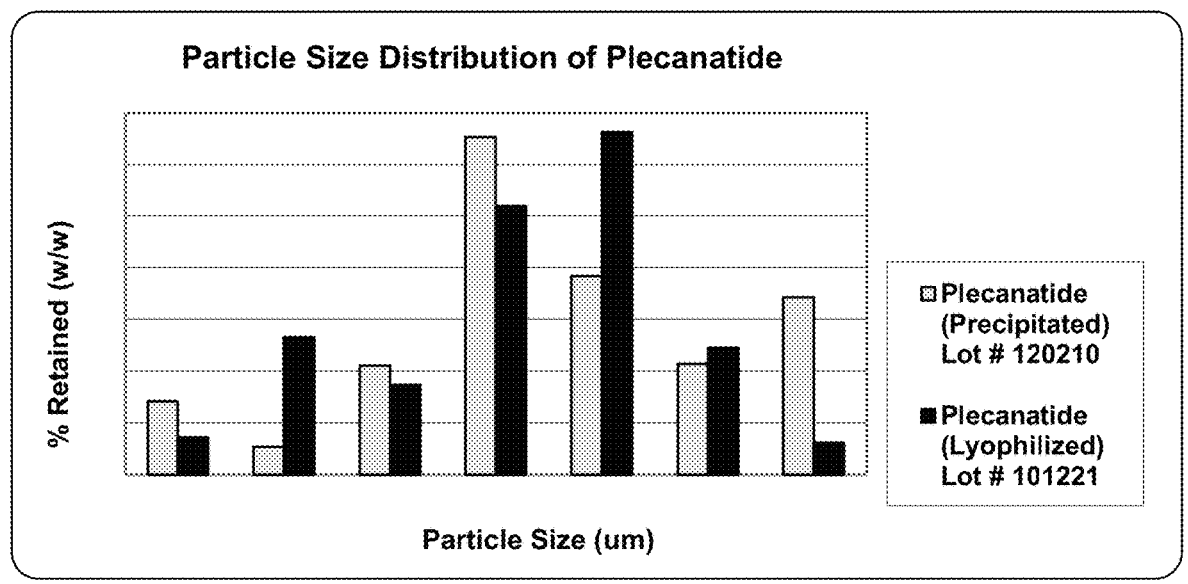
FIG. 1 is a graph showing particle size distribution by sieving analysis for lyophilized plecanatide and precipitated plecanatide.

In one aspect, the present invention provides a solution to various unexpected problems encountered during the purification processes of peptide GCC agonists for pharmaceutical application, such as the lyophilization process and precipitation process described in WO2012/118972.

In particular, it was found that the lyophilization process described in WO2012/118972, which involved use of acetonitrile/water solvent, unexpectedly resulted in enrichment of residual acetamide (a trace level impurity in acetonitrile) in the lyophilized plecanatide product with high acetamide content (i.e., ranging from 88 to 453 ppm among tested batches, or about 300 ppm on average), which hindered commercialization of plecanatide with doses higher than 3 mg/day. In addition, the lyophilized plecanatide product also had a high variability of residual salt levels such as TFA, acetate, and ammonium salts.

On the other hand, while the plecanatide product purified via the precipitation process described in WO2012/118972 had low residual acetamide content (<50 ppm) and higher bulk or tap density (i.e., about ten times higher) than the lyophilized product, the precipitated plecanatide product contained high levels of residual solvents (e.g., IPA as high as 90,000 ppm) due to difficulty in removing the solvents used for peptide precipitation. In addition, while low temperature heating (45° C.) during vacuum drying helped to reduce the residual isopropanol to the amount below the ICH limit of 5000 ppm (e.g., 1700 ppm), a thermal degradant, alpha-Asp-9-plecanatide, having a Relative Retention Time (RRT) of ~1.33 from ultra-performance liquid chromatography (UPLC) analysis, was then formed in the final peptide product at a concentration as high as 0.9%. The content of the RRT 1.33 impurity also increases in plecanatide and tablets thereof during room-temperature storage. Therefore, the initial high level of this RRT 1.33 impurity in plecanatide produced by the precipitation process results in a smaller window of acceptance and hence shortens the usable shelf life of plecanatide drug products.

The purification processes of the invention solves the residual solvent problem and degradation problem by, for example, exchanging the acetonitrile/water solvent with IPA/water solvent followed by rotary evaporation to reduce IPA to a critical low level (e.g., <5%), followed by a first sublot freeze drying, which resulted in low but unacceptable levels of residual solvents, then followed by reconstitution in water and final freeze drying resulting in low and acceptable levels of residual solvents for pharmaceutical application. In addition, the purification processes of the invention are suitable for scale up preparation/purification of peptides.

It was further unexpectedly discovered that adding a small amount of ammonium acetate buffer (e.g., 0.5% to dry peptide) during reconstitution with water (pH 5) prior to final lyophilization improves solubility of final product. Further, ammonium acetate buffer (pH 5) reduces the rate of plecanatide topo-isomerization in solution during lyophilization. The ammonium acetate buffer (pH 5) also controls residual salt levels in the final product with lower variability as compared to the lyophilization product described in WO2012/118972.

The peptide at the end of the purification or isolation processes of the invention has a low residual acetamide level (<50 ppm) and a bulk density of not greater than 0.1 g/mL, as well as an overall lower level of residual solvents (e.g., <500 ppm IPA, <300 ppm ACN), low levels of degradation impurities (e.g., <0.1% alpha-Asp-9-plecanatide (RRT 1.33) degradant) and topoisomers (e.g., 0.4% or less), and low levels of residual salts (e.g., <0.1% TFA, 0.08-0.23% acetate, and 0.11-0.17% ammonium). The comparison among plecanatide products isolated by different methods is presented in Table XX infra.

The invention provides processes of purifying or isolating peptides, e.g., peptide GCC agonists, in particular peptides prepared via a hybrid solution- and solid-phase process, e.g., as described in WO2012/118972, which is hereby incorporated by reference in its entirety. The hybrid process includes providing two or more fragments of a peptide of interest via solid-phase and/or solution-phase syntheses and coupling them via a solution-phase synthesis to obtain the target peptide. The process may further include, if needed, oxidative cyclization of cysteine amino acid residues of a linear peptide formed by the fragment coupling to produce a cyclized peptide.

The fragments described above can be prepared by standard solution phase peptide synthesis or solid phase peptide synthesis techniques in which a peptide linkage occurs through the direct condensation of the amino group (i.e., $NH_2$) of a first amino acid with the carboxy group (i.e., COOH) of a second amino acid with the elimination of a water molecule. In one embodiment, at least one of the fragments is prepared by solid phase peptide synthesis.

Peptide bond synthesis by direct condensation, as formulated above, requires suppression of the reactive character of the amino group of the first and of the carboxyl group of the second amino acid. The masking substituents (i.e., protecting groups) must permit their ready removal, without inducing breakdown of the labile peptide molecule. The term "protected peptide" or "protected peptide fragment" refers to a peptide or peptide fragment, in which all reactive groups on its constituting amino acids, are masked by protecting groups, unless otherwise specified. The term "deprotected peptide" or "deprotected peptide fragment" refers to a peptide or peptide fragment, in which all reactive groups on its constituting amino acids, are free from being masked by protecting groups, unless otherwise specified. The term "reactive groups" refers to the groups forming the peptide bond and those interfering with the peptide bond formation, such as amino, carboxyl, hydroxyl, and thiol (as in cysteine) groups. Examples of protecting groups for amino include and are not limited to 9-fluorenylmethyloxycarbonyl (Fmoc), tert-butoxycarbonyl (Boc), benzoyl (Bz), acetyl (Ac), and benzyl (Bn). Examples of protecting groups for carboxyl include trityl (triphenylmethyl, Trt) and O-tert-butyl (OtBu). Examples of protecting groups for thiol include acetamidomethyl (Acm), tert-butyl (tBu), 3-nitro-2-pyridine sulfenyl (NPYS), 2-pyridine-sulfenyl (Pyr), and trityl (Trt). Additional examples of protecting groups are described in Greene, T. W., Wuts, P. G. M., *Protective Groups in Organic Synthesis,* 3rd edition, John Wiley & Sons: New York, 1999, whose context is incorporated by reference herein.

For example, the hybrid synthetic methods have been used for preparing SP-304 (plecanatide). In particular, three peptide fragments, A, B and C are prepared and then a linear peptide sequence is assembled by the condensation of fragment A, B and C as follows: preparing fragment A, Boc-Asn (Trt)-Asp (OtBu)-Glu (OtBu)-Cys (Trt)-Glu (OtBu)-Leu-OH (i.e. amino acid residues 1-6 SEQ ID NO: 1), by solid phase from 2-chloro-trityl chloride resin; preparing fragment B, Fmoc-Cys (Acm)-Val-Asn-Val-Ala-Cys (Trt)-Thr (tBu)-Gly-OH (i.e. amino acid residues 7-14 of SEQ ID NO: 1), by solid phase from 2-chlorotrityl chloride resin; preparing fragment C, Cys (Acm)-Leu-OtBu, by solution phase synthesis, coupling fragments B and C in solution phase to yield fragment B-C, and coupling fragments A and B-C to yield linear peptide A-B-C.

Figure 7:
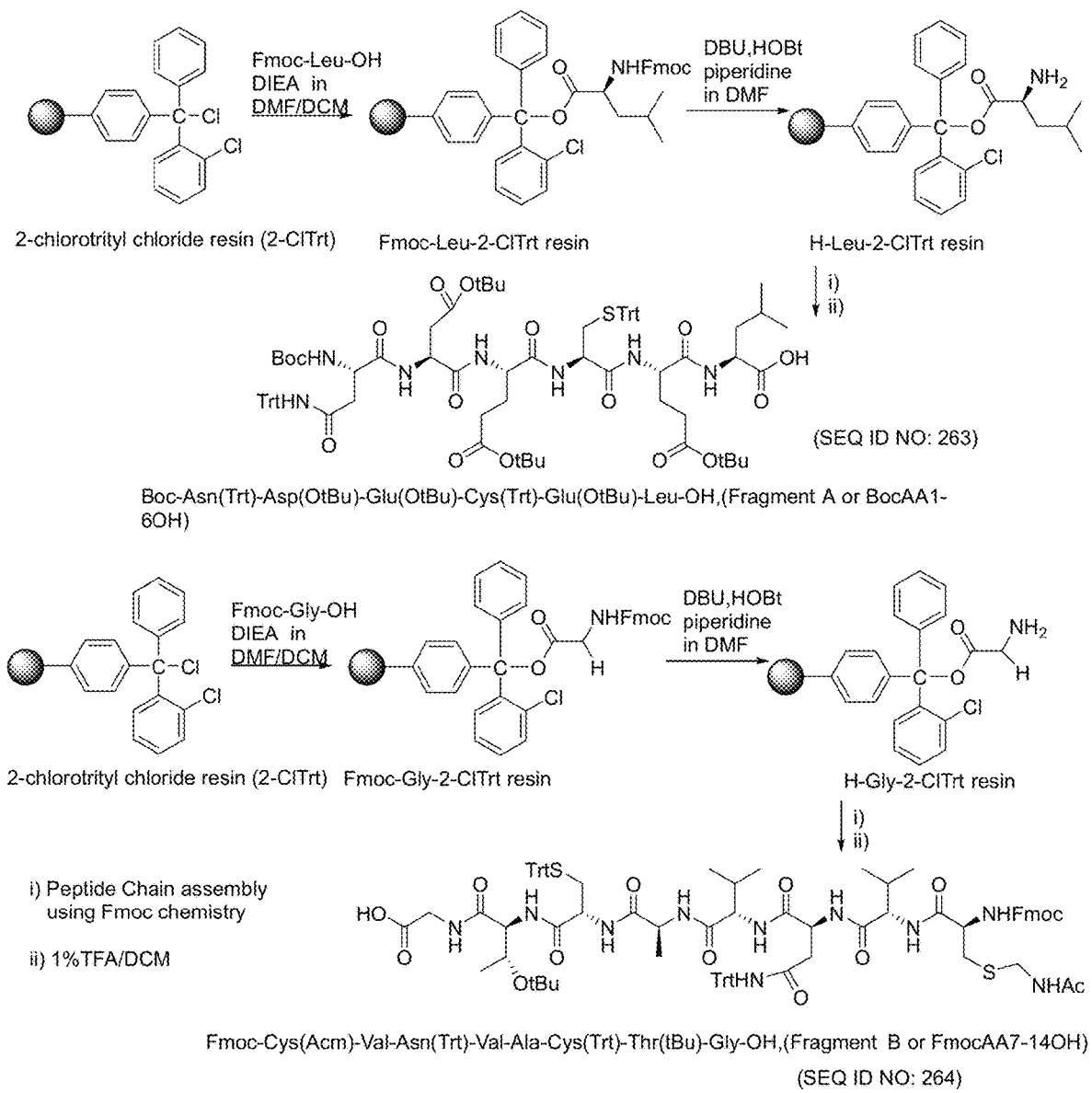
FIG. 7 shows Scheme 1 for the hybrid synthetic methods used for preparing SP-304 (plecanatide).

The side-chain-protected Fragments A (BocAA1-6OH) and B (FmocAA7-14OH) can be prepared by Fmoc SPPS using the super acid-sensitive 2-chlorotrityl chloride (2-ClTrt) resin and Fmoc-protected amino acid derivatives, as shown in Scheme 1 (FIG. 7).

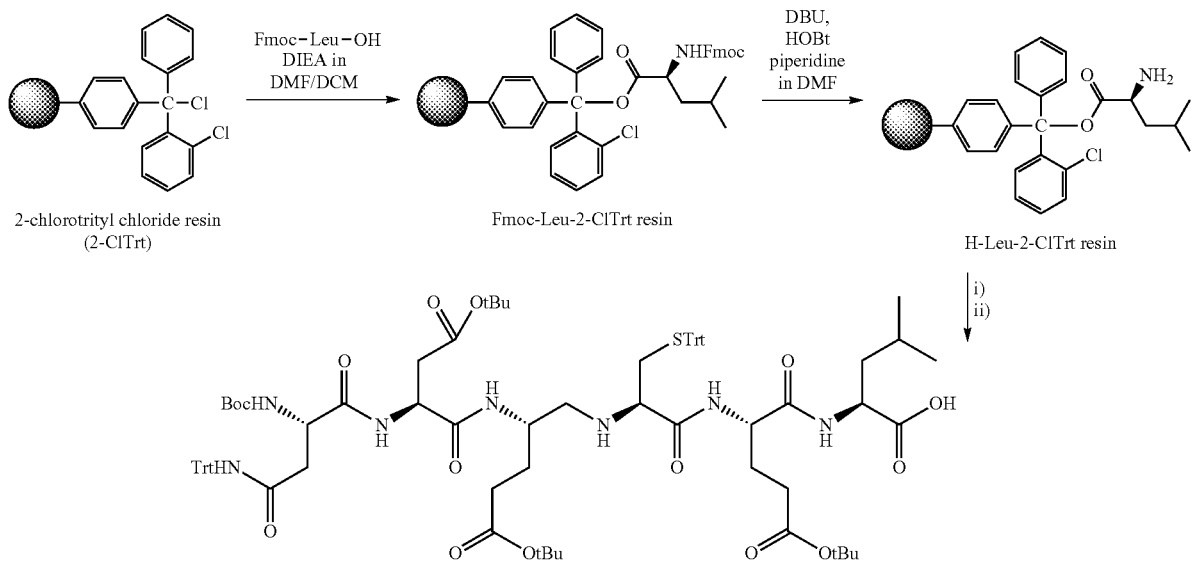

Boc-Asn(Trt)-Asp(OtBu)-Glu(OtBu)-Cys(Trt)-Glu(OtBu)-Leu-OH, (Fragment A or BocAA1-6OH) SEQ ID NO: 263

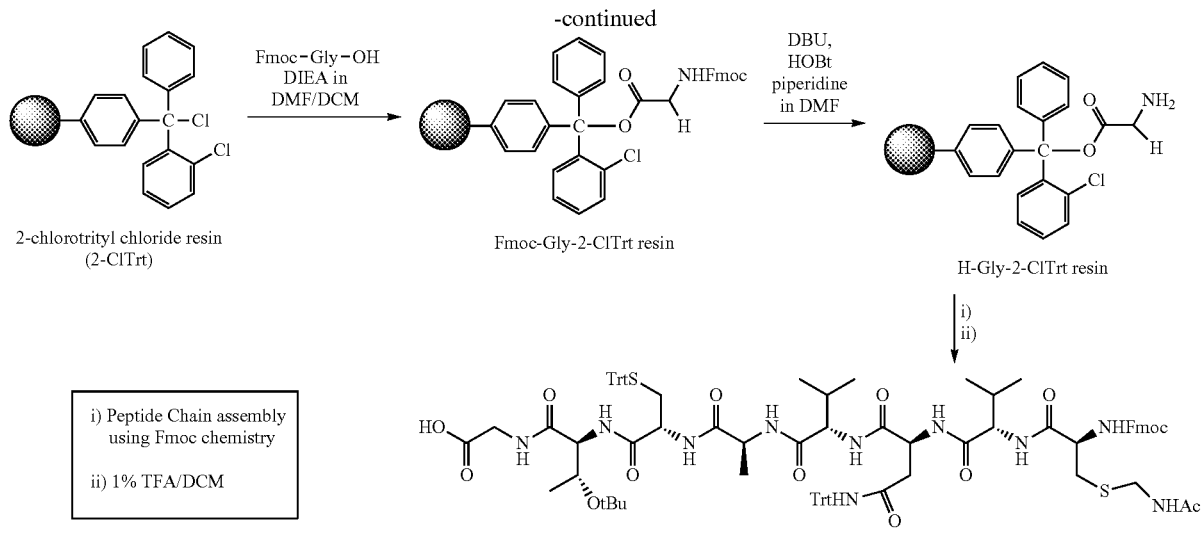

Fmoc-Cys(Acm)-Val-Asn(Trt)-Val-Ala-Cys(Trt)-Thr(tBu)-Gly-OH, (Fragment B or FmocAA7-14OH)
SEQ ID NO: 264

Figure 8:
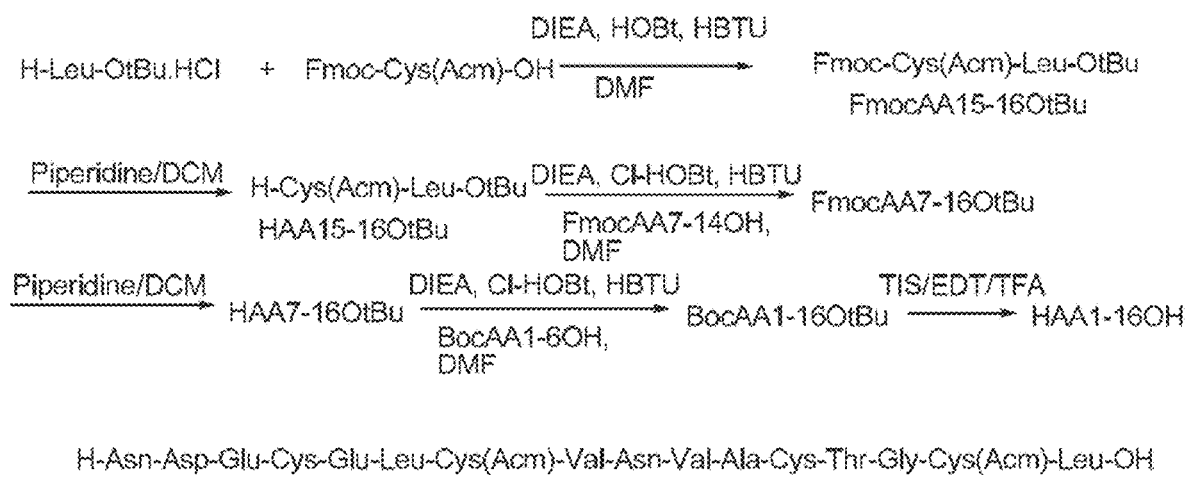
FIG. 8 shows Scheme 2 for the hybrid synthetic methods used for preparing SP-304 (plecanatide).

Fragment C (HAA15-16OtBu) can be prepared by the solution phase synthesis and then be coupled to Fragment B (FmocAA7-14OH) in solution phase to give Fragment B-C (FmocAA7-16OtBu). The Fmoc protecting group can then be removed from Fragment B-C (FmocAA7-16OtBu) to give HAA7-16OtBu, which is then coupled to Fragment A (BocAA1-6OH) to yield side-chain-protected linear SP-304 (BocAA1-16OtBu), as shown in Scheme 2 (FIG. 8).

Scheme 2

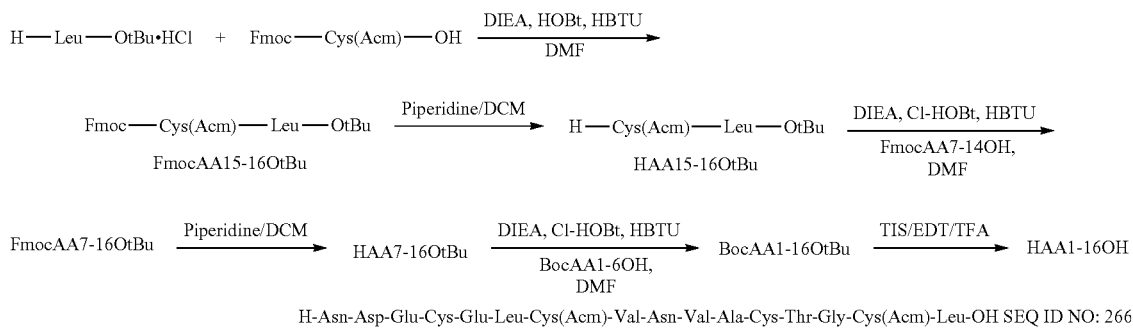

H-Asn-Asp-Glu-Cys-Glu-Leu-Cys(Acm)-Val-Asn-Val-Ala-Cys-Thr-Gly-Cys(Acm)-Leu-OH SEQ ID NO: 266

Figure 9:
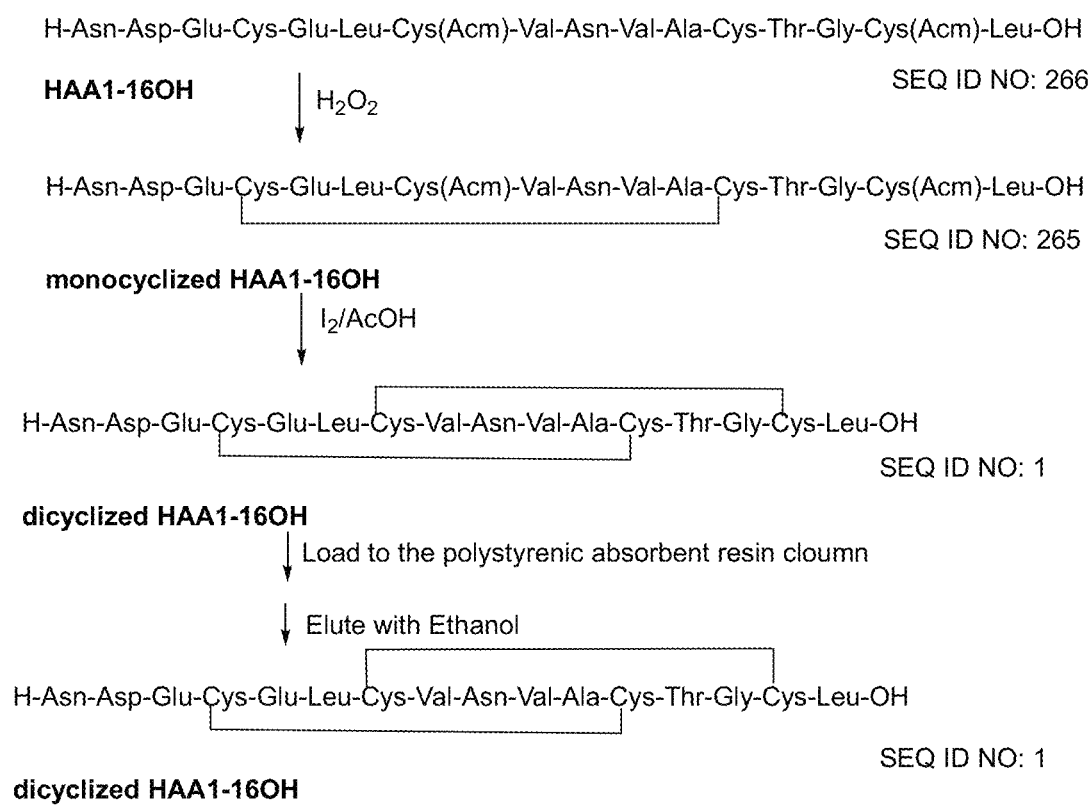
FIG. 9 shows Scheme 3 for the hybrid synthetic methods used for preparing SP-304 (plecanatide).
Figure 10:
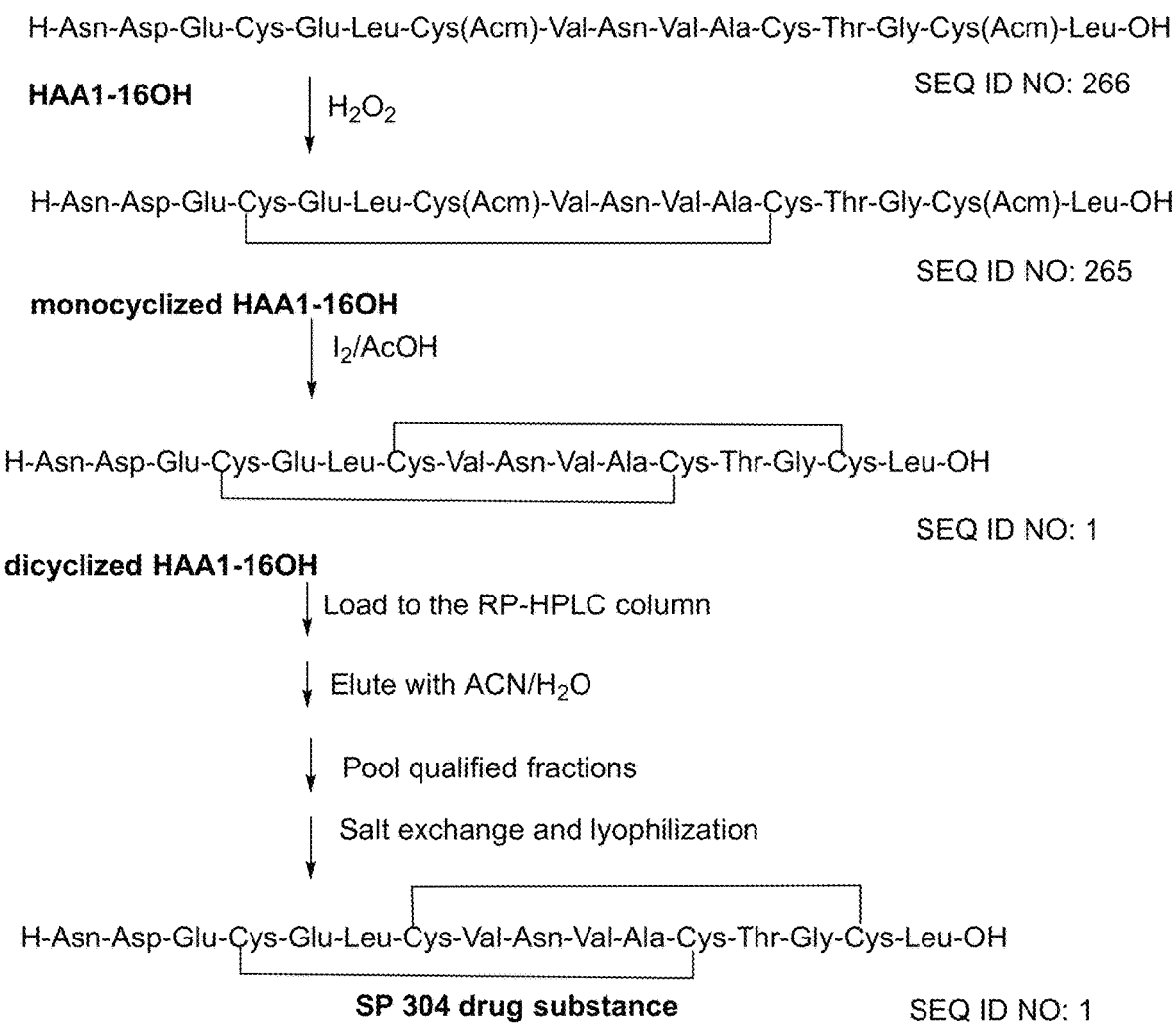
FIG. 10 shows Scheme 4 for the hybrid synthetic methods used for preparing SP-304 (plecanatide).

The side-chain-protected linear SP-304 (BocAA1-16OtBu) can be treated with trifluoroacetic acid/triisopropylsilane/ethanedithiol (TFA/TIS/EDT) to give the partially protected SP-304 (HAA1-16OH) in which the 2 S-Acm groups (as shown in Scheme 2) are intact. The partially protected linear SP-304 (HAA1-16OH) can be oxidized by $H_2O_2$, followed by simultaneous removal of the S-Acm groups and disulfide formation with iodine to give crude dicyclic SP-304, as shown in Schemes 3 and 4 (FIG. 9 and FIG. 10).

Scheme 3

H-Asn-Asp-Glu-Cys-Glu-Leu-Cys(Acm)-Val-Asn-Val-Ala-Cys-Thr-Gly-Cys(Acm)-Leu-OH

HAA1-16OH      SEQ ID NO: 266

-continued

H-Asn-Asp-Glu-Cys-Glu-Leu-Cys(Acm)-Val-Asn-Val-Ala-Cys-Thr-Gly-Cys(Acm)-Leu-OH monocycilzed HAA1-16OH  SEQ ID NO: 265

↓ I₂/AcOH

H-Asn-Asp-Glu-Cys-Glu-Leu-Cys-Val-Asn-Val-Ala-Cys-Thr-Gly-Cys-Leu-OH dicycilzed HAA1-16OH  SEQ ID NO: 1

↓ Load to the polystyrenic absorbent resin cloumn

↓ Elute with Ethanol

H-Asn-Asp-Glu-Cys-Glu-Leu-Cys-Val-Asn-Val-Ala-Cys-Thr-Cys-Leu-OH dicycilzed HAA1-16OH  SEQ ID NO: 1

Scheme 4

H-Asn-Asp-Glu-Cys-Glu-Leu-Cys(Acm)-Val-Asn-Val-Ala-Cys-Thr-Gly-Cys(Acm)-Leu-OH

HAA1-16OH  SEQ ID NO: 266

↓ H₂O₂

H-Asn-Asp-Glu-Cys-Glu-Leu-Cys(Acm)-Val-Asn-Val-Ala-Cys-Thr-Gly-Cys(Acm)-Leu-OH monocyclized HAA1-16OH  SEQ ID NO: 265

↓ I₂/AcOH

H-Asn-Asp-Glu-Cys-Glu-Leu-Cys-Val-Asn-Val-Ala-Cys-Thr-Gly-Cys-Leu-OH dicyclized HAA1-16OH  SEQ ID NO: 1

↓ Load to the RP-HPLC cloumn

↓ Elute with ACN/H₂O

↓ Pool qualified fractions

↓ Salt exchange and lyophilization

H-Asn-Asp-Glu-Cys-Glu-Leu-Cys-Val-Asn-Val-Ala-Cys-Thr-Gly-Cys-Leu-OH

SP 304 drug substance  SEQ ID NO: 1

The solution of crude dicyclic SP-304 can then be purified and concentrated, as shown in Scheme 3, by loading the solution to a polystyrenic adsorbent resin (e.g., D 10 1 (Anhui Sanxing (China); crosslinked polystyrene; surface area 500-550 m²/g; average pore diameter: 9-10 nm; pore volume: 1.18-1.24 ml/g; bulk density: 0.65-0.70 g/ml; specific density: 1.03-1.07 g/ml; moisture: 67-75%; particle size: 0.315~1.25 mm≤95%; effective diameter: 0.4~0.7 mm; uniformity coefficient: <1.6%), DA201C, DA201H, ADS-8, and ADS-5) column, eluting the dicyclic SP-304 from the column with an eluent (e.g., a 90% ethanol aqueous solution), concentrating the collected SP-304 solution under reduced pressure, and precipitating SP-304 with methyl t-butyl ether (MTBE). The precipitate can then be collected by filtration or centrifugation, dried under high vacuum to give SP-304 in solid form.

As illustrated in Scheme 4, the solution of crude dicyclic SP-304 can also be purified directly on preparative HPLC C 18 column with acetonitrile (ACN), methanol, and/or water in various buffer systems. The crude dicyclic SP-304 can also be purified via other methods known to a skilled person in the art.

Those of ordinary skill in the art will recognize that, in solid phase synthesis, deprotection, and coupling reactions must go to completion and the side-chain blocking groups must be stable throughout the synthesis.

Acetylation of the N-terminal can be accomplished by reacting the final peptide with acetic anhydride before cleavage from the resin. C-amidation is accomplished using an appropriate resin such as methylbenzhydrylamine resin using the Boc technology.

In solution phase synthesis, a wide variety of coupling methods and protecting groups may be used (See, Gross and Meienhofer, eds., "The Peptides: Analysis, Synthesis, Biology," Vol. 1-4 (Academic Press, 1979); Bodansky and Bodansky, "The Practice of Peptide Synthesis," 2d ed. (Springer Verlag, 1994)). In addition, intermediate purification and linear scale up are possible. Those of ordinary skill in the art will appreciate that solution synthesis requires consideration of main chain and side chain protecting groups and activation method. In addition, careful fragment selection is necessary to minimize racemization during fragment condensation. For example, racemization is minimized when fragments contain C-terminal Gly or Pro. Solubility considerations are also a factor. Solid phase peptide synthesis uses an insoluble polymer for support during organic synthesis. The polymer-supported peptide chain permits the use of simple washing and filtration steps instead of laborious purifications at intermediate steps. Solid-phase peptide synthesis may generally be performed according to the method of Merrifield et al., *J. Am. Chem. Soc.*, 1963, 85:2149, which involves assembling a linear peptide chain on a resin support using protected amino acids. Solid phase peptide synthesis typically utilizes either the Boc or Fmoc strategy, both of which are well known in the art.

Figure 11:
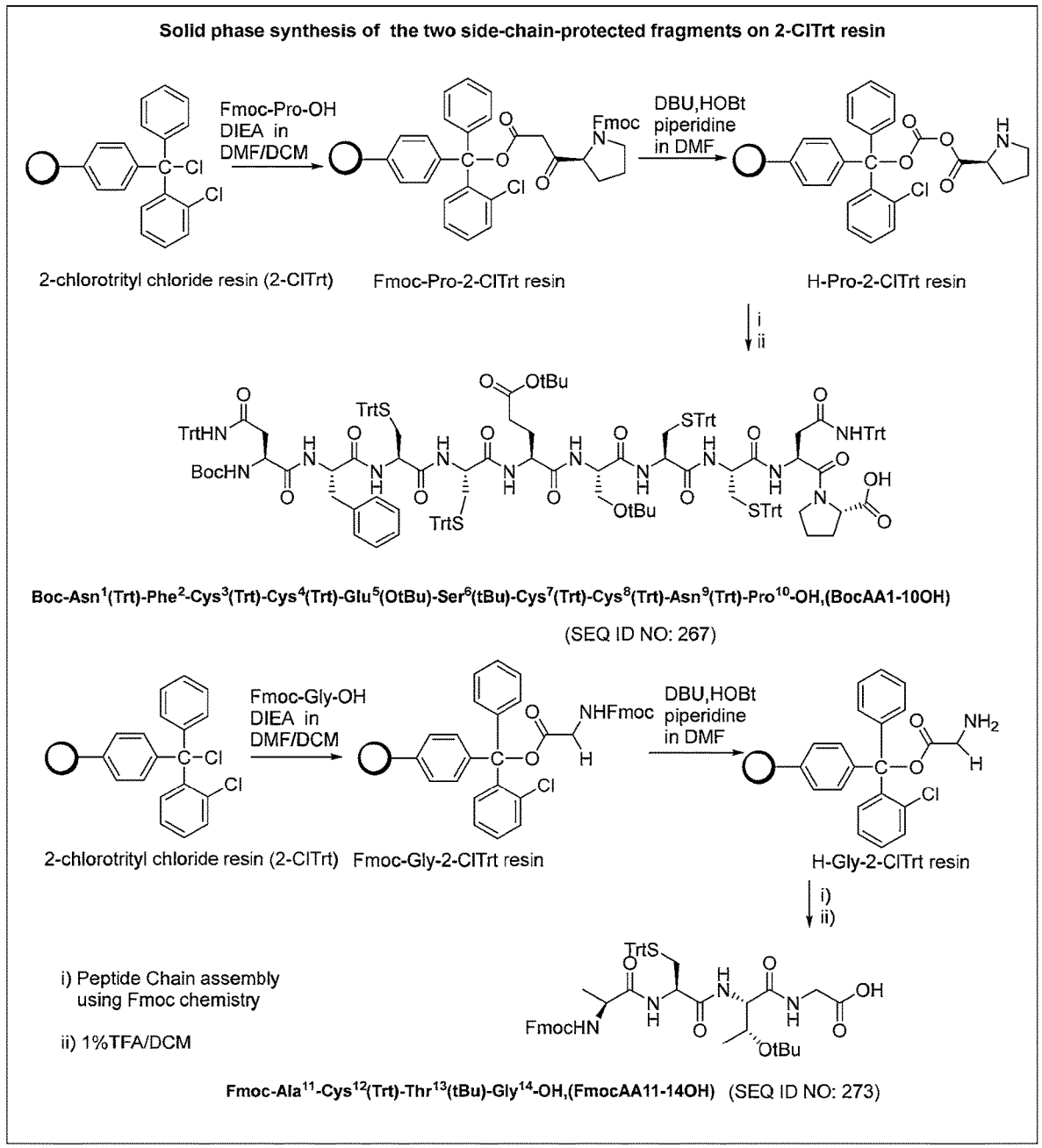
FIG. 11 shows Scheme 5 for the hybrid synthetic methods used for preparing SP-353.
Figure 12:
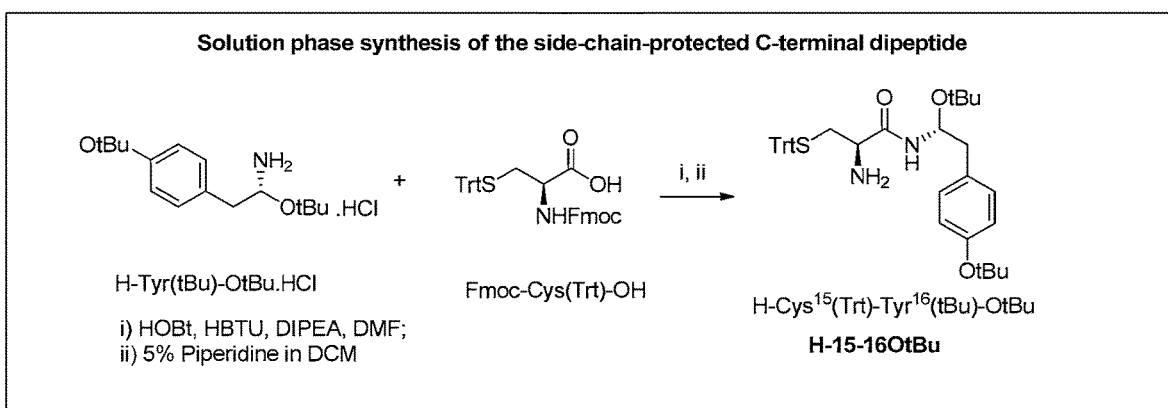
FIG. 12 shows Scheme 6 for the hybrid synthetic methods used for preparing SP-353.
Figure 13:
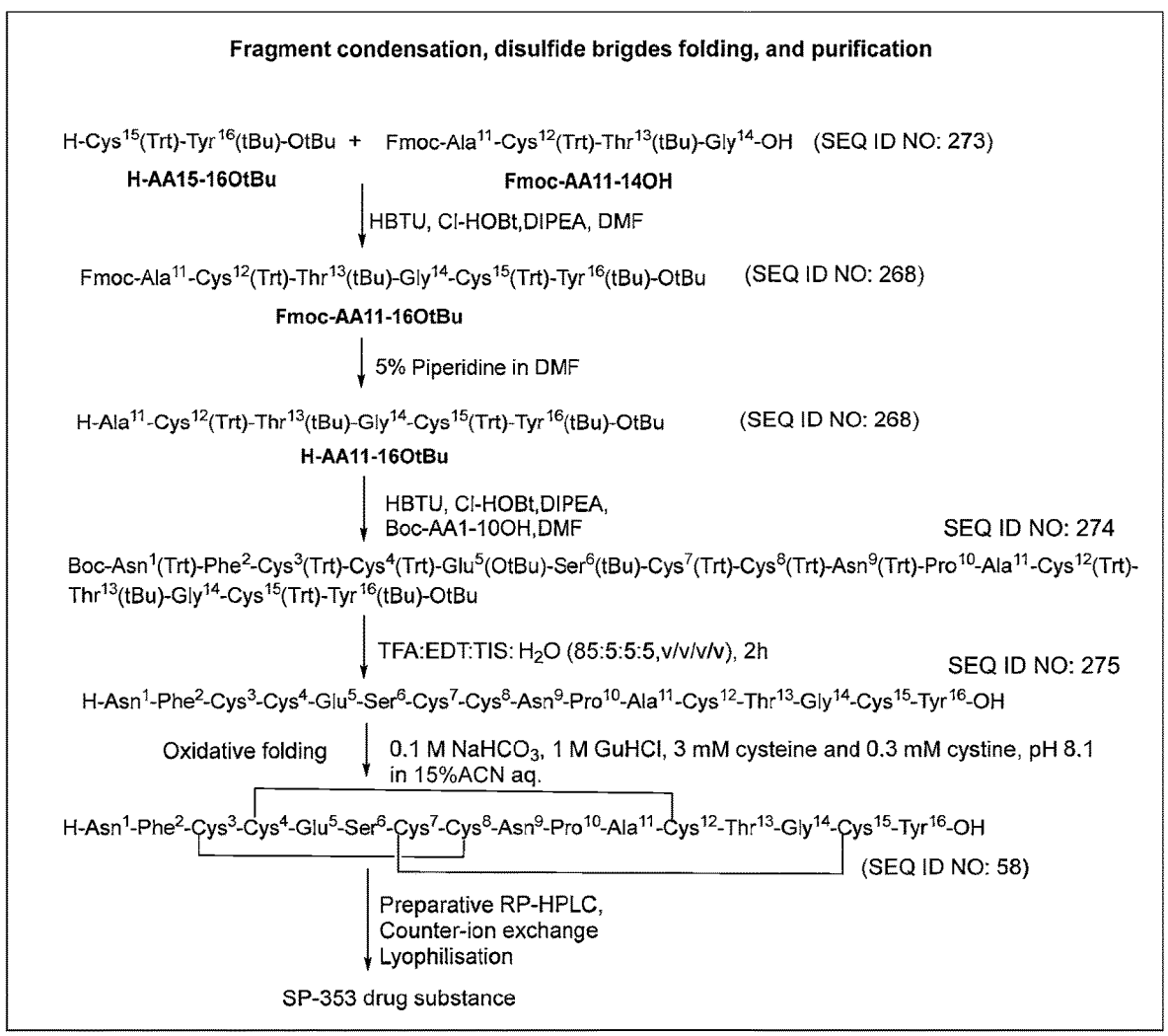
FIG. 13 shows Scheme 7 for the hybrid synthetic methods used for preparing SP-333.

The general strategy for the hybrid synthesis of SP-353 includes solid phase and solution phase syntheses to produce suitable peptide fragments (see Schemes 5 (FIG. 11) and 6 (FIG. 12)), subsequent segment condensation to form the linear crude peptide (see Scheme 7 (FIG. 13)), and natural oxidative folding to form the cyclized final product (see Scheme 7 (FIG. 13)). The same strategy can also be used to produce other ST peptide analogs (such as SP-354, linaclotide, etc.) of similar amino acid sequences shown in Table II.

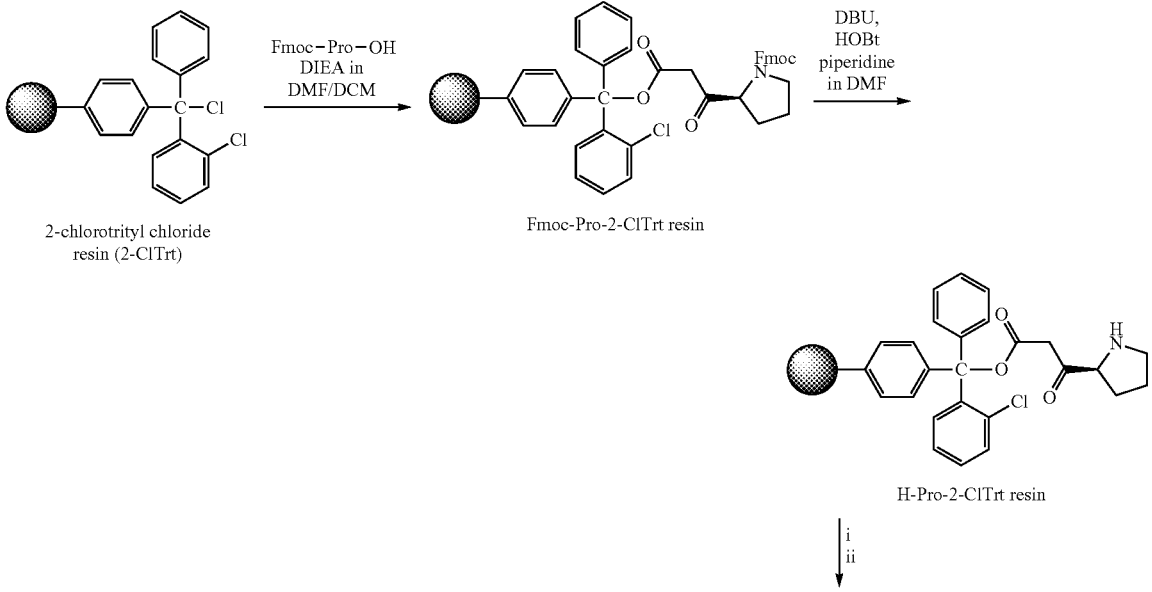

Solid phase synthesis of the two side-chain-protected fragments on 2-ClTrt resin

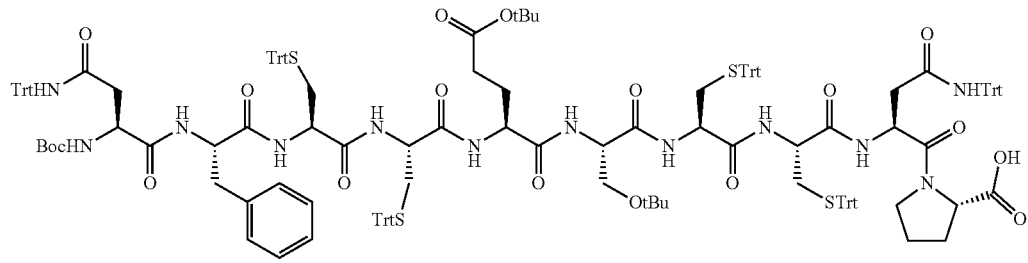

Boc-Asn¹(Trt)-Phe²-Cys³(Trt)-Cys⁴(Trt)-Glu⁵(OtBu)-Ser⁶(tBu)-Cys⁷(Trt)-Cys⁸(Trt)-Asn⁹(Trt)-Pro¹⁰-OH, (BocAA1-10OH)
SEQ ID NO: 267

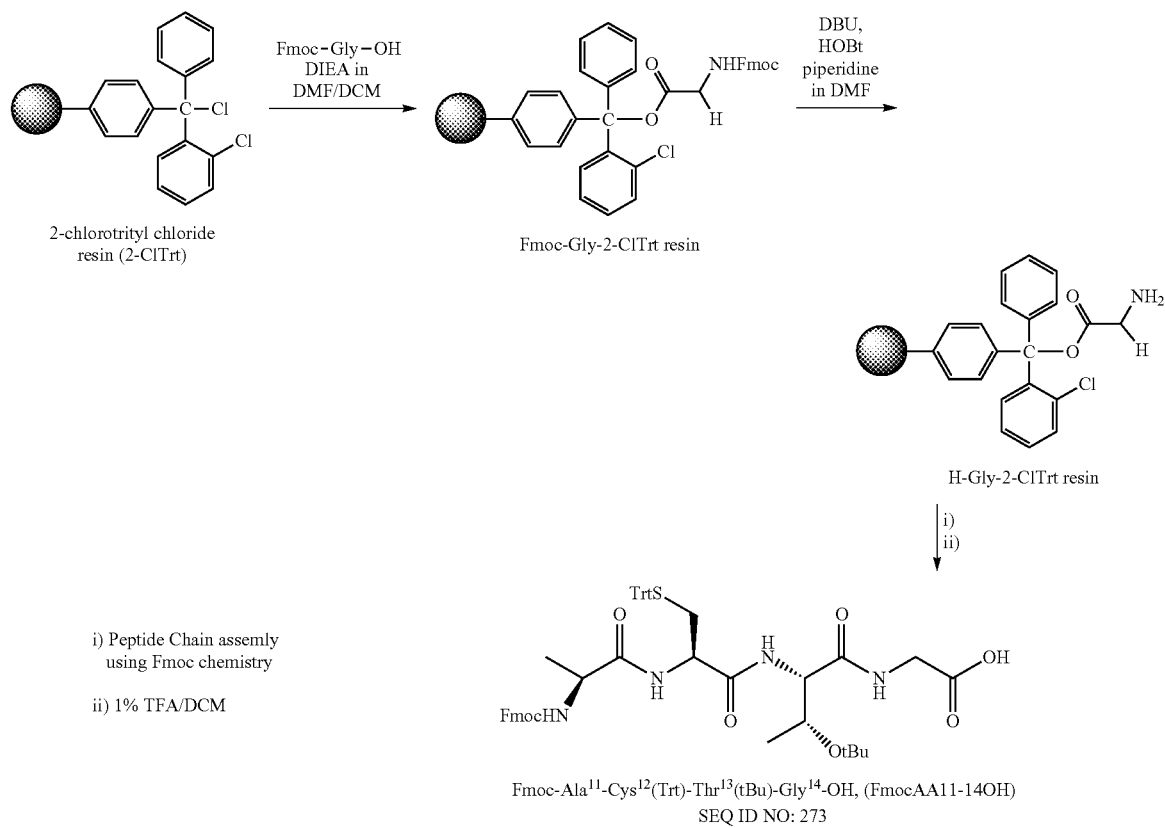

i) Peptide Chain assemly using Fmoc chemistry ii) 1% TFA/DCM

Fmoc-Ala¹¹-Cys¹²(Trt)-Thr¹³(tBu)-Gly¹⁴-OH, (FmocAA11-14OH)
SEQ ID NO: 273

Scheme 6
Solution phase synthesis of the side-chain protected C-terminal dipeptide

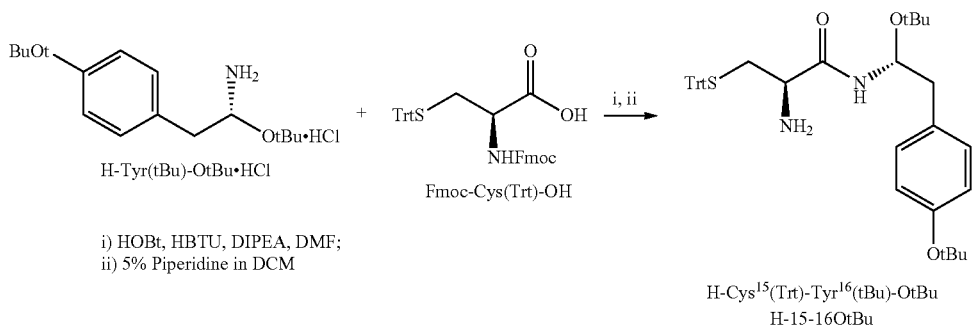

i) HOBt, HBTU, DIPEA, DMF;
ii) 5% Piperidine in DCM

H-Cys¹⁵(Trt)-Tyr¹⁶(tBu)-OtBu
H-15-16OtBu

Figure 14:
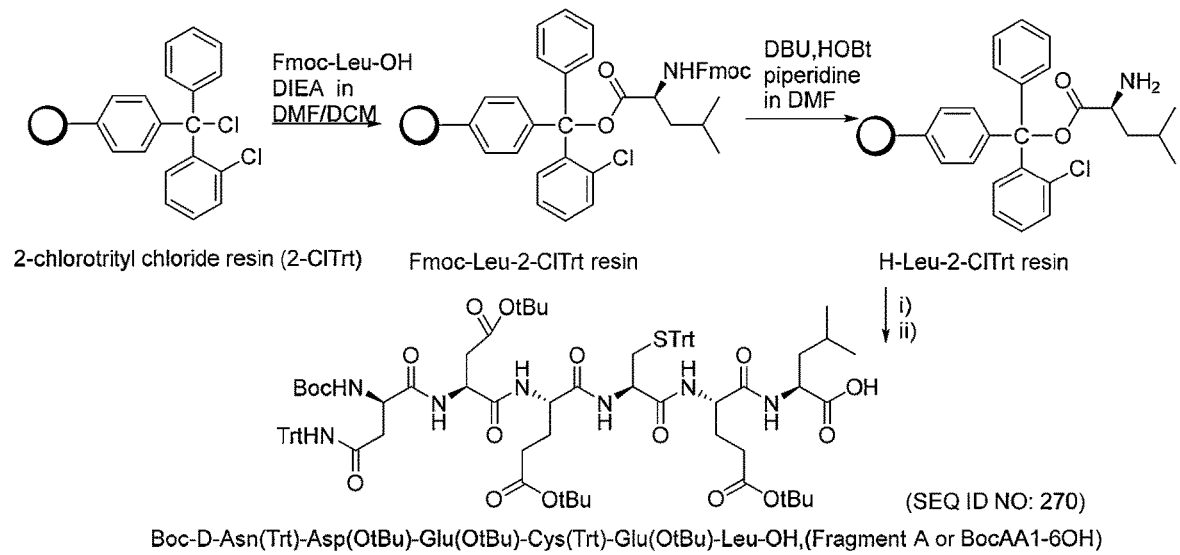
FIG. 14 shows Scheme 8 for the hybrid synthetic methods used for preparing SP-333.
Figure 14:
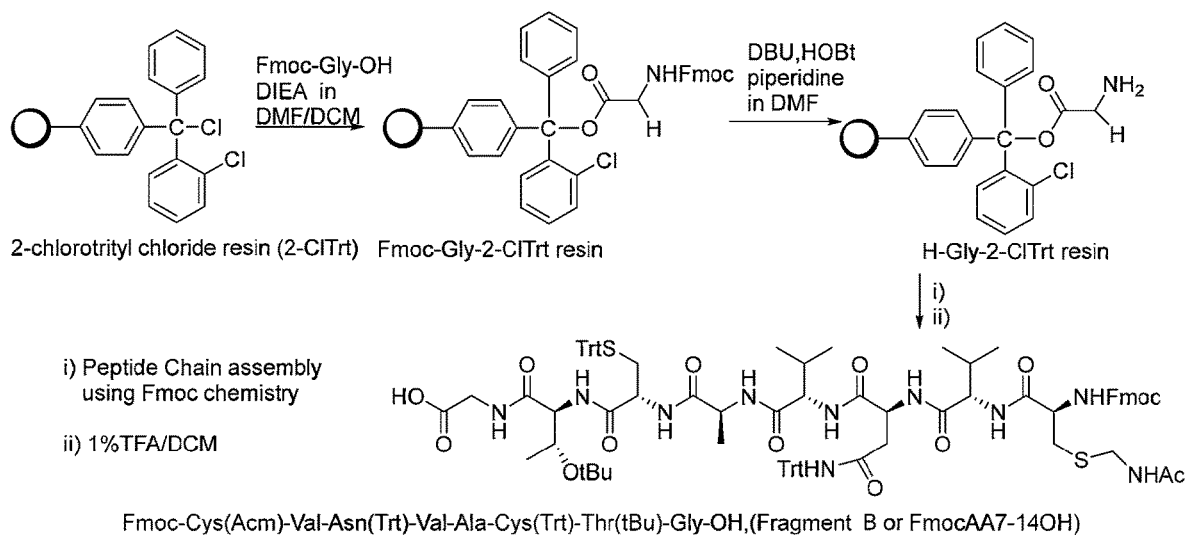
Figure 15:
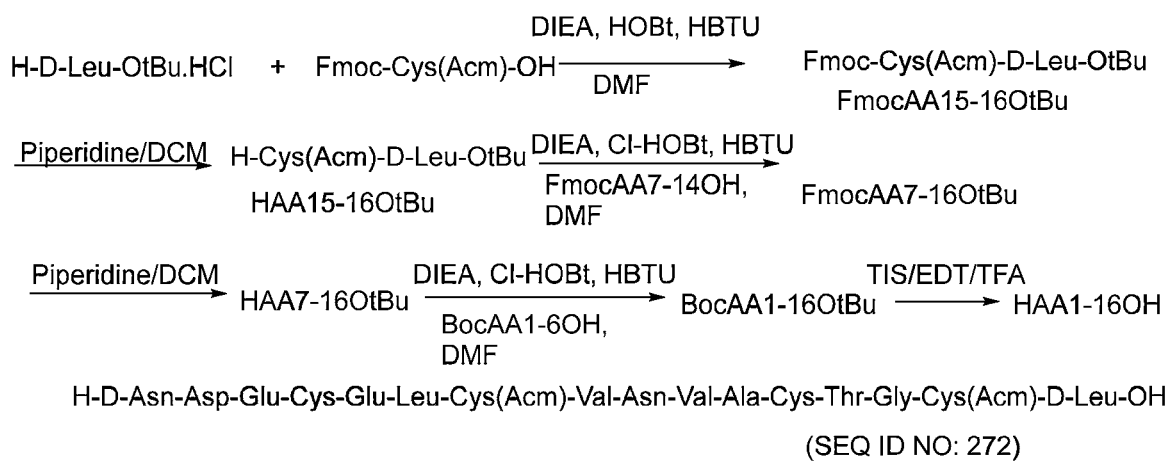
FIG. 15 shows Scheme 9 for the hybrid synthetic methods used for preparing SP-333.
Figure 16:
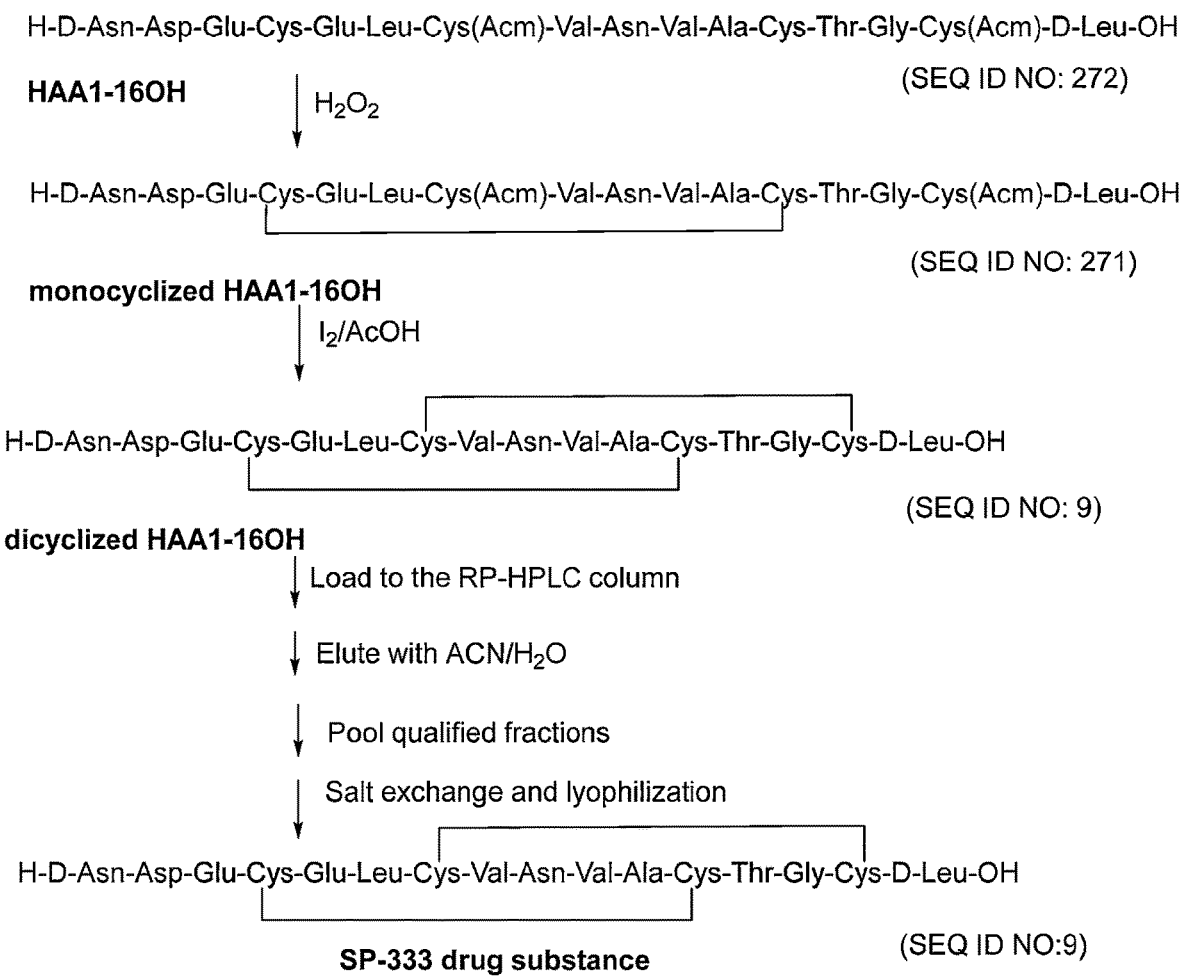
FIG. 16 shows Scheme 10 for the hybrid synthetic methods used for preparing SP-333.

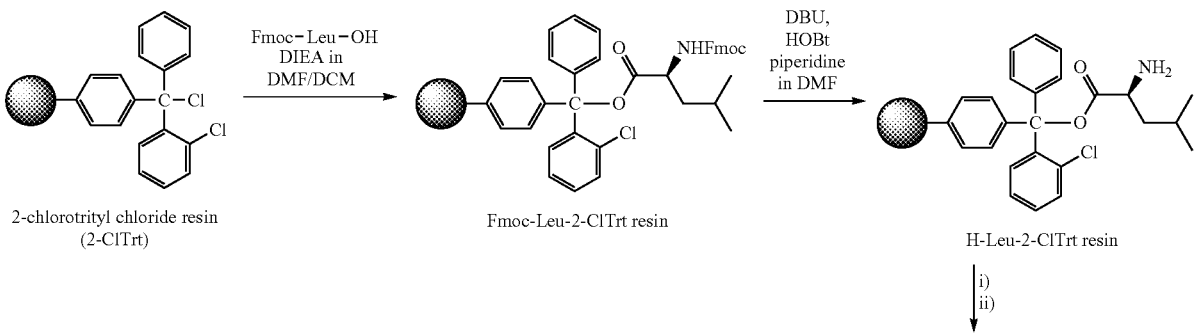
The general strategy for the hybrid synthesis of SP-333 includes solid phase and solution phase syntheses to produce suitable peptide fragments (see Schemes 8 (FIG. 14) and 9 (FIG. 15)), subsequent segment condensation to form the linear crude peptide (see Scheme 9 (FIG. 15)), oxidative folding to form the cyclized final product, purification, and lyophilization (see Scheme 10 (FIG. 16)).

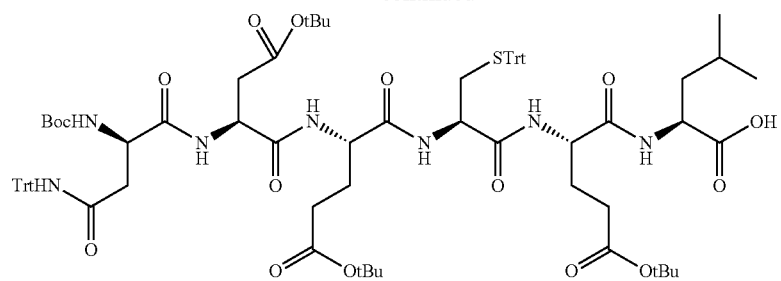
Boc-D-Asn(Trt)-Asp(OtBu)-Glu(OtBu)-Cys(Trt)-Glu(OtBu)-Leu-OH, (Fragment A or BocAA1-6OH)
SEQ ID NO: 270
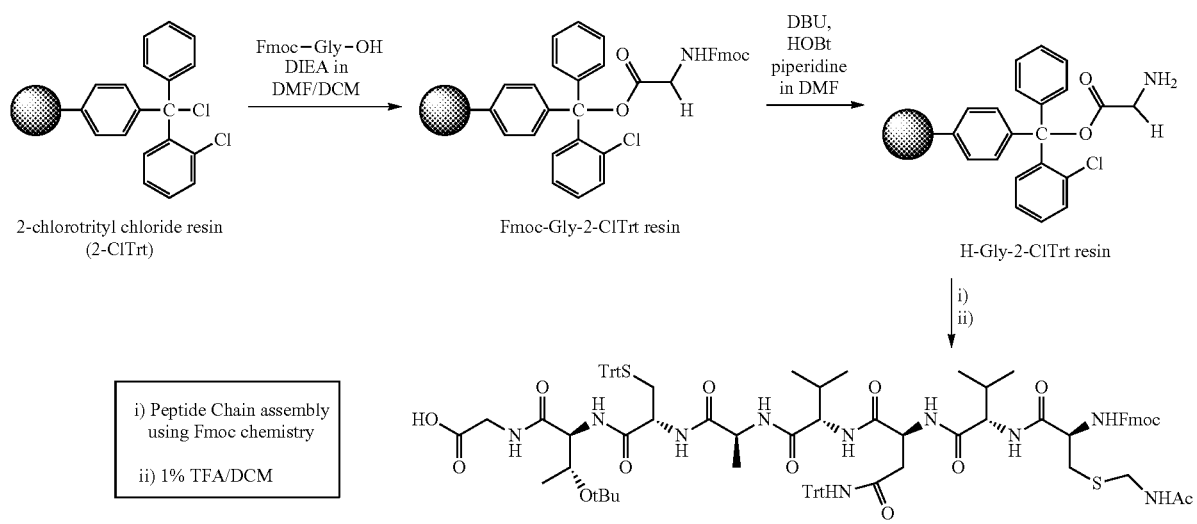
Fmoc-Cys(Acm)-Val-Asn(Trt)-Val-Ala-Cys(Trt)-Thr(tBu)-Gly-OH, (Fragment B or FmocAA7-14OH)
SEQ ID NO: 264
Scheme 9
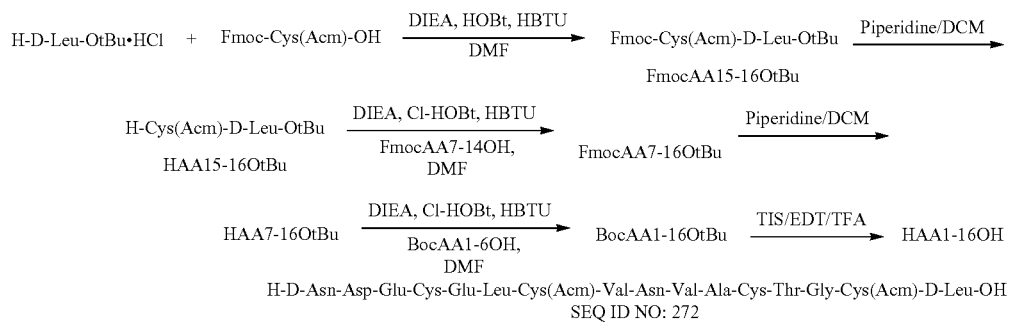
H-D-Asn-Asp-Glu-Cys-Glu-Leu-Cys(Acm)-Val-Asn-Val-Ala-Cys-Thr-Gly-Cys(Acm)-D-Leu-OH
SEQ ID NO: 272
Scheme 10
H-D-Asn-Asp-Glu-Cys-Glu-Leu-Cys(Acm)-Val-Asn-Val-Ala-Cys-Thr-Gly-Cys(Acm)-D-Leu-OH
HAA1-16OH      SEQ ID NO: 272

-continued

H-D-Asn-Asp-Glu-Cys-Glu-Leu-Cys(Acm)-Val-Asn-Val-Ala-Cys-Thr-Gly-Cys(Acm)-D-Leu-OH monocyclized HAA1-16OH     SEQ ID NO: 271

↓ I₂/AcOH

H-D-Asn-Asp-Glu-Cys-Glu-Leu-Cys-Val-Asn-Val-Ala-Cys-Thr-Glu-Cys-D-Leu-OH dicyclized HAA1-16OH     SEQ ID NO: 9

↓ Load to the RP-HPLC cloumn

↓ Elute with ACN/H₂O

↓ Pool qualified fractions

↓ Salt exchange and lyophilization

H-D-Asn-Asp-Glu-Cys-Glu-Leu-Cys-Val-Asn-Val-Ala-Cys-Thr-Gly-Cys-D-Leu-OH

SP-333 drug substance     SEQ ID NO: 9

Figure 5:
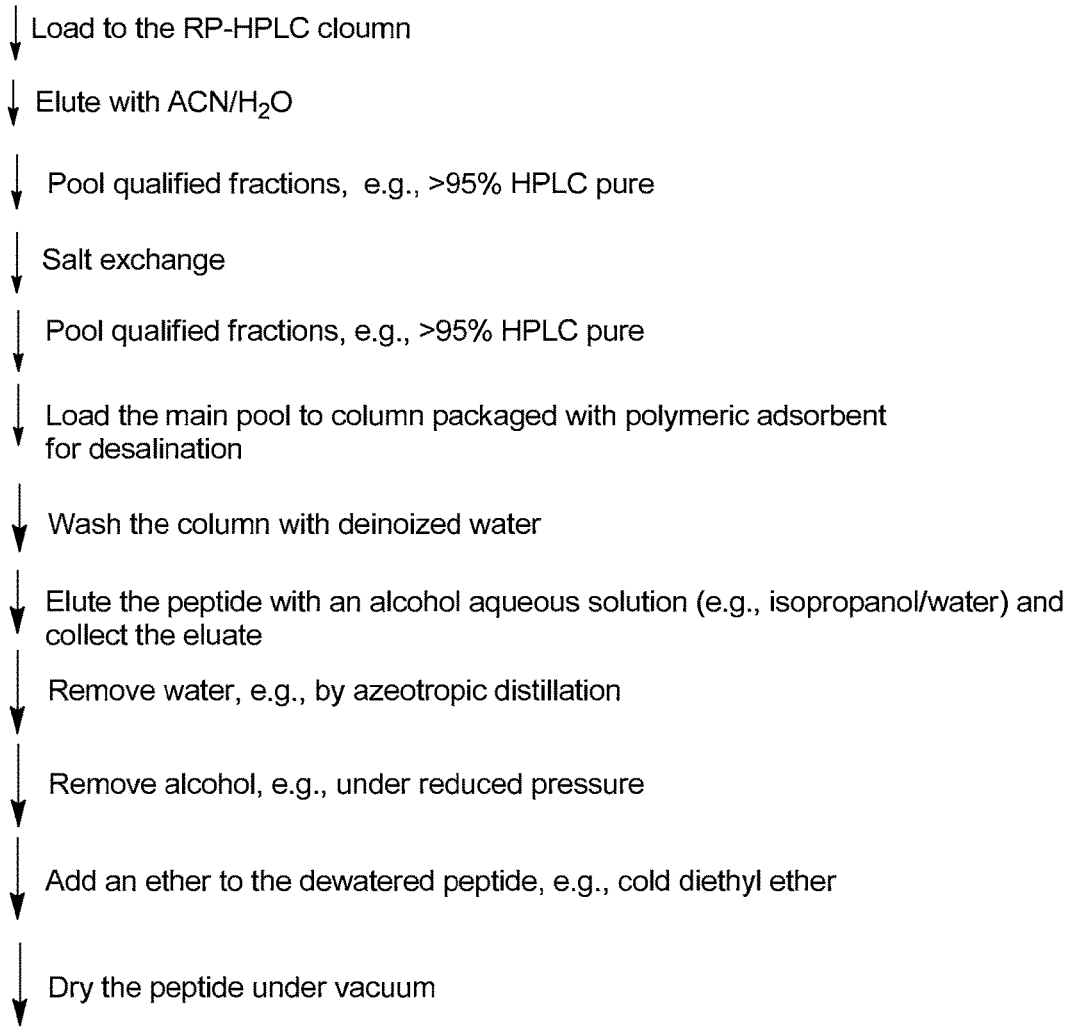
FIG. 5 shows an exemplary general strategy for purifying peptides, including those synthesized by the hybrid methods disclosed herein.

The general strategy for purifying peptides, including those synthesized by the hybrid methods disclosed herein, include, e.g., the steps illustrated in FIG. 5. It is understood that certain steps in FIG. 5 may be repeated (e.g., rinsing column with deionized water) or absent (e.g., salt exchange or alcohol removal after dewatering) to optimize the purification process.

The precipitation process as illustrated in FIG. 5 provides a purified peptide, e.g., peptide GCC agonists. Preferably, the purified peptide is SP-304 (SEQ ID NO: 1) or SP-333 (SEQ ID NO: 9). In one embodiment, the purified SP-304 or SP-333 has a bulk density of no less than 0.05 g/mL, no less than 0.1 g/mL, no less than 0.2 g/mL, no less than 0.3 g/mL, no less than 0.4 g/mL, or no less than 0.5 g/mL. In a preferred embodiment, the purified SP-304 or SP-333 has a bulk density of about 0.05-2 g/mL, about 0.2-0.7 g/mL, about 0.3-0.6 g/mL, or about 0.4-0.5 g/mL. In one embodiment, the purified SP-304 or SP-333 has a tap density of no less than 0.08 g/mL, no less than 0.1 g/mL, no less than 0.15 g/mL, no less than 0.2 g/mL, no less than 0.3 g/mL, no less than 0.4 g/mL, no less than 0.5 g/mL, or no less than 0.6 g/mL. For example, the purified SP-304 or SP-333 has a tap density of 0.08-2 g/mL, about 0.4-0.9 g/mL, about 0.5-0.8 g/mL, or about 0.6-0.7 g/mL. In one embodiment, the purified peptide SP-304 or SP-333 contains <0.01% acetamide (e.g., <28 ppm), <0.3% ammonium ion (e.g., <0.25%), <0.01% acetonitrile (e.g., <20 ppm), and/or <0.1% TFA (e.g., <0.09%). In one embodiment, the purified peptide SP-304 or SP-333 has a bulk density of 0.4-0.5 g/mL, has a tap density of 0.6-0.7 g/mL, and contains <0.01% acetamide (e.g., <28 ppm), <0.3% ammonium ion (e.g., <0.25%), <0.01% acetonitrile (e.g., <20 ppm), and/or <0.1% TFA (e.g., ≤0.09%).

In some embodiments provides a purified peptide having the GCC agonist sequence selected from the group consisting of SEQ ID NOs: 1, 9, and 104, wherein the purified peptide has the following characteristics:

a) has a bulk density of not greater than 0.1 g/mL;
b) contains less than 50 ppm acetamide;
c) less than 0.3% alpha-Asp-9-plecanatide.

The purified peptide can have one or more of the following features.

In one embodiment, the peptide is stable at 25° C. for at least three months.

In one embodiment, the peptide has a particle size distribution having a D10 value of between about 2 tp 15 μm; a D50 value of between about 15-50 μm; and a D90 value of between about 40-80 μm when measured by light scattering with liquid dispersant.

In one embodiment, the purified peptide contains no more than 35 ppm acetamide (e.g., ≤18 ppm).

In one embodiment, the purified peptide contains less than 0.15% alpha-Asp-9-plecanatide (which has a Relative Retention Time (RRT) of ~1.33 from the ultra-performance liquid chromatography (UPLC) analysis described herein).

In some embodiments, the purified peptide has a bulk density of not greater than 0.09 g/mL, not greater than 0.08 g/mL, not greater than 0.07 g/mL, not greater than 0.06 g/mL, not greater than 0.05 g/mL, not greater than 0.04 g/mL, or not greater than 0.03 g/mL.

In some embodiments, the purified peptide is substantially free of water (e.g., water content not exceeding 10%, 9%, 8%, 7%. 6%, 5%, 4%, 3.5%, 3%, 2.5%, 2%, 1.5%, 1%, 0.5%, 0.25%, or 0.1%, of the total weight of the peptide).

In some embodiments, the purified peptide has a chromatographic purity of no less than 95%, no less than 96%, or no less than 97%.

In some embodiments, the total content of impurities in the purified peptide is less than 3% (e.g., <2% or <1%).

In some embodiments, the purified peptide is further substantially free of one or more impurities selected from acetonitrile, alcohols, ammonium, acetates, and TFA.

For example, the purified peptide contains less than 300 ppm acetonitrile (e.g., <250 ppm).

In some embodiments, the purified peptide contains less than 0.2% TFA (e.g., <0.15%, <0.1%, <400 ppm, <300 ppm, <200 ppm, <100 ppm, or <50 ppm).

In some embodiments, the purified peptide contains less than 0.2% isopropanol, i.e., IPA (e.g., <0.15%, <0.1%, <1000 ppm, <900 ppm<800 ppm, <700 ppm, <600 ppm, <500 ppm, <400 ppm, <300 ppm, <200 ppm, <100 ppm, <50 ppm, or <20 ppm).

In some embodiments, the purified peptide contains less than 0.25% acetate (e.g., <0.2% or <0.1%).

In some embodiments, the purified peptide is substantially free of topoisomers (e.g., <0.4%, <0.3%, <0.2% or <0.1%).

In some embodiments, the purified peptide is substantially free of iso-Asp2-plecanatide (RRT 0.96-0.97) (e.g., <0.4%, <0.3%, <0.2% or <0.1%).

In some embodiments, the purified peptide has a chromatographic purity of no less than 96%, no less than 97%, or no less than 98%. For example, the GCC agonist peptide has chromatographic impurity content of no greater than 4%, no greater than 3.5%, no greater than 3%, no greater than 2.5%, no greater than 2%, no greater than 1.5%, or no greater than 1%. The chromatographic impurity content is determined as total area percentages of impurities by HPLC. The chromatographic impurity content includes topoisomer content. The impurities do not include any pharmaceutically acceptable excipient used for drug formulation.

In some embodiments, the purified peptide is substantially free of contaminants resulted from the peptide preparation process such as organic solvents used in the process, e.g., ammonium, acetonitrile, acetamide, alcohol (e.g., methanol, ethanol, or isopropanol), TFA, ether or other contaminants. In this context "substantially" free of contaminants means that the contaminant content of the peptide at the end of the purification process is preferably less than 0.5%, less than 0.3%, less than 0.25%, less than 0.1%, less than 0.05%, less than 0.04%, less than 0.03%, less than 0.02%, less than 0.01%, less than 0.005%, less than 0.003%, or less than 0.001% of the total weight of the peptide. For example, the purified peptide contains <50 ppm acetamide (e.g., ≤35 ppm or ≤18 ppm), <300 ppm acetonitrile (e.g., <250 ppm), <1000 ppm TFA (e.g., <400 ppm, <300 ppm, <200 ppm, <100 ppm, or <50 ppm), <2000 ppm isopropanol (e.g., <1500 ppm, <1000 ppm, <500 ppm, <400 ppm, <300 ppm, <200 ppm, <100 ppm, <50 ppm, or <20 ppm), and/or <0.25% acetate (e.g., <0.2% or <0.1%). The content of contaminants can be determined by conventional methods such as gas chromatography. Preferably, the residual solvents in the purified peptide of the invention are less than the limits set in the ICH guidelines, e.g., IMPURITIES: GUIDELINE FOR RESIDUAL SOLVENTS Q3C (R5) (available at www.ich.org/fileadmin/Public_Web_Site/ICH_Products/Guidelines/Quality/Q3C/Step4/Q3C_R 5_Step4.pdf).

In some embodiments, the purified peptide contains less than 0.3% (e.g., <0.15%) alpha-Asp-9-plecanatide (RRT 1.33).

In some embodiments, the purified peptide has a bulk density of not greater than 0.09 g/mL, not greater than 0.08 g/mL, not greater than 0.07 g/mL, not greater than 0.06 g/mL, not greater than 0.05 g/mL, not greater than 0.04 g/mL, or not greater than 0.03 g/mL.

In some embodiments, the purified peptide is substantially free of iso-Asp2-plecanatide (RRT ~ 0.96-0.97). In this context "substantially" free of iso-Asp2-plecanatide means that the iso-Asp2-plecanatide content of the peptide at the end of the purification process is preferably less than 2%, less than 1.5%, less than 1.25%, less than 1%, less than 0.9%, less than 0.8%, less than 0.7%, less than 0.6%, less than 0.5%, less than 0.4%, less than 0.3%, less than 0.2%, or less than 0.1%, of the total weight of the peptide.

In some embodiments, the purified peptide is substantially free of topoisomers. In this context "substantially" free of topoisomers means that the topoisomer content of the peptide at the end of the purification process is preferably less than 2%, less than 1.5%, less than 1.25%, less than 1%, less than 0.9%, less than 0.8%, less than 0.7%, less than 0.6%, less than 0.5%, less than 0.4%, less than 0.3%, less than 0.2%, or less than 0.1%, of the total weight of the peptide.

In some embodiments, the purified peptide is substantially free of water. In this context "substantially" free of water means that the water content of the peptide at the end of the purification process is preferably less than 10%, 9%, 8%, 7%, less than 6%, less than 5%, less than 4.5%, less than 4.25%, less than 4%, less than 3.5%, less than 3%, less than 2.5%, less than 2%, less than 1.5%, less than 1%, less than 0.5%, less than 0.25%, or less than 0.1%, of the total weight of the peptide.

For example, the purified peptide has a particle size distribution characterized by a D50 value of about 600 µm when measured by light scattering with air dispersant. In comparison, the peptides purified from the lyophilization and precipitation processes described in WO2012/118972 have D50 values of about 180-250 µm and about 300 µm, respectively.

For example, the purified peptide prepared by the processes of the invention has a suitable size distribution for pharmaceutical formulation. In one embodiment, the peptide (e.g., SP-304) has a size distribution (e.g., an average size of 80-120 µm) comparable to that of the pharmaceutical excipient (e.g., microcrystalline cellulose) used in the formulation, for example, in the 3 mg/day unit dose form. The size distribution of the purified peptide may vary based on the unit dose. For example, when unit dose is lower than 3 mg/day, the purified peptide in the pharmaceutical formulation has a smaller average size than that in the 3 mg/day dose. For example, the purified peptide prepared by the processes of the invention is milled to reach the suitable size distribution.

The size distribution of the peptide of the invention can be determined by traditional methods, such as sieve analysis, light obscuration or dynamic light scattering analyses.

Figure 6:
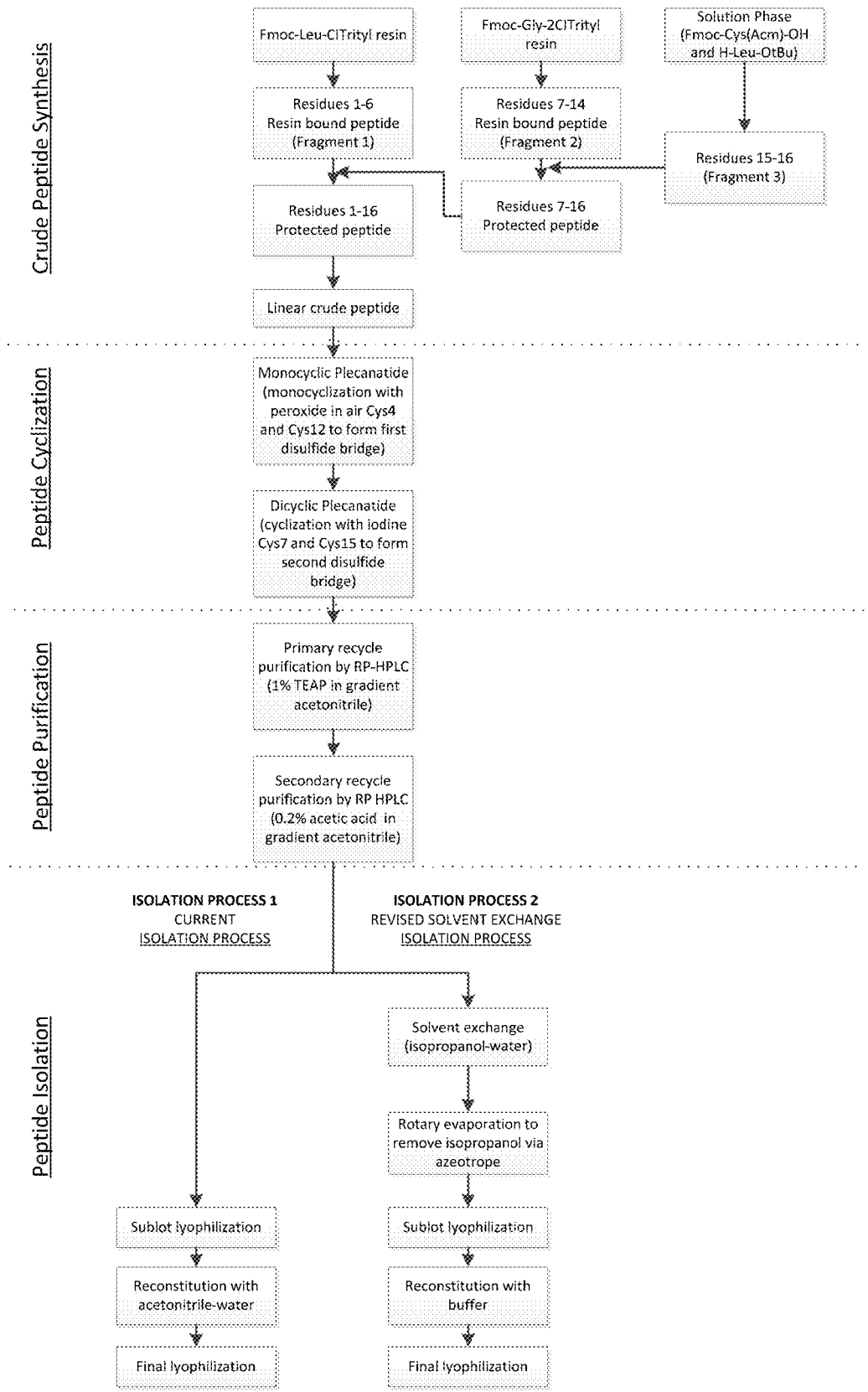
FIG. 6 shows an exemplary purification process of purifying peptides, including those synthesized by the hybrid methods disclosed herein. The process includes, e.g., the steps (referred to as "isolation process 2"), as compared to the isolation steps described in WO2012/118972 (referred to as "isolation process 1").

In one embodiment, the invention provides a purification process of purifying peptides, including those synthesized by the hybrid methods disclosed herein. The process includes, e.g., the steps (referred to as "isolation process 2") illustrated in FIG. 6, as compared to the isolation steps described in WO2012/118972 (referred to as "isolation process 1").

In one embodiment, the purification process of the invention includes the following steps:

Monocyclization of Linear Crude Peptide: The disulfide bond between $Cys^4$ and $Cys^{12}$ of SP-304 is first formed by $H_2O_2$ oxidation at 8.0-8.5 pH to form the monocyclized crude peptide. The linear crude peptide is slowly added and dissolving in 0.5% ammonium acetate in water buffer with pre-added $H_2O_2$ in a ratio of 100:9 gram of peptide to mL $H_2O_2$ to produce a final crude concentration of approximately 1.0 mg/mL. The solution pH is then adjusted to 8.5 with an $NH_4OH$ solution while stirring in the open air. The oxidative monocyclization reaction is monitored, e.g., using HPLC Method 2 as described in Example 8. When the area % of the linear crude peptide is ≤5.0% of the area % of monocyclized peptide, the oxidation reaction is stopped by adjusting the pH of peptide solution to 1.7-2 using a TFA solution. The peptide solution is then transferred to the next step for the formation of the dicyclized peptide.

Dicyclization of Monocyclized Peptide: The disulfide bond between the Cys7 and Cys15 is formed by 3.0% (w/v) $I_2$ in acetonitrile solution. The disulfide bridge is created while simultaneously removing the Acm side-chain protecting groups present on the remaining Cys residues. The oxidative dicyclization reaction is monitored, e.g., using HPLC Method 2. Excess iodine is quenched with a 0.1M ascorbic acid in water solution. Upon completion of the reaction, the dicyclized peptide is adjusted to pH 6.5-7 using an $NH_4OH$ solution and the material is prepared for primary purification.

Primary Purification of Dicyclized Crude Peptide: The dicyclized crude peptide solution resulting from the oxidation steps is then loaded onto a preparative RP-HPLC column packed with C18 reverse phase resin which is operated by a preparative HPLC system. The peptide is eluted in a 1% TEAP in Water, pH7/ACN buffer system. HPLC Method 1 as described in Example 8, for example, is used to ascertain the percent purity of fractions and pools obtained during the primary purification run.

Recycle Pool(s) Purification of Dicyclized Peptide: After primary purification, the fractions that require further purification are purified based on the purity of the fraction pools using a 1% TEAP in Water, pH7/ACN or a 0.2% Acetic Acid in Water/ACN buffer system. The dicyclized crude peptide solution resulting from the oxidation steps is then loaded onto a preparative RP-HPLC column packed with C18 reverse phase resin which is operated by a preparative HPLC system. The peptide is eluted in a 1% TEAP in Water, pH7/ACN buffer system. HPLC Method 1 as described in Example 8, for example, is used to ascertain the percent purity of fractions and pools obtained during the Recycle Purification run.

Secondary Purification and Salt Exchange: After recycle purification, the fractions that require further purification are purified based on the purity of the fraction pools using a 1% TEAP in Water, pH7/ACN or a 0.2% Acetic Acid in Water/ACN buffer system. HPLC Method 1 as described in Example 8, for example, is used to ascertain the percent purity of fractions and pools obtained during the Secondary Purification run. UPLC Method 1 as described in Example 8, for example, is used to ascertain the percent purity of Main Pool obtained during all the Purification run before move to next step.

Solvent Exchange: Material meeting main pool criteria is loaded onto the preparative RP-HPLC column at the flange end in the reverse direction, washed with a water/isopropanol solution (e.g., with a water to isopropanol ratio of 99:1) from the reverse direction, and eluted with a water/isopropanol solution (e.g., with a water to isopropanol ratio of 60:40) in the forward direction. The collected peptide solution is tested by UPLC Method 1 to ascertain the purity, then the peptide solution is filtered, undergoes rotary evaporation to remove excess isopropanol (to e.g., below 5%), followed by sublot lyophilization for, e.g., no less than 96 hours.

Reconstitution and Final Lyophilization: The sublot lyophilized dry peptide undergoes reconstitution in water to form a homogenous lot. A buffer, such as ammonium acetate (e.g., 0.5% (w/w) to dry peptide), is added to the solution and it is mixed until the ammonium acetate and the peptide are dissolved. The material can be analyzed by UPLC Method 1 to verify the purity. The dissolved material can be installed onto the tray lyophilizer and kept under vacuum for, e.g., no less than 120 hours to comprise the final dry peptide material.

1.1 GCC Agonists

The GCC agonists prepared by the processes of the invention can bind to guanylate cyclase C and stimulate intracellular production of cGMP. Optionally, the GCC agonists induce apoptosis and inhibit proliferation of epithelial cells. The term, "guanylate cyclase C" refers to a transmembrane form of guanylate cyclase that acts as the intestinal receptor for the heat-stable toxin (ST) peptides secreted by enteric bacteria. Guanylate cyclase C is also the receptor for the naturally occurring peptides guanylin and uroguanylin. The possibility that there may be different receptors for each of these peptides has not been excluded. Hence, the term "guanylate cyclase C" may also encompass a class of transmembrane guanylate cyclase receptors expressed on epithelial cells lining the gastrointestinal mucosa.

The term "GCC agonist" refers to both peptides and non-peptide compounds such as that bind to an intestinal guanylate cyclase C and stimulate the intracellular production of cGMP. Where the GCC agonist is a peptide, the term encompasses biologically active fragments of such peptides and pro-peptides that bind to guanylate cyclase C and stimulate the intracellular production of cGMP.

1.1.1 GCC Agonist Peptides

The GCC agonists suitable for the methods of the invention are preferably peptides. In some embodiments, the GCC agonist peptide is less than 30 amino acids in length. In particular embodiments, the GCC agonist peptide is less than or equal to 30, 25, 20, 15, 14, 13, 12, 11, 10, or 5 amino acids in length. Examples of GCC agonist peptides for use in the formulations and methods of the invention include those described in U.S. Pat. Nos. 7,879,802 and 8,034,782, and U.S. Publication Nos. US 2010-0069306 and US 2010-0120694, each of which is incorporated by reference herein in its entirety.

Specific examples of GCC agonist peptides that can be purified or prepared by the methods of the invention include those described in Tables I-VII below. As used Tables I-VII, the terms "PEG3" or "3PEG" refer to a polyethylene glycol such as aminoethyloxy-ethyloxy-acetic acid (AeeA), and polymers thereof. As used herein, the term "AMIDE" is meant to denote that the terminal carboxylic acid is replaced with an amide group, i.e., the terminal COOH is replaced with CONH2.

The term "$X_{aa}$" refers to any natural or unnatural amino acid or amino acid analogue. The term "$M_{aa}$" refers to a cysteine (Cys), penicillamine (Pen) homocysteine, or 3-mercaptoproline. The term "$Xaa_{n1}$" is meant to denote an amino acid sequence of any natural or unnatural amino acid or amino acid analogue that is one, two or three residues in length; $Xaa_{n2}$ is meant to denote an amino acid sequence that is zero or one residue in length; and $Xaa_{n3}$ is meant to denote an amino acid sequence zero, one, two, three, four, five or six residues in length. Additionally, any amino acid represented by Xaa, $Xaa_{n1}$, $Xaa_{n2}$, or $Xaa_{n3}$ may be an L-amino acid, a D-amino acid, a methylated amino acid or any combination of thereof. Optionally, any GCC agonist peptide represented by Formulas I to XX in the tables may contain one or more polyethylene glycol residues at the N-terminus, C-terminus or both.

In certain embodiments, a GCC agonist purified or prepared by the methods of the invention comprises a peptide selected from SEQ ID NOs: 1-251, the sequences of which are set forth below in Tables I to VII below. In one embodiment, a GCC agonist purified by the methods of the invention comprises the peptide designated by SEQ ID NOs: 1, 9, or 104.

In certain embodiments, a GCC agonist prepared by the methods of the invention comprises a peptide that is substantially equivalent to a peptide selected from SEQ ID NOs: 1-251. The term "substantially equivalent" refers to a peptide that has an amino acid sequence equivalent to that of the binding domain where certain residues may be deleted or replaced with other amino acids without impairing the peptide's ability to bind to an intestinal guanylate cyclase receptor and stimulate fluid and electrolyte transport.

In certain embodiments, a GCC agonist prepared by the methods of the invention comprises a peptide that are analogs to a peptide selected from SEQ ID NOs: 1-251. Particularly, these analogs contain an a-aminoadipic acid (Aad), preferably at the $3^{rd}$ position from the N-terminus of each peptide or at the position to the N-terminal side next to the first cysteine ("Cys") residue.251

In certain embodiments, the GCC agonist peptides are analogues of uroguanylin or a bacterial ST peptide. Uroguanylin is a circulating peptide hormone with natriuretic activity. An ST peptide is a member of a family of heat stable enterotoxins (ST peptides) secreted by pathogenic strains of E. coli and other enteric bacteria that activate guanylate cyclase receptor and cause secretory diarrhea. Unlike bacterial ST peptides, the binding of uroguanylin to guanylate cyclase receptor is dependent on the physiological pH of the gut. Therefore, uroguanylin is expected to regulate fluid and electrolyte transport in a pH dependent manner and without causing severe diarrhea.

The GCC agonist peptides prepared by the methods of the invention can be polymers of L-amino acids, D-amino acids, or a combination of both. For example, in various embodiments, the peptides are D retro-inverso peptides. The term "retro-inverso isomer" refers to an isomer of a linear peptide in which the direction of the sequence is reversed and the chirality of each amino acid residue is inverted. See, e.g., Jameson et al., Nature, 368, 744-746 (1994); Brady et al., Nature, 368, 692-693 (1994). The net result of combining D-enantiomers and reverse synthesis is that the positions of carbonyl and amino groups in each amide bond are exchanged, while the position of the side-chain groups at each alpha carbon is preserved. Unless specifically stated otherwise, it is presumed that any given L-amino acid sequence of the invention may be made into a D retro-inverso peptide by synthesizing a reverse of the sequence for the corresponding native L-amino acid sequence.

The GCC agonist peptides prepared by the methods of the invention are able to induce intracellular cGMP production in cells and tissues expressing guanylate cyclase C. In certain embodiments, the GCC agonist peptide stimulates 5%, 10%, 20%, 30%, 40%, 50%, 75%, 90% or more intracellular cGMP compared to naturally occurring GCC agonists such as uroguanylin, guanylin, or ST peptides. Optionally, the GCC agonist peptide stimulates 5%, 10%, 20%, 30%, 40%, 50%, 75%, 90% or more intracellular cGMP compared to SP-304 (SEQ ID NO: 1). In further embodiments, the GCC agonist peptide stimulates apoptosis, e.g., programmed cell death, or activate the cystic fibrosis transmembrane conductance regulator (CFTR).

In some embodiments, the GCC agonist peptides prepared by the methods of the invention are more stable than naturally occurring GCC agonists and/or SP-304 (SEQ ID NO: 1), SP-339 (linaclotide) (SEQ ID NO: 55) or SP-340 (SEQ ID NO: 56). For example, the GCC agonist peptide degrades 2%, 3%, 5%, 10%, 15%, 20%, 30%, 40%, 50%, 75%, 90% or less compared to naturally occurring GCC agonists and/or SP-304, SP-339 (linaclotide) or SP-340. In certain embodiments, the GCC agonist peptides for use in the formulations and methods of the invention are more stable to proteolytic digestion than naturally occurring GCC agonists and/or SP-304 (SEQ ID NO: 1), SP-339 (linaclotide) (SEQ ID NO: 55) or SP-340 (SEQ ID NO: 56). In one embodiment, a GCC agonist peptide is pegylated in order to render the peptides more resistant towards proteolysis by enzymes of the gastrointestinal tract. In a preferred embodiment, the GCC agonist peptide is pegylated with the aminoethyloxy-ethyloxy-acetic acid (Aeea) group at its C-terminal end, at its N-terminal end, or at both termini.

Specific examples of GCC agonist peptides that can be prepared by the methods of the invention include a peptide selected from the group designated by SEQ ID NOs: 1-251.

In one embodiment, the GCC agonist peptide is a peptide having the amino acid sequence of any one of Formulas X-XVII (e.g. SEQ ID NOs: 87-98).

In some embodiments, GCC agonist peptides include peptides having the amino acid sequence of Formula I, wherein at least one amino acid of Formula I is a D-amino acid or a methylated amino acid and/or the amino acid at position 16 is a serine. Preferably, the amino acid at position 16 of Formula I is a D-amino acid or a methylated amino acid. For example, the amino acid at position 16 of Formula I is a d-leucine or a d-serine. Optionally, one or more of the amino acids at positions 1-3 of Formula I are D-amino acids or methylated amino acids or a combination of D-amino acids or methylated amino acids. For example, $Asn^1$, $Asp^2$ or $Glu^3$ (or a combination thereof) of Formula I is a D-amino acid or a methylated amino acid. Preferably, the amino acid at position $Xaa^6$ of Formula I is a leucine, serine or tyrosine.

In alternative embodiments, GCC agonist peptides include peptides having the amino acid sequence of Formula II, wherein at least one amino acid of Formula II is a D-amino acid or a methylated amino acid. Preferably, the amino acid denoted by $Xaa_{n2}$ of Formula II is a D-amino acid or a methylated amino acid. In some embodiments, the amino acid denoted by $Xaa_{n2}$ of Formula II is a leucine, a d-leucine, a serine, or a d-serine. Preferably, the one or more amino acids denoted by $Xaa_{n1}$ of Formula II is a D-amino acid or a methylated amino acid. Preferably, the amino acid at position $Xaa^6$ of Formula II is a leucine, a serine, or a tyrosine.

In some embodiments, GCC agonist peptides include peptides having the amino acid sequence of Formula III, wherein at least one amino acid of Formula III is a D-amino acid or a methylated amino acid and/or Maa is not a cysteine. Preferably, the amino acid denoted by $Xaa_{n2}$ of Formula III is a D-amino acid or a methylated amino acid. In some embodiments the amino acid denoted by $Xaa_{n2}$ of Formula III is a leucine, a d-leucine, a serine, or a d-serine. Preferably, the one or more amino acids denoted by $Xaa_{n1}$ of Formula III is a D-amino acid or a methylated amino acid. Preferably, the amino acid at position $Xaa^6$ of Formula III is a leucine, a serine, or a tyrosine.

In other embodiments, GCC agonist peptides include peptides having the amino acid sequence of Formula IV, wherein at least one amino acid of Formula IV is a D-amino acid or a methylated amino acid, and/or Maa is not a cysteine. Preferably, the $Xaa_{n2}$ of Formula IV is a D-amino acid or a methylated amino acid. In some embodiments, the amino acid denoted by $Xaa_{n2}$ of Formula IV is a leucine, a d-leucine, a serine, or a d-serine. Preferably, the one or more of the amino acids denoted by $Xaa_{n1}$ of Formula IV is a D-amino acid or a methylated amino acid. Preferably, the amino acid denoted Xaa6 of Formula IV is a leucine, a serine, or a tyrosine.

In further embodiments, GCC agonist peptides include peptides having the amino acid sequence of Formula V, wherein at least one amino acid of Formula V is a D-amino acid or a methylated amino acid. Preferably, the amino acid at position 16 of Formula V is a D-amino acid or a methylated amino acid. For example, the amino acid at position 16 (i.e., $Xaa^{16}$) of Formula V is a d-leucine or a d-serine. Optionally, one or more of the amino acids at position 1-3 of Formula V are D-amino acids or methylated amino acids or a combination of D-amino acids or methylated amino acids. For example, $Asn^1$, $Asp^2$ or $Glu^3$ (or a combination thereof) of Formula V is a D-amino acids or a methylated amino acid. Preferably, the amino acid denoted at $Xaa^6$ of Formula V is a leucine, a serine, or a tyrosine.

In additional embodiments, GCC agonist peptides include peptides having the amino acid sequence of Formula VI, VII, VIII, or IX. Preferably, the amino acid at position 6 of Formula VI, VII, VIII, or IX is a leucine, a serine, or a tyrosine. In some aspects the amino acid at position 16 of Formula VI, VII, VIII, or IX is a leucine or a serine. Preferably, the amino acid at position 16 of Formula V is a D-amino acid or a methylated amino acid.

In additional embodiments, GCC agonist peptides include peptides having the amino acid sequence of Formula X, XI, XII, XIII, XIV, XV, XVI or XVII. Optionally, one or more amino acids of Formulas X, XI, XII, XIII, XIV, XV, XVI or XVII is a D-amino acid or a methylated amino acid. Preferably, the amino acid at the carboxy terminus of the peptides according to Formulas X, XI, XII, XIII, XIV, XV, XVI or XVII is a D-amino acid or a methylated amino acid. For example the amino acid at the carboxy terminus of the peptides according to Formulas X, XI, XII, XIII, XIV, XV, XVI or XVII is a D-tyrosine.

Preferably, the amino acid denoted by $Xaa^6$ of Formula XIV is a tyrosine, phenylalanine or a serine. Most preferably the amino acid denoted by $Xaa^6$ of Formula XIV is a phenylalanine or a serine. Preferably, the amino acid denoted by $Xaa^4$ of Formula XV, XVI or XVII is a tyrosine, a phenylalanine, or a serine. Most preferably, the amino acid position $Xaa^4$ of Formula V, XVI or XVII is a phenylalanine or a serine.

In some embodiments, GCRA peptides include peptides containing the amino acid sequence of Formula XVIII. Preferably, the amino acid at position 1 of Formula XVIII is a glutamic acid, aspartic acid, glutamine or lysine. Preferably, the amino acid at position 2 and 3 of Formula XVIII is a glutamic acid, or an aspartic acid. Preferably, the amino acid at position 5 a glutamic acid. Preferably, the amino acid at position 6 of Formula XVIII is an isoleucine, valine, serine, threonine, or tyrosine. Preferably, the amino acid at position 8 of Formula XVIII is a valine or isoleucine. Preferably, the amino acid at position 9 of Formula XVIII is an asparagine. Preferably, the amino acid at position 10 of Formula XVIII is a valine or a methionine. Preferably, the amino acid at position 11 of Formula XVIII is an alanine. Preferably, the amino acid at position 13 of Formula XVIII is a threonine. Preferably, the amino acid at position 14 of Formula XVIII is a glycine. Preferably, the amino acid at position 16 of Formula XVIII is a leucine, serine or threonine In alternative embodiments, GCRA peptides include peptides containing the amino acid sequence of Formula XIX. Preferably, the amino acid at position 1 of Formula XIX is a serine or asparagine. Preferably, the amino acid at position 2 of Formula XIX is a histidine or an aspartic acid. Preferably, the amino acid at position 3 of Formula XIX is a threonine or a glutamic acid. Preferably, the amino acid at position 5 of Formula XIX is a glutamic acid. Preferably, the amino acid at position 6 of Formula XIX is an isoleucine, leucine, valine, or tyrosine. Preferably, the amino acid at position 8, 10, 11, or 13 of Formula XIX is an alanine. Preferably, the amino acid at position 9 of Formula XIX is an asparagine or a phenylalanine. Preferably, the amino acid at position 14 of Formula XIX is a glycine.

In further embodiments, GCRA peptides include peptides containing the amino acid sequence of Formula XX. Preferably, the amino acid at position 1 of Formula XX is a glutamine. Preferably, the amino acid at position 2 or 3 of Formula XX is a glutamic acid or an aspartic acid. Preferably, the amino acid at position 5 of Formula XX is a glutamic acid. Preferably, the amino acid at position 6 of Formula XX is threonine, glutamine, tyrosine, isoleucine, or leucine. Preferably, the amino acid at position 8 of Formula XX is isoleucine or valine. Preferably, the amino acid at position 9 of Formula XX is asparagine. Preferably, the amino acid at position 10 of Formula XX is methionine or valine. Preferably, the amino acid at position 11 of Formula XX is alanine. Preferably, the amino acid at position 13 of Formula XX is a threonine. Preferably, the amino acid at position 1 of Formula XX is a glycine. Preferably, the amino acid at position 15 of Formula XX is a tyrosine. Optionally, the amino acid at position 15 of Formula XX is two amino acid in length and is Cysteine (Cys), Penicillamine (Pen) homocysteine, or 3-mercaptoproline and serine, leucine or threonine.

In certain embodiments, one or more amino acids of the GCC agonist peptides are replaced by a non-naturally occurring amino acid or a naturally or non-naturally occurring amino acid analog. Such amino acids and amino acid analogs are known in the art. See, for example, Hunt, "The Non-Protein Amino Acids," in *Chemistry and Biochemistry of the Amino Acids*, Barrett, Chapman, and Hall, 1985. In some embodiments, an amino acid is replaced by a naturally-occurring, non-essential amino acid, e.g., taurine. Non-limiting examples of naturally occurring amino acids that can be replaced by non-protein amino acids include the following: (1) an aromatic amino acid can be replaced by 3,4-dihydroxy-L-phenylalanine, 3-iodo-L-tyrosine, triiodothyronine, L-thyroxine, phenylglycine (Phg) or nor-tyrosine (norTyr); (2) Phg and norTyr and other amino acids including Phe and Tyr can be substituted by, e.g., a halogen, —CH3, —OH, —CH2NH3, —C(O)H, —CH2CH3, —CN, —CH2CH2CH3, —SH, or another group; (3) glutamine residues can be substituted with gamma-Hydroxy-Glu or gamma-Carboxy-Glu; (4) tyrosine residues can be substituted with an alpha substituted amino acid such as L-alpha-methylphenylalanine or by analogues such as: 3-Amino-Tyr; Tyr (CH3); Tyr (PO3 (CH3) 2); Tyr (SO3H); beta-Cyclo-hexyl-Ala; beta-(1-Cyclopentenyl)-Ala; beta-Cyclopentyl-Ala; beta-Cyclopropyl-Ala; beta-Quinolyl-Ala; beta-(2-Thiazolyl)-Ala; beta-(Triazole-1-yl)-Ala; beta-(2-Pyridyl)-Ala; beta-(3-Pyridyl)-Ala; Amino-Phe; Fluoro-Phe; Cyclohexyl-Gly; tBu-Gly; beta-(3-benzothienyl)-Ala; beta-(2-thienyl)-Ala; 5-Methyl-Trp; and A-Methyl-Trp; (5) proline residues can be substituted with homopro (L-pipecolic acid); hydroxy-Pro; 3,4-Dehydro-Pro; 4-fluoro-Pro; or alpha-methyl-Pro or an N (alpha)-C(alpha) cyclized amino acid analogues with the structure: n=0, 1, 2, 3; and (6) alanine residues can be substituted with alpha-substituted or N-methylated amino acid such as alpha-amino isobutyric acid (aib), L/D-alpha-ethylalanine (L/D-isovaline), L/D- methylvaline, or L/D-alpha-methylleucine or a non-natural amino acid such as beta-fluoro-Ala. Alanine can also be substituted with: n=0, 1, 2, 3 Glycine residues can be substituted with alpha-amino isobutyric acid (aib) or L/D-alpha-ethylalanine (L/D-isovaline).

Further examples of non-natural amino acids include: an unnatural analog of tyrosine; an unnatural analogue of glutamine; an unnatural analogue of phenylalanine; an unnatural analogue of serine; an unnatural analogue of threonine; an alkyl, aryl, acyl, azido, cyano, halo, hydrazine, hydrazide, hydroxyl, alkenyl, alkynyl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; an amino acid that is amidated at a site that is not naturally amidated, a metal-containing amino acid; a radioactive amino acid; a photocaged and/or photoisomerizable amino acid; a biotin or biotin-analogue containing amino acid; a glycosylated or carbohydrate modified amino acid; a keto containing amino acid; amino acids comprising polyethylene glycol or polyether; a heavy atom substituted amino acid (e.g., an amino acid containing deuterium, tritium, $^{13}C$, $^{15}N$, or $^{18}O$); a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an a-hydroxy containing acid; an amino thio acid containing amino acid; an α, α disubstituted amino acid; a β-amino acid; a cyclic amino acid other than proline; an O-methyl-L-tyrosine; an L-3-(2-naphthyl) alanine; a 3-methyl-phenylalanine; a ρ-acetyl-L-phenylalanine; an O-4-allyl-L-tyrosine; a 4-propyl-L-tyrosine; a tri-O-acetyl-GlcNAc β-serine; an L-Dopa; a fluorinated phenylalanine; an isopropyl-L-phenylalanine; a p-azido-L-phenylalanine; a p-acyl-L-phenylalanine; a p-benzoyl-L-phenylalanine; an L-phosphoserine; a phosphonoserine; a phosphonotyrosine; a p-iodo-phenylalanine; a 4-fluorophenylglycine; a p-bromophenylalanine; a p-amino-L-phenylalanine; an isopropyl-L-phenylalanine; L-3-(2-naphthyl) alanine; D-3-(2-naphthyl) alanine (dNal); an amino-, isopropyl-, or O-allyl-containing phenylalanine analogue; a dopa, 0-methyl-L-tyrosine; a glycosylated amino acid; a p-(propargyloxy) phenylalanine; dimethyl-Lysine; hydroxy-proline; mercaptopropionic acid; methyl-lysine; 3-nitro-tyrosine; norleucine; pyro-glutamic acid; Z (Carbobenzoxyl); ε-Acetyl-Lysine; β-alanine; aminobenzoyl derivative; aminobutyric acid (Abu); citrulline; aminohexanoic acid; aminoisobutyric acid (AIB); cyclohexylalanine; d-cyclohexylalanine; hydroxyproline; nitro-arginine; nitro-phenylalanine; nitro-tyrosine; norvaline; octahydroindole carboxylate; ornithine (Orn); penicillamine (PEN); tetrahydroisoquinoline; acetamidomethyl protected amino acids and pegylated amino acids. Further examples of unnatural amino acids and amino acid analogs can be found in U.S. 20030108885, US20030082575, US20060019347 (paragraphs 410-418) and the references cited therein. The polypeptides of the invention can include further modifications including those described in US20060019347, paragraph 589. Exemplary GCC agonist peptides which include a non-naturally occurring amino acid include for example SP-368 and SP-369.

In some embodiments, the GCC agonist peptides are cyclic peptides. GCC agonist cyclic peptides can be prepared by methods known in the art. For example, macrocyclization is often accomplished by forming an amide bond between the peptide N- and C-termini, between a side chain and the N- or C-terminus [e.g., with $K_3Fe(CN)_6$ at pH 8.5] (Samson et al., *Endocrinology*, 137:5182-5185 (1996)), or between two amino acid side chains, such as cysteine. See, e.g., DeGrado, *Adv Protein Chem*, 39:51-124 (1988). In various embodiments, the GCC agonist peptides are [4,12; 7,15] bicycles.

In certain embodiments, one or both Cys residues which normally form a disulfide bond in a GCC agonist peptide are replaced with homocysteine, penicillamine, 3-mercaptoproline (Kolodziej et al. 1996 *Int. J. Pept. Protein Res.* 48:274), β, β dimethylcysteine (Hunt et al. 1993 *Int. J. Pept. Protein Res.* 42:249), or diaminopropionic acid (Smith et al. 1978 *J. Med. Chem.* 2 1:117) to form alternative internal cross-links at the positions of the normal disulfide bonds.

In certain embodiments, one or more disulfide bonds in a GCC agonist peptide are replaced by alternative covalent cross-links, e.g., an amide linkage ($—CH_2CH(O)NHCH_2—$ or $—CH_2NHCH(O)CH_2—$), an ester linkage, a thioester linkage, a lactam bridge, a carbamoyl linkage, a urea linkage, a thiourea linkage, a phosphonate ester linkage, an alkyl linkage ($—CH_2CH_2CH_2CH_2—$), an alkenyl linkage ($—CH_2CH=CHCH_2—$), an ether linkage ($—CH_2CH_2OCH_2—$ or $—CH_2OCH_2CH_2—$), a thioether linkage ($—CH_2CH_2SCH_2—$ or $—CH_2SCH_2CH_2—$), an amine linkage ($—CH_2CH_2NHCH_2—$ or $—CH2NHCH_2CH_2—$) or a thioamide linkage ($—CH_2C(S)NHCH_2—$ or $—CH_2NHC(S)CH_2—$). For example, Ledu et al. (*Proc. Natl. Acad. Sci.* 100:11263-78, 2003) describe methods for preparing lactam and amide cross-links. Exemplary GCC agonist peptides which include a lactam bridge include, for example, SP-370.

In certain embodiments, the GCC agonist peptides have one or more conventional polypeptide bonds replaced by an alternative bond. Such replacements can increase the stability of the polypeptide. For example, replacement of the polypeptide bond between a residue amino terminal to an aromatic residue (e.g. Tyr, Phe, Trp) with an alternative bond can reduce cleavage by carboxy peptidases and may increase half-life in the digestive tract. Bonds that can replace polypeptide bonds include: a retro-inverso bond (C(O)—NH instead of NH—C(O); a reduced amide bond (NH—$CH_2$); a thiomethylene bond (S—$CH_2$ or $CH_2$-S); an oxomethylene bond (O—$CH_2$ or $CH_2$-O); an ethylene bond ($CH_2$-$CH_2$); a thioamide bond (C(S)—NH); a trans-olefine bond (CH=CH); a fluoro substituted trans-olefine bond (CF=CH); a ketomethylene bond (C(O)—CHR or CHR—C(O) wherein R is H or $CH_3$; and a fluoro-ketomethylene bond (C(O)—CFR or CFR—C(O) wherein R is H or F or $CH_3$.

In certain embodiments, the GCC agonist peptides are modified using standard modifications. Modifications may occur at the amino (N—), carboxy (C—) terminus, internally or a combination of any of the preceding. In one aspect described herein, there may be more than one type of modification on the polypeptide. Modifications include but are not limited to: acetylation, amidation, biotinylation, cinnamoylation, farnesylation, formylation, myristoylation, palmitoylation, phosphorylation (Ser, Tyr or Thr), stearoylation, succinylation, sulfurylation and cyclisation (via disulfide bridges or amide cyclisation), and modification by Cys3 or Cys5. The GCC agonist peptides described herein may also be modified by 2, 4-dinitrophenyl (DNP), DNP-lysine, modification by 7-Amino-4-methyl-coumarin (AMC), flourescein, NBD (7-Nitrobenz-2-Oxa-1,3-Diazole), p-nitro-anilide, rhodamine B, EDANS (5-((2-aminoethyl)amino) naphthalene-1-sulfonic acid), dabcyl, dabsyl, dansyl, texas red, FMOC, and Tamra (Tetramethylrhodamine). The GCC agonist peptides described herein may also be conjugated to, for example, polyethylene glycol (PEG); alkyl groups (e.g., C1-C20 straight or branched alkyl groups); fatty acid moieties; combinations of PEG, alkyl groups and fatty acid moieties (See, U.S. Pat. No. 6,309,633; Soltero et al., 2001 Innovations in Pharmaceutical Technology 106-110); BSA and KLH (Keyhole Limpet Hemocyanin). The addition of PEG and other polymers which can be used to modify polypeptides of the invention is described in US20060 19347 section IX.

A GCC agonist peptide can also be a derivative of a GCC agonist peptide described herein. For example, a derivative includes hybrid and modified forms of GCC agonist peptides in which certain amino acids have been deleted or replaced. A modification may also include glycosylation. Preferably, where the modification is an amino acid substitution, it is a conservative substitution at one or more positions that are predicted to be non-essential amino acid residues for the biological activity of the peptide. A "conservative substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

In one embodiment, a GCC agonist peptide prepared by the methods described herein is subjected to random mutagenesis in order to identify mutants having biological activity.

In one embodiment, the methods of the invention can be used to prepare a GCC agonist peptide that is substantially homologous to a GCC agonist peptide described herein. Such substantially homologous peptides can be isolated by virtue of cross-reactivity with antibodies to a GCC agonist peptide described herein.

Further examples of GCC agonist peptides that can be prepared by the methods of the invention are found in Tables I-VII below.

1.1.2 Alternative Preparation Methods of GCC Agonist Peptides and their Fragments GCC agonist peptides and their fragments can be prepared using art recognized techniques such as molecular cloning, peptide synthesis, or site-directed mutagenesis.

In addition to the conventional solution- or solid-phase peptide synthesis described above, the GCC agonist peptides or their fragments can be produced by modern cloning techniques. For example, the GCC agonist peptides are produced either in bacteria including, without limitation, *E. coli*, or in other existing systems for polypeptide or protein production (e.g., *Bacillus subtilis*, baculovirus expression systems using *Drosophila* Sf9 cells, yeast or filamentous fungal expression systems, mammalian cell expression systems), or they can be chemically synthesized. If the GCC agonist peptide or variant peptide is to be produced in bacteria, e.g., *E. coli*, the nucleic acid molecule encoding the polypeptide may also encode a leader sequence that permits the secretion of the mature polypeptide from the cell. Thus, the sequence encoding the polypeptide can include the pre sequence and the pro sequence of, for example, a naturally-occurring bacterial ST polypeptide. The secreted, mature polypeptide can be purified from the culture medium.

The sequence encoding a GCC agonist peptide described herein can be inserted into a vector capable of delivering and maintaining the nucleic acid molecule in a bacterial cell. The DNA molecule may be inserted into an autonomously replicating vector (suitable vectors include, for example, pGEM3Z and pcDNA3, and derivatives thereof). The vector nucleic acid may be a bacterial or bacteriophage DNA such as bacteriophage lambda or M13 and derivatives thereof. Construction of a vector containing a nucleic acid described herein can be followed by transformation of a host cell such as a bacterium. Suitable bacterial hosts include but are not limited to, *E. coli, B. subtilis, Pseudomonas, Salmonella*. The genetic construct also includes, in addition to the encoding nucleic acid molecule, elements that allow expression, such as a promoter and regulatory sequences. The expression vectors may contain transcriptional control sequences that control transcriptional initiation, such as promoter, enhancer, operator, and repressor sequences.

A variety of transcriptional control sequences are well known to those in the art. The expression vector can also include a translation regulatory sequence (e.g., an untranslated 5' sequence, an untranslated 3' sequence, or an internal ribosome entry site). The vector can be capable of autonomous replication or it can integrate into host DNA to ensure stability during polypeptide production.

The protein coding sequence that includes a GCC agonist peptide described herein can also be fused to a nucleic acid encoding a polypeptide affinity tag, e.g., glutathione S-transferase (GST), maltose E binding protein, protein A, FLAG tag, hexa-histidine, myc tag or the influenza HA tag, in order to facilitate purification. The affinity tag or reporter fusion joins the reading frame of the polypeptide of interest to the reading frame of the gene encoding the affinity tag such that a translational fusion is generated. Expression of the fusion gene results in translation of a single polypeptide that includes both the polypeptide of interest and the affinity tag. In some instances where affinity tags are utilized, DNA sequence encoding a protease recognition site will be fused between the reading frames for the affinity tag and the polypeptide of interest.

Genetic constructs and methods suitable for production of immature and mature forms of the GCC agonist peptides and variants described herein in protein expression systems other than bacteria, and well known to those skilled in the art, can also be used to produce polypeptides in a biological system.

The peptides disclosed herein may be modified by attachment of a second molecule that confers a desired property upon the peptide, such as increased half-life in the body, for example, pegylation. Such modifications also fall within the scope of the term "variant" as used herein.

TABLE I

GCRA Peptides (SP-304 and Derivatives)

| Name | Position of Disulfide bonds | Structure | SEQ ID NO: |
|---|---|---|---|
| SP-304 | C4:C12, C7:C15 | $Asn^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Leu^{16}$ | 1 |
| SP-326 | C3:C11, C6:C14 | $Asp^1$-$Glu^2$-$Cys^3$-$Glu^4$-$Leu^5$-$Cys^6$-$Val^7$-$Asn^8$-$Val^9$-$Ala^{10}$-$Cys^{11}$-$Thr^{12}$-$Gly^{13}$-$Cys^{14}$-$Leu^{15}$ | 2 |
| SP-327 | C2:C10, C5:C13 | $Asp^1$-$Glu^2$-$Cys^3$-$Glu^4$-$Leu^5$-$Cys^6$-$Val^7$-$Asn^8$-$Val^9$-$Ala^{10}$-$Cys^{11}$-$Thr^{12}$-$Gly^{13}$-$Cys^{14}$ | 3 |
| SP-328 | C2:C10, C5:C13 | $Glu^1$-$Cys^2$-$Glu^3$-$Leu^4$-$Cys^5$-$Val^6$-$Asn^7$-$Val^8$-$Ala^9$-$Cys^{10}$-$Thr^{11}$-$Gly^{12}$-$Cys^{13}$-$Leu^{14}$ | 4 |
| SP-329 | C2:C10, C5:C13 | $Glu^1$-$Cys^2$-$Glu^3$-$Leu^4$-$Cys^5$-$Val^6$-$Asn^7$-$Val^8$-$Ala^9$-$Cys^{10}$-$Thr^{11}$-$Gly^{12}$-$Cys^{13}$ | 5 |
| SP-330 | C1:C9, C4:C12 | $Cys^1$-$Glu^2$-$Leu^3$-$Cys^4$-$Val^5$-$Asn^6$-$Val^7$-$Ala^8$-$Cys^9$-$Thr^{10}$-$Gly^{11}$-$Cys^{12}$-$Leu^{13}$ | 6 |
| SP-331 | C1:C9, C4:C12 | $Cys^1$-$Glu^2$-$Leu^3$-$Cys^4$-$Val^5$-$Asn^6$-$Val^7$-$Ala^8$-$Cys^9$-$Thr^{10}$-$Gly^{11}$-$Cys^{12}$ | 7 |
| SP332 | C4:C12, C7:C15 | $Asn^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dLeu^{16}$ | 8 |
| SP-333 | C4:C12, C7:C15 | $dAsn^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dLeu^{16}$ | 9 |
| SP-334 | C4:C12, C7:C15 | $dAsn^1$-$dAsp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dLeu^{16}$ | 10 |
| SP-335 | C4:C12, C7:C15 | $dAsn^1$-$dAsp^2$-$dGlu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dLeu^{16}$ | 11 |
| SP-336 | C4:C12, C7:C15 | $dAsn^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Leu^{16}$ | 12 |
| SP-337 | C4:C12, C7:C15 | $dAsn^1$-$Asp^2$-$Glu^3$-$Cys^4$-$Glu^5$-$dLeu^6$-$Cys^7$-$Val^8$-$Asn^9$-$Val^{10}$-$Ala^{11}$-$Cys^{12}$-$Thr^{13}$-$Gly^{14}$-$Cys^{15}$-$dLeu^{16}$ | 13 |
| SP-338 | C4:C12, C7:C15 | $Asn^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys15$ | 14 |
| SP-342 | C4:C12, C7:C15 | PEG3-$Asn^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dLeu^{16}$-PEG3 | 15 |
| SP-343 | C4:C12, C7:C15 | PEG3-$dAsn^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dLeu^{16}$-PEG3 | 16 |
| SP-344 | C4:C12, C7:C15 | PEG3-$dAsn^1$-$dAsp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dLeu^{16}$-PEG3 | 17 |
| SP-347 | C4:C12, C7:C15 | $dAsn^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dLeu^{16}$-PEG3 | 18 |
| SP-348 | C4:C12, C7:C15 | PEG3-$Asn^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dLeu^{16}$ | 19 |
| SP-350 | C4:C12, C7:C15 | PEG3-$dAsn^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dLeu^{16}$ | 20 |
| SP-352 | C4:C12, C7:C15 | $Asn^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dLeu^{16}$-PEG3 | 21 |
| SP-358 | C4:C12, C7:C15 | PEG3-$dAsn^1$-$dAsp^2$-$dGlu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dLeu^{16}$-PEG3 | 22 |
| SP-359 | C4:C12, C7:C15 | PEG3-$dAsn^1$-$dAsp^2$-$dGlu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dLeu^{16}$ | 23 |
| SP-360 | C4:C12, C7:C15 | $dAsn^1$-$dAsp^2$-$dGlu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dLeu^{16}$-PEG3 | 24 |
| SP-361 | C4:C12, C7:C15 | $dAsn^1$-$dAsp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dLeu^{16}$-PEG3 | 25 |

TABLE I-continued

GCRA Peptides (SP-304 and Derivatives)

| Name | Position of Disulfide bonds | Structure | SEQ ID NO: |
|---|---|---|---|
| SP-362 | C4:C12, C7:C15 | PEG3-dAsn$^1$-dAsp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 26 |
| SP-368 | C4:C12, C7:C15 | dAsn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dNal$^{16}$ | 27 |
| SP-369 | C4:C12, C7:C15 | dAsn$^1$-Asp$^2$-Glu$^3$-Cys$^4$-Glu$^5$-Leu$^6$-Cys$^7$-AIB$^8$-Asn$^9$-AIB$^{10}$-Ala$^{11}$-Cys$^{12}$-Thr$^{13}$-Gly$^{14}$-Cys$^{15}$-dLeu$^{16}$ | 28 |
| SP-370 | C4:C12, C7:C15 | dAsn$^1$-Asp$^2$-Glu$^3$-Cys$^4$-Glu$^5$-Leu$^6$-Asp[Lactam]$^7$-Val$^8$-Asn$^9$-Val$^{10}$-Ala$^{11}$-Cys$^{12}$-Thr$^{13}$-Gly$^{14}$-Orn$^{15}$-dLeu$^1$ | 29 |
| SP-371 | C4:C12, C7:C15 | dAsn$^1$-Asp$^2$-Glu$^3$-Cys$^4$-Glu$^5$-Tyr$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 30 |
| SP-372 | C4:C12, C7:C15 | dAsn$^1$-Asp$^2$-Glu$^3$-Cys$^4$-Glu$^5$-Ser$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 31 |
| N1 | C4:C12, C7:C15 | PEG3-dAsn$^1$-Asp$^2$-Glu$^3$-Cys$^4$-Glu$^5$-Tyr$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$-PEG3 | 32 |
| N2 | C4:C12, C7:C15 | PEG3-dAsn$^1$-Asp$^2$-Glu$^3$-Cys$^4$-Glu$^5$-Tyr$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 33 |
| N3 | C4:C12, C7:C15 | dAsn$^1$-Asp$^2$-Glu$^3$-Cys$^4$-Glu$^5$-Tyr$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$PEG3 | 34 |
| N4 | C4:C12, C7:C15 | PEG3-dAsn$^1$-Asp$^2$-Glu$^3$-Cys$^4$-Glu$^5$-Ser$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$-PEG3 | 35 |
| N5 | C4:C12, C7:C15 | PEG3-dAsn$^1$-Asp$^2$-Glu$^3$-Cys$^4$-Glu$^5$-Ser$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$ | 36 |
| N6 | C4:C12, C7:C15 | dAsn$^1$-Asp$^2$-Glu$^3$-Cys$^4$-Glu$^5$-Ser$^6$-Cys$^7$-Val$^8$-Asn$^9$-Val$^{10}$-Ala$^{11}$-Cys$^{12}$-Thr$^{13}$-Gly$^{14}$-Cys$^{15}$-dLeu$^{16}$-PEG3 | 37 |
| N7 | C4:C12, C7:C15 | Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$ | 38 |
| N8 | C4:C12, C7:C15 | PEG3-Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$-PEG3 | 39 |
| N9 | C4:C12, C7:C15 | PEG3-Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$ | 40 |
| N10 | C4:C12, C7:C15 | Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$-PEG3 | 41 |
| N11 | C4:C12, C7:C15 | PEG3-Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dSer$^{16}$-PEG3 | 42 |
| N12 | C4:C12, C7:C15 | PEG3-Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dSer$^{16}$ | 43 |
| N13 | C4:C12, C7:C15 | Asn$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-dSer$^{16}$-PEG3 | 44 |
| Formula I | C4:C12, C7:C15 | Asn$^1$-Asp$^2$-Glu$^3$-Cys$^4$-Xaa$^5$-Xaa$^6$-Cys$^7$-Xaa$^8$-Xaa$^9$-Xaa$^{10}$-Xaa$^{11}$-Cys$^{12}$-Xaa$^{13}$-Xaa$^{14}$-Cys$^{15}$-Xaa$^{16}$ | 45 |
| Formula II | C4:C12, C7:C15 | Xaa$_{n1}$-Cys$^4$-Xaa$^5$-Xaa$^6$-Cys$^7$-Xaa$^8$-Xaa$^9$-Xaa$^{10}$-Xaa$^{11}$-Cys$^{12}$-Xaa$^{13}$-Xaa$^{14}$-Cys$^{15}$-Xaa$_{n2}^{16}$ | 46 |
| Formula III | 4:12, 7:15 | Xaa$_{n1}$-Maa$^4$-Glu$^5$-Xaa$^6$-Maa$^7$-Val$^8$-Asn$^9$-Val$^{10}$-Ala$^{11}$-Maa$^{12}$-Thr$^{13}$-Gly$^{14}$-Maa$^{15}$-Xaa$_{n2}$ | 47 |
| Formula IV | 4:12, 7:15 | Xaa$_{n1}$-Maa$^4$-Xaa$^5$-Xaa$^6$-Maa$^7$-Xaa$^8$-Xaa$^9$-Xaa$^{10}$-Xaa$^{11}$-Maa$^{12}$-Xaa$^{13}$-Xaa$^{14}$-Maa$^{15}$-Xaa$_{n2}$ | 48 |
| Formula V | C4:C12, C7:C15 | Asn$^1$-Asp$^2$-Asp$^3$-Cys$^4$-Xaa$^5$-Xaa$^6$-Cys$^7$-Xaa$^8$-Asn$^9$-Xaa$^{10}$-Xaa$^{11}$-Cys$^{12}$-Xaa$^{13}$-Xaa$^{14}$-Cys$^{15}$-Xaa$^{16}$ | 49 |
| Formula VI | C4:C12, C7:C15 | dAsn$^1$-Glu$^2$-Glu$^3$-Cys$^4$-Xaa$^5$-Xaa$^6$-Cys$^7$-X$^{38}$-Asn$^9$-Xaa$^{10}$-Xaa$^{11}$-Cys$^{12}$-Xaa$^{13}$-Xaa$^{14}$-Cys$^{15}$-d-Xaa$^{16}$ | 50 |

TABLE I-continued

GCRA Peptides (SP-304 and Derivatives)

| Name | Position of Disulfide bonds | Structure | SEQ ID NO: |
|---|---|---|---|
| Formula VII | C4:C12, C7:C15 | dAsn$^1$-dGlu$^2$-Asp$^3$-Cys$^4$-Xaa$^5$-Xaa$^6$-Cys$^7$-Xaa$^8$-Asn$^9$-Xaa$^{10}$-Xaa$^{11}$-Cys$^{12}$-Xaa$^{13}$-Xaa$^{14}$-Cys$^{15}$-d-Xaa$^{16}$ | 51 |
| Formula VII | C4:C12, C7:C15 | dAsn$^1$-dAsp$^2$-Glu$^3$-Cys$^4$-Xaa$^5$-Xaa$^6$-Cys$^7$-Xaa$^8$-Asn$^9$-Xaa$^{10}$-Xaa$^{11}$-Cys$^{12}$-Xaa$^{13}$-Xaa$^{14}$-Cys$^{15}$-d-Xaa$^{16}$ | 52 |
| Formula III | C4:C12, C7:C15 | dAsn$^1$-dAsp$^2$-dGlu$^3$-Cys$^4$-Xaa$^5$-Xaa$^6$-Cys$^7$-Xaa$^8$-Tyr$^9$-Xaa$^{10}$-Xaa$^{11}$-Cys$^{12}$-Xaa$^{13}$-Xaa$^{14}$-Cys$^{15}$-d-Xaa$^{16}$ | 53 |
| Formula IX | C4:C12, C7:C15 | dAsn$^1$-dGlu$^2$-dGlu$^3$-Cys$^4$-Xaa$^5$-Xaa$^6$-Cys$^7$-Xaa$^8$-Tyr$^9$-Xaa$^{10}$-Xaa$^{11}$-Cys$^{12}$-Xaa$^{13}$-Xaa$^{14}$-Cys$^{15}$-d-Xaa$^{16}$ | 54 |
| Formula XXI | C4:C12, C7:C15 | Xaa$_{n1}$-Cys$^4$-Xaa$^5$-Xaa$^6$-Xaa$^7$-Xaa$^8$-Xaa$^9$-Xaa$^{10}$-Xaa$^{11}$-Cys$^{12}$-Xaa$^{13}$-Xaa$^{14}$-Xaa$^{15}$-Xaa$_{n2}^{16}$ | 250 |

TABLE II

Linaclotide and Derivatives

| Name | Position of Disulfide bonds | Structure | SEQ ID NO: |
|---|---|---|---|
| SP-339 (linaclotide) | C1:C6, C2:C10, C5:13 | Cys$^1$-Cys$^2$-Glu$^3$-Tyr$^4$-Cys$^5$-Cys$^6$-Asn$^7$-Pro$^8$-Ala$^9$-Cys$^{10}$-Thr$^{11}$-Gly$^{12}$-Cys$^{13}$-Tyr14 | 55 |
| SP-340 | C1:C6, C2:C10, C5:13 | Cys$^1$-Cys$^2$-Glu$^3$-Tyr$^4$-Cys$^5$-Cys$^6$-Asn$^7$-Pro$^8$-Ala$^9$-Cys$^{10}$-Thr$^{11}$-Gly$^{12}$-Cys$^{13}$ | 56 |
| SP-349 | C1:C6, C2:C10, C5:13 | PEG3-Cys$^1$-Cys$^2$-Glu$^3$-Tyr$^4$-Cys$^5$-Cys$^6$-Asn$^7$-Pro$^8$-Ala$^9$-Cys$^{10}$-Thr$^{11}$-Gly$^{12}$-Cys$^{13}$-Tyr$^{14}$-PEG3 | 57 |
| SP-353 | C3:C8, C4:C12, C7:15 | Asn$^1$-Phe$^2$-Cys$^3$-Cys$^4$-Glu$^5$-Ser$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr$^{16}$ | 58 |
| SP-354 | C3:C8, C4:C12, C7:15 | Asn$^1$-Phe$^2$-Cys$^3$-Cys$^4$-Glu$^5$-Phe$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr$^{16}$ | 59 |
| SP-355 | C1:C6, C2:C10, C5:13 | Cys$^1$-Cys$^2$-Glu$^3$-Tyr$^4$-Cys$^5$-Cys$^6$-Asn$^7$-Pro$^8$-Ala$^9$-Cys$^{10}$-Thr$^{11}$-Gly$^{12}$-Cys$^{13}$-dTyr$^{14}$ | 60 |
| SP-357 | C1:C6, C2:C10, C5:13 | PEG3-Cys$^1$-Cys$^2$-Glu$^3$-Tyr$^4$-Cys$^5$-Cys$^6$-Asn$^7$-Pro$^8$-Ala$^9$-Cys$^{10}$-Thr$^{11}$-Gly$^{12}$-Cys$^{13}$-Tyr$^{14}$ | 61 |
| SP-374 | C3:C8, C4:C12, C7:15 | Asn$^1$-Phe$^2$-Cys$^3$-Cys$^4$-Glu$^5$-Thr$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr | 62 |
| SP-375 | C3:C8, C4:C12, C7:15 | Asn$^1$-Phe$^2$-Cys$^3$-Cys$^4$-Glu$^5$-Ser$^6$-Cys$^7$-Cys$^8$-Asn$^9$-Pro$^{10}$-Ala$^{11}$-Cys$^{12}$-Thr$^{13}$-Gly$^{14}$-Cys$^{15}$-dTyr$^{16}$ | 63 |
| SP-376 | C3:C8, C4:C12, C7:15 | dAsn$^1$-Phe$^2$-Cys$^3$-Cys$^4$-Glu$^5$-Ser$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr$^{16}$ | 64 |
| SP-377 | C3:C8, C4:C12, C7:15 | dAsn$^1$-Phe$^2$-Cys$^3$-Cys$^4$-Glu$^5$-Ser$^6$-Cys$^7$-Cys$^8$-Asn$^9$-Pro$^{10}$-Ala$^{11}$-Cys$^{12}$-Thr$^{13}$-Gly$^{14}$-Cys$^{15}$-dTyr$^{16}$ | 65 |
| SP-378 | C3:C8, C4:C12, C7:15 | Asn$^1$-Phe$^2$-Cys$^3$-Cys$^4$-Glu$^5$-Thr$^6$-Cys$^7$-Cys$^8$-Asn$^9$-Pro$^{10}$-Ala$^{11}$-Cys$^{12}$-Thr$^{13}$-Gly$^{14}$-Cys$^{15}$-dTyr$^{16}$ | 66 |
| SP-379 | C3:C8, C4:C12, C7:15 | dAsn$^1$-Phe$^2$-Cys$^3$-Cys$^4$-Glu$^5$-Thr$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr$^{16}$ | 67 |
| SP-380 | C3:C8, C4:C12, C7:15 | dAsn$^1$-Phe$^2$-Cys$^3$-Cys$^4$-Glu$^5$-Thr$^6$-Cys$^7$-Cys$^8$-Asn$^9$-Pro$^{10}$-Ala$^{11}$-Cys$^{12}$-Thr$^{13}$-Gly$^{14}$-Cys$^{15}$-dTyr$^{16}$ | 68 |
| SP-381 | C3:C8, C4:C12, C7:15 | Asn$^1$-Phe$^2$-Cys$^3$-Cys$^4$-Glu$^5$-Phe$^6$-Cys$^7$-Cys$^8$-Asn$^9$-Pro$^{10}$-Ala$^{11}$-Cys$^{12}$-Thr$^{13}$-Gly$^{14}$-Cys$^{15}$-dTyr$^{16}$ | 69 |
| SP-382 | C3:C8, C4:C12, C7:15 | dAsn$^1$-Phe$^2$-Cys$^3$-Cys$^4$-Glu$^5$-Phe$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr$^{16}$ | 70 |

TABLE II-continued

Linaclotide and Derivatives

| Name | Position of Disulfide bonds | Structure | SEQ ID NO: |
|---|---|---|---|
| SP-383 | C3:C8, C4:C12, C7:15 | dAsn$^1$-Phe$^2$-Cys$^3$-Cys$^4$-Glu$^5$-Phe$^6$-Cys$^7$-Cys$^8$-Asn$^9$-Pro$^{10}$-Ala$^{11}$-Cys$^{12}$-Thr$^{13}$-Gly$^{14}$-Cys$^{15}$-dTyr$^{16}$ | 71 |
| SP-384 | C1:C6, C2:C10, C5:13 | Cys$^1$-Cys$^2$-Glu$^3$-Tyr$^4$-Cys$^5$-Cys$^6$-Asn$^7$-Pro$^8$-Ala$^9$-Cys$^{10}$-Thr$^{11}$-Gly$^{12}$-Cys$^{13}$-Tyr$^{14}$-PEG3 | 72 |
| N14 | C1:C6, C2:C10, C5:13 | PEG3-Cys$^1$-Cys$^2$-Glu$^3$-Tyr$^4$-Cys$^5$-Cys$^6$-Asn$^7$-Pro$^8$-Ala$^9$-Cys$^{10}$-Thr$^{11}$-Gly$^{12}$-Cys$^{13}$-PEG3 | 73 |
| N15 | C1:C6, C2:C10, C5:13 | PEG3-Cys$^1$-Cys$^2$-Glu$^3$-Tyr$^4$-Cys$^5$-Cys$^6$-Asn$^7$-Pro$^8$-Ala$^9$-Cys$^{10}$-Thr$^{11}$-Gly$^{12}$-Cys$^{13}$ | 74 |
| N16 | C1:C6, C2:C10, C5:13 | Cys$^1$-Cys$^2$-Glu$^3$-Tyr$^4$-Cys$^5$-Cys$^6$-Asn$^7$-Pro$^8$-Ala$^9$-Cys$^{10}$-Thr$^{11}$-Gly$^{12}$-Cys$^{13}$-PEG3 | 75 |
| N17 | C3:C8, C4:C12, C7:15 | PEG3-Asn$^1$-Phe$^2$-Cys$^3$-Cys$^4$-Glu$^5$-Ser$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr$^{16}$-PEG3 | 76 |
| N18 | C3:C8, C4:C12, C7:15 | PEG3-Asn$^1$-Phe$^2$-Cys$^3$-Cys$^4$-Glu$^5$-Ser$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr$^{16}$ | 77 |
| N19 | C3:C8, C4:C12, C7:15 | Asn$^1$-Phe$^2$-Cys$^3$-Cys$^4$-Glu$^5$-Ser$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr$^{16}$-PEG3 | 78 |
| N20 | C3:C8, C4:C12, C7:15 | PEG3-Asn$^1$-Phe$^2$-Cys$^3$-Cys$^4$-Glu$^5$-Phe$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr$^{16}$-PEG3 | 79 |
| N21 | C3:C8, C4:C12, C7:15 | PEG3-Asn$^1$-Phe$^2$-Cys$^3$-Cys$^4$-Glu$^5$-Phe$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr$^{16}$ | 80 |
| N22 | C3:C8, C4:C12, C7:15 | Asn$^1$-Phe$^2$-Cys$^3$-Cys$^4$-Glu$^5$-Phe$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr$^{16}$-PEG3 | 81 |
| N23 | C3:C8, C4:C12, C7:15 | PEG3-Asn$^1$-Phe$^2$-Cys$^3$-Cys$^4$-Glu$^5$-Tyr$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr$^{16}$-PEG3 | 82 |
| N24 | C3:C8, C4:C12, C7:15 | PEG3-Asn$^1$-Phe$^2$-Cys$^3$-Cys$^4$-Glu$^5$-Tyr$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr$^{16}$ | 83 |
| N25 | C3:C8, C4:C12, C7:15 | Asn$^1$-Phe$^2$-Cys$^3$-Cys$^4$-Glu$^5$-Tyr$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr$^{16}$-PEG3 | 84 |
| N26 | C1:C6, C2:C10, C5:13 | Cys$^1$-Cys$^2$-Glu$^3$-Ser$^4$-Cys$^5$-Cys$^6$-Asn$^7$-Pro$^8$-Ala$^9$-Cys$^{10}$-Thr$^{11}$-Gly$^{12}$-Cys$^{13}$-Tyr$^{14}$ | 85 |
| N27 | C1:C6, C2:C10, C5:13 | Cys$^1$-Cys$^2$-Glu$^3$-Phe$^4$-Cys$^5$-Cys$^6$-Asn$^7$-Pro$^8$-Ala$^9$-Cys$^{10}$-Thr$^{11}$-Gly$^{12}$-Cys$^{13}$-Tyr$^{14}$ | 86 |
| N28 | C1:C6, C2:C10, C5:13 | Cys$^1$-Cys$^2$-Glu$^3$-Ser$^4$-Cys$^5$-Cys$^6$-Asn$^7$-Pro$^8$-Ala$^9$-Cys$^{10}$-Thr$^{11}$-Gly$^{12}$-Cys$^{13}$- | 87 |
| N29 | C1:C6, C2:C10, C5:13 | Cys$^1$-Cys$^2$-Glu$^3$-Phe$^4$-Cys$^5$-Cys$^6$-Asn$^7$-Pro$^8$-Ala$^9$-Cys$^{10}$-Thr$^{11}$-Gly$^{12}$-Cys$^{13}$ | 88 |
| N30 | 1:6, 2:10, 5:13 | Pen$^1$-Pen$^2$-Glu$^3$-Tyr$^4$-Pen$^5$-Pen$^6$-Asn$^7$-Pro$^8$-Ala$^9$-Pen$^{10}$-Thr$^{11}$-Gly$^{12}$-Pen$^{13}$-Tyr$^{14}$ | 89 |
| N31 | 1:6, 2:10, 5:13 | Pen$^1$-Pen$^2$-Glu$^3$-Tyr$^4$-Pen$^5$-Pen$^6$-Asn$^7$-Pro$^8$-Ala$^9$-Pen$^{10}$-Thr$^{11}$-Gly$^{12}$-Pen$^{13}$ | 90 |
| Formula X | C9:C14, C10:C18, C13:21 | Xaa$^1$-Xaa$^2$-Xaa$^3$-Xaa$^4$-Xaa$^5$-Xaa$^6$-Asn$^7$-Tyr$^8$-Cys$^9$-Cys$^{10}$-Xaa$^{11}$-Tyr$^{12}$-Cys$^{13}$-Cys$^{14}$-Xaa$^{15}$-Xaa$^{16}$-Xaa$^{17}$-Cys$^{18}$-Xaa$^{19}$-Xaa$^{20}$-Cys$^{21}$-Xaa$^{22}$ | 91 |
| Formula XI | C9:C14, C10:C18, C13:21 | Xaa$^1$-Xaa$^2$-Xaa$^3$-Xaa$^4$-Xaa$^5$-Xaa$^6$-Asn$^7$-Phe$^8$-Cys$^9$-Cys$^{10}$-Xaa$^{11}$-Phe$^{12}$-Cys$^{13}$-Cys$^{14}$-Xaa$^{15}$-Xaa$^{16}$-Xaa$^{17}$-Cys$^{18}$-Xaa$^{19}$-Xaa$^{20}$-Cys$^{21}$-Xaa$^{22}$ | 92 |
| Formula XII | C3:C8, C4:C12, C7:15 | Asn$^1$-Phe$^2$-Cys$^3$-Cys$^4$-Xaa$^5$-Phe$^6$-Cys$^7$-Cys$^8$-Xaa$^9$-Xaa$^{10}$-Xaa$^{11}$-Cys$^{12}$-Xaa$^{13}$-Xaa$^{14}$-Cys$^{15}$-Xaa$^{16}$ | 93 |
| Formula XIII | 3:8, 4:12, C:15 | Asn$^1$-Phe$^2$-Pen$^3$-Cys$^4$-Xaa$^5$-Phe$^6$-Cys$^7$-Pen$^8$-Xaa$^9$-Xaa$^{10}$-Xaa$^{11}$-Cys$^{12}$-Xaa$^{13}$-Xaa$^{14}$-Cys$^{15}$-Xaa$^{16}$ | 94 |

TABLE II-continued

Linaclotide and Derivatives

| Name | Position of Disulfide bonds | Structure | SEQ ID NO: |
|---|---|---|---|
| Formula XIV | 3:8, 4:12, 7:15 | $Asn^1$-$Phe^2$-$Maa^3$-$Maa^4$-$Xaa^5$-$Xaa^6$-$Maa^7$-$Maa^8$-$Xaa^9$-$Xaa^{10}$-$Xaa^{11}$-$Maa^{12}$-$Xaa^{13}$-$Xaa^{14}$-$Maa^{15}$-$Xaa^{16}$ | 95 |
| Formula XV | 1:6, 2:10, 5:13 | $Maa^1$-$Maa^2$-$Glu^3$-$Xaa^4$-$Maa^5$-$Maa^6$-$Asn^7$-$Pro^8$-$Ala^9$-$Maa^{10}$-$Thr^{11}$-$Gly^{12}$-$Maa^{13}$-$Tyr^{14}$ | 96 |
| Formula XVI | 1:6, 2:10, 5:13 | $Maa^1$-$Maa^2$-$Glu^3$-$Xaa^4$-$Maa^5$-$Maa^6$-$Asn^7$-$Pro^8$-$Ala^9$-$Maa^{10}$-$Thr^{11}$-$Gly^{12}$-$Maa^{13}$- | 97 |
| Formula XVII | 1:6, 2:10, 5:13 | $Xaa_{n3}$-$Maa^1$-$Maa^2$-$Xaa^3$-$Xaa^4$-$Maa^5$-$Maa^6$-$Xaa^7$-$Xaa^8$-$Xaa^9$-$Maa^{10}$-$Xaa^{11}$-$Xaa^{12}$-$Maa^{13}$-$Xaa_{n2}$ | 98 |

TABLE III

GCRA Peptides

| Name | Position of Disulfide bonds | Structure | SEQ ID NO: |
|---|---|---|---|
| SP-363 | C4:C12, C7:C15 | $dAsn^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dLeu$-$AMIDE^{16}$ | 99 |
| SP-364 | C4:C12, C7:C15 | $dAsn^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dSer^{16}$ | 100 |
| SP-365 | C4:C12, C7:C15 | $dAsn^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dSer$-$AMIDE^{16}$ | 101 |
| SP-366 | C4:C12, C7:C15 | $dAsn^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dTyr^{16}$ | 102 |
| SP-367 | C4:C12, C7:C15 | $dAsn^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dTyr$-$AMIDE^{16}$ | 103 |
| SP-373 | C4:C12, C7:C15 | $Pyglu^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$dLeu$-$AMIDE^{16}$ | 104 |
| / | C4:C12, C7:C15 | $Pyglu^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Leu^{16}$ | 251 |
| SP-304 di PEG | C4:C12, C7:C15 | PEG3-$Asn^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Leu^{16}$-PEG3 | 105 |
| SP-304 N-PEG | C4:C12, C7:C15 | PEG3-$Asn^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Leu^{16}$ | 106 |
| SP-304 C-PEG | C4:C12, C7:C15 | $Asn^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Leu^{16}$-PEG3 | 107 |

TABLE IV

SP304 Analogs, Uroguanylin, and Uroguanylin Analogs

| Name | Position of Disulfide bonds | Structure | SEQ ID NO: |
|---|---|---|---|
| Formula XVIII | C4:C12, C7:C15 | $Xaa^1$-$Xaa^2$-$Xaa^3$-$Maa^4$-$Xaa^5$-$Xaa^6$-$Maa^7$-$Xaa^8$-$Xaa^9$-$Xaa^{10}$-$Xaa^{11}$-$Maa^{12}$-$Xaa^{13}$-$Xaa^{14}$-$Maa^{15}$-$Xaa^{16}$ | 108 |
| Uroguanylin | C4:C12, C7:C15 | $Asn^1$-$Asp^2$-$Asp^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Leu^{16}$ | 109 |
| N32 | C4:C12, C7:C15 | $Glu^1$-$Asp^2$-$Asp^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Leu^{16}$ | 110 |
| N33 | C4:C12, C7:C15 | $Glu^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Leu^{16}$ | 111 |

TABLE IV-continued

SP304 Analogs, Uroguanylin, and Uroguanylin Analogs

| Name | Position of Disulfide bonds | Structure | SEQ ID NO: |
|---|---|---|---|
| N34 | C4:C12, C7:C15 | $Glu^1$-$Glu^2$-$Asp^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Leu^{16}$ | 112 |
| N35 | C4:C12, C7:C15 | $Glu^1$-$Glu^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Leu^{16}$ | 113 |
| N36 | C4:C12, C7:C15 | $Asp^1$-$Asp^2$-$Asp^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Leu^{16}$ | 114 |
| N37 | C4:C12, C7:C15 | $Asp^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Leu^{16}$ | 115 |
| N38 | C4:C12, C7:C15 | $Asp^1$-$Glu^2$-$Asp^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Leu^{16}$ | 116 |
| N39 | C4:C12, C7:C15 | $Asp^1$-$Glu^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Leu^{16}$ | 117 |
| N40 | C4:C12, C7:C15 | $Gln^1$-$Asp^2$-$Asp^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Leu^{16}$ | 118 |
| N41 | C4:C12, C7:C15 | $Gln^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Leu^{16}$ | 119 |
| N42 | C4:C12, C7:C15 | $Gln^1$-$Glu^2$-$Asp^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Leu^{16}$ | 120 |
| N43 | C4:C12, C7:C15 | $Gln^1$-$Glu^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Leu^{16}$ | 121 |
| N44 | C4:C12, C7:C15 | $Lys^1$-$Asp^2$-$Asp^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Leu^{16}$ | 122 |
| N45 | C4:C12, C7:C15 | $Lys^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Leu^{16}$ | 123 |
| N46 | C4:C12, C7:C15 | $Lys^1$-$Glu^2$-$Asp^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Leu^{16}$ | 124 |
| N47 | C4:C12, C7:C15 | $Lys^1$-$Glu^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Leu^{16}$ | 125 |
| N48 | C4:C12, C7:C15 | $Glu^1$-$Asp^2$-$Asp^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Ser^{16}$ | 126 |
| N49 | C4:C12, C7:C15 | $Glu^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Ser^{16}$ | 127 |
| N50 | C4:C12, C7:C15 | $Glu^1$-$Glu^2$-$Asp^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Ser^{16}$ | 128 |
| N51 | C4:C12, C7:C15 | $Glu^1$-$Glu^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Ser^{16}$ | 129 |
| N52 | C4:C12, C7:C15 | $Asp^1$-$Asp^2$-$Asp^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Ser^{16}$ | 130 |
| N53 | C4:C12, C7:C15 | $Asp^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Ser^{16}$ | 131 |
| N54 | C4:C12, C7:C15 | $Asp^1$-$Glu^2$-$Asp^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Ser^{16}$ | 132 |
| N55 | C4:C12, C7:C15 | $Asp^1$-$Glu^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Ser^{16}$ | 133 |
| N56 | C4:C12, C7:C15 | $Gln^1$-$Asp^2$-$Asp^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Ser^{16}$ | 134 |
| N57 | C4:C12, C7:C15 | $Gln^1$-$Asp^2$-$Glu^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Ser^{16}$ | 135 |
| N58 | C4:C12, C7:C15 | $Gln^1$-$Glu^2$-$Asp^3$-$Cys^4$-$Glu^5$-$Leu^6$-$Cys^7$-$Val^8$-$Asn^9$-$Val^{10}$-$Ala^{11}$-$Cys^{12}$-$Thr^{13}$-$Gly^{14}$-$Cys^{15}$-$Ser^{16}$ | 136 |

TABLE IV-continued

SP304 Analogs, Uroguanylin, and Uroguanylin Analogs

| Name | Position of Disulfide bonds | Structure | SEQ ID NO: |
|---|---|---|---|
| N59 | C4:C12, C7:C15 | Gln$^1$-Glu$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$ | 137 |
| N60 | C4:C12, C7:C15 | Lys$^1$-Asp$^2$-Asp$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$ | 138 |
| N61 | C4:C12, C7:C15 | Lys$^1$-Asp$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$ | 139 |
| N62 | C4:C12, C7:C15 | Lys$^1$-Glu$^2$-Asp$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$ | 140 |
| N63 | C4:C12, C7:C15 | Lys$^1$-Glu$^2$-Glu$^3$-Cys$^4$-Glu$^5$-Leu$^6$-Cys$^7$-Val$^8$-Asn$^9$-Val$^{10}$-Ala$^{11}$-Cys$^{12}$-Thr$^{13}$-Gly$^{14}$-Cys$^{15}$-Ser$^{16}$ | 141 |
| N65 | C4:C12, C7:C15 | Glu$^1$-Asp$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 142 |
| N66 | C4:C12, C7:C15 | Glu$^1$-Asp$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 143 |
| N67 | C4:C12, C7:C15 | Glu$^1$-Glu$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 144 |
| N68 | C4:C12, C7:C15 | Glu$^1$-Glu$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 145 |
| N69 | C4:C12, C7:C15 | Asp$^1$-Asp$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 146 |
| N70 | C4:C12, C7:C15 | Asp$^1$-Asp$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 147 |
| N71 | C4:C12, C7:C15 | Asp$^1$-Glu$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 148 |
| N72 | C4:C12, C7:C15 | Asp$^1$-Glu$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 149 |
| N73 | C4:C12, C7:C15 | Gln$^1$-Asp$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 150 |
| N74 | C4:C12, C7:C15 | Gln$^1$-Asp$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 151 |
| N75 | C4:C12, C7:C15 | Gln$^1$-Glu$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 152 |
| N76 | C4:C12, C7:C15 | Gln$^1$-Glu$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 153 |
| N77 | C4:C12, C7:C15 | Lys$^1$-Asp$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 154 |
| N78 | C4:C12, C7:C15 | Lys$^1$-Asp$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 155 |
| N79 | C4:C12, C7:C15 | Lys$^1$-Glu$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 156 |
| N80 | C4:C12, C7:C15 | Lys$^1$-Glu$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Leu$^{16}$ | 157 |
| N81 | C4:C12, C7:C15 | Glu$^1$-Asp$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 158 |
| N82 | C4:C12, C7:C15 | Glu$^1$-Asp$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 159 |
| N83 | C4:C12, C7:C15 | Glu$^1$-Glu$^2$-Asp$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 160 |
| N84 | C4:C12, C7:C15 | Glu$^1$-Glu$^2$-Glu$^3$-Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 161 |

TABLE IV-continued

SP304 Analogs, Uroguanylin, and Uroguanylin Analogs

| Name | Position of Disulfide bonds | Structure | SEQ ID NO: |
|---|---|---|---|
| N85 | C4:C12, C7:C15 | $Asp^1$-$Asp^2$-$Asp^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Ser^{16}$ | 162 |
| N86 | C4:C12, C7:C15 | $Asp^1$-$Asp^2$-$Glu^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Ser^{16}$ | 163 |
| N87 | C4:C12, C7:C15 | $Asp^1$-$Glu^2$-$Asp^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Ser^{16}$ | 164 |
| N88 | C4:C12, C7:C15 | $Asp^1$-$Glu^2$-$Glu^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Ser^{16}$ | 165 |
| N89 | C4:C12, C7:C15 | $Gln^1$-$Asp^2$-$Asp^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Ser^{16}$ | 166 |
| N90 | C4:C12, C7:C15 | $Gln^1$-$Asp^2$-$Glu^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Ser^{16}$ | 167 |
| N91 | C4:C12, C7:C15 | $Gln^1$-$Glu^2$-$Asp^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Ser^{16}$ | 168 |
| N92 | C4:C12, C7:C15 | $Gln^1$-$Glu^2$-$Glu^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Ser^{16}$ | 169 |
| N93 | C4:C12, C7:C15 | $Lys^1$-$Asp^2$-$Asp^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Ser^{16}$ | 170 |
| N94 | C4:C12, C7:C15 | $Lys^1$-$Asp^2$-$Glu^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Ser^{16}$ | 171 |
| N95 | C4:C12, C7:C15 | $Lys^1$-$Glu^2$-$Asp^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Ser^{16}$ | 172 |
| N96 | C4:C12, C7:C15 | $Lys^1$-$Glu^2$-$Glu^3$-$Cys^4$-$Glu^5$-$Leu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Ser^{16}$ | 173 |

TABLE V

Guanylin and Analogs

| Name | Position of Disulfide bonds | Structure | SEQ ID NO: |
|---|---|---|---|
| Formula XIX | 4:12, 7:15 | $Xaa^1$-$Xaa^2$-$Xaa^3$-$Maa^4$-$Xaa^5$-$Xaa^6$-$Maa^7$-$Xaa^8$-$Xaa^9$-$Xaa^{10}$-$Xaa^{11}$-$Maa^{12}$-$Xaa^{13}$-$Xaa^{14}$-$Maa^{15}$ | 174 |
| Guanylin | C4:C12, C7:C15 | $Ser^1$-$His^2$-$Thr^3$-$Cys^4$-$Glu^5$-$Ile^6$-$Cys^7$-$Ala^8$-$Phe^9$-$Ala^{10}$-$Ala^{11}$-$Cys^{12}$-$Ala^{13}$-$Gly^{14}$-$Cys^{15}$ | 175 |
| Human Guanylin | C4:C12, C7:C15 | $Pro^1$-$Gly^2$-$Thr^3$-$Cys^4$-$Glu^5$-$Ile^6$-$Cys^7$-$Ala^8$-$Tyr^9$-$Ala^{10}$-$Ala^{11}$-$Cys^{12}$-$Thr^{13}$-$Gly^{14}$-$Cys^{15}$ | 252 |
| N97 | C4:C12, C7:C15 | $Ser^1$-$His^2$-$Thr^3$-$Cys^4$-$Glu^5$-$Ile^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 176 |
| N98 | C4:C12, C7:C15 | $Ser^1$-$His^2$-$Thr^3$-$Cys^4$-$Glu^5$-$Leu^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 177 |
| N99 | C4:C12, C7:C15 | $Ser^1$-$His^2$-$Thr^3$-$Cys^4$-$Glu^5$-$Val^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 178 |
| N100 | C4:C12, C7:C15 | $Ser^1$-$His^2$-$Thr^3$-$Cys^4$-$Glu^5$-$Tyr^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 179 |
| N101 | C4:C12, C7:C15 | $Ser^1$-$His^2$-$Thr^3$-$Cys^4$-$Glu^5$-$Ile^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 180 |
| N102 | C4:C12, C7:C15 | $Ser^1$-$His^2$-$Thr^3$-$Cys^4$-$Glu^5$-$Leu^6$-$Cys^7$-$Ala^8$-$Asn^9$-$Ala^{10}$-$Ala^{11}$-$Cys^{12}$-$Ala^{13}$-$Gly^{14}$-$Cys^{15}$ | 181 |

TABLE V-continued

Guanylin and Analogs

| Name | Position of Disulfide bonds | Structure | SEQ ID NO: |
|---|---|---|---|
| N103 | C4:C12, C7:C15 | Ser$^1$-His$^2$-Thr$^3$-Cys$^4$-Glu$^5$-Val$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 182 |
| N104 | C4:C12, C7:C15 | Ser$^1$-His$^2$-Thr$^3$-Cys$^4$-Glu$^5$-Tyr$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 183 |
| N105 | C4:C12, C7:C15 | Ser$^1$-His$^2$-Thr$^3$-Cys$^4$-Glu$^5$-Ile$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 184 |
| N106 | C4:C12, C7:C15 | Ser$^1$-His$^2$-Thr$^3$-Cys$^4$-Glu$^5$-Leu$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 185 |
| N107 | C4:C12, C7:C15 | Ser$^1$-His$^2$-Thr$^3$-Cys$^4$-Glu$^5$-Val$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 186 |
| N108 | C4:C12, C7:C15 | Ser$^1$-His$^2$-Thr$^3$-Cys$^4$-Glu$^5$-Tyr$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 187 |
| N109 | C4:C12, C7:C15 | Ser$^1$-His$^2$-Thr$^3$-Cys$^4$-Glu$^5$-Ile$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 188 |
| N110 | C4:C12, C7:C15 | Ser$^1$-His$^2$-Thr$^3$-Cys$^4$-Glu$^5$-Leu$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 189 |
| N111 | C4:C12, C7:C15 | Ser$^1$-His$^2$-Thr$^3$-Cys$^4$-Glu$^5$-Val$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 190 |
| N112 | C4:C12, C7:C15 | Ser$^1$-His$^2$-Thr$^3$-Cys$^4$-Glu$^5$-Tyr$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 191 |
| N113 | C4:C12, C7:C15 | Asn$^1$-Asp$^2$-Glu$^3$-Cys$^4$-Glu$^5$-Ile$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 192 |
| N114 | C4:C12, C7:C15 | Asn$^1$-Asp$^2$-Glu$^3$-Cys$^4$-Glu$^5$-Leu$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 193 |
| N115 | C4:C12, C7:C15 | Asn$^1$-Asp$^2$-Glu$^3$-Cys$^4$-Glu$^5$-Val$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 194 |
| N116 | C4:C12, C7:C15 | Asn$^1$-Asp$^2$-Glu$^3$-Cys$^4$-Glu$^5$-Tyr$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 195 |
| N117 | C4:C12, C7:C15 | Asn$^1$-Asp$^2$-Glu$^3$-Cys$^4$-Glu$^5$-Ile$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 196 |
| N118 | C4:C12, C7:C15 | Asn$^1$-Asp$^2$-Glu$^3$-Cys$^4$-Glu$^5$-Leu$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 197 |
| N119 | C4:C12, C7:C15 | Asn$^1$-Asp$^2$-Glu$^3$-Cys$^4$-Glu$^5$-Val$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 198 |
| N120 | C4:C12, C7:C15 | Asn$^1$-Asp$^2$-Glu$^3$-Cys$^4$-Glu$^5$-Tyr$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 199 |
| N121 | C4:C12, C7:C15 | Asn$^1$-Asp$^2$-Glu$^3$-Cys$^4$-Glu$^5$-Ile$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 200 |
| N122 | C4:C12, C7:C15 | Asn$^1$-Asp$^2$-Glu$^3$-Cys$^4$-Glu$^5$-Leu$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 201 |
| N123 | C4:C12, C7:C15 | Asn$^1$-Asp$^2$-Glu$^3$-Cys$^4$-Glu$^5$-Val$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 202 |
| N124 | C4:C12, C7:C15 | Asn$^1$-Asp$^2$-Glu$^3$-Cys$^4$-Glu$^5$-Tyr$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 203 |
| N125 | C4:C12, C7:C15 | Asn$^1$-Asp$^2$-Glu$^3$-Cys$^4$-Glu$^5$-Ile$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 204 |
| N126 | C4:C12, C7:C15 | Asn$^1$-Asp$^2$-Glu$^3$-Cys$^4$-Glu$^5$-Leu$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 205 |
| N127 | C4:C12, C7:C15 | Asn$^1$-Asp$^2$-Glu$^3$-Cys$^4$-Glu$^5$-Val$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 206 |

TABLE V-continued

Guanylin and Analogs

| Name | Position of Disulfide bonds | Structure | SEQ ID NO: |
|---|---|---|---|
| N128 | C4:C12, C7:C15 | Asn$^1$-Asp$^2$-Glu$^3$-Cys$^4$-Glu$^5$-Tyr$^6$-Cys$^7$-Ala$^8$-Asn$^9$-Ala$^{10}$-Ala$^{11}$-Cys$^{12}$-Ala$^{13}$-Gly$^{14}$-Cys$^{15}$ | 207 |

TABLE VI

Lymphoguanylin and Analogs

| Name | Position of Disulfide bonds | Structure | SEQ ID NO: |
|---|---|---|---|
| Formula XX | 4:12,7:15 | Xaa$^1$-Xaa$^2$-Xaa$^3$-Maa$^4$-Xaa$^5$-Xaa$^6$-Maa$^7$-Xaa$^8$-Xaa$^9$-Xaa$^{10}$-Xaa$^{11}$-Maa$^{12}$-Xaa$^{13}$-Xaa$^{14}$-Xaa$_{n1}^{15}$ | 208 |
| Lymphoguanylin | C4:C12 | Gln$^1$-Glu$^2$-Glu-3Cys$^4$-Glu$^5$-Leu$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 209 |
| N129 | C4:C12 | Gln$^1$-Glu$^2$-Glu$^3$-Cys$^4$-Glu$^5$-Thr$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 210 |
| N130 | C4:C12 | Gln$^1$-Asp$^2$-Glu$^3$-Cys$^4$-Glu$^5$-Thr$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 211 |
| N131 | C4:C12 | Gln$^1$-Asp$^2$-Asp$^3$-Cys$^4$-Glu$^5$-Thr$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 212 |
| N132 | C4:C12 | Gln$^1$-Glu$^2$-Asp$^3$-Cys$^4$-Glu$^5$-Thr$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 213 |
| N133 | C4:C12 | Gln$^1$-Glu$^2$-Glu$^3$-Cys$^4$-Glu$^5$-Glu$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 214 |
| N134 | C4:C12 | Gln$^1$-Asp$^2$-Glu$^3$-Cys$^4$-Glu$^5$-Glu$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 215 |
| N135 | C4:C12 | Gln$^1$-Asp$^2$-Asp$^3$-Cys$^4$-Glu$^5$-Glu$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 216 |
| N136 | C4:C12 | Gln$^1$-Glu$^2$-Asp$^3$-Cys$^4$-Glu$^5$-Glu$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 217 |
| N137 | C4:C12 | Gln$^1$-Glu$^2$-Glu$^3$-Cys$^4$-Glu$^5$-Tyr$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 218 |
| N138 | C4:C12 | Gln$^1$-Asp$^2$-Glu$^3$-Cys$^4$-Glu$^5$-Tyr$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 219 |
| N139 | C4:C12 | Gln$^1$-Asp$^2$-Asp$^3$-Cys$^4$-Glu$^5$-Tyr$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 220 |
| N140 | C4:C12 | Gln$^1$-Glu$^2$-Asp$^3$-Cys$^4$-Glu$^5$-Tyr$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 221 |
| N141 | C4:C12 | Gln$^1$-Glu$^2$-Glu$^3$-Cys$^4$-Glu$^5$-Ile$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 222 |
| N142 | C4:C12 | Gln$^1$-Asp$^2$-Glu$^3$-Cys$^4$-Glu$^5$-Ile$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 223 |
| N143 | C4:C12 | Gln$^1$-Asp$^2$-Asp$^3$-Cys$^4$-Glu$^5$-Ile$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 224 |
| N144 | C4:C12 | Gln$^1$-Glu$^2$-Asp$^3$-Cys$^4$-Glu$^5$-Ile$^6$-Cys$^7$-Ile$^8$-Asn$^9$-Met$^{10}$-Ala$^{11}$-Cys$^{12}$-Thr$^{13}$-Gly$^{14}$-Tyr$^{15}$ | 225 |
| N145 | C4:C12, C7:C15 | Gln$^1$-Glu$^2$-Glu$^3$-Cys$^4$-Glu$^5$-Thr$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 226 |
| N146 | C4:C12, C7:C15 | Gln$^1$-Asp$^2$-Glu$^3$-Cys$^4$-Glu$^5$-Thr$^6$-Cys$^7$-Ile$^8$-Asn$^9$-Met$^{10}$-Ala$^{11}$-Cys$^{12}$-Thr$^{13}$-Gly$^{14}$-Cys$^{15}$-Ser$^{16}$ | 227 |

TABLE VI-continued

Lymphoguanylin and Analogs

| Name | Position of Disulfide bonds | Structure | SEQ ID NO: |
|---|---|---|---|
| N147 | C4:C12, C7:C15 | $Gln^1$-$Asp^2$-$Asp^3$-$Cys^4$-$Glu^5$-$Thr^6$-$Cys^7$-$Ile^8$-$Asn^9$-$Met^{10}$-$Ala^{11}$-$Cys^{12}$-$Thr^{13}$-$Gly^{14}$-$Cys^{15}$-$Ser^{16}$ | 228 |
| N148 | C4:C12, C7:C15 | $Gln^1$-$Glu^2$-$Asp^3$-$Cys^4$-$Glu^5$-$Thr^6$-$Cys^7$-$Ile^8$-$Asn^9$-$Met^{10}$-$Ala^{11}$-$Cys^{12}$-$Thr^{13}$-$Gly^{14}$-$Cys^{15}$-$Ser^{16}$ | 229 |
| N149 | C4:C12, C7:C15 | $Gln^1$-$Glu^2$-$Glu^3$-$Cys^4$-$Glu^5$-$Glu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Ser^{16}$ | 230 |
| N150 | C4:C12, C7:C15 | $Gln^1$-$Asp^2$-$Glu^3$-$Cys^4$-$Glu^5$-$Glu^6$-$Cys^7$-$Ile^8$-$Asn^9$-$Met^{10}$-$Ala^{11}$-$Cys^{12}$-$Thr^{13}$-$Gly^{14}$-$Cys^{15}$-Ser | 231 |
| N151 | C4:C12, C7:C15 | $Gln^1$-$Asp^2$-$Asp^3$-$Cys^4$-$Glu^5$-$Glu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Ser^{16}$ | 232 |
| N152 | C4:C12, C7:C15 | $Gln^1$-$Glu^2$-$Asp^3$-$Cys^4$-$Glu^5$-$Glu^6$-$Cys^7$-$Ile^8$-$Asn^9$-$Met^{10}$-$Ala^{11}$-$Cys^{12}$-$Thr^{13}$-$Gly^{14}$-$Cys^{15}$-$Ser^{16}$ | 233 |
| N153 | C4:C12, C7:C15 | $Gln^1$-$Glu^2$-$Glu^3$-$Cys^4$-$Glu^5$-$Tyr^6$-$Cys^7$-$Ile^8$-$Asn^9$-$Met^{10}$-$Ala^{11}$-$Cys^{12}$-$Thr^{13}$-$Gly^{14}$-$Cys^{15}$-$Ser^{16}$ | 234 |
| N154 | C4:C12, C7:C15 | $Gln^1$-$Asp^2$-$Glu^3$-$Cys^4$-$Glu^5$-$Tyr^6$-$Cys^7$-$Ile^8$-$Asn^9$-$Met^{10}$-$Ala^{11}$-$Cys^{12}$-$Thr^{13}$-$Gly^{14}$-$Cys^{15}$-$Ser^{16}$ | 235 |
| N155 | C4:C12, C7:C15 | $Gln^1$-$Asp^2$-$Asp^3$-$Cys^4$-$Glu^5$-$Tyr^6$-$Cys^7$-$Ile^8$-$Asn^9$-$Met^{10}$-$Ala^{11}$-$Cys^{12}$-$Thr^{13}$-$Gly^{14}$-$Cys^{15}$-$Ser^{16}$ | 236 |
| N156 | C4:C12, C7:C15 | $Gln^1$-$Glu^2$-$Asp^3$-$Cys^4$-$Glu^5$-$Tyr^6$-$Cys^7$-$Ile^8$-$Asn^9$-$Met^{10}$-$Ala^{11}$-$Cys^{12}$-$Thr^{13}$-$Gly^{14}$-$Cys^{15}$-$Ser^{16}$ | 237 |
| N157 | C4:C12, C7:C15 | $Gln^1$-$Glu^2$-$Glu^3$-$Cys^4$-$Glu^5$-$Ile^6$-$Cys^7$-$Ile^8$-$Asn^9$-$Met^{10}$-$Ala^{11}$-$Cys^{12}$-$Thr^{13}$-$Gly^{14}$-$Cys^{15}$-$Ser^{16}$ | 238 |
| N158 | C4:C12, C7:C15 | $Gln^1$-$Asp^2$-$Glu^3$-$Cys^4$-$Glu^5$-$Ile^6$-$Cys^7$-$Ile^8$-$Asn^9$-$Met^{10}$-$Ala^{11}$-$Cys^{12}$-$Thr^{13}$-$Gly^{14}$-$Cys^{15}$-$Ser^{16}$ | 239 |
| N159 | C4:C12, C7:C15 | $Gln^1$-$Asp^2$-$Asp^3$-$Cys^4$-$Glu^5$-$Ile^6$-$Cys^7$-$Ile^8$-$Asn^9$-$Met^{10}$-$Ala^{11}$-$Cys^{12}$-$Thr^{13}$-$Gly^{14}$-$Cys^{15}$-$Ser^{16}$ | 240 |
| N160 | C4:C12, C7:C15 | $Gln^1$-$Glu^2$-$Asp^3$-$Cys^4$-$Glu^5$-$Ile^6$-$Cys^7$-$Ile^8$-$Asn^9$-$Met^{10}$-$Ala^{11}$-$Cys^{12}$-$Thr^{13}$-$Gly^{14}$-$Cys^{15}$-$Ser^{16}$ | 241 |

TABLE VII

ST Peptide and Analogues

| Name | Position of Disulfide bonds | Structure | SEQ ID NO: |
|---|---|---|---|
| ST Peptide | C3:C8, C4:C12, C7:15 | $Asn^1$-$Ser^2$-$Ser^3$-$Asn^4$-$Ser^5$-$Ser^6$-$Asn^7$-$Tyr^8$-$Cys^9$-$Cys^{10}$-$Glu^{11}$-$Lys^{12}$-$Cys^{13}$-$Cys^{14}$-$Asn^{15}$-$Pro^{16}$-$Ala^{17}$-$Cys^{18}$-$Thr^{19}$-$Gly^{20}$-$Cys^{21}$-$Tyr^{22}$ | 242 |
| N161 | C3:C8, C4:C12, C7:15 | PEG3-$Asn^1$-$Phe^2$-$Cys^3$-$Cys^4$-$Glu^5$-$Thr^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$-PEG3 | 243 |
| N162 | C3:C8, C4:C12, C7:15 | PEG3-$Asn^1$-$Phe^2$-$Cys^3$-$Cys^4$-$Glu^5$-$Thr^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$ | 244 |
| N163 | C3:C8, C4:C12, C7:15 | $Asn^1$-$Phe^2$-$Cys^3$-$Cys^4$-$Glu^5$-$Thr^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$-PEG3 | 245 |
| N164 | C3:C8, C4:C12, C7:15 | $Asn^1$-$Phe^2$-$Cys^3$-$Cys^4$-$Glu^5$-$Tyr^6$-$Cys^7$-$Cys^8$-$Asn^9$-$Pro^{10}$-$Ala^{11}$-$Cys^{12}$-$Thr^{13}$-$Gly^{14}$-$Cys^{15}$-$Tyr^{16}$ | 246 |
| N165 | C3:C8, C4:C12, C7:15 | $dAsn^1$-$Phe^2$-$Cys^3$-$Cys^4$-$Glu^5$-$Tyr^6$-$Cys^7$-$Cys^8$-$Asn^9$-$Pro^{10}$-$Ala^{11}$-$Cys^{12}$-$Thr^{13}$-$Gly^{14}$-$Cys^{15}$-$dTyr^{16}$ | 247 |
| N166 | C3:C8, C4:C12, C7:15 | $Asn^1$-$Phe^2$-$Cys^3$-$Cys^4$-$Glu^5$-$Tyr^6$-$Cys^7$-$Cys^8$-$Asn^9$-$Pro^{10}$-$Ala^{11}$-$Cys^{12}$-$Thr^{13}$-$Gly^{14}$-$Cys^{15}$-$dTyr^{16}$ | 248 |

TABLE VII-continued

ST Peptide and Analogues

| Name | Position of Disulfide bonds | Structure | SEQ ID NO: |
|------|----------------------------|-----------|------------|
| N167 | C3:C8, C4:C12, C7:15 | dAsn$^1$-Phe$^2$-Cys$^3$-Cys$^4$-Glu$^5$-Tyr$^6$-Cys$^7$-Cys$^8$-Asn$^9$-Pro$^{10}$-Ala$^{11}$-Cys$^{12}$-Thr$^{13}$-Gly$^{14}$-Cys$^{15}$-Tyr$^{16}$ | 249 |

1.2 Methods of Use

The invention provides methods for treating or preventing gastrointestinal disorders and increasing gastrointestinal motility in a subject in need thereof by administering an effective amount of a GCC agonist or a formulation thereof to the subject. Non-limiting examples of gastrointestinal disorders that can be treated or prevented according to the methods of the invention include irritable bowel syndrome (IBS), non-ulcer dyspepsia, H. pylori infection related ulcers, chronic intestinal pseudo-obstruction, functional dyspepsia, colonic pseudo-obstruction, duodenogastric reflux, gastroesophageal reflux disease (GERD), ileus (e.g., post-operative ileus), gastroparesis, heartburn (high acidity in the GI tract), constipation (e.g., constipation associated with use of medications such as opioids, osteoarthritis drugs, or osteoporosis drugs); post surgical constipation, constipation associated with neuropathic disorders, Crohn's disease, and ulcerative colitis.

In one embodiment, the invention provides methods for treating or preventing gastrointestinal motility disorder, irritable bowel syndrome, a functional gastrointestinal disorder, gastroesophageal reflux disease, duodenogastric reflux, functional heartburn, dyspepsia, functional dyspepsia, non-ulcer dyspepsia, gastroparesis, chronic intestinal pseudo-obstruction, colonic pseudo-obstruction, obesity, congestive heart failure, or benign prostatic hyperplasia.

In one embodiment, the invention provides methods for treating or preventing constipation and/or increasing gastrointestinal motility in a subject in need thereof by administering an effective amount of a GCC agonist or a formulation thereof to the subject. Clinically accepted criteria that define constipation range from the frequency of bowel movements, the consistency of feces and the ease of bowel movement. One common definition of constipation is less than three bowel movements per week. Other definitions include abnormally hard stools or defecation that requires excessive straining (Schiller 2001 Aliment Pharmacol Ther 15:749-763). Constipation may be idiopathic (functional constipation or slow transit constipation) or secondary to other causes including neurologic, metabolic or endocrine disorders. These disorders include diabetes mellitus, hypothyroidism, hyperthyroidism, hypocalcaemia, Multiple sclerosis, Parkinson's disease, spinal cord lesions, Neurofibromatosis, autonomic neuropathy, Chagas disease, Hirschsprung disease and cystic fibrosis. Constipation may also be the result of surgery or due to the use of drugs such as analgesics (like opioids), antihypertensives, anticonvulsants, antidepressants, antispasmodics and antipsychotics.

In various embodiments, the constipation is associated with use of a therapeutic agent; the constipation is associated with a neuropathic disorder; the constipation is postsurgical constipation; the constipation is associated with a gastrointestinal disorder; the constipation is idiopathic (functional constipation or slow transit constipation); the constipation is associated with neuropathic, metabolic or endocrine disorder (e.g., diabetes mellitus, hypothyroidism, hyperthyroidism, hypocalcaemia, Multiple Sclerosis, Parkinson's disease, spinal cord lesions, neurofibromatosis, autonomic neuropathy, Chagas disease, Hirschsprung disease or cystic fibrosis). Constipation may also be the result of surgery or due to the use of drugs such as analgesics (e.g., opioids), antihypertensives, anticonvulsants, antidepressants, antispasmodics and antipsychotics.

In one embodiment, the invention provides methods for treating or preventing chronic idiopathic constipation and increasing gastrointestinal motility in a subject in need thereof by administering an effective amount of a GCC agonist or a formulation thereof to the subject.

The term "treating" as used herein refers to a reduction, a partial improvement, amelioration, or a mitigation of at least one clinical symptom associated with the gastrointestinal disorders being treated. The term "preventing" refers to an inhibition or delay in the onset or progression of at least one clinical symptom associated with the gastrointestinal disorders to be prevented. The term "effective amount" as used herein refers to an amount that provides some improvement or benefit to the subject. In certain embodiments, an effective amount is an amount that provides some alleviation, mitigation, and/or decrease in at least one clinical symptom of the gastrointestinal disorder to be treated. In other embodiments, the effective amount is the amount that provides some inhibition or delay in the onset or progression of at least one clinical symptom associated with the gastrointestinal disorder to be prevented. The therapeutic effects need not be complete or curative, as long as some benefit is provided to the subject. The term "subject" preferably refers to a human subject but may also refer to a non-human primate or other mammal preferably selected from among a mouse, a rat, a dog, a cat, a cow, a horse, or a pig.

The invention also provides methods for treating gastrointestinal cancer in a subject in need thereof by administering an effective amount of a GCC agonist or a formulation thereof to the subject. Non-limiting examples of gastrointestinal cancers that can be treated according to the methods of the invention include gastric cancer, esophageal cancer, pancreatic cancer, colorectal cancer, intestinal cancer, anal cancer, liver cancer, gallbladder cancer, or colon cancer.

The invention also provides methods for treating lipid metabolism disorders, biliary disorders, inflammatory disorders, lung disorders, cancer, cardiac disorders including cardiovascular disorders, eye disorders, oral disorders, blood disorders, liver disorders, skin disorders, prostate disorders, endocrine disorders, and obesity.

Lipid metabolism disorders include, but are not limited to, dyslipidemia, hyperlipidemia, hypercholesterolemia, hypertriglyceridemia, sitosterolemia, familial hypercholesterolemia, xanthoma, combined hyperlipidemia, lecithin cholesterol acyltransferase deficiency, tangier disease, abetalipoproteinemia, erectile dysfunction, fatty liver disease, and hepatitis.

Biliary disorders include gallbladder disorders such as for example, gallstones, gall bladder cancer cholangitis, or primary sclerosing cholangitis; or bile duct disorders such as for example, cholecystitis, bile duct cancer or fascioliasis.

Inflammatory disorders include tissue and organ inflammation such as kidney inflammation (e.g., nephritis), gastrointestinal system inflammation (e.g., Crohn's disease and ulcerative colitis); necrotizing enterocolitis (NEC); pancreatic inflammation (e.g., pancreatis), pancreatic insufficiency, lung inflammation (e.g., bronchitis or asthma) or skin inflammation (e.g., psoriasis, eczema).

Lung Disorders include for example chronic obstructive pulmonary disease (COPD), and fibrosis.

Cancer includes tissue and organ carcinogenesis including metastases such as for example gastrointestinal cancer, (e.g., gastric cancer, esophageal cancer, pancreatic cancer colorectal cancer, intestinal cancer, anal cancer, liver cancer, gallbladder cancer, or colon cancer; lung cancer; thyroid cancer; skin cancer (e.g., melanoma); oral cancer; urinary tract cancer (e.g. bladder cancer or kidney cancer); blood cancer (e.g. myeloma or leukemia) or prostate cancer.

Cardiac disorders include for example, congestive heart failure, trachea cardia hypertension, high cholesterol, or high triglycerides. Cardiovascular disorders include for example aneurysm, angina, atherosclerosis, cerebrovascular accident (stroke), cerebrovasculardisease, congestive heart failure, coronary artery disease, myocardial infarction (heart attack), or peripheral vascular disease.

Liver disorders include for example cirrhosis and fibrosis. In addition, GC-C agonist may also be useful to facilitate liver regeneration in liver transplant patients. Eye disorders include for example increased intra-ocular pressure, glaucoma, dry eyes, retinal degeneration, disorders of tear glands or eye inflammation. Skin disorders include for example xerosis. Oral disorders include for example dry mouth (xerostomia), Sjögren's syndrome, gum diseases (e.g., periodontal disease), or salivary gland duct blockage or malfunction. Prostate disorders include for example benign prostatic hyperplasia (BPH). Endocrine disorders include for example diabetes mellitus, hyperthyroidism, hypothyroidism, and cystic fibrosis.

1.2.1 Therapeutically Effective Dosages

Disorders are treated, prevented or alleviated by administering to a subject, e.g., a mammal such as a human in need thereof, a therapeutically effective dose of a GCC agonist peptide. The present invention is based in part on the unexpected results of clinical trials in humans which demonstrated that the formulations of the invention are therapeutically effective at much lower doses than predicted based on animal studies. In accordance with one aspect of the invention, the therapeutically effective dose is between 0.01 milligrams (mg) and 10 mg per unit dose. The term "unit dose" refers to a single drug delivery entity, e.g., a tablet, capsule, solution, inhalation, controlled release or extended release formulation (e.g. MMX® technology of Cosmo Pharmaceuticals). In one embodiment, the effective dose is between 0.01 mg and 9 mg. In another embodiment, the effective dose is between 0.01 mg and 5 mg. In another embodiment, the effective dose is between 0.01 mg and 3 mg. In another embodiment, the effective dose is between 0.10 mg and 5 mg. In another embodiment, the effective dose is between 0.10 mg and 3 mg. In one embodiment, the unit dose is .01 mg, .05 mg, 0.1 mg, 0.2 mg, 0.3 mg, 0.5 mg, 1.0 mg, 1.5 mg, 2.0 mg, 2.5 mg, 3.0 mg, 5 mg, or 10 mg. In one embodiment, the unit dose is 0.3 mg, 1.0 mg, 3.0 mg, 9.0 mg, or 9.5 mg.

The GCC agonist peptides may be in a pharmaceutical composition in unit dose form, together with one or more pharmaceutically acceptable excipients. The amount of peptide present should be sufficient to have a positive therapeutic effect when administered to a patient. What constitutes a "positive therapeutic effect" will depend upon the particular condition being treated and will include any significant improvement in a condition readily recognized by one of skill in the art.

The GCC agonists for use in the methods described above are preferably administered orally. Dosage forms include solutions, suspensions, emulsions, tablets, and capsules.

The total daily dose can be administered to the patient in a single dose, or in multiple sub-doses. Typically, sub-doses can be administered two to six times per day, preferably two to four times per day, and even more preferably two to three times per day. Preferably, a single daily dose is administered.

The GCC agonists may be administered as either the sole active agent or in combination with one or more additional active agents. In all cases, additional active agents should be administered at a dosage that is therapeutically effective using the existing art as a guide. The GCC agonists may be administered in a single composition or sequentially with the one or more additional active agents. In one embodiment, the GCC agonist is administered in combination with one or more inhibitors of cGMP dependent phosphodiesterase such as suldinac sulfone, zaprinast, motapizone, vardenafil, or sildenifil. In another embodiment, the GCC agonist is administered in combination with one or more chemotherapeutic agents. In another embodiment, the GCC agonist is administered in combination with one or more or anti-inflammatory drugs such as steroids or non-steroidal anti-inflammatory drugs (NSAIDS), such as aspirin.

Combination therapy can be achieved by administering two or more agents, e.g., a GCC agonist peptide described herein and another compound, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within 1, 2, 3, 6, 9, 12, 15, 18, or 24 hours of each other or within 1, 2, 3, 4, 5, 6, 7, 8, 9, 10, 12, 14 days of each other or within 2, 3, 4, 5, 6, 7, 8, 9, or 10 weeks of each other. In some cases even longer intervals are possible. While in many cases it is desirable that the two or more agents used in a combination therapy be present in within the patient's body at the same time, this need not be so.

The GCC agonist peptides described herein may be combined with phosphodiesterase inhibitors, e.g., sulindae sulfone, Zaprinast, sildenafil, vardenafil or tadalafil to further enhance levels of cGMP in the target tissues or organs.

Combination therapy can also include two or more administrations of one or more of the agents used in the combination. For example, if agent X and agent Y are used in a combination, one could administer them sequentially in any combination one or more times, e.g., in the order X-Y-X, X-X-Y, Y-X-Y, Y-Y-X, X-X-Y-Y, etc.

1.2.2 Exemplary Agents for Combination Therapy

The GCC agonist formulations of the invention may be administered alone or in combination with one or more additional therapeutic agents as part of a therapeutic regimen for the treatment or prevention of a gastrointestinal disease or disorder. In some embodiments, the GCC agonist formulation comprises one or more additional therapeutic agents.

In other embodiments, the GCC agonist is formulated separately from the one or more additional therapeutic agents. In accordance with this embodiment, the GCC agonist is administered either simultaneously, sequentially, or at a different time than the one or more additional therapeutic agents. In one embodiment, the GCC agonist formulation is administered in combination with one or more additional therapeutic agents selected from the group consisting of phosphodiesterase inhibitors, cyclic nucleotides (such as cGMP and cAMP), a laxative (such as SENNA or METAMUCIL), a stool softner, an anti-tumor necrosis factor alpha therapy for IBD (such as REMICADE, ENBREL, or HUMIRA), and anti-inflammatory drugs (such as COX-2 inhibitors, sulfasalazine, 5-ASA derivatives and NSAIDS). In certain embodiments, the GCC agonist formulation is administered in combination with an effective dose of an inhibitor of cGMP-specific phosphodiesterase (cGMP-PDE) either concurrently or sequentially with said GCC agonist. cGMP-PDE inhibitors include, for example, suldinac sulfone, zaprinast, motapizone, vardenifil, and sildenafil. In another embodiment, the GCC agonist formulation is administered in combination with inhibitors of cyclic nucleotide transporters. Further examples of therapeutic agents that may be administered in combination with the GCC agonist formulations of the invention are given in the following sections.

1.2.2.1 Agents to Treat Gastrointestinal Cancers

The GCC agonist formulations described herein can be used in combination with one or more antitumor agents including but not limited to alkylating agents, epipodophyllotoxins, nitrosoureas, anti-metabolites, *vinca* alkaloids, anthracycline antibiotics, nitrogen mustard agents, and the like. Particular antitumor agents include tamoxifen, taxol, etoposide, and 5-fluorouracil. In one embodiment, the GCC agonist formulations are used in combination with an antiviral agent or a monoclonal antibody.

Non-limiting examples of antitumor agents that can be used in combination with the GCC agonist formulations of the invention for the treatment of colon cancer include anti-proliferative agents, agents for DNA modification or repair, DNA synthesis inhibitors, DNA/RNA transcription regulators, RNA processing inhibitors, agents that affect protein expression, synthesis and stability, agents that affect protein localization or their ability to exert their physiological action, agents that interfere with protein-protein or protein-nucleic acid interactions, agents that act by RNA interference, receptor binding molecules of any chemical nature (including small molecules and antibodies), targeted toxins, enzyme activators, enzyme inhibitors, gene regulators, HSP-90 inhibitors, molecules interfering with microtubules or other cytoskeletal components or cell adhesion and motility, agents for phototherapy, and therapy adjuncts.

Representative anti-proliferative agents include N-acetyl-D-sphingosine ($C_2$ ceramide), apigenin, berberine chloride, dichloromethylenediphosphonic acid disodium salt, loe-emodine, emodin, HA 14-1, N-hexanoyl-D-sphingosine ($C_6$ ceramide), 7b-hydroxycholesterol, 25-hydroxycholesterol, hyperforin, parthenolide, and rapamycin.

Representative agents for DNA modification and repair include aphidicolin, bleomycin sulfate, carboplatin, carmustine, chlorambucil, cyclophosphamide monohydrate, cyclophosphamide monohydrate ISOPAC.RTM, cis-diamminepatinum (II) dichloride (Cisplatin), esculetin, melphalan, methoxyamine hydrochloride, mitomycin C, mitoxantrone dihydrochloride, oxaliplatin, and streptozocin.

Representative DNA synthesis inhibitors include (.+−.) amethopterin (methotrexate), 3-amino-1,2,4-benzotriazine 1,4-dioxide, aminopterin, cytosine b-D-arabinofurdnoside (Ara-C), cytosine b-D-arabinofuranoside (Ara-C) hydrochloride, 2-fluoroadenine-9-b-D-arabinofuranoside (Fludarabine des-phosphate; F-ara-A), 5-fluoro-5'-deoxyuridinc, 5-fluorouracil, ganciclovir, hydroxyurea, 6-mercaptopurine, and 6-thioguanine.

Representative DNA/RNA transcription regulators include actinomycin D, daunorubicin hydrochloride, 5,6-dichlorobenzimidazole 1-b-D-ribofuranoside, doxorubicin hydrochloride, homoharringtonine, and idarubicin hydrochloride.

Representative enzyme activators and inhibitors include forskolin, DL-aminoglutethimide, apicidin, Bowman-Birk Inhibitor, butein, (S)-(+)-camptothecin, curcumin, (−)-deguelin, (−)-depudecin, doxycycline hyclate, etoposide, formestane, fostriecin sodium salt, hispidin, 2-imino-1-imidazolidineacetic acid (Cyclocreatine), oxamflatin, 4-phenylbutyric acid, roscovitine, sodium valproate, trichostatin A, tyrphostin AG 34, tyrphostin AG 879, urinary trypsin inhibitor fragment, valproic acid (2-propylpentanoic acid), and XK469.

Representative gene regulators include 5-aza-2'-deoxycytidine, 5-azacytidine, cholecalciferol (Vitamin D3), ciglitizone, cyproterone acetate, 15-deoxy-D.sup. 12,14-prostaglandin $J_2$, epitestosterone, flutamide, glycyrrhizic acid ammonium salt (glycyrrhizin), 4-hydroxytamoxifen, mifepristone, procainamide hydrochloride, raloxifene hydrochloride, all trans-retinal (vitamin A aldehyde), retinoic acid (vitamin A acid), 9-cis-retinoic acid, 13-cis-retinoic acid, retinoic acid p-hydroxyanilide, retinol (Vitamin A), tamoxifen, tamoxifen citrate salt, tetradecylthioacetic acid, and troglitazone.

Representative HSP-90 inhibitors include 17-(allylamino)-17-demethoxygeldanamycin and geldanamycin.

Representative microtubule inhibitors include colchicines, dolastatin 15, nocodazole, taxanes and in particular paclitaxel, podophyllotoxin, rhizoxin, vinblastine sulfate salt, vincristine sulfate salt, and vindesine sulfate salt and vinorelbine (Navelbine) ditartrate salt.

Representative agents for performing phototherapy include photoactive porphyrin rings, hypericin, 5-methoxypsoralen, 8-methoxypsoralen, psoralen and ursodeoxycholic acid.

Representative agents used as therapy adjuncts include amifostine, 4-amino-1,8-naphthalimide, brefeldin A, cimetidine, phosphomycin disodium salt, leuprolide (leuprorelin) acetate salt, luteinizing hormone-releasing hormone (LH-RH)acetate salt, lectin, papaverine hydrochloride, pifithrin-a, (−)-scopolamine hydrobromide, and thapsigargin.

The agents can also be anti-VEGF (vascular endothelial growth factor) agents, as such are known in the art. Several antibodies and small molecules are currently in clinical trials or have been approved that function by inhibiting VEGF, such as Avastin (Bevacizumab), SU5416, SU11248 and BAY 43-9006. The agents can also be directed against growth factor receptors such as those of the EGF/Erb-B family such as EGF Receptor (Iressa or Gefitinib, and Tarceva or Erlotinib), Erb-B2, receptor (Herceptin or Trastuzumab), other receptors (such as Rituximab or Rituxan/MabThera), tyrosine kinases, non-receptor tyrosine kinases, cellular serine/threonine kinases (including MAP kinases), and various other proteins whose deregulation contribute to oncogenesis (such as small/Ras family and large/heterotrimeric G proteins). Several antibodies and small molecules targeting those molecules are currently at various stages of development (including approved for treatment or in clinical trials).

In a preferred embodiment, the invention provides a method for treating colon cancer in a subject in need thereof by administering to the subject a GCC agonist formulation in combination with one or more antitumor agent selected from the group consisting of paclitaxel, docetaxel, tamoxifen, vinorelbine, gemcitabine, cisplatin, etoposide, topotecan, irinotecan, anastrozole, rituximab, trastuzumab, fludarabine, cyclophosphamide, gentuzumab, carboplatin, interferons, and doxorubicin. In a particular embodiment the antitumor agent is paclitaxel. In a further embodiment, the method further comprises an antitumor agent selected from the group consisting of 5-FU, doxorubicin, vinorelbine, cytoxan, and cisplatin.

1.2.2.2 Agents that Treat Crohn's Disease

In one embodiment, a GCC agonist formulation of the invention is administered as part of a combination therapy with one or more additional therapeutic agents for the treatment of Crohn's disease. Non-limiting examples of the one or more additional therapeutic agents include sulfasalazine and other mesalamine-containing drugs, generally known as 5-ASA agents, such as Asacol, Dipentum, or Pentasa, or infliximab (REMICADE). In certain embodiments, the one or more additional agents is a corticosteroid or an immunosuppressive agent such as 6-mercaptopurine or azathioprine. In another embodiment, the one or more additional agents is an antidiarrheal agent such as diphenoxylate, loperamide, or codeine.

1.2.2.3 Agents that Treat Ulcerative Colitis

In one embodiment, a GCC agonist formulation of the invention is administered as part of a combination therapy with one or more additional therapeutic agents for the treatment of ulcerative colitis. The agents that are used to treat ulcerative colitis overlap with those used to treat Chrohn's Disease. Non-limiting examples of the one or more additional therapeutic agents that can be used in combination with a GCC agonist formulation of the invention include aminosalicylates (drugs that contain 5-aminosalicyclic acid (5-ASA)) such as sulfasalazine, olsalazine, mesalamine, and balsalazide. Other therapeutic agents that can be used include corticosteroids, such as prednisone and hydrocortisone, immunomodulators, such as azathioprine, 6-mercapto-purine (6-MP), cytokines, interleukins, and lymphokines, and anti-TNF-alpha agents, including the thiazolidinediones or glitazones such as rosiglitazone and pioglitazone. In one embodiment, the one or more additional therapeutic agents includes both cyclosporine A and 6-MP or azathioprine for the treatment of active, severe ulcerative colitis.

1.2.2.4 Agents that Treat Constipation/Irritable Bowel Syndrome

In one embodiment, a GCC agonist formulation of the invention is administered as part of a combination therapy with one or more additional therapeutic agents for the treatment of constipation, such as that associated with irritable bowel syndrome. Non-limiting examples of the one or more additional therapeutic agents include laxatives such as SENNA, MIRALAX, LACTULOSE, PEG, or calcium polycarbophil), stool softeners (such as mineral oil or COLACE), bulking agents (such as METAMUCIL or bran), agents such as ZELNORM (also called tegaserod), and anticholinergic medications such as BENTYL and LEVSIN.

1.2.2.5 Agents for the Treatment of Postoperative Ileus

In one embodiment, a GCC agonist formulation of the invention is administered as part of a combination therapy with one or more additional therapeutic agents for the treatment of postoperative ileus. Non-limiting examples of the one or more additional therapeutic agents include ENTEREG (alvimopan; formerly called ado lor/ADL 8-2698), conivaptan, and related agents describes in U.S. Pat. No. 6,645,959.

1.2.2.6 Anti-Obesity Agents

In one embodiment, a GCC agonist formulation of the invention is administered as part of a combination therapy with one or more additional therapeutic agents for the treatment of obesity. Non-limiting examples of the one or more additional therapeutic agents include 1 1β HSD-I (11-beta hydroxy steroid dehydrogenase type 1) inhibitors, such as BVT 3498, BVT 2733, 3-(1-adamantyl)-4-ethyl-5-(ethylthio)-4H-1,2,4-triazole, 3-(1-adamantyl)-5-(3,4,5-trimethoxyphenyl)-4-methyl-4H-1,2,4-triazole, 3-adamantanyl-4,5,6,7,8,9,10, 11, 12,3a-decahydro-1,2,4-triazolo[4, 3-a][11] annulene, and those compounds disclosed in WO01/90091, WO01/90090, WO01/90092 and WO02/072084; 5HT antagonists such as those in WO03/037871, WO03/037887, and the like; 5HTIa modulators such as carbidopa, benserazide and those disclosed in U.S. Pat. No. 6,207,699, WO03/031439, and the like; 5HT2c (serotonin receptor 2c) agonists, such as BVT933, DPCA37215, IK264, PNU 22394, WAY161503, R-1065, SB 243213 (Glaxo Smith Kline) and YM 348 and those disclosed in U.S. Pat. No. 3,914,250, WO00/77010, WO02/36596, WO02/48124, WO02/10169, WO01/66548, WO02/44152, WO02/51844, WO02/40456, and WO02/40457; 5HT6 receptor modulators, such as those in WO03/030901, WO03/035061, WO03/039547, and the like; acyl-estrogens, such as oleoyl-estrone, disclosed in del Mar-Grasa, M. et al, Obesity Research, 9:202-9 (2001) and Japanese Patent Application No. JP 2000256190; anorectic bicyclic compounds such as 1426 (Aventis) and 1954 (Aventis), and the compounds disclosed in WO00/18749, WO01/32638, WO01/62746, WO01/62747, and WO03/015769; CB 1 (cannabinoid-1 receptor) antagonist/inverse agonists such as rimonabant (Acomplia; Sanofi), SR-147778 (Sanofi), SR-141716 (Sanofi), BAY 65-2520 (Bayer), and SLV 319 (Solvay), and those disclosed in patent publications U.S. Pat. Nos. 4,973,587, 5,013,837, 5,081,122, 5,112,820, 5,292, 736, 5,532,237, 5,624,941, 6,028,084, 6,509,367, 6,509,367, WO96/33159, WO97/29079, WO98/31227, WO98/33765, WO98/37061, WO98/41519, WO98/43635, WO98/43636, WO99/02499, WO00/10967, WO00/10968, WO01/09120, WO01/58869, WO01/64632, WO01/64633, WO01/64634, WO01/70700, WO01/96330, WO02/076949, WO03/006007, WO03/007887, WO03/020217, WO03/026647, WO03/026648, WO03/027069, WO03/027076, WO03/027114, WO03/037332, WO03/040107, WO03/086940, WO03/084943 and EP658546; CCK-A (cholecystokinin-A) agonists, such as AR-R 15849, GI 181771 (GSK), JMV-180, A-71378, A-71623 and SR146131 (Sanofi), and those described in U.S. Pat. No. 5,739,106; CNTF (Ciliary neurotrophic factors), such as GI-181771 (Glaxo-SmithKline), SRI 46131 (Sanofi Synthelabo), butabindide, PD 170,292, and PD 149164 (Pfizer); CNTF derivatives, such as Axokine® (Regeneron), and those disclosed in WO94/09134, WO98/22128, and WO99/43813; dipeptidyl peptidase IV (DP-IV) inhibitors, such as isoleucine thiazolidide, valine pyrrolidide, NVP-DPP728, LAF237, P93/01, P 3298, TSL 225 (tryptophyl-1,2,3,4-tetrahydroisoquinoline-3-carboxylic acid; disclosed by Yamada et al, Bioorg. & Med. Chem. Lett. 8 (1998) 1537-1540), TMC-2A/2B/2C, CD26 inhibitors, FE 999011, P9310/K364, VIP 0177, SDZ 274-444, 2-cyanopyrrolidides and 4-cyanopyrrolidides as disclosed by Ashworth et al, Bioorg. & Med. Chem. Lett., Vol. 6, No. 22, pp 1163-1166 and 2745-2748 (1996) and the compounds disclosed patent publications. WO99/38501, WO99/46272, WO99/67279 (Probiodrug), WO99/67278 (Probiodrug), WO99/61431 (Probiodrug), WO02/083128, WO02/062764, WO03/000180, WO03/000181, WO03/000250, WO03/002530, WO03/002531, WO03/002553, WO03/002593, WO03/004498, WO03/004496, WO03/017936, WO03/024942, WO03/024965, WO03/033524, WO03/037327 and EP1258476; growth hormone secretagogue receptor agonists/antagonists, such as NN703, hexarelin, MK-0677 (Merck), SM-130686, CP-424391 (Pfizer), LY 444,711 (Eli Lilly), L-692,429 and L-163,255, and such as those disclosed in U.S. Ser. No. 09/662,448, U.S. provisional application 60/203,335, U.S. Pat. No. 6,358,951, US2002049196, US2002/022637, WO01/56592 and WO02/32888; H3 (histamine H3) antagonist/inverse agonists, such as thioperamide, 3-(1H-imidazol-4-yl) propyl N-(4-pentenyl) carbamate), clobenpropit, iodophenpropit, imoproxifan, GT2394 (Gliatech), and A331440, O-[3-(IH-imidazol-4-yl) propanol]carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)) and histamine H3 receptor modulators such as those disclosed in WO02/15905, WO03/024928 and WO03/024929; leptin derivatives, such as those disclosed in U.S. Pat. Nos. 5,552,524, 5,552,523, 5,552,522, 5,521,283, WO96/23513, WO96/23514, WO96/23515, WO96/23516, WO96/23517, WO96/23518, WO96/23519, and WO96/23520; leptin, including recombinant human leptin (PEG-OB, Hoffman La Roche) and recombinant methionyl human leptin (Amgen); lipase inhibitors, such as tetrahydrolipstatin (orlistat/Xenical®), Triton WRI 339, RHC80267, lipstatin, teasaponin, diethylumbelliferyl phosphate, FL-386, WAY-121898, Bay-N-3176, valilactone, esteracin, ebelactone A, ebelactone B, and RHC 80267, and those disclosed in patent publications WO01/77094, U.S. Pat. Nos. 4,598,089, 4,452,813, USUS5512565, U.S. Pat. Nos. 5,391,571, 5,602,151, 4,405,644, 4,189,438, and 4,242,453; lipid metabolism modulators such as maslinic acid, erythrodiol, ursolic acid uvaol, betulinic acid, betulin, and the like and compounds disclosed in WO03/011267; Mc4r (melanocortin 4 receptor) agonists, such as CHIR86036 (Chiron), ME-10142, ME-10145, and HS-131 (Melacure), and those disclosed in PCT publication Nos. WO99/64002, WO00/74679, WO01/991752, WO01/25192, WO01/52880, WO01/74844, WO01/70708, WO01/70337, WO01/91752, WO02/059095, WO02/059107, WO02/059108, WO02/059117, WO02/06276, WO02/12166, WO02/11715, WO02/12178, WO02/15909, WO02/38544, WO02/068387, WO02/068388, WO02/067869, WO02/081430, WO03/06604, WO03/007949, WO03/009847, WO03/009850, WO03/013509, and WO03/031410; Mc5r (melanocortin 5 receptor) modulators, such as those disclosed in WO97/19952, WO00/15826, WO00/15790, US20030092041; melanin-concentrating hormone 1 receptor (MCHR) antagonists, such as T-226296 (Takeda), SB 568849, SNP-7941 (Synaptic), and those disclosed in patent publications WO01/21169, WO01/82925, WO01/87834, WO02/051809, WO02/06245, WO02/076929, WO02/076947, WO02/04433, WO02/51809, WO02/083134, WO02/094799, WO03/004027, WO03/13574, WO03/15769, WO03/028641, WO03/035624, WO03/033476, WO03/033480, JP13226269, and JP1437059; mGluR5 modulators such as those disclosed in WO03/029210, WO03/047581, WO03/048137, WO03/051315, WO03/051833, WO03/053922, WO03/059904, and the like; serotoninergic agents, such as fenfluramine (such as Pondimin® (Benzeneethanamine, N-ethyl-alpha-methyl-3-(trifluoromethyl)-, hydrochloride), Robbins), dexfenfluramine (such as Redux® (Benzeneethanamine, N-ethyl-alpha-methyl-3-(trifluoromethyl)-, hydrochloride), Interneuron) and sibutramine ((Meridia®, Knoll/Reductil™) including racemic mixtures, as optically pure isomers (+) and (−), and pharmaceutically acceptable salts, solvents, hydrates, clathrates and prodrugs thereof including sibutramine hydrochloride monohydrate salts thereof, and those compounds disclosed in U.S. Pat. Nos. 4,746,680, 4,806,570, and 5,436,272, 20,020,006964, WO01/27068, and WO01/62341; NE (norepinephrine) transport inhibitors, such as GW 320659, despiramine, talsupram, and nomifensine; NPY 1 antagonists, such as BIBP3226, J-115814, BIBO 3304, LY-357897, CP-671906, GI-264879A, and those disclosed in U.S. Pat. No. 6,001,836, WO96/14307, WO01/23387, WO99/51600, WO01/85690, WO01/85098, WO01/85173, and WO01/89528; NPY5 (neuropeptide Y Y5) antagonists, such as 152,804, GW-569180A, GW-594884A, GW-587081X, GW-548118X, FR235208, FR226928, FR240662, FR252384, 1229U91, GI-264879A, CGP71683A, LY-377897, LY-366377, PD-160170, SR-120562A, SR-120819A, JCF-104, and H409/22 and those compounds disclosed in patent publications U.S. Pat. Nos. 6,140,354, 6,191,160, 6,218,408, 6,258,837, 6,313,298, 6,326,375, 6,329,395, 6,335,345, 6,337,332, 6,329,395, 6,340,683, EP01010691, EP-01044970, WO97/19682, WO97/20820, WO97/20821, WO97/20822, WO97/20823, WO98/27063, WO00/107409, WO00/185714, WO00/185730, WO00/64880, WO00/68197, WO00/69849, WO/0113917, WO01/09120, WO01/14376, WO01/85714, WO01/85730, WO01/07409, WO01/02379, WO01/23388, WO01/23389, WO01/44201, WO01/62737, WO01/62738, WO01/09120, WO02/20488, WO02/22592, WO02/48152, WO02/49648, WO02/051806, WO02/094789, WO03/009845, WO03/014083, WO03/022849, WO03/028726 and Norman et al, J. Med. Chem. 43:4288-4312 (2000); opioid antagonists, such as nalmefene (REVEX®), 3-methoxynaltrexone, methylnaltrexone, naloxone, and naltrexone (e.g. PT901; Pain Therapeutics, Inc.) and those disclosed in US20050004155 and WO00/21509; orexin antagonists, such as SB-334867-A and those disclosed in patent publications WO01/96302, WO01/68609, WO02/44172, WO02/51232, WO02/51838, WO02/089800, WO02/090355, WO03/023561, WO03/032991, and WO03/037847; PDE inhibitors (e.g. compounds which slow the degradation of cyclic AMP (cAMP) and/or cyclic GMP (cGMP) by inhibition of the phosphodiesterases, which can lead to a relative increase in the intracellular concentration of cAMP and cGMP; possible PDE inhibitors are primarily those substances which are to be numbered among the class consisting of the PDE3 inhibitors, the class consisting of the PDE4 inhibitors and/or the class consisting of the PDE5 inhibitors, in particular those substances which can be designated as mixed types of PDE3/4 inhibitors or as mixed types of PDE3/4/5 inhibitors) such as those disclosed in patent publications DE1470341, DE2108438, DE2123328, DE2305339, DE2305575, DE2315801, DE2402908, DE2413935, DE2451417, DE2459090, DE2646469, DE2727481, DE2825048, DE2837161, DE2845220, DE2847621, DE2934747, DE3021792, DE3038166, DE3044568, EP000718, EP0008408, EP0010759, EP0059948, EP0075436, EP0096517, EP0112987, EP0116948, EP0150937, EP0158380, EP0161632, EP0161918, EP0167121, EP0199127, EP0220044, EP0247725, EP0258191, EP0272910, EP0272914, EP0294647, EP0300726, EP0335386, EP0357788, EP0389282, EP0406958, EP0426180, EP0428302, EP0435811, EP0470805, EP0482208, EP0490823, EP0506194, EP0511865, EP0527117, EP0626939, EP0664289, EP0671389, EP0685474, EP0685475, EP0685479, JP92234389, JP94329652, JP95010875, U.S. Pat. Nos. 4,963,561, 5,141,931, WO9117991, WO9200968, WO9212961, WO9307146, WO9315044, WO9315045, WO9318024, WO9319068, WO9319720, WO9319747, WO9319749, WO9319751, WO9325517, WO9402465, WO9406423, WO9412461, WO9420455, WO9422852, WO9425437, WO9427947, WO9500516, WO9501980, WO9503794, WO9504045, WO9504046, WO9505386, WO9508534, WO9509623, WO9509624, WO9509627, WO9509836, WO9514667, WO9514680, WO9514681, WO9517392, WO9517399, WO9519362, WO9522520, WO9524381, WO9527692, WO9528926, WO9535281, WO9535282, WO9600218, WO9601825, WO9602541, WO9611917, DE3142982, DEI 116676, DE2162096, EP0293063, EP0463756, EP0482208, EP0579496, EP0667345 U.S. Pat. No. 6,331,543, US20050004222 (including those disclosed in formulas I—XIII and paragraphs 37-39, 85-0545 and 557-577), WO9307124, EP0163965, EP0393500, EP0510562, EP0553174, WO9501338 and WO9603399, as well as PDE5 inhibitors (such as RX-RA-69, SCH-51866, KT-734, vesnarinone, zaprinast, SKF-96231, ER-21355, BF/GP-385, NM-702 and sildenafil (Viagra™)), PDE4 inhibitors (such as etazolate, ICI63197, RP73401, imazolidinone (RO-20-1724), MEM 1414 (R1 533/R1500; Pharmacia Roche), denbufylline, rolipram, oxagrelate, nitraquazone, Y-590, DH-6471, SKF-94120, motapizone, lixazinone, indolidan, olprinone, atizoram, KS-506-G, dipamfylline, BMY-43351, atizoram, arofylline, filaminast, PDB-093, UCB-29646, CDP-840, SKF-107806, piclamilast, RS-17597, RS-25344-000, SB-207499, TIBENELAST, SB-210667, SB-211572, SB-211600, SB-212066, SB-212179, GW-3600, CDP-840, mopidamol, anagrelide, ibudilast, amrinone, pimobendan, cilostazol, quazinone and N-(3,5-dichloropyrid-4-yl)-3-cyclopropyl-methoxy4-difluoromethoxybenzamide, PDE3 inhibitors (such as ICI153, 100, bemorandane (RWJ 22867), MCI-154, UD-CG 212, sulmazole, ampizone, cilostamide, carbazeran, piroximone, imazodan, CI-930, siguazodan, adibendan, saterinone, SKF-95654, SDZ-MKS-492, 349-U-85, emora- dan, EMD-53998, EMD-57033, NSP-306, NSP-307, revizinone, NM-702, WIN-62582 and WIN-63291, enoximone and milrinone, PDE3/4 inhibitors (such as benafentrine, trequinsin, ORG-30029, zardaverine, L-686398, SDZ-ISQ-844, ORG-20241, EMD-54622, and tolafentrine) and other PDE inhibitors (such as vinpocetin, papaverine, enprofylline, cilomilast, fenoximone, pentoxifylline, roflumilast, tadalafil (Cialis®), theophylline, and vardenafil (Levitra®); Neuropeptide Y2 (NPY2) agonists include but are not limited to: polypeptide YY and fragments and variants thereof (e.g. YY3-36 (PYY3-36) (N. Engl. J. Med. 349:941, 2003; IKPEAPGE DASPEELNRY YASLRHYLNL VTRQRY (SEQ ID NO: 253)) and PYY agonists such as those disclosed in WO02/47712, WO03/026591, WO03/057235, and WO03/027637; serotonin reuptake inhibitors, such as, paroxetine, fluoxetine (Prozac™), fluvoxamine, sertraline, citalopram, and imipramine, and those disclosed in U.S. Pat. Nos. 6,162,805, 6,365,633, WO03/00663, WO01/27060, and WO01/162341; thyroid hormone β agonists, such as KB-2611 (KaroBioBMS), and those disclosed in WO02/15845, WO97/21993, WO99/00353, GB98/284425, U.S. Provisional Application No. 60/183,223, and Japanese Patent Application No. JP 2000256190; UCP-I (uncoupling protein-1), 2, or 3 activators, such as phytanic acid, 4-[(E)-2-(5, 6,7,8-tetrahydro-5, 5,8,8-tetramethyl-2-napthalenyl)-1-propenyl]benzoic acid (TTNPB), retinoic acid, and those disclosed in WO99/00123; β3 (beta adrenergic receptor 3) agonists, such as AJ9677/TAK677 (Dainippon/Takeda), L750355 (Merck), CP331648 (Pfizer), CL-316,243, SB 418790, BRL-37344, L-796568, BMS-196085, BRL-35135A, CGP12177A, BTA-243, GW 427353, Trecadrine, Zeneca D7114, N-5984 (Nisshin Kyorin), LY-377604 (Lilly), SR 59119A, and those disclosed in U.S. Pat. Nos. 5,541,204, 5,770,615, 5,491,134, 5,776,983, U.S. Pat. No. 488,064, U.S. Pat. Nos. 5,705,515, 5,451,677, WO94/18161, WO95/29159, WO97/46556, WO98/04526 and WO98/32753, WO01/74782, WO02/32897, WO03/014113, WO03/016276, WO03/016307, WO03/024948, WO03/024953 and WO03/037881; noradrenergic agents including, but not limited to, diethylpropion (such as Tenuate® (1-propanone, 2-(diethylamino)-1-phenyl-, hydrochloride), Merrell), dextroamphetamine (also known as dextroamphetamine sulfate, dexamphetamine, dexedrine, Dexampex, Ferndex, Oxydess II, Robese, Spancap #1), mazindol ((or 5-(p-chlorophenyl)-2,5-dihydro-3H-imidazo [2,1-a]isoindol-5-ol) such as Sanorex®, Novartis or Mazanor®, Wyeth Ayerst), phenylpropanolamine (or Benzenemethanol, alpha-(1-aminoethyl)-, hydrochloride), phentermine ((or Phenyl-tertiary-butylamine) such as Adipex-P®, Lemmon, FASTIN®, Smith-Kline Beecham and Ionamin®, Medeva), Phenol, 3-[4,5-dihydro-1H-imidazol-2-yl)ethyl](4-methylphenyl)amino], monohydrochloride, phendimetrazine ((or (2S,3S)-3,4-Dimethyl-2phenylmorpholine L-(+)-tartrate (1:1)) such as Metra® (Forest), Plegine® (Wyeth-Ay erst), Prelu-2® (Boehringer Ingelheim), and Statobex® (Lemmon), phendamine tartrate (such as Thephorin® (2,3,4,9-Tetrahydro-2-methyl-9-phenyl-IH-indenol [2,1-c]pyridine L-(+)-tartrate (1:1)), Hoffmann-LaRoche), methamphetamine (such as Desoxyn®, Abbot ((S)-N, (alpha)-dimethylbenzeneethanamine hydrochloride)), and phendimetrazine tartrate (such as Bontril® Slow-Release Capsules, Amarin (−3,4-Dimethyl-2-phenylmorpholine Tartrate); fatty acid oxidation upregulator/inducers such as Famoxin® (Genset); monamine oxidase inhibitors including but not limited to befloxatone, moclobemide, brofaromine, phenoxathine, esuprone, befol, toloxatone, pirlindol, ami-flamine, serclorenine, bazinaprine, lazabemide, milacemide, caroxazone and other certain compounds as disclosed by WO01/12176; and other anti-obesity agents such as 5HT-2 agonists, ACC (acetyl-CoA carboxylase) inhibitors such as those described in WO03/072197, alpha-lipoic acid (alpha-LA), AOD9604, appetite suppressants such as those in WO03/40107, ATL-962 (Alizyme PLC), benzocaine, benzphetamine hydrochloride (Didrex), bladderwrack (focus vesiculosus), BRS3 (bombesin receptor subtype 3) agonists, bupropion, caffeine, CCK agonists, chitosan, chromium, conjugated linoleic acid, corticotropin-releasing hormone agonists, dehydroepiandrosterone, DGATI (diacylglycerol acyltransferase 1) inhibitors, DGAT2 (diacylglycerol acyltransferase 2) inhibitors, dicarboxylate transporter inhibitors, ephedra, exendin-4 (an inhibitor of glp-1) FAS (fatty acid synthase) inhibitors (such as Cerulenin and C75), fat resorption inhibitors (such as those in WO03/053451, and the like), fatty acid transporter inhibitors, natural water soluble fibers (such as *psyllium, plantago*, guar, oat, pectin), galanin antagonists, galega (Goat's Rue, French Lilac), garcinia cambogia, germander (*teucrium chamaedrys*), ghrelin antibodies and ghrelin antagonists (such as those disclosed in WO01/87335, and WO02/08250), polypeptide hormones and variants thereof which affect the islet cell secretion, such as the hormones of the secretin/gastric inhibitory polypeptide (GIP)/vasoactive intestinal polypeptide (VIP)/pituitary adenylate cyclase activating polypeptide (PACAP)/glucagon-like polypeptide II (GLP-II)/glicentin/ glucagon gene family and/or those of the adrenomedullin/ amylin/calcitonin gene related polypeptide (CGRP) gene family includingGLP-1 (glucagon-like polypeptide 1) agonists (e.g. (1) exendin-4, (2) those GLP-I molecules described in US20050130891 including GLP-1 (7-34), GLP-1 (7-35), GLP-1 (7-36) or GLP-1 (7-37) in its C-terminally carboxylated or amidated form or as modified GLP-I polypeptides and modifications thereof including those described in paragraphs 17-44 of US20050130891, and derivatives derived from GLP-1-(7-34) COOH and the corresponding acid amide are employed which have the following general formula: R-NH-HAEGTFTSDV-SYLEGQAAKEFIAWLVK-CONH$_2$ (SEQ ID NO: 254) wherein R=H or an organic compound having from 1 to 10 carbon atoms. Preferably, R is the residue of a carboxylic acid. Particularly preferred are the following carboxylic acid residues: formyl, acetyl, propionyl, isopropionyl, methyl, ethyl, propyl, isopropyl, n-butyl, sec-butyl, tert-butyl.) and glp-1 (glucagon-like polypeptide-1), glucocorticoid antagonists, glucose transporter inhibitors, growth hormone secretagogues (such as those disclosed and specifically described in U.S. Pat. No. 5,536,716), interleukin-6 (IL-6) and modulators thereof (as in WO03/057237, and the like), L-carnitine, Mc3r (melanocortin 3 receptor) agonists, MCH2R (melanin concentrating hormone 2R) agonist/antagonists, melanin concentrating hormone antagonists, melanocortin agonists (such as Melanotan II or those described in WO 99/64002 and WO 00/74679), nomame herba, phosphate transporter inhibitors, phytopharm compound 57 (CP 644, 673), pyruvate, SCD-I (stearoyl-CoA desaturase-1) inhibitors, T71 (Tularik, Inc., Boulder CO), Topiramate (Topimax®, indicated as an anti-convulsant which has been shown to increase weight loss), transcription factor modulators (such as those disclosed in WO03/026576), 0-hydroxy steroid dehydrogenase-1 inhibitors (β-HSD-I), β-hydroxy-β-methylbutyrate, p57 (Pfizer), Zonisamide (Zonegran™ indicated as an anti-epileptic which has been shown to lead to weight loss), and the agents disclosed in US20030119428 paragraphs 20-26.

1.2.2.7 Phosphodiesterase inhibitors

In certain embodiments, the regimen of combination therapy includes the administration of one or more phosphodiesterase ("PDE") inhibitors. PDE inhibitors slow the degradation of cyclic AMP (CAMP) and/or cyclic GMP (cGMP) by inhibiting phosphodiesterases, which can lead to a relative increase in the intracellular concentration of cAMP and/or cGMP. Non-limiting examples of PDE inhibitors that can be used in combination with the GCC agonists of the invention include PDE3 inhibitors, PDE4 inhibitors and/or PDE5 inhibitors, in particular those substances which can be designated as mixed types of PDE3/4 inhibitors or as mixed types of PDE3/4/5 inhibitors. Non-limiting examples of such PDE inhibitors are described in the following patent applications and patents: DE1470341, DE2108438, DE2123328, DE2305339, DE2305575, DE2315801, DE2402908, DE2413935, DE2451417, DE2459090, DE2646469, DE2727481, DE2825048, DE2837161, DE2845220, DE2847621, DE2934747, DE3021792, DE3038166, DE3044568, EP000718, EP0008408, EP0010759, EP0059948, EP0075436, EP0096517, EPO1 12987, EPO1 16948, EP0150937, EP0158380, EP0161632, EP0161918, EP0167121, EP0199127, EP0220044, EP0247725, EP0258191, EP0272910, EP0272914, EP0294647, EP0300726, EP0335386, EP0357788, EP0389282, EP0406958, EP0426180, EP0428302, EP0435811, EP0470805, EP0482208, EP0490823, EP0506194, EP0511865, EP0527117, EP0626939, EP0664289, EP0671389, EP0685474, EP0685475, EP0685479, JP92234389, JP94329652, JP95010875, U.S. Pat. Nos. 4,963,561, 5, 141,931, WO9117991, WO9200968, WO9212961, WO9307146, WO9315044, WO9315045, WO9318024, WO9319068, WO9319720, WO9319747, WO9319749, WO9319751, WO9325517, WO9402465, WO9406423, WO9412461, WO9420455, WO9422852, WO9425437, WO9427947, WO9500516, WO9501980, WO9503794, WO9504045, WO9504046, WO9505386, WO9508534, WO9509623, WO9509624, WO9509627, WO9509836, WO9514667, WO9514680, WO9514681, WO9517392, WO9517399, WO9519362, WO9522520, WO9524381, WO9527692, WO9528926, WO9535281, WO9535282, WO9600218, WO9601825, WO9602541, WO9611917, DE3142982, DEI 116676, DE2162096, EP0293063, EP0463756, EP0482208, EP0579496, EP0667345 U.S. Pat. No. 6,331,543, US20050004222 (including those disclosed in formulas I—XIII and paragraphs 37-39, 85-0545 and 557-577) and WO9307124, EP0163965, EP0393500, EP0510562, EP0553174, WO9501338 and WO9603399. PDE5 inhibitors which may be mentioned by way of example are RX-RA-69, SCH-51866, KT-734, vesnarinone, zaprinast, SKF-96231, ER-21355, BF/GP-385, NM-702 and sildenafil (Viagra®). PDE4 inhibitors which may be mentioned by way of example are RO-20-1724, MEM 1414 (R1 533/R1500; Pharmacia Roche), DENBUFYLLINE, ROLIPRAM, OXAGRELATE, NITRAQUAZONE, Y-590, DH-6471, SKF-94120, MOTAPIZONE, LIXAZINONE, INDOLIDAN, OLPRINONE, ATIZORAM, KS-506-G, DIPAMFYLLINE, BMY-43351, ATIZORAM, AROFYLLINE, FILAMINAST, PDB-093, UCB-29646, CDP-840, SKF-107806, PICLAMILAST, RS-17597, RS-25344-000, SB-207499, TIBENELAST, SB-210667, SB-211572, SB-211600, SB-212066, SB-212179, GW-3600, CDP-840, MOPIDAMOL, ANAGRELIDE, IBUDILAST, AMRINONE, PIMOBENDAN, CILOSTAZOL, QUAZINONE and N-(3,5-dichloro-pyrid-4-yl)-3-cyclopropylmethoxy4-difluoromethoxybenz-amide. PDE3 inhibitors which may be mentioned by way of example are SULMAZOLE, AMPIZONE, CILOSTAMIDE, CARBAZERAN, PIROXIMONE, IMAZODAN, CI-930, SIGUAZODAN, ADIBENDAN, SATERINONE, SKF-95654, SDZ-MKS-492, 349-U-85, EMORADAN, EMD-53998, EMD-57033, NSP-306, NSP-307, REVIZINONE, NM-702, WIN-62582 and WIN-63291, ENOXIMONE and MILRINONE. PDE3/4 inhibitors which may be mentioned by way of example are BENAFENTRINE, TREQUINSIN, ORG-30029, ZARDAVERINE, L-686398, SDZ-ISQ-844, ORG-20241, EMD-54622, and TOLAFENTRINE. Other PDE inhibitors include: cilomilast, pentoxifylline, roflumilast, tadalafil (Cialis®), theophylline, and vardenafil (Levitra®), zaprinast (PDE5 specific).

1.2.2.8 Analgesic Agents

In certain embodiments, the regimen of combination therapy includes the administration of one or more analgesic agents, e.g., an analgesic compound or an analgesic polypeptide. In some embodiments, the GCC agonist formulation is administered simultaneously or sequentially with one or more analgesic agents. In other embodiments, the GCC agonist is covalently linked or attached to an analgesic agent to create a therapeutic conjugate. Non-limiting examples of analgesic agents that can be used include calcium channel blockers, 5HT receptor antagonists (for example 5HT3, 5HT4 and 5HT1 receptor antagonists), opioid receptor agonists (loperamide, fedotozine, and fentanyl), NK1 receptor antagonists, CCK receptor agonists (e.g., loxiglumide), NK1 receptor antagonists, NK3 receptor antagonists, norepinephrine-serotonin reuptake inhibitors (NSRI), vanilloid and cannabanoid receptor agonists, and sialorphin. Further examples of analgesic agents in the various classes are known in the art.

In one embodiment, the analgesic agent is an analgesic polypeptide selected from the group consisting of sialorphin-related polypeptides, including those comprising the amino acid sequence QHNPR (SEQ ID NO: 255), including: VQHNPR (SEQ ID NO: 256); VRQHNPR (SEQ ID NO: 257); VRGQHNPR (SEQ ID NO: 258); VRGPQHNPR (SEQ ID NO: 259); VRGPRQHNPR (SEQ ID NO: 260); VRGPRRQHNPR (SEQ ID NO: 261); and RQHNPR (SEQ ID NO: 262). Sialorphin-related polypeptides bind to neprilysin and inhibit neprilysin-mediated breakdown of substance P and Met-enkephalin. Thus, compounds or polypeptides that are inhibitors of neprilysin are useful analgesic agents which can be administered with the GCC agonists described herein or covalently linked to a GCC agonist to form a therapeutic conjugate. Sialorphin and related polypeptides are described in U.S. Pat. No. 6,589,750; US20030078200 A1; and WO 02/051435 A2.

In another embodiment, a GCC agonist formulation of the invention is administered as part of a regimen of combination therapy with an opioid receptor antagonist or agonist. In one embodiment, the GCC agonist and the opioid receptor antagonist or agonist are linked via a covalent bond. Non-limiting examples of opioid receptor antagonists include naloxone, naltrexone, methyl nalozone, nalmefene, cypridime, beta funaltrexamine, naloxonazine, naltrindole, norbinaltorphimine, enkephalin pentapeptide (HOE825; Tyr-D-Lys-Gly-Phe-L-homoserine), trimebutine, vasoactive intestinal polypeptide, gastrin, glucagons. Non-limiting examples of opioid receptor agonists include fedotozine, asimadoline, and ketocyclazocine, the compounds described in WO03/097051 and WO05/007626, morphine, diphenyloxylate, frakefamide (H-Tyr-D-Ala-Phe (F)-Phe-NH 2; WO 01/019849 A1), and loperamide.

Further non-limiting examples of analgesic agents that can be used in a regimen of combination therapy along with the GCC agonist formulations of the invention include the dipeptide Tyr-Arg (kyotorphin); the chromogranin-derived polypeptide (CgA 47-66; See, e.g., Ghia et al. 2004 Regulatory polypeptides 119:199); CCK receptor agonists such as caerulein; conotoxin polypeptides; peptide analogs of thymulin (FR Application 2830451); CCK (CCKa or CCKb) receptor antagonists, including loxiglumide and dexloxiglumide (the R-isomer of loxiglumide) (WO 88/05774); 5-HT4 agonists such as tegaserod (Zelnorm®), mosapride, metoclopramide, zacopride, cisapride, renzapride, benzimidazolone derivatives such as BIMU 1 and BIMU 8, and lirexapride; calcium channel blockers such as ziconotide and related compounds described in, for example, EP625162B1, U.S. Pat. Nos. 5,364,842, 5,587,454, 5,824,645, 5,859,186, 5,994,305, 6,087,091, 6,136,786, WO 93/13128 A1, EP 1336409 A1, EP 835126 A1, EP 835126 BI, U.S. Pat. Nos. 5,795,864, 5,891,849, 6,054,429, WO 97/01351 A1; NK-I, receptor antagonists such as aprepitant (Merck & Co Inc), vofopitant, ezlopitant (Pfizer, Inc.), R-673 (Hoffmann-La Roche Ltd), SR-48968 (Sanofi Synthelabo), CP-122,721 (Pfizer, Inc.), GW679769 (Glaxo Smith Kline), TAK-637 (Takeda/Abbot), SR-14033, and related compounds described in, for example, EP 873753 A1, US20010006972 A1, US 20030109417 A1, WO 01/52844 A1 (for a review see Giardina et al. 2003.Drugs 6:758); NK-2 receptor antagonists such as nepadutant (Menarini Ricerche SpA), saredutant (Sanofi Synthelabo), GW597599 (Glaxo Smith Kline), SR-144190 (Sanof~-Synthelabo) and UK-290795 (Pfizer Inc); NK3 receptor antagonists such as osanetant (SR-142801; Sanof~-Synthelabo), SSR-241586, talnetant and related compounds described in, for example, WO 02/094187 A2, EP 876347 A1, WO 97/21680 A1, U.S. Pat. No. 6,277,862, WO 98/1 1090, WO 95/28418, WO 97/19927, and Boden et al. (J Med Chem. 39:1664-75, 1996); norepinephrine-serotonin reuptake inhibitors (NSRI) such as milnacipran and related compounds described in WO 03/077897; and vanilloid receptor antagonists such as arvanil and related compouds described in WO 01/64212 A1.

In addition to sialorphin-related polypeptides, analgesic polypeptides include: AspPhe, endomorphin-1, endomorphin-2, nocistatin, dalargin, lupron, ziconotide, and substance P.

1.2.2.9 Insulin and Insulin Modulating Agents

The GCC agonist peptides described herein can be used in combination therapy with insulin and related compounds including primate, rodent, or rabbit insulin including biologically active variants thereof including allelic variants, more preferably human insulin available in recombinant form. Sources of human insulin include pharmaceutically acceptable and sterile formulations such as those available from Eli Lilly (Indianapolis, Ind. 46285) as Humulin™ (human insulin rDNA origin). See, the THE PHYSICIAN'S DESK REFERENCE, 55.sup.th Ed. (2001) Medical Economics, Thomson Healthcare (disclosing other suitable human insulins).

The GCC peptides described herein can also be used in combination therapy with agents that can boost insulin effects or levels of a subject upon administration, e.g. glipizide and/or rosiglitazone. The polypeptides and agonists described herein can be used in combitherapy with SYMLIN® (pramlintide acetate) and Exenatide® (synthetic exendin-4; a 39 aa polypeptide).

1.2.2.10 Anti-Hypertensive Agents

The GCC agonist peptides described herein can be used in combination therapy with an anti-hypertensive agent including but not limited to: (1) diuretics, such as thiazides, including chlorthalidone, chlorthiazide, dichlorophenamide, hydroflumethiazide, indapamide, polythiazide, and hydrochlorothiazide; loop diuretics, such as bumetanide, ethacrynic acid, furosemide, and torsemide; potassium sparing agents, such as amiloride, and triamterene; carbonic anhydrase inhibitors, osmotics(such as glycerin) and aldosterone antagonists, such as spironolactone, epirenone, and the like; (2) beta-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil, and the like; (4) angiotensin converting enzyme (ACE) inhibitors such as benazepril; captopril; ceranapril; cilazapril; delapril; enalapril; enalopril; fosinopril; imidapril; lisinopril; losinopril; moexipril; quinapril; quinaprilat; ramipril; perindopril; perindropril; quanipril; spirapril; tenocapril; trandolapril, and zofenopril, and the like; (5) neutral endopeptidase inhibitors such as omapatrilat, cadoxatril and ecadotril, fosidotril, sampatrilat, AVE7688, ER4030, and the like; (6) endothelin antagonists such as tezosentan, A308165, and YM62899, and the like; (7) vasodilators such as hydralazine, clonidine, minoxidil, and nicotinyl alcohol, and the like; (8) angiotensin II receptor antagonists such as aprosartan, candesartan, eprosartan, irbesartan, losartan, olmesartan, pratosartan, tasosartan, telmisartan, valsartan, and EXP-3137, FI6828K, and RNH6270, and the like; (9) α/β adrenergic blockers such as nipradilol, arotinolol and amosulalol, and the like; (10) alpha 1 blockers, such as terazosin, urapidil, prazosin, tamsulosin, bunazosin, trimazosin, doxazosin, naftopidil, indoramin, WHP 164, and XENOIO, and the like; (11) alpha 2 agonists such as lofexidine, tiamenidine, moxonidine, rilmenidine and guanobenz, and the like; (12) aldosterone inhibitors, and the like; and (13) angiopoietin-2-binding agents such as those disclosed in WO03/030833. Specific anti-hypertensive agents that can be used in combination with polypeptides and agonists described herein include, but are not limited to: diuretics, such as thiazides (e.g., chlorthalidone, cyclothiazide (CAS RN 2259-96-3), chlorothiazide (CAS RN 72956-09-3, which may be prepared as disclosed in U.S. Pat. No. 2,809,194), dichlorophenamide, hydroflumethiazide, indapamide, polythiazide, bendroflumethazide, methyclothazide, polythiazide, trichlormethazide, chlorthalidone, indapamide, metolazone, quinethazone, althiazide (CAS RN 5588-16-9, which may be prepared as disclosed in British Patent No. 902,658), benzthiazide (CAS RN 91-33-8, which may be prepared as disclosed in U.S. Pat. No. 3,108,097), buthiazide (which may be prepared as disclosed in British Patent Nos. 861,367), and hydrochlorothiazide), loop diuretics (e.g. bumetanide, ethacrynic acid, furosemide, and torasemide), potassium sparing agents (e.g. amiloride, and triamterene (CAS Number 396-01-O)), and aldosterone antagonists (e.g. spironolactone (CAS Number 52-01-7), epirenone, and the like); 0-adrenergic blockers such as Amiodarone (Cordarone, Pacerone), bunolol hydrochloride (CAS RN 31969-05-8, Parke-Davis), acebutolol (±N-[3-Acetyl-4-[2-hydroxy-3-[(1 methylethyl)amino] propoxy]phenyl]-butanamide, or (±)-3'-Acetyl-4'-[2-hydroxy-3-(isopropylamino) propoxy]butyranilide), acebutolol hydrochloride (e.g. Sectral®, Wyeth-Ayerst), alprenolol hydrochloride (CAS RN 13707-88-5 see Netherlands Patent Application No. 6,605,692), atenolol (e.g. Tenormin®, AstraZeneca), carteolol hydrochloride (e.g. Cartrol® Filmtab®, Abbott), Celiprolol hydrochloride (CAS RN 57470-78-7, also see in U.S. Pat. No. 4,034,009), cetamolol hydrochloride (CAS RN 77590-95-5, see also U.S. Pat. No. 4,059,622), labetalol hydrochloride (e.g. Normodyne®, Schering), esmolol hydrochloride (e.g. Brevibloc®, Baxter), levobetaxolol hydrochloride (e.g. Betaxon™ Ophthalmic Suspension, Alcon), levobunolol hydrochloride (e.g. Betagan® Liquifilm® with CCAP® Compliance Cap, Allergan), nadolol (e.g. Nadolol, Mylan), practolol (CAS RN 6673-35-4, see also U.S. Pat. No. 3,408,387), propranolol hydrochloride (CAS RN 318-98-9), sotalol hydrochloride (e.g. Betapace AF™,Berlex), timolol (2-Propanol,l-[(1,1-dimethylethyl)amino]-3-[[4-4(4-morpholinyl)-1,2,5-thiadiazol-3-yl]oxy]-, hemihydrate, (S)-, CAS RN 91524-16-2), timolol maleate (S)-I-[(1,1-dimethylethyl)amino]-3-[[4-(4-morpholinyl)-1,2,5-thiadiazol-3-yl] oxy]-2-propanol (Z)-2-butenedioate (1:1) salt, CAS RN 26921-17-5), bisoprolol (2-Propanol, 1-[4-[[2-(1-methylethoxy)ethoxy]-methyl]phenoxy]-3-[(1-meth-ylethyl) amino]-, (±), CAS RN 66722-44-9), bisoprolol fumarate (such as (±)-1-[4-[[2-(1-Methylethoxy) ethoxy]methyl]phenoxy]-3-[(1-methylethyl)amino]-2-propanol (E)-2-butenedioate (2:1) (salt), e.g., Zebeta™, Lederle Consumer), nebivalol (2H-1-Benzopyran-2-methanol, αα'-[iminobis (methylene)]bis[6-fluoro-3,4-dihydro-, CAS RN 99200-09-6 see also U.S. Pat. No. 4,654,362), cicloprolol hydrochloride, such 2-Propanol, 1-[4-[2-(cyclopropylmethoxy) ethoxy]phenoxy]-3-[1-methylethyl)amino]-, hydrochloride, A.A.S. RN 63686-79-3), dexpropranolol hydrochloride (2-Propanol,l-[1-methylethy)-amino]-3-(1-naphthyloxy)-hydrochloride (CAS RN 13071-11-9), diacetolol hydrochloride (Acetamide, N-[3-acetyl-4-[2-hydroxy-3-[(1-methylethyl)amino]propoxy][phenyl]-, monohydrochloride CAS RN 69796-04-9), dilevalol hydrochloride (Benzamide, 2-hydroxy-5-[1-hydroxy-2-[1-methyl-3-phenylpropyl)amino] ethyl]-, monohydrochloride, CAS RN 75659-08-4), exaprolol hydrochloride (2-Propanol, 1-(2-cyclohexylphenoxy)-3-[(1-methylethyl)amino]-, hydrochloride CAS RN 59333-90-3), flestolol sulfate (Benzoic acid, 2-fluro-,3-[[2-[aminocarbonyl)amino]-dimethylethyl]amino]-2-hydroxy-propyl ester, (+)-sulfate (1:1) (salt), CAS RN 88844-73-9; metalol hydrochloride (Methanesulfonamide, N-[4-[l-hydroxy-2-(methylamino)propyl]phenyl]-, monohydrochloride CAS RN 7701-65-7), metoprolol 2-Propanol, 1-[4-(2-methoxyethyl)phenoxy]-3-[1-methylethyl)amino]-; CAS RN 37350-58-6), metoprolol tartrate (such as 2-Propanol, 1-[4-(2-methoxyethyl)phenoxy]-3-[(1-methylethyl)amino]-, e.g., Lopressor®, Novartis), pamatolol sulfate (Carbamic acid, [2-[4-[2-hydroxy-3-[(1-methylethyl)amino]propoxyl] phenyl]-ethyl]-, methyl ester, (±) sulfate (salt) (2:1), CAS RN 59954-01-7), penbutolol sulfate (2-Propanol, 1-(2-cyclopentylphenoxy)-3-[1,1-dimethyle-thyl)amino]1, (S)-, sulfate (2:1) (salt), CAS RN 38363-32-5), practolol (Acetamide, N-[4-[2-hydroxy-3-[(1-methylethyl)amino]-propoxy]phenyl]-, CAS RN 6673-35-4;) tiprenolol hydrochloride (Propanol, 1-[(1-methylethyl)amino]-3-[2-(methylthio)-phenoxy]-, hydrochloride, (±), CAS RN 39832-43-4), tolamolol (Benzamide, 4-[2-[[2-hydroxy-3-(2-methylphenoxy)-propyl]amino]ethoxyl]-, CAS RN 38103-61-6), bopindolol, indenolol, pindolol, propanolol, tertatolol, and tilisolol, and the like; calcium channel blockers such as besylate salt of amlodipine (such as 3-ethyl-5-methyl-2-(2-aminoethoxymethyl)-4-(2-chlorophenyl)-1,4-dihydro-6-methyl-3,5-pyridinedicarboxylate benzenesulphonate, e.g., Norvasc®, Pfizer), clentiazem maleate (1,5-Benzothiazepin-4(5H)-one, 3-(acetyloxy)-8-chloro-5-[2-(dimethylamino)ethyl]-2,3-dihydro-2-(4-methoxyphenyl)-(2S-cis)-, (Z)-2-butenedioate (1:1), see also U.S. Pat. No. 4,567,195), isradipine (3,5-Pyridinedicarboxylic acid, 4-(4-benzofurazanyl)-1,4-dihydro-2,6-dimethyl-, methyl 1-methylethyl ester, (±)-4(4-benzofurazanyl)-1,4-dihydro-2, 6-dimethyl-3,5-pyridinedicarboxylate, see also U.S. Pat. No. 4,466,972); nimodipine (such as is isopropyl (2-methoxyethyl) 1, 4-dihydro-2,6-dimethyl-4-(3-nitrophenyl)-3,5-pyridine-dicarboxylate, e.g. Nimotop®, Bayer), felodipine (such as ethyl methyl 4-(2,3-dichlorophenyl)-1,4-dihydro-2, 6-dimethyl-3,5-pyridinedicarboxylate-, e.g. Plendil® Extended-Release, AstraZeneca LP), nilvadipine (3,5-Pyridinedicarboxylic acid, 2-cyano-1,4-dihydro-6-methyl-4-(3-nitrophenyl)-,3-methyl 5-(1-methylethyl) ester, also see U.S. Pat. No. 3,799,934), nifedipine (such as 3, 5-pyridinedicarboxylic acid,1,4-dihydro-2,6-dimethyl-4-(2-nitrophenyl)-, dimethyl ester, e.g., Procardia XL® Extended Release Tablets, Pfizer), diltiazem hydrochloride (such as 1,5-Benzothiazepin-4(5H)-one,3-(acetyloxy)-5[2-(dimethylamino) ethyl]-2,-3-dihydro-2(4-methoxyphenyl)-, monohydrochloride, (+)-cis, e.g., Tiazac®, Forest), verapamil hydrochloride (such as benzeneacetonitrile, (alpha)-[[3-[[2-(3,4-dimethoxyphenyl)ethyl]methylamino]propyl]-3,4-dimethoxy-(alpha)-(1-methylethyl) hydrochloride, e.g., Isoptin® SR, Knoll Labs), teludipine hydrochloride (3,5-Pyridinedicarboxylic acid, 2-[(dimethylamino)methyl]4-[2-[(1E)-3-(1,1-dimethylethoxy)-3-oxo-1-propenyl]phenyl]-1,4-dihydro-6-methyl-, diethyl ester, monohydrochloride CAS RN 108700-03-4), belfosdil (Phosphonic acid, [2-(2-phenoxy ethyl)-1,3-propane-diyl]bis-, tetrabutyl ester CAS RN 103486-79-9), fostedil (Phosphonic acid, [[4-(2-benzothiazolyl)phenyl]methyl]-, diethyl ester CAS RN 75889-62-2), aranidipine, azelnidipine, barnidipine, benidipine, bepridil, cinaldipine, clevidipine, efonidipine, gallopamil, lacidipine, lemildipine, lercanidipine, monatepil maleate (1-Piperazinebutanamide, N-(6, 11-dihydrodibenzo(b,e)thiepin-11-yl)4-(4-fluorophenyl)-, (+)-, (Z)-2-butenedioate (1:1) (±)-N-(6,11-Dihydrodibenzo(b,e)thiep-in-l 1-yl)-4-(p-fluorophenyl)-1-piperazinebutyramide maleate (1:1) CAS RN 132046-06-1), nicardipine, nisoldipine, nitrendipine, manidipine, pranidipine, and the like; T-channel calcium antagonists such as mibefradil; angiotensin converting enzyme (ACE) inhibitors such as benazepril, benazepril hydrochloride (such as 3-[[1-(ethoxycarbonyl)-3-phenyl-(1 S)-propyl]amino]-2,3,4,5-tetrahydro-2-oxo-1H-1-(3 S)-benzazepine-1-acetic acid monohydrochloride, e.g., Lotrel®, Novartis), captopril (such as 1-[(2S)-3-mercapto-2-methylpropionyl]-L-proline, e.g., Captopril, Mylan, CAS RN 62571-86-2 and others disclosed in U.S. Pat. No. 4,046, 889), ceranapril (and others disclosed in U.S. Pat. No. 4,452,790), cetapril (alacepril, Dainippon disclosed in Eur. Therap. Res. 39:671 (1986); 40:543 (1986)), cilazapril (Hoffman-LaRoche) disclosed in J. Cardiovasc. Pharmacol. 9:39 (1987), indalapril (delapril hydrochloride (2H-1,2,4-Benzothiadiazine-7-sulfonamide, 3-bicyclo[2.2.1]hept-5-en-2-yl-6-chloro-3,4-dihydro-, 1,1-dioxide CAS RN 2259-96-3); disclosed in U.S. Pat. No. 4,385,051), enalapril (and others disclosed in U.S. Pat. No. 4,374,829), enalopril, enaloprilat, fosinopril, ((such as L-proline, 4-cyclohexyl-l-[[[2-methyl-1-(1-oxopropoxy) propoxy](4-phenylbutyl) phosphinyl]acetyl]-, sodium salt, e.g., Monpril, Bristol-Myers Squibb and others disclosed in U.S. Pat. No. 4,168, 267), fosinopril sodium (L-Proline, 4-cyclohexyl-l-[[(R)-[(1S)-2-methyl-l-(1-ox-opropoxy)propox), imidapril, indolapril (Schering, disclosed in J. Cardiovasc. Pharmacol. 5:643, 655 (1983)), lisinopril (Merck), losinopril, moexipril, moexipril hydrochloride (3-Isoquinolinecarboxylic acid, 2-[(2S)-2-[[(1S)-1-(ethoxycarbonyl)-3-phenylpropyl] amino]-1 oxopropyl]-1,-2,3,4-tetrahydro-6,7-dimethoxy-, monohydrochloride, (3S)-CAS RN 82586-52-5), quinapril, quinaprilat, ramipril (Hoechsst) disclosed in EP 79022 and Curr. Ther. Res. 40:74 (1986), perindopril erbumine (such as 2S,3aS,7aS-1-[(S)-N-[(S)-1-Carboxybutyl]alanyl]hexahydro/\-indolinecarboxylic acid, 1-ethyl ester, compound with tert-butylamine (1:1), e.g., Aceon®, Solvay), perindopril (Servier, disclosed in Eur. J. clin. Pharmacol. 31:519 (1987)), quanipril (disclosed in U.S. Pat. No. 4,344,949), spirapril (Schering, disclosed in Acta. Pharmacol. Toxicol. 59 (Supp. 5): 173 (1986)), tenocapril, trandolapril, zofenopril (and others disclosed in U.S. Pat. No. 4,316,906), rentiapril (fentiapril, disclosed in Clin. Exp. Pharmacol. Physiol. 10:131 (1983)), pivopril, YS980, teprotide (Bradykinin potentiator BPP9a CAS RN 35115-60-7), BRL 36,378 (Smith Kline Beecham, see EP80822 and EP60668), MC-838 (Chugai, see CA. 102:72588v and Jap. J. Pharmacol. 40:373 (1986), CGS 14824 (Ciba-Geigy, 3-([1-ethoxycarbonyl-3-phenyl-(1S)-propyl]amino)-2,3,4,5-tetrahydro-2-ox-o-1-(3S)-benzazepine-1 acetic acid HCl, see U.K. Patent No. 2103614), CGS 16,617 (Ciba-Geigy, 3(S)-[[(1S)-5-amino-1-carboxypentyl]amino]-2,3,4,-5-tetrahydro-2-oxo-1H-1-benzazepine-1-ethanoic acid, see U.S. Pat. No. 4,473,575), Ru 44570 (Hoechst, see Arzneimittelforschung 34:1254 (1985)), R 31-2201 (Hoffman-LaRoche see FEBS Lett. 165:201 (1984)), CI925 (Pharmacologist 26:243, 266 (1984)), WY-44221 (Wyeth, see J. Med. Chem. 26:394 (1983)), and those disclosed in US2003006922 (paragraph 28), US4337201, US4432971 (phosphonamidates); neutral endopeptidase inhibitors such as omapatrilat (Vanlev®), CGS 30440, cadoxatril and ecadotril, fasidotril (also known as aladotril or alatriopril), sampatrilat, mixanpril, and gemopatrilat, AVE7688, ER4030, and those disclosed in US5362727, US5366973, US5225401, US4722810, US5223516, US4749688, US5552397, US5504080, US5612359, US5525723, EP0599444, EP0481522, EP0599444, EP0595610, EP0534363, EP534396, EP534492, EP0629627; endothelin antagonists such as tezosentan, A308165, and YM62899, and the like; vasodilators such as hydralazine (apresoline), clonidine (clonidine hydrochloride (1H-Imidazol-2-amine, N-(2,6-dichlorophenyl)4,5-dihydro-, monohydrochloride CAS RN 4205-91-8), catapres, minoxidil (loniten), nicotinyl alcohol (roniacol), diltiazem hydrochloride (such as 1,5-Benzothiazepin 4(5H)-one,3-(acetyloxy)-5[2-(dimethylamino)ethyl]-2,-3-dihydro-2(4-methoxyphenyl)-, monohydrochloride, (+)-cis, e.g., Tiazac®, Forest), isosorbide dinitrate (such as 1,4:3,6-dianhydro-D-glucitol 2,5-dinitrate e.g., Isordil® Titradose®, Wyeth-Ayerst), sosorbide mononitrate (such as 1,4:3,6-dianhydro-D-glucito-1,5-nitrate, an organic nitrate, e.g., Ismo®, Wyeth-Ayerst), nitroglycerin (such as 2,3 propanetriol trinitrate, e.g., Nitrostat® Parke-Davis), verapamil hydrochloride (such as benzeneacetonitrile, (±)-(alpha)[3-[[2-(3,4 dimethoxypheny l)ethyl]methylamino]propyl]-3,4-dimethoxy-(alpha)-(1-methylethyl) hydrochloride, e.g., Covera HS® Extended-Release, Searle), chromonar (which may be prepared as disclosed in U.S. Pat. No. 3,282,938), clonitate (Annalen 1870 155), droprenilamine (which may be prepared as disclosed in DE2521113), lidoflazine (which may be prepared as disclosed in U.S. Pat. No. 3,267,104); prenylamine (which may be prepared as disclosed in U.S. Pat. No. 3,152,173), propatyl nitrate (which may be prepared as disclosed in French Patent No. 1, 103,113), mioflazine hydrochloride (1-Piperazineacetamide, 3-(aminocarbonyl)4-[4,4-bis(4-fluorophenyl)butyl]-N-(2,6-dichlorophenyl)-, dihydrochloride CAS RN 83898-67-3), mixidine (Benzeneethanamine, 3,4-dimethoxy-N-(1-methyl-2-pyrrolidinylidene)-Pyrrolidine, 2-[(3,4-dimethoxyphenethyl)imino]-1-methyl-1-Methyl-2-[(3, 4-dimethoxyphenethyl)imino]pyrrolidine CAS RN 27737-38-8), molsidomine (1,2,3-Oxadiazolium, 5-[(ethoxycarbonyl) amino]-3-(4-morpholinyl)-, inner salt CAS RN 25717-80-0), isosorbide mononitrate (D-Glucitol, 1,4:3,6-dianhydro-, 5-nitrate CAS RN 16051-77-7), erythrityl tetranitrate (1,2, 3,4-Butanetetrol, tetranitrate, (2R,3S)-rel-CAS RN 7297-25-8), clonitrate(1,2-Propanediol, 3-chloro-, dinitrate (7CI, 8CI, 9CI) CAS RN 2612-33-1), dipyridamole Ethanol, 2,2', 2",2'"-[(4,8-di-1-piperidinylpyrimido[5,4-d]pyrimidine-2,6-diyl)dinitrilo]tetrakis-CAS RN 58-32-2), nicorandil (CAS RN 65141-46-0 3-), pyridinecarboxamide (N-[2-(nitrooxy) ethyl]-Nisoldipine3,5-Pyridinedicarboxylic acid, 1,4-dihydro-2,6-dimethyl-4-(2-nitrophenyl)-, methyl 2-methylpropyl ester CAS RN 63675-72-9), nifedipine3,5-Pyridinedicarboxylic acid, 1,4-dihydro-2,6-dimethyl-4-(2-nitrophenyl)-, dimethyl ester CAS RN 21829-25-4), perhexiline maleate (Piperidine, 2-(2,2-dicyclohexylethyl)-, (2Z)-2-butenedioate (1:1) CAS RN 6724-53-4), oxprenolol hydrochloride (2-Propanol, 1-[(1-methylethyl)amino]-3-[2-

(2-propenyloxy)phenoxy]-, hydrochloride CAS RN 6452-73-9), pentrinitrol (1,3-Propanediol, 2,2-bis[(nitrooxy)methyl]-, mononitrate (ester) CAS RN 1607-17-6), verapamil (Benzeneacetonitrile, α-[3-[[2-(3,4-dimethoxyphenyl)ethyl]-methylamino]propyl]-3, 4-dimethoxy-a-(1-methylethyl)-CAS RN 52-53-9) and the like; angiotensin II receptor antagonists such as, aprosartan, zolasartan, olmesartan, pratosartan, FI6828K, RNH6270, candesartan (1 H-Benzimidazole-7-carboxylic acid, 2-ethoxy-l-[[2'-(1H-tetrazol-5-yl)[1,1'-biphenyl]4-yl]methyl]-CAS RN 139481-59-7), candesartan cilexetil ((+/−)-1-(cyclohexylcarbonyloxy)ethyl-2-ethoxy-1-[[2'-(1H-tetrazol-5-yl)biphenyl-4-yl]-1H-benzimidazole carboxylate, CAS RN 145040-37-5, US5703110 and US5196444), eprosartan (3-[1-4-carboxyphenylmethyl)-2-n-butyl-imidazol-5-yl]-(2-thienylmethyl) propenoic acid, US5185351 and US5650650), irbesartan (2-n-butyl-3-[[2'-(1h-tetrazol-5-yl)biphenyl-4-yl]methyl]1, 3-diazazspiro[4,4]non-l-en-4-one, US5270317 and US5352788), losartan (2-N-butyl-4-chloro-5-hydroxymethyl-l-[(2'-(1H-tetrazol-5-yl)biphenyl-4-yl)-methyl]imidazole, potassium salt, U.S. Pat. Nos. 5,138,069, 5,153,197 and 5,128,355), tasosartan (5,8-dihydro-2,4-dimethyl-8-[[2'-(1H-tetrazol-5-yl)[1,r-biphenyl]4-yl]methyl]-pyrido[2,3-d] pyrimidin-7(6H)-one, US5149699), telmisartan (4'-[(1,4-dimethyl-2'-propyl-(2,6'-bi-1H-benzimidazol)-r-yl)]-[1 , 1'-biphenyl]-2-carboxylic acid, CAS RN 144701-48-4, U.S. Pat. No. 5,591,762), milfasartan, abitesartan, valsartan (Diovan® (Novartis), (S)-N-valeryl-N-[[2'-(1H-tetrazol-5-yl)biphenyl-4-yl]methyl]valine, U.S. Pat. No. 5,399,578), EXP-3137 (2-N-butyl-4-chloro-l-[(2'-(1H-tetrazol-5-yl)biphenyl-4-yl)-methyl]imidazole-5-carboxylic acid, U.S. Pat. Nos. 5,138,069, 5,153,197 and 5,128,355), 3-(2'-(tetrazol-5-yl)-1,r-biphen-4-yl)methyl-5,7-dimethyl-2-ethyl-3H-imidazo[4, 5-b]pyridine, 4'[2-ethyl-4-methyl-6-(5, 6, 7, 8-tetrahydroimidazo [1, 2-a]pyridin-2-yl]-benzimidazol-l-yl]-methyl]-1, r-biphenyl]-2-carboxylic acid, 2-butyl-6-(1-methoxy-1-methylethyl)-2-[2'-)IH-tetrazol-5-yl)biphenyl-4-ylmethyl] guinazolin-4(3H)-one, 3-[2'-carboxybiphenyl-4-yl)methyl]-2-cyclopropyl-7-methyl-3H-imidazo[4,5-b]pyridine, 2-butyl-4-chloro-l-[(2'-tetrazol-5-yl)biphenyl-4-yl)methyl] imidazole-carboxylic acid, 2-butyl-4-chloro-l-[[2'-(1H-tetrazol-5-yl) [1, 1'-biphenyl]-4-yl]methyl]-1 H-imidazole-5-carboxylic acid-1-(ethoxycarbonyl-oxy)ethyl ester potassium salt, dipotassium 2-butyl-4-(methylthio)-1-[[2-[[[(propylamino)carbonyl]amino]-sulfonyl](1,1'-biphenyl)-4-yl]methyl]-1 H-imidazole-5-carboxylate, methyl-2-[[4-butyl-2-methyl-6-oxo-5-[[2'-(1H-tetrazol-5-yl)-[1,1'-biphenyl]-4-yl]methyl]-1-(6H)-pyrimidinyl]methyl]-3-thiophencarboxylate, 5-[(3,5-dibutyl-1H-1,2,4-triazol-1-yl) methyl]-2-[2-(1 H-tetrazol-5-ylphenyl)]pyridine, 6-butyl-2-(2-phenylethyl)-5 [[2'-(I H-tetrazol-5-yl)[1,1'-biphenyl]-4-methyl]pyrimidin-4-(3H)-one D,L lysine salt, 5-methyl-7-n-propyl-8-[[2'-(1H-tetrazol-5-yl)biphenyl-4-yl]methyl]-[1 ,2,4]-triazolo[1,5-c]pyrimidin-2(3H)-one, 2,7-diethyl-5-[[2'-(5-tetrazoly)biphenyl-4-yl]methyl]-5H-pyrazolo[1,5-b] [1,2,4]triazole potassium salt, 2-[2-butyl-4,5-dihydro-4-oxo-3-[2'-(1H-tetrazol-5-yl)-4-biphenylmethyl]-3H-imidazol[4,5-c]pyridine-5-ylmethyl]benzoic acid, ethyl ester, potassium salt, 3-methoxy-2,6-dimethyl-4-[[2'(1H-tetrazol-5-yl)-1,1'-biphenyl-4-yl]methoxy]pyridine, 2-ethoxy-l-[[2'-(5-oxo-2,5-dihydro-1,2,4-oxadiazol-3 yl)biphenyl-4-yl]methyl]-1 H-benzimidazole-7-carboxylic acid, 1-[N-(2'-(1 H-tetrazol-5-yl)biphenyl-4-yl-methyl)-N-valerolylaminomethyl)cyclopentane-1-carboxylic acid, 7-methyl-2n-propyl-3-[[2' 1H-tetrazol-5-yl)biphenyl-4-yl] methyl]-3H-imidazo[4,5-6]pyridine, 2-[5-[(2-ethyl-5,7-dimethyl-3H-imidazo[4,5-b]pyridine-3-yl)methyl]-2-quinolinyl]sodium benzoate, 2-butyl-6-chloro-4-hydroxymethyl-5-methyl-3-[[2'-(I H-tetrazol-5-yl)biphenyl-4-yl]methyl] pyridine, 2-[[[2-butyl-1-[(4-carboxyphenyl)methyl]-1 H-imidazol-5-yl]methyl]amino]benzoic acid tetrazol-5-yl) biphenyl-4-yl]methyl]pyrimidin-6-one, 4(S)-[4-(carboxymethyl)phenoxy]-N-[2(R)-[4-(2-sulfobenzamido)imidazol-1-yl]octanoyl]-L-proline, 1 (2,6-dimethylphenyl)-4-butyl-1,3-dihydro-3-[[6-[2-(1H-tetrazol-5-yl)phenyl]-3-pyridinyl] methyl]-2H-imidazol-2-one, 5,8-ethano-5,8-dimethyl-2-n-propyl-5,6,7,8-tetrahydro-1-[[2'(1H-tetrazol-5-yl)biphenyl-4-yl]methyl]-1H,4H-1,3,4a,8a-tetrazacyclopentanaphthalene-9-one, 4-[1-[2'-(1,2,3,4-tetrazol-5-yl)biphen-4-yl)methylamino]-5,6,7,8-tetrahydro-2-trifylquinazoline, 2-(2-chlorobenzoyl)imino-5-ethyl-3-[2'-(1H-tetrazole-5-yl)biphenyl-4-yl)methyl-1,3,4-thiadiazoline, 2-[5-ethyl-3-[2-(1H-tetrazole-5-yl)biphenyl-4-yl]methyl-1,3,4-thiazoline-2-ylidene]aminocarbonyl-1-cyclopentencarboxylic acid dipotassium salt, and 2-butyl-4-[N-methyl-N-(3-methylcrotonoyl)amino]-1-[[2'-(1 H-tetrazol-5-yl)biphenyl-4-yl]methyl]-1 H-imidzole-5-carboxylic acid 1-ethoxycarbonyloxyethyl ester, those disclosed in patent publications EP475206, EP497150, EP539086, EP539713, EP535463, EP535465,EP542059, EP497121, EP535420, EP407342, EP415886, EP424317, EP435827, EP433983, EP475898, EP490820, EP528762, EP324377, EP323841, EP420237, EP500297, EP426021, EP480204, EP429257, EP430709, EP434249, EP446062, EP505954, EP524217, EP514197, EP514198, EP514193, EP514192, EP450566, EP468372, EP485929, EP503162, EP533058, EP467207 EP399731, EP399732, EP412848, EP453210, EP456442, EP470794, EP470795, EP495626, EP495627, EP499414, EP499416, EP499415, EP511791, EP516392, EP520723, EP520724, EP539066, EP438869, EP505893, EP530702, EP400835, EP400974, EP401030, EP407102, EP411766, EP409332, EP412594, EP419048, EP480659, EP481614, EP490587, EP467715, EP479479, EP502725, EP503838, EP505098, EP505111 EP513,979 EP507594, EP510812, EP511767, EP512675, EP512676, EP512870, EP517357, EP537937, EP534706, EP527534, EP540356, EP461040, EP540039, EP465368, EP498723, EP498722, EP498721, EP515265, EP503785, EP501892, EP519831, EP532410, EP498361, EP432737, EP504888, EP508203, EP508445, EP403159, EP403158, EP425211, EP427463, EP437103, EP481448, EP488532, EP501269, EP500409, EP540400, EP005528, EP028834, EP028833, EP411507, EP425921, EP430300, EP434038, EP442473, EP443568, EP445811, EP459136, EP483683, EP518033, EP520423, EP531876, EP531874, EP392317, EP468470, EP470543, EP502314, EP529253, EP543263, EP540209, EP449699, EP465323, EP521768, EP415594, WO92/14468, WO93/08171, WO93/08169, WO91/00277, WO91/00281, WO91/14367, WO92/00067, WO92/00977, WO92/20342, WO93/04045, WO93/04046, WO91/15206, WO92/14714, WO92/09600, WO92/16552, WO93/05025, WO93/03018, WO91/07404, WO92/02508, WO92/13853, WO91/19697, WO91/11909, WO91/12001, WO91/11999, WO91/15209, WO91/15479, WO92/20687, WO92/20662, WO92/20661, WO93/01177, WO91/14679, WO91/13063, WO92/13564, WO91/17148, WO91/18888, WO91/19715, WO92/02257, WO92/04335, WO92/05161, WO92/07852, WO92/15577, WO93/03033, WO91/16313, WO92/00068, WO92/02510, WO92/09278, WO9210179, WO92/10180, WO92/10186, WO92/10181, WO92/10097, WO92/10183, WO92/10182, WO92/10187, WO92/10184, WO92/10188, WO92/10180, WO92/10185, WO92/20651, WO93/03722, WO93/06828, WO93/03040, WO92/19211, WO92/22533, WO92/06081, WO92/05784, WO93/00341, WO92/04343, WO92/

04059, U.S. Pat. Nos. 5,104,877, 5,187,168, 5,149,699, 5,185,340, 4,880,804, 5,138,069, 4,916,129, 5,153,197, 5,173,494, 5,137,906, 5,155,126, 5,140,037, 5,137,902, 5,157,026, 5,053,329, 5,132,216, 5,057,522, 5,066,586, 5,089,626, 5,049,565, 5,087,702, 5,124,335, 5,102,880, 5,128,327, 5,151,435, 5,202,322, 5,187,159, 5,198,438, 5,182,288, 5,036,048, 5,140,036, 5,087,634, 5,196,537, 5,153,347, 5,191,086, 5,190,942, 5,177,097, 5,212,177, 5,208,234, 5,208,235, 5,212,195, 5,130,439, 5,045,540, 5,041,152, and 5,210,204, and pharmaceutically acceptable salts and esters thereof; α/β adrenergic blockers such as nipradilol, arotinolol, amosulalol, bretylium tosylate (CAS RN: 61-75-6), dihydroergtamine mesylate (such as ergotaman-3', 6',18-trione,9,-10-dihydro-12'-hydroxy-2'-methyl-5'-(phenylmethyl)-,(5'(α))-, monomethanesulfonate, e.g., DHE 45® Injection, Novartis), carvedilol (such as (±)-1-(Carbazol-4-yloxy)-3-[[2-(o-methoxyphenoxy)ethyl]amino]-2-propanol, e.g., Coreg®, SmithKline Beecham), labetalol (such as 5-[1-hydroxy-2-[(1-methyl-3-phenylpropyl)amino]ethyl]salicylamide monohydrochloride, e.g., Normodyne®, Schering), bretylium tosylate (Benzenemethanaminium, 2-bromo-N-ethyl-N,N-dimethyl-, salt with 4-methylbenzenesulfonic acid (1:1) CAS RN 61-75-6), phentolamine mesylate (Phenol, 3-[[(4,5-dihydro-1H-imidazol-2-yl)methyl](4-methylphenyl)amino]-, monomethanesulfonate (salt) CAS RN 65-28-1), solypertine tartrate (5H-1,3-Dioxolo[4,5-f]indole, 7-[2-[4-(2-methoxyphenyl)-1-piperazinyl]ethyl]-, (2R,3R)-2,3-dihydroxybutanedioate (1:1) CAS RN 5591-43-5), zolertine hydrochloride (Piperazine, 1-phenyl4-[2-(1H-tetrazol-5-yl)ethyl]-, monohydrochloride (8Cl, 9Cl) CAS RN 7241-94-3) and the like; a adrenergic receptor blockers, such as alfuzosin (CAS RN: 81403-68-1), terazosin, urapidil, prazosin (Minipress®), tamsulosin, bunazosin, trimazosin, doxazosin, naftopidil, indoramin, WHP 164, XENOIO, fenspiride hydrochloride (which may be prepared as disclosed in U.S. Pat. No. 3,399,192), proroxan (CAS RN 33743-96-3), and labetalol hydrochloride and combinations thereof, α 2 agonists such as methyldopa, methyldopa HCL, lofexidine, tiamenidine, moxonidine, rilmenidine, guanobenz, and the like; aldosterone inhibitors, and the like; renin inhibitors including Aliskiren (SPPlOO; Novartis/Speedel); angiopoietin-2-binding agents such as those disclosed in WO03/030833; anti-angina agents such as ranolazine (hydrochloride 1-Piperazineacetamide, N-(2,6-dimethylphenyl)-4-[2-hydroxy-3-(2-methoxyphenoxy)propyl]-, dihydrochloride CAS RN 95635-56-6), betaxolol hydrochloride (2-Propanol, 1-[4-[2(cyclopropylmethoxy)ethyl]phenoxy]-3-[(1-methylethyl) amino]-, hydrochloride CAS RN 63659-19-8), butoprozine hydrochloride (Methanone, [4-[3(dibutylamino)propoxy] phenyl](2-ethyl-3-indolizinyl)-, monohydrochloride CAS RN 62134-34-3), cinepazet maleatel-Piperazineacetic acid, 4-[1-oxo-3-(3,4,5-trimethoxyphenyl)-2-propenyl]-, ethyl ester, (2Z)-2-butenedioate (1:1) CAS RN 50679-07-7), tosifen (Benzenesulfonamide, 4-methyl-N-[[[(1S)-1-methyl-2-phenylethyl]amino]carbonyl]-CAS RN 32295-184), verapamilhydrochloride (Benzeneacetonitrile, α-[3-[[2-(3,4-dimethoxyphenyl)ethyl]methylamino]propyl]-3,4-dimethoxy-a-(1-methylethyl)-, monohydrochloride CAS RN 152-114), molsidomine (1,2,3-Oxadiazolium, 5-[(ethoxycarbonyl)amino]-3-(4-morpholinyl)-, inner salt CAS RN 25717-80-0), and ranolazine hydrochloride (1-Piperazineacetamide, N-(2,6-dimethylphenyl)4-[2-hydroxy-3-(2-meth-oxyphenoxy)propyl]-, dihydrochloride CAS RN 95635-56-6); tosifen (Benzenesulfonamide, 4-methyl-N-[[[(1S)-1-methyl-2-phenylethyl]amino]carbonyl]-CAS RN 32295-184); adrenergic stimulants such as guanfacine hydrochloride (such as N-amidino-2-(2,6-dichlorophenyl) acetamide hydrochloride, e.g., Tenex® Tablets available from Robins); methyldopa-hydrochlorothiazide (such as levo-3-(3,4-dihydroxyphenyl)-2-methylalanine) combined with Hydrochlorothiazide (such as 6-chloro-3,4-dihydro-2H-1,2,4-benzothiadiazine-7-sulfonamide 1,1-dioxide, e.g., the combination as, e.g., Aldoril® Tablets available from Merck), methyldopa-chlorothiazide (such as 6-chloro-2H-1, 2,4-benzothiadiazine-7-sulfonamide 1,1-dioxide and methyldopa as described above, e.g., Aldoclor®, Merck), clonidine hydrochloride (such as 2-(2,6-dichlorophenylamino)-2-imidazoline hydrochloride and chlorthalidone (such as 2-chloro-5-(1-hydroxy-3-oxo-1-isoindolinyl)benzenesulfonamide), e.g., Combipres®, Boehringer Ingelheim), clonidine hydrochloride (such as 2-(2,6-dichlorophenylamino)-2-imidazoline hydrochloride, e.g., Catapres®, Boehringer Ingelheim), clonidine (1H-Imidazol-2-amine, N-(2,6-dichlorophenyl)4,5-dihydro-CAS RN 4205-90-7), Hyzaar (Merck; a combination of losartan and hydrochlorothiazide), Co-Diovan (Novartis; a combination of valsartan and hydrochlorothiazide, Lotrel (Novartis; a combination of benazepril and amlodipine) and Caduet (Pfizer; a combination of amlodipine and atorvastatin), and those agents disclosed in US20030069221.

1.2.2.11 Agents for the Treatment of Respiratory Disorders

The GCC agonist peptides described herein can be used in combination therapy with one or more of the following agents useful in the treatment of respiratory and other disorders including but not limited to: (1) β-agonists including but not limited to: albuterol (PRO VENTIL®, S ALBUT AMOl®, VENTOLIN®), bambuterol, bitoterol, clenbuterol, fenoterol, formoterol, isoetharine (BRONKOSOL®, BRONKOMETER®), metaproterenol (ALUPENT®, METAPREL®), pirbuterol (MAXAIR®), reproterol, rimiterol, salmeterol, terbutaline (BRETHAIRE®, BRETHINE®, BRICANYL®), adrenalin, isoproterenol (ISUPREL®), epinephrine bitartrate (PRIMATENE®), ephedrine, orciprenline, fenoterol and isoetharine; (2) steroids, including but not limited to beclomethasone, beclomethasone dipropionate, betamethasone, budesonide, bunedoside, butixocort, dexamethasone, flunisolide, fluocortin, fluticasone, hydrocortisone, methyl prednisone, mometasone, predonisolone, predonisone, tipredane, tixocortal, triamcinolone, and triamcinolone acetonide; (3) β2-agonist-corticosteroid combinations [e.g., salmeterol-fluticasone (AD V AIR®), formoterol-budesonid (S YMBICORT®)]; (4) leukotriene D4 receptor antagonists/leukotriene antagonists/LTD4 antagonists (i.e., any compound that is capable of blocking, inhibiting, reducing or otherwise interrupting the interaction between leukotrienes and the Cys LTI receptor) including but not limited to: zafhiukast, montelukast, montelukast sodium (SINGULAIR®), pranlukast, iralukast, pobilukast, SKB-106,203 and compounds described as having LTD4 antagonizing activity described in U.S. Pat. No. 5,565,473; (5) 5-lipoxygenase inhibitors and/or leukotriene biosynthesis inhibitors [e.g., zileuton and BAY1005 (CA registry 128253-31-6)]; (6) histamine H1 receptor antagonists/antihistamines (i.e., any compound that is capable of blocking, inhibiting, reducing or otherwise interrupting the interaction between histamine and its receptor) including but not limited to: astemizole, acrivastine, antazoline, azatadine, azelastine, astamizole, bromopheniramine, bromopheniramine maleate, carbinoxamine, carebastine, cetirizine, chlorpheniramine, chlorpheniramine maleate, cimetidine clemastine, cyclizine, cyproheptadine, descarboethoxyloratadine, dexchlorpheniramine, dimethindene, diphenhydramine, diphenylpyraline, doxylamine succinate, doxylarnine, ebastine, efletirizine, epinastine, famotidine, fexofenadine, hydroxyzine, hydroxyzine, ketotifen, levocabastine, levocetirizine, levocetirizine, loratadine, meclizine, mepyramine, mequitazine, methdilazine, mianserin, mizolastine, noberastine, norasternizole, noraztemizole, phenindamine, pheniramine, picumast, promethazine, pynlamine, pyrilamine, ranitidine, temelastine, terfenadine, trimeprazine, tripelenamine, and triprolidine; (7) an anticholinergic including but not limited to: atropine, benztropine, biperiden, flutropium, hyoscyamine (e.g. Levsin®; Levbid®; Levsin/SL®, Anaspaz®, Levsinex timecaps®, NuLev®), ilutropium, ipratropium, ipratropium bromide, methscopolamine, oxybutinin, rispenzepine, scopolamine, and tiotropium; (8) an anti-tussive including but not limited to: dextromethorphan, codeine, and hydromorphone; (9) a decongestant including but not limited to: pseudoephedrine and phenylpropanolamine; (10) an expectorant including but not limited to: guafenesin, guaicolsulfate, terpin, ammonium chloride, glycerol guaicolate, and iodinated glycerol; (11) a bronchodilator including but not limited to: theophylline and aminophylline; (12) an anti-inflammatory including but not limited to: fluribiprofen, diclophenac, indomethacin, ketoprofen, S-ketroprophen, tenoxicam; (13) a PDE (phosphodiesterase) inhibitor including but not limited to those disclosed herein; (14) a recombinant humanized monoclonal antibody [e.g. xolair (also called omalizumab), rhuMab, and talizumab]; (15) a humanized lung surfactant including recombinant forms of surfactant proteins SP—B, SP—C or SP-D [e.g. SURFAXIN®, formerly known as dsc-104 (Discovery Laboratories)], (16) agents that inhibit epithelial sodium channels (ENaC) such as amiloride and related compounds; (17) antimicrobial agents used to treat pulmonary infections such as acyclovir, amikacin, amoxicillin, doxycycline, trimethoprin sulfamethoxazole, amphotericin B, azithromycin, clarithromycin, roxithromycin, clarithromycin, cephalosporins (ceffoxitin, cefmetazole etc), ciprofloxacin, ethambutol, gentimycin, ganciclovir, imipenem, isoniazid, itraconazole, penicillin, ribavirin, rifampin, rifabutin,amantadine, rimantidine, streptomycin, tobramycin, and vancomycin; (18) agents that activate chloride secretion through Ca++dependent chloride channels (such as purinergic receptor (P2Y(2) agonists); (19) agents that decrease sputum viscosity, such as human recombinant DNase 1, (Pulmozyme®); (20) nonsteroidal anti-inflammatory agents (acemetacin, acetaminophen, acetyl salicylic acid, alclofenac, alminoprofen, apazone, aspirin, benoxaprofen, bezpiperylon, bucloxic acid, carprofen, clidanac, diclofenac, diclofenac, diflunisal, diflusinal, etodolac, fenbufen, fenbufen, fenclofenac, fenclozic acid, fenoprofen, fentiazac, feprazone, flufenamic acid, flufenisal, flufenisal, fluprofen, flurbiprofen, flurbiprofen, furofenac, ibufenac, ibuprofen, indomethacin, indomethacin, indoprofen, isoxepac, isoxicam, ketoprofen, ketoprofen, ketorolac, meclofenamic acid, meclofenamic acid, mefenamic acid, mefenamic acid, miroprofen, mofebutazone, nabumetone oxaprozin, naproxen, naproxen, niflumic acid, oxaprozin, oxpinac, oxyphenbutazone, phenacetin, phenylbutazone, phenylbutazone, piroxicam, piroxicam, pirprofen, pranoprofen, sudoxicam, tenoxican, sulfasalazine, sulindac, sulindac, suprofen, tiaprofenic acid, tiopinac, tioxaprofen, tolfenamic acid, tolmetin, tolmetin, zidometacin, zomepirac, and zomepirac); and (21) aerosolized antioxidant therapeutics such as S-Nitrosoglutathione.

1.2.2.12 Anti-Diabetic Agents

The GCC agonist peptides described herein can be used in therapeutic combination with one or more anti-diabetic agents, including but not limited to: PPARγ agonists such as glitazones (e.g., WAY-120,744, AD 5075, balaglitazone, ciglitazone, darglitazone (CP-86325, Pfizer), englitazone (CP-68722, Pfizer), isaglitazone (MIT/J&J), MCC-555 (Mitsibishi disclosed in U.S. Pat. No. 5,594,016), pioglitazone (such as such as Actos™ pioglitazone; Takeda), rosiglitazone (Avandia™; Smith Kline Beecham), rosiglitazone maleate, troglitazone (Rezulin®, disclosed in U.S. Pat. No. 4,572,912), rivoglitazone (CS-01 1, Sankyo), GL-262570 (Glaxo Welcome), BRL49653 (disclosed in WO98/0533 1), CLX-0921, 5-BTZD, GW-0207, LG-100641, JJT-501 (JPNT/P&U), L-895645 (Merck), R-119702 (Sankyo/Pfizer), NN-2344 (Dr. Reddy/NN), YM-440 (Yamanouchi), LY-300512, LY-519818, R483 (Roche), T131 (Tularik), and the like and compounds disclosed in U.S. Pat. Nos. 4,687,777, 5,002,953, 5,741,803, 5,965,584, 6,150,383, 6,150,384, 6,166,042, 6,166,043, 6,172,090, 6,211,205, 6,271,243, 6,288,095, 6,303,640, 6,329,404, 5,994,554, WO97/10813, WO97/27857, WO97/28115, WO97/28137,WO97/27847, WO00/76488, WO03/000685,WO03/027112,WO03/035602, WO03/048130, WO03/055867, and pharmaceutically acceptable salts thereof, biguanides such as metformin hydrochloride (N,N-dimethylimidodicarbonimidic diamide hydrochloride, such as Glucophage™, Bristol-Myers Squibb); metformin hydrochloride with glyburide, such as Glucovance™, Bristol-Myers Squibb); buformin (Imidodicarbonimidic diamide, N-butyl-); etoformine (1-Butyl-2-ethylbiguanide, Schering A. G.); other metformin salt forms (including where the salt is chosen from the group of, acetate, benzoate, citrate, ftimarate, embonate, chlorophenoxyacetate, glycolate, palmoate, aspartate, methanesulphonate, maleate, parachlorophenoxyisobutyrate, formate, lactate, succinate, sulphate, tartrate, cyclohexanecarboxylate, hexanoate, octanoate, decanoate, hexadecanoate, octodecanoate, benzenesulphonate, trimethoxybenzoate, paratoluenesulphonate, adamantanecarboxylate, glycoxylate, glutarnate, pyrrolidonecarboxylate, naphthalenesulphonate, 1-glucosephosphate, nitrate, sulphite, dithionate and phosphate), and phenformin; protein tyrosine phosphatase-IB (PTP-IB) inhibitors, such as A-401,674, KR 61639, OC-060062, OC-83839, OC-297962, MC52445, MC52453, ISIS 113715, and those disclosed in WO99/585521, WO99/58518, WO99/58522, WO99/61435, WO03/032916, WO03/032982, WO03/041729, WO03/055883, WO02/26707, WO02/26743, JP2002114768, and pharmaceutically acceptable salts and esters thereof; sulfonylureas such as acetohexamide (e.g. Dymelor, Eli Lilly), carbutamide, chlorpropamide (e.g. Diabinese®, Pfizer), gliamilide (Pfizer), gliclazide (e.g. Diamcron, Servier Canada Inc), glimepiride (e.g. disclosed in U.S. Pat. No. 4,379,785, such as Amaryl, Aventis), glipentide, glipizide (e.g. Glucotrol or Glucotrol XL Extended Release, Pfizer), gliquidone, glisolamide, glyburide/glibenclamide (e.g. Micronase or Glynase Prestab, Pharmacia & Upjohn and Diabeta, Aventis), tolazamide (e.g. Tolinase), and tolbutamide (e.g. Orinase), and pharmaceutically acceptable salts and esters thereof; meglitinides such as repaglinide (e.g. Pranidin®, Novo Nordisk), KAD1229 (PF/Kissei), and nateglinide (e.g. Starlix®, Novartis), and pharmaceutically acceptable salts and esters thereof; α glucoside hydrolase inhibitors (or glucoside inhibitors) such as acarbose (e.g. Precose™, Bayer disclosed in U.S. Pat. No. 4,904,769), miglitol (such as GLYSET™ Pharmacia & Upjohn disclosed in U.S. Pat. No. 4,639,436), camiglibose (Methyl 6-deoxy-6-[(2R,3R,4R,5S)-3,4,5-trihydroxy-2-(hydroxymethyl)piperidino]-alpha-D-glucopyranoside, Marion Merrell Dow), voglibose (Takeda), adiposine, emiglitate, pradimicin-Q, salbostatin, CKD-711, MDL-25,637, MDL-73,945, and MOR 14, and the compounds disclosed in U.S. Pat. Nos. 4,062,950, 4,174,439, 4,254,256, 4,701,559, 4,639,436, 5,192,772, 4,634,765, 5,157,116, 5,504,078, 5,091,418, 5,217,877, US51091 and WO01/47528 (polyamines); α-amylase inhibitors such as tendamistat, trestatin, and A1-3688, and the compounds disclosed in U.S. Pat. Nos. 4,451,455, 4,623,714, and 4,273,765; SGLT2 inhibtors including those disclosed in U.S. Pat. Nos. 6,414, 126 and 6,515,117; an aP2 inhibitor such as disclosed in U.S. Pat. No. 6,548,529; insulin secreatagogues such as linogliride, A-4166, forskilin, dibutyrl cAMP, isobutylmethylxanthine (IBMX), and pharmaceutically acceptable salts and esters thereof; fatty acid oxidation inhibitors, such as clomoxir, and etomoxir, and pharmaceutically acceptable salts and esters thereof; A2 antagonists, such as midaglizole, isaglidole, deriglidole, idazoxan, earoxan, and fluparoxan, and pharmaceutically acceptable salts and esters thereof; insulin and related compounds (e.g. insulin mimetics) such as biota, LP-100, novarapid, insulin detemir, insulin lispro, insulin glargine, insulin zinc suspension (lente and ultralente), Lys-Pro insulin, GLP-I (1-36)amide, GLP-I (73-7) (insulintropin, disclosed in U.S. Pat. No. 5,614,492), LY-315902 (Lilly), GLP-I (7-36)-NH2), AL-401 (Autoimmune), certain compositions as disclosed in U.S. Pat. Nos. 4,579,730, 4,849,405, 4,963,526, 5,642,868, 5,763,396, 5,824,638, 5,843,866, 6,153,632, 6,191,105, and WO 85/05029, and primate, rodent, or rabbit insulin including biologically active variants thereof including allelic variants, more preferably human insulin available in recombinant form (sources of human insulin include pharmaceutically acceptable and sterile formulations such as those available from Eli Lilly (Indianapolis, Ind. 46285) as Humulin™ (human insulin rDNA origin), also see the THE PHYSICIAN'S DESK REFERENCE, 55.sup.th Ed. (2001) Medical Economics, Thomson Healthcare (disclosing other suitable human insulins); non-thiazolidinediones such as JT-501 and farglitazar (GW-2570/GI-262579), and pharmaceutically acceptable salts and esters thereof, PPARα/γ dual agonists such as AR-H039242 (Aztrazeneca), GW-409544 (Glaxo-Wellcome), BVT-142, CLX-0940, GW-1536, GW-1929, GW-2433, KRP-297 (Kyorin Merck; 5-[(2,4-Dioxo thiazolidinyl)methyl]methoxy-N-[[4-(trifluoromethyl)phenyl]methyl]benzamide), L-796449, LR-90, MK-0767 (Merck/Kyorin/Banyu), SB 219994, muraglitazar (BMS), tesaglitzar (Astrazeneca), reglitazar (JTT-501) and those disclosed in WO99/16758, WO99/19313, WO99/20614, WO99/38850, WO00/23415, WO00/23417, WO00/23445, WO00/50414, WO01/00579, WO01/79150, WO02/062799, WO03/004458, WO03/016265, WO03/018010, WO03/033481, WO03/033450, WO03/033453, WO03/043985, WO 031053976, U.S. application Ser. No. 09/664, 598, filed Sep. 18, 2000, Murakami et al. Diabetes 47, 1841-1847 (1998), and pharmaceutically acceptable salts and esters thereof; other insulin sensitizing drugs; VPAC2 receptor agonists; GLK modulators, such as those disclosed in WO03/015774; retinoid modulators such as those disclosed in WO03/000249; GSK 3β/GSK 3 inhibitors such as 4-[2-(2-bromophenyl)-4-(4-fluorophenyl-1H-imidazol-5-yl] pyridine and those compounds disclosed in WO03/024447, WO03/037869, WO03/037877, WO03/037891, WO03/068773, EP1295884, EP1295885, and the like; glycogen phosphorylase (HGLPa) inhibitors such as CP-368,296, CP-316,819, BAYR3401, and compounds disclosed in WO01/94300, WO02/20530, WO03/037864, and pharmaceutically acceptable salts or esters thereof; ATP consumption promotors such as those disclosed in WO03/007990; TRB3 inhibitors; vanilloid receptor ligands such as those disclosed in WO03/049702; hypoglycemic agents such as those disclosed in WO03/015781 and WO03/040114; glycogen synthase kinase 3 inhibitors such as those disclosed in WO03/035663 agents such as those disclosed in WO99/51225, US20030134890, WO01/24786, and WO03/059870; insulin-responsive DNA binding protein-1 (IRDBP-I) as disclosed in WO03/057827, and the like; adenosine A2 antagonists such as those disclosed in WO03/035639, WO03/035640, and the like; PPARδagonists such as GW 501516, GW 590735, and compounds disclosed in JP10237049 and WO02/14291; dipeptidyl peptidase IV (DP-IV) inhibitors, such as isoleucine thiazolidide, NVP-DPP728A (1-[[[2-[(5-cyanopyridin-2-yl)amino]ethyl]amino]acetyl]-2-cyano-(S)-pyrrolidine, disclosed by Hughes et al, Biochemistry, 38(36), 11597-11603, 1999), P32/98, NVP-LAF-237, P3298, TSL225 (tryptophyl-1,2,3,4-tetrahydro-isoquinoline-3-carboxylic acid, disclosed by Yamada et al, Bioorg. & Med. Chem. Lett. 8 (1998) 1537-1540), valine pyrrolidide, TMC-2A/2B/2C, CD-26 inhibitors, FE999011, P93 10/K364, VIP 0177, DPP4, SDZ 274-444, 2-cyanopyrrolidides and 4-cyanopyrrolidides as disclosed by Ashworth et al, Bioorg. & Med. Chem. Lett., Vol. 6, No. 22, pp 1163-1166 and 2745-2748 (1996),and the compounds disclosed in U.S. Pat. Nos. 6,395,767, 6,573, 287, 6,395,767 (compounds disclosed include BMS-477118, BMS-471211 and BMS 538,305), WO99/38501, WO99/46272, WO99/67279, WO99/67278, WO99/61431 WO03/004498, WO03/004496, EP1258476, WO02/083128, WO02/062764, WO03/000250, WO03/002530, WO03/002531, WO03/002553, WO03/002593, WO03/000180, and WO03/000181; GLP-I agonists such as exendin-3 and exendin-4 (including the 39 aa polypeptide synthetic exendin-4 called Exenatide ®), and compounds disclosed in US2003087821 and NZ 504256, and pharmaceutically acceptable salts and esters thereof, peptides including amlintide and Symlin® (pramlintide acetate); and glycokinase activators such as those disclosed in US2002103199 (fused heteroaromatic compounds) and WO02/48106 (isoindolin-1-one-substituted propionamide compounds).

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application. In the case of conflict, the present specification, including definitions, will control. The references cited herein are not admitted to be prior art to the invention.

It is to be understood that while the invention has been described in conjunction with the preferred specific embodiments thereof, that the foregoing description is intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains.

Examples

Example 1: Preparation of Side-Chain Protected Fragments of SP-304 (as in WO 2012/118972)

Attachment Fmoc-AA-OH to 2-ClTrt Resin

2-ClTrt resin (10 g, substitution=1.0 mmol/g resin) was suspended in 100 mL of dichloromethane (DCM) for 5 minutes, and then drained. The esterification was performed using 1.5 equiv. of Fmoc-amino acid and 1.7 equiv. Diisopropylethylamine (DIEA) in 80 mL of DCM (with minimum quantity of dimethylformamide (DMF) to dissolve the amino acid completely) for 2 hours. The resulting resin was washed with 60 mL of DCM and endcapped with 60 mL of DIEA/methanol (1:9, v/v) solution for 30 minutes. The loaded resin was then washed with DCM (6 vol.) for 2 times, DMF (6 vol.) for 3 times and methyl t-butylether (MTBE) (6 vol.) for 3 times, and dried under high vacuum. The substitution of the Fmoc-protected resin was determined by Fmoc release assay. Finally, the Fmoc group was deprotected with a mixture of 5% piperidine, 1% 1,8-diazobicyclo [5.4.0]undec-7-ene (DBU) and 1% N-Hydroxybenzotriazole (HOBt) in DMF (10 vol.) for 2 times and the resin was washed and dried under high vacuum to give the final resin for peptide synthesis. The results of the experiments are listed in Table VIII below.

TABLE VIII

Preparation of H-Gly-2ClTrt and H-Leu-2ClTrt resin

| Amino acid 2-ClTrt resin | Synthesis scale (mmol) | Substitution of the loaded resin from Fmoc release assay | Yield (Weight, % yield) |
| --- | --- | --- | --- |
| H-Gly-2ClTrt resin | 4.16 | 0.57 mmol/g resin | 6 g, 82% |
| H-Leu-2ClTrt resin | 5.20 | 0.81 mmol/g resin | 6.4 g, 100% |
| H-Gly-2ClTrt resin | 300 | 0.80 mmol/g resin | 328.6 g, 88% |
| H-Leu-2ClTrt resin | 300 | 0.75 mmol/g resin | 338.5 g, 84% |

Synthesis of Side-Chain-Protected Fragments A and B

H-Gly-2-ClTrt resin or H-Leu-2-ClTrt resin was suspended in DMF (10 vol.) for 20 minutes, then drained. The resulting resin was washed with DMF (10 vol.) for 5 minutes. The chain assembly was conducted using the standard Fmoc chemistry. Generally, 1.5 equiv. of Fmoc amino acid and 1.5 equiv. of HOBt were dissolved in DMF (4.5 vol.), followed by addition of 1.5 equiv. of DIEA. Then, the resulting solution was cooled to below 5° C. with an ice water bath, and activated by addition of 1.5 equiv. of HBTU. DCM (1.5 vol.) was added to the resin, followed by addition of the activated Fmoc amino acid solution. The resulting mixture was stirred at room temperature for 2 hours and the completion of the acylation was monitored by Kaiser Test. If Kaiser Test indicated the presence of unreacted amine after 2 hours, recoupling with the same protocol using 1.0 equiv. of Fmoc amino acid, 1.0 equiv. of HOBt and 1.0 equiv. of DIEA was required. Capping was generally achieved by acetylating the unreacted amine with a mixture of acetic anhydride/pyridine/DMF solution. The peptide sequence was assembled by repeating the above capping procedure with the corresponding Fmoc-amino acid derivatives in the sequence from C- to N-terminal. The coupling of Fmoc-Cys(Trt)-OH or Fmoc-Cys(Acm)-OH residue was achieved by using 2.0 equiv. of Fmoc-Cys(Trt)-OH or Fmoc-Cys(Acm)-OH, 2.0 of equiv. HOBt and 2.0 equiv. of DIC in situ activation in DCM/DMF protocol to minimize racemization of cysteine.

After completion of the synthetic step, the peptide resin was thoroughly washed with DMF (10 vol.), MTBE (10 vol.), DMF (10 vol. 3 times) and MTBE (10 vol. 3 times) and subsequently dried in a vacuum oven to a constant weight.

The side-chain-protected peptide was cleaved from the resin using 1TFA/DCM (10 vol.) for 3 times, 5 minutes for each time and the cleavage fractions were collected onto pyridine each time (1:1 volume ratio to TFA in each cleavage fraction). The peptide resin was washed with DCM (7.5 vol.). The fractions were combined and concentrated under vacuum to 10% of the original volume, and the resulting solution was reconstituted with ethanol (3 vol.) and concentrated to 50% of the original volume. Finally, the peptide was precipitated out by addition of water (1 vol.). The solid was collected by vacuum filtration or centrifugation and washed with water twice. The product was dried in vacuum to a constant weight and subjected to TIPLC and ES-MS analysis. The results of the experiments are presented in Table IX below.

TABLE IX

Preparation of Fragments A and B

| Fragment | Synthesis scale (mmol) | Final peptide resin weight and yield from the weight gain of the resin | Yield of Fragment obtained (% yield) | Purity (HPLC) | Fragment Masses Calculated/Found* |
| --- | --- | --- | --- | --- | --- |
| FmocAA7-14OH (1) | 3.4 | 9.5 g, 66.4% | 3.337 g (61.3%) | 87.8% | 1599.95/1598.86 |
| BocAA1-6OH (2) | 5.2 | 11.8 g, 76.3% | 5.896 g (76.9%) | 94.6% | 1474.80/1473.94 |
| FmocAA7-14OH (1') | 200 | 479.7 g, 74.4% | 213.7 g (66.8%) | 90.1% | 1599.95/1598.81 |
| BocAA1-6OH (2') | 200 | 544.0 g, 101.3% | 247.0 g (83.7%) | 94.2% | 1474.80/1473.94 |

*Calculated = average molecular mass; Found = mono-isotopic mass by ES-MS

Example 2: Condensation of Fragments of SP-304 in Solution (as in WO 2012/118972)

Synthesis of Fragment C: H-AA15-16OtBu (1-1)

A solution of Fmoc-Cys(Acm)-OH (124.38 µm, 0.3 mol), H-Leu-OtBu·HCl (67.12 gm, 0.3 mol), and HOBt (40.54 µm, 0.3 mol) in DMF (600 mL) was cooled to −5° C. 2-[1H-Benzotriazole-1-yl]-1,1,3,3-tetramethyluronium hexafluorophosphate (HBTU) (113.79 µm, 0.3 mol) was added and dissolved completely. DIEA (183.1 mL, 1.05 mol) was added dropwise over a period of 105 minutes at the same temperature with good stirring, keeping the pH of the mixture between 6 and 7. Stirring was continued for 15 minutes at 0° C. and the reaction was monitored with TLC. The reaction mixture was diluted with ethyl acetate (EtOAc) (600 mL) and 5% $H_3PO_4$ (300 mL). The organic layer was separated and the aqueous layer was extracted with EtOAc (600 mL). The combined extracts were washed with 5% $H_3PO_4$ (2 times), $H_2O$ (1 time), saturated $NaHCO_3$ (3 times), $H_2O$ (2 times), and brine (2 times). The solution was dried over $MgSO_4$ anhydrous, filtered, and evaporated in vacuo to dryness. The product was recrystallized from petroleum ether/EtOAc (3:1) and dried: 166.75 µm (yield 95.0%, purity 99.0%).

Fmoc-Cys(Acm)-Leu-OtBu (166.75 µm, 0.277 mol) was dissolved in a 10% piperidine/DCM solution (8 10 mL) with stirring. The reaction was monitored with TLC. After the reaction was completed in 3 hours, the solvent and the volatile materials were removed using a rotavap. The oily material obtained was triturated with petroleum ether to remove the by-products by decantation. The residue, a syrup, was taken up in EtOAc, and washed with a mixture solution of $NaH_2PO_4/Na_2HPO_4$ (pH=6), then saturated $NaHCO_3$, purified $H_2O$, and brine. The organic layer was dried over $MgSO_4$ anhydrous. Evaporation of the solvent and the volatile materials yielded an oily product H-Cys (Acm)-Leu-OtBu (1-1) (73.23 µm, yield: 73.1%, purity: 98.0%).

Synthesis of Fragment B-C: HAA7-16OtBu (2-3)

A solution of Fmoc-AA7-14OH (1') (198.3 µm, 124.0 mmol), H-AA15-16OtBu (1-1) (52.3 gm, 148.8 mmol) and Cl-HOBt (21.0 µm, 124.0 mmol) in DMF (2500 mL) was cooled to −5° C. HBTU (51.7 µm, 136.4 mmol) was added and dissolved completely. DIEA (54.1 mL, 310 mmol) was then added with stirring, keeping the pH of the mixture between 6 and 7. Stirring was continued for 30 minutes at 0-5° C. The reaction mixture was allowed to warm up to 20-27° C. slowly and stirring was continued for one and a half hours. Then, the mixture was poured into precooled (10-20° C.) 0.5 N HCl aq. (20 L).The suspension was stored at 20-25° C. for 45 minutes. The solid was collected by filtering the suspension through a fritted-glass funnel of medium porosity and subsequent washing with 0.5 N HCl aq.(3500 mL, 2 times), purified water (3500 mL), saturated $NaHCO_3$aq. (3500 mL, 2 times) and purified water (3500 mL, 2 times) and diethyl ether (2000 mL, 2 times). Finally, the wet, crude peptide FmocAA7-16OtBu was dried in a desiccator under high vacuum at room temperature to yield product 238.22 µm (purity, 85.27%, yield 98.9%).

To a solution of FmocAA7-16OtBu (234.88 µm, 120.9 mmol) in DMF (2350 mL) was added piperidine (123 mL, 1245.2 mmol). The reaction mixture was stirred at 25° C. for two and a half hours, and then the mixture was poured into n-hexane (20.OL). The resulting sticky precipitate was triturated with n-hexane (3500 mL, 7 times). The sticky precipitate was dissolved in minimal amount of DMF (2000 mL), and then poured into 0.5N HCl aq. (10 vol.). The solid was collected by filtration and washed with purified water (3 times), and then diethyl ether (3000 mL, 3 times), dried in air overnight and then dried in vacuo to give product (2-3) (HAA7-16OtBu) (183.67 µm, purity: 68.4%, yield %: 88.33%, ES-MS, MW: calculated=1721.2, found=1719.84).

Synthesis of the Fully Protected A-B-C: BocAA1-16OtBu (3-3)

A solution of HAA7-16OtBu (2-3) (183.67 gm, 106.71 mmol), BocAA1-6-OH (2') (157.65 µm, 106.71 mmol), and 6-Cl-HOBt (18.141 gm, 106.71 mmol) in DMF (3 L) were cooled to at −3 to 0° C. HBTU (44.523 µm, 117.38 mmol) was added and dissolved completely. DIEA (55.8 mL, 320.13 mmol) was then added with stirring, keeping the pH of the mixture 6. Stirring was continued for 20 minutes at −5 to 0° C. The reaction mixture was allowed to warm up to 25° C. slowly and stirring was continued for 2.5 hours, followed by further addition of HBTU (4.048 gm, 10.671 mmol) and DIEA (2 mL). Stirring was continued for another 1.5 hours. The resulting mixture was poured into MeOH (15 L), and the precipitate was collected and washed with MeOH/DMF mixture (5:1, v/v) (2 times, 3 L), 0.1 N HCl (3 L, 2 times), saturated $NaHCO_3$ (2 times), purified water (3 times), diethyl ether (2 times) and dried in vacuo to yield the product BocAA1-16OtBu (3-3) (278.0 µm, yield 82.0%. Note: the purity was determined after the deprotection).

Synthesis of the Partially Protected Linear SP-304: HAA1-160H (4-4)

A mixture of TFA/TIS/EDT (8:1:1, 2400 mL) was cooled to (0-5° C.) under nitrogen and Boc-AA1-16OtBu (3-3) (201 gm) was added in portions. The resulting suspension was stirred at 0-10° C. for 30 min, then the reaction solution was allowed to warm up to 20-25° C. with a water bath (10 minutes) and stirring was continued for additional 1 hr and 50 min at the same temperature. The reaction mixture was poured into pre-cooled (10° C.) MTBE (18 L). Some heat was evolved during the addition of the peptide/TFA solution and the internal temperature went up to 25° C. The resulting suspension was then stored in an ice-water bath (5-10° C.) for 40 min. The precipitate was collected by filtration and washed with MTBE (2000 mL, 4 times), and dried in vacuum over $P_2O_5$, yielding 148.37 µm of off-white product, HAA1-160H (4-4) (purity: 62.23%, ES-MS, MW: calculated=1828.07, found=1826.67).

Example 3: Oxidative Cyclization and Purification of SP-304 by Polystyrenic Absorbent Resin (as in WO 2012/118972)

HAA1-160H (4-4) (0.58 gm) was dissolved in 5 mL of acetonitrile and diluted with 575 mL of purified water. The solution was adjusted to pH 8-9 with 25% ammonia solution, and 3% hydrogen peroxide (0.58 mL) was added, then the reaction mixture was kept for an hour with monitoring the disulfide formation by HPLC. Nitrogen was then passed through the reaction mixture and the solution was acidified to pH 3-4 with acetic acid (71.8% HPLC, recovery 98.5% estimated from peak area). The resulting mixture was added 1% iodine/ACN dropwise over a period of 10 minutes with good stirring until the yellow color of the iodine persisted. Stirring was continued for 30 minutes at 17-20° C. The iodine was quenched by addition of 0.5 M ascorbic acid aq. until the yellow disappeared. Then, the pH of the mixture was adjusted to 6-7 with 25% ammonia solution (51.0% HPLC, recovery 50% estimated from peak area).

The polystyrenic absorbent resin (D101) was packed to a 3(ID)×9(L) CM column and well equilibrated with 6 column volume (CV) of ethanol, 4 CV of purified water, 2 CV of 5% HCl aq., 4 CV of purified water, 2 CV of 2% NaOH aq. and 4 CV of purified water at the flow rate of 3 CV/hour. The oxidized peptide solution was then loaded to the column at 2 CV/h. After loading, the column was washed with 2 CV purified water at 2 CV/h. The elution was conducted by applying 80% ethanol aq. to the column at 2 CV/h. The fractions with UV absorbents at 215 nm, was collected and combined (125 mL). The combined fractions were then evaporated in vacuum to 10% of the original volume and the suspension was precipitated with 125 mL of cold MTBE (10 vol). The solid was collected by filtration and dried in vacuum to yield the crude SP-304 (0.282 g, 55.0% HPLC).

Example 4: Oxidative Cyclization and Purification of SP-304 by RP-HPLC (as in WO 2012/118972)

Crude peptide (4-4), prepared as described in Example 2 was dissolved in 10% ACN aqueous to an approximate concentration of 1.25 g/L with continuous stirring via a mechanical stirrer. The pH of the peptide solution was adjusted to 8.5-9.0 with 20% ammonia aqueous and the resulting solution was stirred vigorously open to the atmosphere. Hydrogen peroxide (3%, 0.25 equiv.) was added and stirring was continued at room temperature for 60 minutes. The HPLC analysis showed complete consumption of the linear peptide. Then, the solution was acidified to pH 3-4 with 10% AcOH aqueous. The resulting solution was diluted to a concentration of about 1 g/L with purified water. Iodine (1.3% in ACN) was added in with vigorous stirring over a period of 10 minutes until the yellow color of the iodine persisted. At about half-hourly intervals samples were taken from the mixture and analyzed by RP-HPLC. The monocyclized peptide peak decreased gradually and a new peak (dicyclized peptide) emerged. Oxidation was complete when no monocyclized peptide peak left. The excess iodine was neutralized by a small amount of ascorbic acid. The resulting solution was loaded on a C18 RP-HPLC column packed with Kromasil 1 00 Å, 10 µm silica gel. After the dicyclized peptide solution was loaded, a 3 column volume of a solution of 90% mobile phase A (1.0% TEA, 0.5% $H_3PO_4$ in $H_2O$, pH=7) and 10% mobile phase B (acetonitrile) was loaded to wash out lines. Then, gradient was operated from 10% B to 30% B in 80 minutes. Fractions were collected at recorded intervals when main peak began to elute. The purity of each fraction was monitored by analytical RP-HPLC. Fractions of purity ≤95% (not meeting the Main Pool criteria) were pooled accordingly and forward processed using the same buffer system and gradient elution parameters stated above. All fractions with purity ≥95% were pooled and stored at 2-8° C. The purified peptide solution was diluted in a 1:1 ratio with purified water and then loaded to the same RP-HPLC column. The counter-ion exchange was accomplished by washing the column with 2-3 column volumes of 0.5M ammonium acetate aqueous, followed by gradient elution from 90% C (0.2% AcOH aqueous solution) and 10% mobile phase D (ACN) to 50% mobile phase C and 50% mobile phase D in 50 minutes. Fractions were collected at recorded intervals and monitored by analytical RP-HPLC. The fractions (≥95%) were collected and lyophilized to obtain final dry peptide, 68.0g (96.1% pure).

Example 5: Desalination and Isolation of SP-304 after Purification by RP-HPLC (as in WO 2012/118972)

After plecanatide was purified by RP-HPLC as described in Example 4, it was desalinated and isolated. Briefly, the purified plecanatide in ammonium acetate/acetonitrile/water buffer was loaded onto a column packed with polymeric absorbent (macroporous adsorption resin) and then eluted by a mixture of alcohol/water. Finally, the peptide alcohol solution was concentrated under reduced pressure, precipitated with an ether, e.g., diethyl ether or MTBE, and dried under vacuum to give the final product.

Resin (Polymeric Adsorbents) Screening

Resin pre-treatment: Polymeric adsorbents, DA201-C (from Jiangsu Suqing, China; crosslinked polystyrene; surface area 1200-1400 $m^2/g$; average pore diameter: 3-4 nm; pore volume: 1.1-1.2 ml/g; bulk density: 0.68-0.75 g/ml; specific density: 1.03-1.1 g/ml; moisture: 50-60%; particle size: 0.315~1.25 mm ≥95%; effective diameter: 0.4~0.7 mm; uniformity coefficient: ≤1.6%), DA201-H (from Jiangsu Suqing, China; crosslinked polystyrene; surface area ≥800 $m^2/g$; average pore diameter: 6-8 nm; pore volume: 1.5-1.8 ml/g; bulk density: 0.65-0.70 g/ml; specific density: 1.02-1.07 g/ml; moisture: 55-65%; particle size: 0.315~1.25 mm ≥95%; effective diameter: 0.4-0.7 mm; uniformity coefficient: ≤1.6% ), ADS-5 (from Nankai Hecheng, China; crosslinked polystyrene; surface area 520-600 m2/g; average pore diameter: 25-30 nm; bulk density: 0.7-0.8 g/ml; moisture: 60-70%; particle size: 0.315~1.25 mm ≥95%; uniformity coefficient: ≤1.6% ), and ADS-8 (from Nankai Hecheng, China; crosslinked polystyrene; surface area 450-500 $m^2/g$; average pore diameter: 12-16 nm; bulk density: 0.65-0.75 g/ml; moisture: 60-70%; particle size: 0.315~1.25 mm ≥95%; uniformity coefficient: ≤1.6%) were suspended in 4-6 volume of ethanol overnight. Decant or suction off the supernatant from the settled resin. Add 6-8 volume of deionized water and resuspend the resin with gentle overhead stirring. Again, decant or suction off the supernatant from the settled resin. Repeat the above water treatment and decantation steps until fines appearance is minimal.

Column packing and regeneration: Resuspend the pre-treated resins above with 1-2 volume of deionized water to form the resin slurry respectively by using gentle agitation. Pour the resin slurry slowly down the inside of the column to prevent air entrapment. After the resin slurry has been fully transferred to the column, rinse the inside of the column using a squirt bottle containing deionized water. Open the column outlet to from a settled resin bed (ID=4 cm, H=10 cm). Then the resin beds were washed successively at a flow rate of 3CV per hour by 4 CV of deionized water, 2CV of 5% HCl aq, 4CV of deionized water, 2CV of 2% NaOH aq and finally 4 CV of deionized water till the pH of the elute was around 7.

Preparation of loading samples: 2000 mg of lyophilized plecanatide was dissolved in a mixture of 60 mL of ACN and 150 mL of 0.2% AcOH aq (the pH of the AcOH aq was adjusted to 4 with 10% ammonia aq.). After filtration with 1.2 µm Nylon membrane, the filtrate was diluted to 250 mL with 0.2% AcOH aq (pH4) and split into 4 parts (62.5 mL each) for loading.

Loading the sample to the columns: 62.5 mL of peptide solution above was loaded onto the above 4 columns at a flow rate of 2CV/h respectively. The loading elute was collected and tested by RP-HPLC to evaluate the absorbent capacity of each resin. The absorbent capacity results of each resin were demonstrated in Table X below.

TABLE X

| Resins | Peptide in loading sample | Peptide absorbed | Absorbent ratio |
|---|---|---|---|
| DA201-C | 500 mg | 303.5 mg | 60.7% |
| DA201-H | 500 mg | 493.4 mg | 98.7% |
| ADS-5 | 500 mg | 450.5 mg | 90.1% |
| ADS-8 | 500 mg | 466.1 mg | 93.2% |

HPLC Method: HPLC machine: Shimadzu LC-10 AD vp; column: Kromasil, C18, 4.6×250 mm; mobile phase A: 0.1% TFA in water; mobile phase B: 0.1% TFA in ACN; detect at: 215 nm; column temperature: 40° C.; flow rate: 1.0 mL/min; gradient: 25% B to 45% B in 30 min.

Absorbent Capacity Calculation: The absorbent capacity of each resin was demonstrated by the absorbent ratio of the peptide loaded onto each column, which was calculated by the quantity of the peptide absorbed in each resin column divided by the peptide quantity in each loading sample (500 mg). The quantity of peptide absorbed in each column was calculated by the formula below:

Quantity of peptide absorbed=Quantity of peptide in the loading sample-Quantity of peptide in the loading elute=500 mg−62.5 mL×(1.6 mg/mL×HPLC peak area of the eluate/HPLC peak area of the peptide standard solution)

Washing the Column with Deionized Water: The loaded columns above were then washed with 2CV of deionized water at 2CV/h to remove the salts. The washing eluates were collected and analyzed by RP-HPLC to determine the peptide quantity desorbed by water using the same method above. The desorbed peptide ratios of each resin were listed in Table XI below.

TABLE XI

| Resins | Peptide absorbed in resin | Peptide desorbed | Desorption ratio |
|---|---|---|---|
| DA201-C | 303.5 mg | 184.5 mg | 60.8% |
| DA201-H | 493.4 mg | 40.9 mg | 8.3% |
| ADS-5 | 450.5 mg | 41.9 mg | 9.3% |
| ADS-8 | 466.1 mg | 40.1 mg | 8.6% |

Desorbing the Peptide with 90% Ethanol/Water: After 2CV of water washes, the peptide absorbed in each column was then eluted by 1-2CV of 90% ethanol in water at 2 CV/h. The elution was collected and analyzed by RP-HPLC to determine the peptide quantity desorbed by 90% ethanol using the same method above. The desorbed peptide ratios of each resin were listed in Table XII below.

TABLE XII

| Resins | Peptide absorbed in resin after 2CV water washes | Peptide desorbed | Desorption ratio |
|---|---|---|---|
| DA201-C | 119.0 mg | 47.6 mg (by 2CV ethanol) | 40% |
| DA201-H | 452.5 mg | 452.5 mg (by 1.5CV ethanol) | 100% |
| ADS-5 | 408.6 mg | 408.6 mg (by 1.5 CV ethanol) | 100% |
| ADS-8 | 426.0 mg | 426.0 mg (by 1.5 CV ethanol) | 100% |

Isolation of the Peptide from the Ethanol Solution: The collected peptide/ethanol/water solution from each column was concentrated under reduced pressure, precipitated with MTBE, filtered and dried in vacuo to give the final product.

The overall yield of the peptide processed by each column was demonstrated in Table XIII below.

TABLE XIII

| Resins | Peptide in loading sample | Final product obtained | Overall yield |
|---|---|---|---|
| DA201-C | 500 mg | 52 mg | 10.4% |
| DA201-H | 500 mg | 460 mg | 92.0% |
| ADS-5 | 500 mg | 400 mg | 80.0% |
| ADS-8 | 500 mg | 430 mg | 86.0% |

Resin Screening Conclusion: From the data above (Table X to Table XIII), the DA201-H resin presented the best absorbent capacity and the best desorption (by ethanol) performance for plecanatide among the resins in the experiment.

Desalination and Isolation Process Optimization

Eluting Solvents Selection: Isopropanol and ethanol are two commonly used solvents for eluting the peptide from the polymeric absorbents. Table XIV shows the amount of plecanatide that is able to be dissolved in aqueous ethanol or isopropanol solution depending on the v/v % isopropanol (or ethanol): water.

TABLE XIV

| Solvent | Solubility |
|---|---|
| 90% IPA/Water | 67.5 mg/mL |
| 75% IPA/Water | 596.1 mg/mL |
| 50% IPA/Water | 635.0 mg/mL |
| 90% EtOH/Water | 302.0 mg/mL |
| 75% EtOH/Water | 700.0 mg/mL |

The water in the peptide/alcohol solution can be removed by azeotropic distillation. Table XV shows the property of the binary azeotropes of ethanol/water and isopropanol/water.

TABLE XV

| Component A | Component B | Boiling Point A | Boiling Point B | Azeotrope Boiling Point | Azeotrope Wt. % A |
|---|---|---|---|---|---|
| Water | Ethanol | 100° C. | 78.3° C. | 78.2° C. | 4% |
| Water | Isopropanol | 100° C. | 82.3° C. | 80.3° C. | 12.6% |

Degradation of plecanatide will occur during the long time storage of the peptide/alcohol/water solution and the concentration process. Table XVI demonstrates the stability data of plecanatide in 75% IPA/water solution and 90% EtOH/water at 23° C.

TABLE XVI

| Duration | Purity (in 90% EtOH aq.)* | Purity (in 75% IPA aq.)* |
|---|---|---|
| 0 hours | 98.5% | 98.7% |
| 2 hours | 98.4% | 98.7% |
| 4 hours | N/A | 98.3% |
| 6 hours | 98.1% | 97.5% |
| 8 hours | N/A | 96.6% |
| 10 hours | 95.5% | N/A |
| 24 hours | 92.0% | N/A |
| 25 hours | N/A | 96.1% |

*HPLC Method: HPLC machine: Shimadzu LC-10AD vp: column: Kromasil, C18, 4.6 × 250 mm; mobile phase A: 0.1% TFA in water; mobile phase B: 0.1% TFA in ACN; detect at: 215 nm; column temperature: 40° C.; flow rate: 1.0 mL/min; gradient: 25% B to 45% B in 30 min.

From the testing data obtained, plecanatide was fairly stable at 23° C. in alcohol/water solution within 6 hours.

Elution experiments were conducted using isopropanol/water mixtures with different v/v %. The desorption ratio and water content of the peptide eluates were listed in Table XVII below.

TABLE XVII

| v/v % IPA/Water | 75% IPA/water | 95% IPA/water | 100% IPA/water |
|---|---|---|---|
| Water content in peptide | 65.9% | 53.0% | 49.8% |
| Desorption ratio | 100% | 100% | 90% |

75% Isopropanol/water as eluting solution: 500 mg of plecanatide (98.1% pure) was dissolved in a mixture of 16 mL ACN and 49 mL of 0.2% AcOH aqueous (the pH of the 0.2% AcOH solution was adjusted to 4.0 by addition of 10% NH4OH aq). After filtration by 1.2 μm nylon membrane, the peptide solution was loaded onto a column packed with DA201-H resin (ID=4 cm, H=10 cm, packed and pre-treated by the procedure mentioned previously) at 2CV/h. After loading, the column was washed with 2 CV deionized water at 2CV/h. Then, the peptide was eluted by 1.5CV of 75% IPA/water at 2CV/h. The elution was monitored by RP-HPLC. The eluate was collected (124 mL, 98.3% pure). Karl Fisher analysis indicated water (65.9% wt. %). Into a 1-neck, 500-mL round bottom flask was placed 124 mL of peptide/IPA/water eluate collected above (97.6% pure, slight degradation occurred during storage at 2-8° C. for 2 days). The flask was then placed under reduced pressure (60 Pa) on a rotary evaporator and partially immersed in a 23° C. water bath. A whitish suspension was formed by feed-stripping approximately 622 mL of isopropanol in 2 hours to about 1/3 of the initial volume of the solution (97.7% pure). Karl Fisher analysis indicated water (0.17% wt. %). To the concentrate was added 350 mL of pre-chilled diethyl ether, the solid was collected by centrifugation at 3500 rpm for 3 minutes and dried under vacuum to yield 333 mg of final product (yield 66.6%, 97.2% HPLC purity).

95% Isopropanol/water as eluting solution I: 500 mg of plecanatide (98.1% pure) was dissolved in a mixture of 16 mL ACN and 49 mL of 0.2% AcOH aqueous (the pH of the 0.2% AcOH solution was adjusted to 4.0 by addition of 10% NH4OH aq). After filtration by 1.2 μm nylon membrane, the peptide solution was loaded onto a column packed with DA201-H resin (ID=4 cm, H=10 cm, pre-treated by the procedure mentioned previously) at 2CV/h. After loading, the column was washed with 2 CV deionized water at 2CV/h. Then, the peptide was eluted by 1.5CV of 95% IPA/water at 2CV/h. The elution was monitored by RP-HPLC. The eluate was collected (117 mL, 98.1% pure). Karl Fisher analysis indicated water (52% wt. %). Into a 1-neck, 500-mL round bottom flask was placed 117 mL of peptide/IPA/water eluate collected above. The flask was then placed under reduced pressure (50 Pa) on a rotary evaporator and partially immersed in a 23° C. water bath. A whitish solid was formed by feed-stripping approximately 470 mL of isopropanol in 130 min (97.9% pure). To the solid above was added 50 mL of pre-chilled diethyl ether to form a suspension and evaporated under reduced pressure (50 Pa) on a rotary evaporator at 23° C. to dryness. Yield was 430 mg of final product (86%). HPLC purity was 97.9%.

95% Isopropanol/water as eluting solution II: 500 mg of plecanatide (98.1% pure) was dissolved in a mixture of 16 mL ACN and 49 mL of 0.2% AcOH aqueous (the pH of the 0.2% AcOH solution was adjusted to 4.0 by addition of 10% NH4OH aq). After filtration by 1.2 μm nylon membrane, the peptide solution was loaded onto a column packed with DA201-H resin (ID=4 cm, H=10 cm, packed and pre-treated by the procedure mentioned previously) at 2CV/h. After loading, the column was washed with 2 CV deionized water at 2CV/h. Then, the peptide was eluted by 1.5CV of 95% IPA/water at 2CV/h. The elution was monitored by RP-HPLC. The eluate was collected (118 mL, 98.2% pure). Karl Fisher analysis indicated water (53% wt. %). Into a 1-neck, 500-mL round bottom flask was placed 118 mL of peptide/IPA/water eluate collected above. The flask was then placed under reduced pressure (50 Pa) on a rotary evaporator and partially immersed in a 23° C. water bath. A whitish suspension (~40 mL) was formed by feed-stripping approximately 330 mL of isopropanol in 100 min (97.7% pure). To the suspension above was added 400 mL of pre-chilled diethyl ether to form a suspension. After standing at ambient temperature for 1 hour, the solid was collected by centrifugation at 3500 rpm for 3 minutes, and dried under vacuum to yield 370 mg of final product. Yield was 74%. HPLC purity was 97.9%.

95% Isopropanol/water as eluting solution III 10 g of plecanatide was desalted and precipitated in a manner similar to that described above. Interestingly, the precipitation yield was improved to 93%, which is a significant increase in yield. HPLC purity after precipitation was 98.47%.

Example 6: Characterization of Lyophilized SP-304 and Precipitated SP-304 (as in WO 2012/118972)

The plecanatide purified by lyophilization as described in Example 4 and plecanatide purified by precipitation as described in Example 5 were analyzed to determine significant chemical impurity values such as the levels of acetamide, TFA, ammonium ion, and acetonitrile. The results are listed in the table below.

|  | Acetamide | TFA | Ammonium ion | Acetonitrile |
|---|---|---|---|---|
| Lyophilized plecanatide | 356 ppm | 0.14% | 1.58% | 40 ppm |
| Precipitated plecanatide | <28 ppm (LOQ of method) | 0.09% | 0.23% | Not Detected (20 ppm LOQ) |

As demonstrated by results above, the precipitation process provided significantly reduced levels of undesirable process impurities.

The plecanatide purified by lyophilization as described in Example 4 and plecanatide purified by precipitation as described in Example 5 were measured to obtain their bulk densities, tap densities, particle size distribution, and shape.

EQUIPMENT: (1) Tap Density Tester Model TD-1020; (2) Sonic Sifter Separator Model L3P; (3) Optical Microscope LINITRON 2850.

Methods

1) Bulk and Tap Density Measurements: Modified USP 1 Method
   a. 100.0 mL graduate cylinder was used for lyophilized plecanatide
   b. 10.0 mL graduated cylinder was used for precipitated plecanatide 2) Particle Size Distribution Analysis
   a) a. Screens used: 200, 140, 100, 60, 40 and 30 meshes.
   b. Sample size: 2g of lyophilized plecanatide and 6.4g of precipitated plecanatide
3) Optical Microscopic Analysis: Particle Size and Shape
   a. Dry powder was manually dispersed onto a microscopic plate
   b. Magnification: 100×
   c. Under normal light condition (no polarized filters)

Results (1) Physical Appearance: lyophilized plecanatide is a light, fluffy and white powder. Precipitated plecanatide is a slightly off-white powder.

(2) Bulk and Tap Density: Table XVIII provides bulk and tap density data for Plecanatide samples of both lyophilized and precipitated:

TABLE XVIII

| Plecanatide Sample | Bulk Density, g/mL | Tap Density, g/mL |
|---|---|---|
| Lyophilized, Lot 101221 | 0.0332 | 0.0680 |
| Precipitated, Lot 120210 | 0.486 | 0.641 |

As seen from the data, the precipitated plecanatide is unexpectedly significantly denser than the lyophilized plecanatide. The precipitated plecanatide has less tendency of dust generation during processing, which affords the advantages of increased safety and reduced processing losses.

(3) Particle Size Distribution: Table XIX summarizes the particle size distribution analysis. FIG. 1 presents the data graphically.

TABLE XIX

| # Mesh Size | Particle Size (μm) | Weight Retained (g) Lyophilized | Weight Retained (g) Precipitated | Percent Retained Lyophilized | Percent Retained Precipitated |
|---|---|---|---|---|---|
| 30 | 600 | 0.07 | 0.45 | 3.6% | 7.1% |
| 40 | 425 | 0.26 | 0.17 | 13.3% | 2.7% |
| 60 | 250 | 0.17 | 0.67 | 8.7% | 10.5% |
| 100 | 150 | 0.51 | 2.08 | 26.0% | 32.7% |
| 140 | 106 | 0.65 | 1.22 | 33.2% | 19.2% |
| 200 | 75 | 0.24 | 0.68 | 12.2% | 10.7% |
| Pan | <75 | 0.06 | 1.09 | 3.1% | 17.1% |
| Total | | 1.96 | 6.36 | 100.0% | 100.0% |

As demonstrated by Table XIX and FIG. 1, the particle size distributions are different for both types of plecanatide. During analysis, it was observed that the precipitated plecanatide contained some larger particles, which could be broken up easily. It was also noticed that the lyophilized plecanatide appeared to be flaky and sticking onto top and bottom of sieves, whereas no sticking was observed for the precipitated plecanatide. It indicates a better processing property of the precipitated plecanatide.

Figure 2:
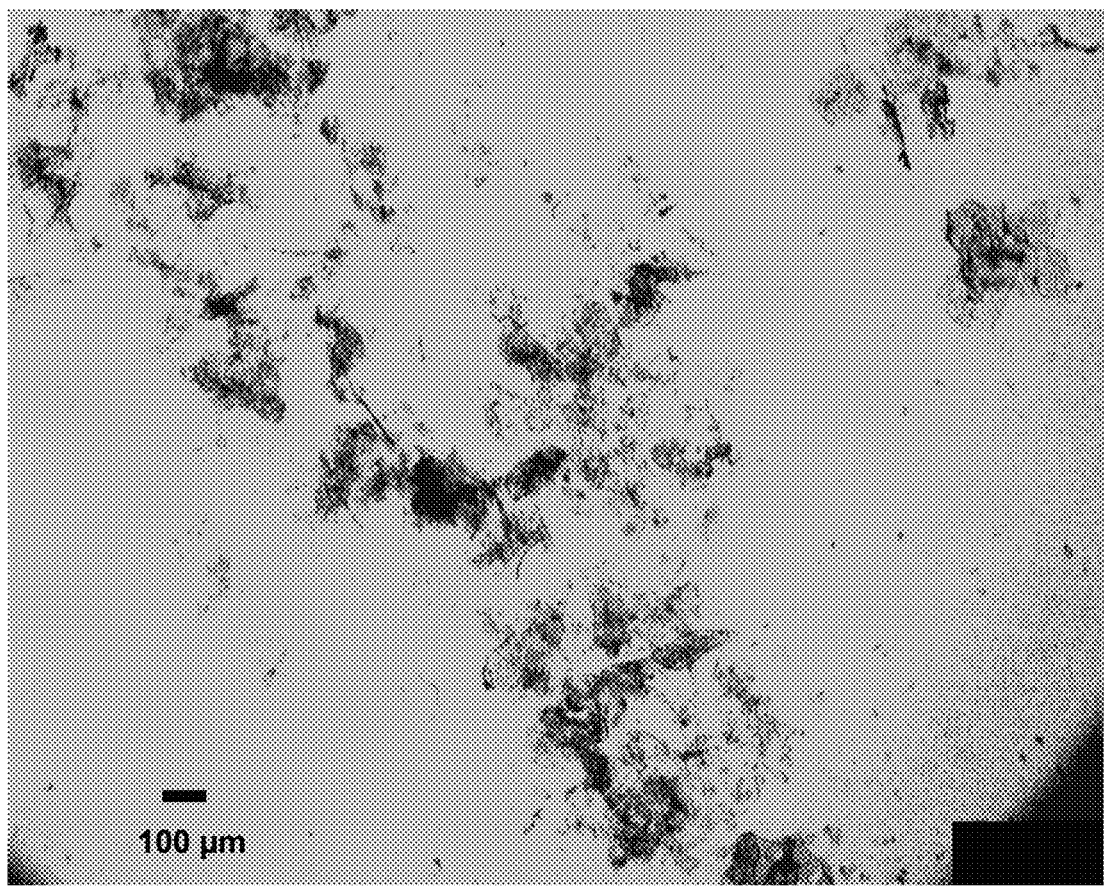
FIG. 2 is an optical microscopic image of lyophilized plecanatide.
Figure 3:
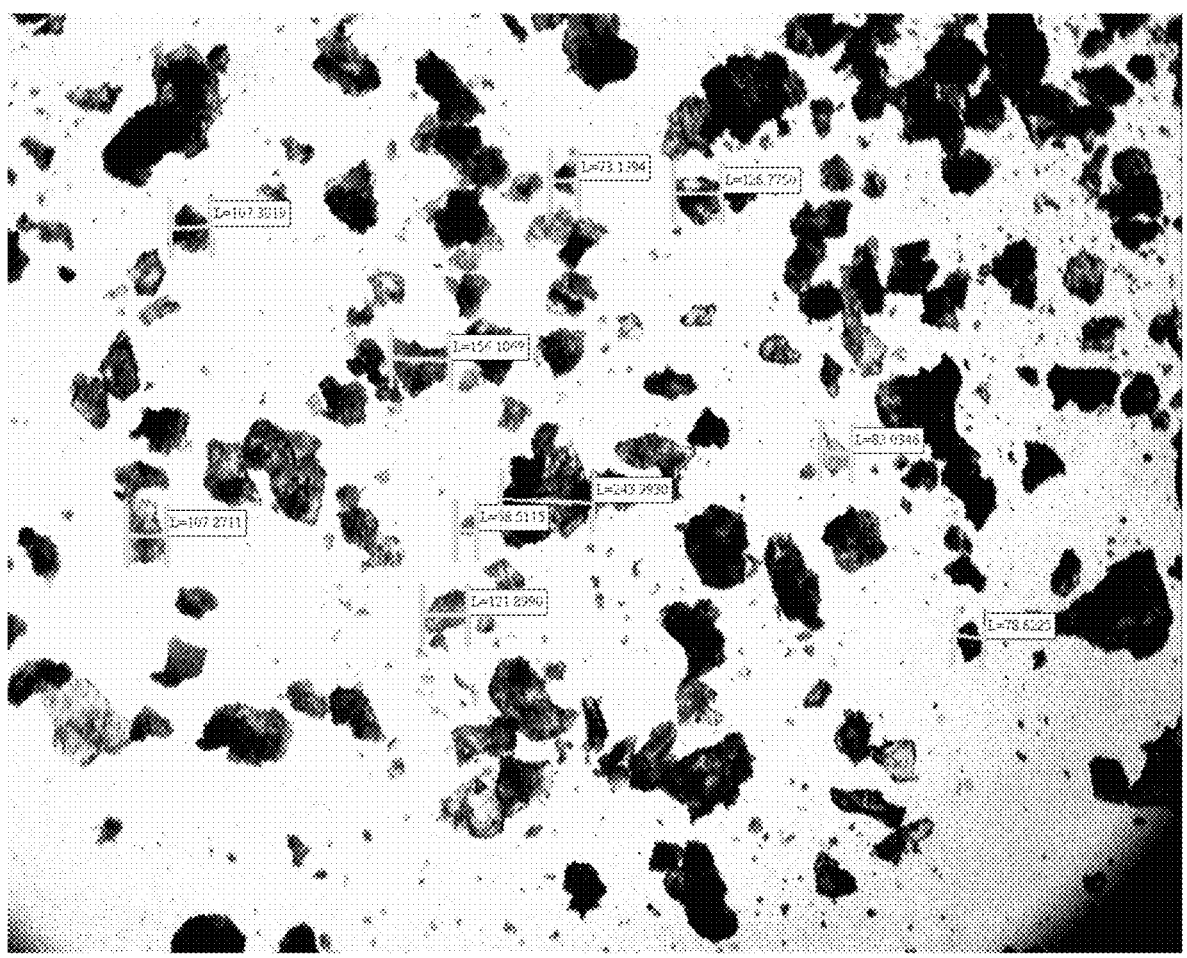
FIG. 3 is an optical microscopic image of precipitated plecanatide.

(4) Particle Size and Shape: FIGS. 2 and 3 provide optical microscopic analysis of samples of lyophilized and precipitated plecanatide, respectively. As seen in FIG. 2, the lyophilized plecanatide is in amorphous form and has irregular shapes of particles. They form physical aggregates with particles lying on top of each other. In FIG. 3, the precipitated plecanatide shows distinguishable individual particles. From the particle appearances and shapes, the precipitated plecanatide will have better flow property and therefore can facilitate solid processing during manufacturing.

The lyophilized and precipitated forms of plecanatide have shown distinguishable physical appearances and properties by density, particle size distribution and shape analyses. The precipitated form is more suitable for solid dosage form processing during manufacturing in terms of reducing dust generation, less sticking onto processing equipment, and potentially less processing losses.

The precipitated form is more suitable for processing solid dosage form during manufacture (e.g., a low-dose solid dosage form). The higher density of the precipitated material will reduce aerosol or "dust" losses during weighing, transferring, and blending. The different particle shape has been shown to reduce loss caused by sticking to screens or sieves. The higher density should improve content uniformity since the size and density of the drug particles more closely match those of the excipients.

Example 7: Low-Dose Formulation of Precipitated SP-304 (as in WO 2012/118972)

The plecanatide purified by precipitation as described in Example 5 is processed further to make low-dose formulations as described below.

| Composition of dry-blending batch | | |
|---|---|---|
| Item No. | Ingredient | Concentration % w/w |
| 1 | SP-304 | 0.3246 |
| 2 | Microcrystalline cellulose (Avicel PH 102) | 99.43 |
| 3 | Magnesium stearate | 0.2500 |
| 4 | HPMC capsule shells | n/a |
| | Total | 100 |

Blending:

Avicel PH 102 is screened through a 60 mesh screen. V-blenders (1 Qt, 4Qt, and 16 Qt) are then dusted by the screened Avicel PH 102. SP-304 is screened through a 200 mesh screen and loaded into the 1-Qt V-blender. Then, about 80 g Avicel PH 102 is added into the 1-Qt blender and the mixture is blended for 10 minutes at 25 rpm. The mixture is then transferred to the 4-Qt V-blender which is pre-dusted by the screened Avicel PH 102. The 1-Qt blender is rinsed with Avicel and the rinse material is transferred to the 4-Qt blender. The rinsing is repeated until all SP-304 is transferred to the 4-Qt blender. About 200g Avicel is added to the 4-Qt V-blender and the mixture is blended for 10 minutes. The resulting blend is then screened through a 60 mesh screen and then transferred into the pre-dusted 16-Qt blender (dusted with 1500g Avicel). The 4-Qt blender is rinsed with Avicel and the rinse material is transferred to the 16-Qt blender. The remaining Avicel is added to the 16-Qt blender and the mixture is blended for 10 minutes. The resulting blend is passed through Comil, rinsed with excess of Avicel, and then returned to the 16-Qt blender and is further blended for 5 minutes. Proper amount of magnesium stearate is weighed, screened through a 60 mesh screen, and added into the 16-Qt blender. The resulting mixture is blended for 2 minutes. The resulting mixture is then either packaged in capsules or compressed to form tablets.

Encapsulation

A MG2 Planeta capsule filler is set up. Average weight of the empty capsule shells is determined and target capsule fill weight was calculated (±5%). The blend from the above process is added into the hopper of the capsule filler and encapsulation is started. Run weight parameters are manually adjusted. Resulting capsules are then sorted according to the target fill weight.

Compression

A Fette tablet press is set up. Then the blend mixture is loaded into the powder hopper and tooling is installed. The weight of each tablet is set to be 100 mg±5% and hardness to be 4-6 Kp. The weight, hardness, and thickness of tablets are measured and recorded every 5 to 10 minutes. Friability measurement is also performed to ensure satisfactory product.

Example 8: Synthesis and Purification of SP-304 by Solvent Exchange-Lyophilization Monocyclization of Linear Crude Peptide: The disulfide bond between $Cys^4$ and $Cys^{12}$ was first formed by $H_2O_2$ oxidation at 8.0-8.5 pH to form the monocyclized crude peptide. The linear crude peptide was slowly added and dissolving in 0.5% ammonium acetate in water buffer with pre-added $H_2O_2$ in a ratio of 100:9 gram of peptide to mL $H_2O_2$ to produce a final crude concentration of approximately 1.0 mg/mL. The solution pH was then adjusted to 8.5 with an $NH_4OH$ solution while stirring in the open air. The oxidative monocyclization reaction was monitored using HPLC Method 2. When the area % of the linear crude peptide was <5.0% of the area % of monocyclized peptide, the oxidation reaction was stopped by adjusting the pH of peptide solution to 1.7-2 using a TFA solution. The peptide solution was then transferred to the next step for the formation of the dicyclized peptide.

Dicyclization of Monocyclized Peptide: The disulfide bond between the Cys7 and Cys15 was formed by 3.0% (w/v) $I_2$ in acetonitrile solution. The disulfide bridge was created while simultaneously removing the Acm side-chain protecting groups present on the remaining Cys residues. The oxidative dicyclization reaction was monitored using HPLC Method 2. Excess iodine was quenched with a 0.1 M ascorbic acid in water solution. Upon completion of the reaction, the dicyclized peptide was adjusted to pH 6.5-7 using an NH4OH solution and the material was prepared for primary purification.

Primary Purification of Dicyclized Crude Peptide: The dicyclized crude peptide solution resulting from the oxidation steps was then loaded onto a preparative RP-HPLC column packed with $C_{18}$ reverse phase resin which was operated by a preparative HPLC system. The peptide was eluted in a 1% triethylamine phosphate (TEAP) in water, pH7/ACN buffer system. HPLC Method 1 was used to ascertain the percent purity of fractions and pools obtained during the primary purification run.

Recycle Pool(s) Purification of Dicyclized Peptide: After primary purification, the fractions that required further purification were purified based on the purity of the fraction pools using a 1% TEAP in water, pH7/ACN or a 0.2% acetic acid in water/ACN buffer system. The dicyclized crude peptide solution resulting from the oxidation steps was then loaded onto a preparative RP-HPLC column packed with $C_{18}$ reverse phase resin which was operated by a preparative HPLC system. The peptide was eluted in a 1% TEAP in water, pH7/ACN buffer system. HPLC Method 1 was used to ascertain the percent purity of fractions and pools obtained during the Recycle Purification run.

Secondary Purification and Salt Exchange: After recycle purification, the fractions that required further purification were purified based on the purity of the fraction pools using a 1% TEAP in water, pH7/ACN or a 0.2% acetic acid in water/ACN buffer system. UPLC Method 1 was used to ascertain the percent purity of fractions and pools obtained during the Secondary Purification run. HPLC Method 1 was used to ascertain the percent purity of Main Pool obtained during all the Purification runs before moving to next step.

Solvent Exchange: Material meeting main pool criteria was loaded onto the preparative RP-HPLC column at the flange end in the reverse direction, washed with a 99:1 water to isopropanol solution from the reverse direction, and eluted with a 40:60 isopropanol:water solution in the forward direction. The collected peptide solution was tested by UPLC Method 1 to ascertain the purity, then the peptide solution was filtered, underwent rotary evaporation to remove excess isopropanol to below 5%, followed by sublot lyophilization for no less than 96 hours.

Reconstitution and Final Lyophilization: The sublot lyophilized dry peptide underwent reconstitution in water to form a homogenous lot. An amount of 0.5% (w/w) ammonium acetate to dry peptide was added to the solution and mixed until the ammonium acetate/peptide was dissolved. The material underwent analysis by UPLC Method 1 to verify the purity. The dissolved material was installed onto the tray lyophilizer and kept under vacuum for no less than 120 hours to comprise the final dry peptide material.

In Process Testing Methods

HPLC Method 1: The following RP-HPLC analytical method will be used to verify the HPLC percent purity of the primary and recycling purification steps or batch record indicated.

HPLC Parameters:
    Column: Waters SunFire™ C8, 3.5 µm, 4.6×150 mm or equivalent
    Wavelength: 215 nm
    Mobile Phase A: 0.02M TEAP in Water pH 6.5 (Analytical Buffer BA)
    Mobile Phase B: 100% ACN
    Injection Volume: 5-50 µL
    Column Temp.: 40° C.

Gradient Elution Parameters:

| Time (min.) | Flow Rate (mL/min.) | % A | % B |
|---|---|---|---|
| 0.0 | 1.0 | 87.0 | 13.0 |
| 25.0 | 1.0 | 70.0 | 30.0 |
| 25.1 | 1.0 | 20.0 | 80.0 |
| 30.0 | 1.0 | 20.0 | 80.0 |
| 30.1 | 1.0 | 87.0 | 13.0 |
| 35.0 | 1.0 | 87.0 | 13.0 |

HPLC Method 2: The following RP-HPLC analytical method will be used to verify the HPLC percent purity of the linear crude peptide and to monitor the progress of the oxidative cyclization steps.

HPLC Parameters:
    Column: Kromasil C18 5g 100 Å 4.5×250 mm, or equivalent
    Wavelength: 215 nm
    Mobile Phase A: 0.02M TEAP in Water pH 6.5 (Analytical Buffer BA)
    Mobile Phase B: 100% ACN Injection Volume: 5-50 μL
Column Temp.: 40° C.
Gradient Elution Parameters:

| Time (min.) | Flow Rate (mL/min.) | % A | % B |
|---|---|---|---|
| 0.0 | 1.0 | 85.0 | 15.0 |
| 15.0 | 1.0 | 75.0 | 25.0 |
| 16.1 | 1.0 | 20.0 | 80.0 |
| 20.0 | 1.0 | 20.0 | 80.0 |
| 20.1 | 1.0 | 85.0 | 15.0 |
| 25.0 | 1.0 | 85.0 | 15.0 |

UPLC Method 1: The following RP-UPLC analytical method will be used to verify the Main Pool percent purity and final product peptide material before lyophilization.
UPLC Parameters:
  Column: Waters Acquity BEH C18, 1.7 μm, 150×2.1 mm, P/N 186002353 with a Waters
  Acquity column in-line filter unit, 0.2 μm, P/N 205000343

Wavelength: 215 nm
Mobile Phase A: 48/52/0.16-MeOH/Water/TFA
Injection Volume: 5 μL
Column Temp.: 10° C.
Isocratic Elution Parameters:

| Time (min.) | Flow Rate (mL/min.) | % A |
|---|---|---|
| 0.0 | 0.16 | 100.0 |
| 85.0 | 0.16 | 100.0 |

Figure 4:
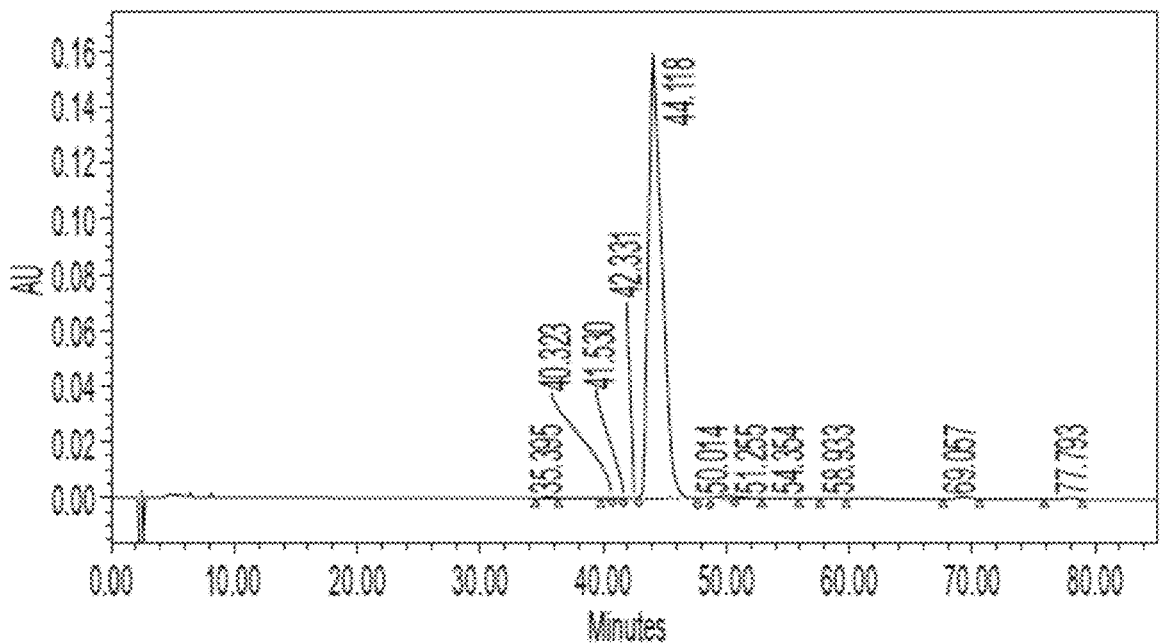
FIG. 4 is a UPLC chromatogram of plecanatide isolated by one embodiment of the purification process of the invention.

Two batches were prepared by the method described in the Example: lot #121026 IPA2 with a batch size of 50 g and lot #121026 B with a batch size of 930 g. As illustrated in FIG. 4, lot #121026 IPA2 peptide had a UPLC chromatographic purity of ~98%. Other characteristics of the two batches are summarized in Table XX below, as compared to the batches prepared by the methods described in WO 2012/118972.

TABLE XX

| | ACN Lyophilization Process (Average or range) | ACN Lyophilization Process (lot 101221) WO 2012/118972 | ACN Lyophilization Process (lot 110425) WO 2012/118972 | Preceipitation Process (lot February 2012) WO 2012/118972 |
|---|---|---|---|---|
| Batch size | 1110-2580 g | 1142 g | 1110 g | 0.5 g |
| Acetamide | 88-453 ppm | 350 ppm | 356 ppm | <28 ppm |
| TFA | <0.04-0.25% | 0.2% | 0.14% | |
| Acetate | 0.6-4.7% | <0.6% | 0.6% | |
| Ammonium | 0.02-1.94% | 1.05% | 1.58% | 0.23% |
| Degradation product (RRT 1.33) | <0.10-0.15% | <0.10% | 0.10% | |
| Chromatographic purity UPLC | | 97.3% | 97.6% | |
| Total impurities | 2.24% (n = 7) 1.46-2.71% | 2.33% | 1.87% | |
| ROS (residual organic solvent) | ACN 0-40 ppm | All <20 ppm | ACN 40 ppm | Ethylacetate 20 ppm IPA 27,000 ppm Methanol 250 ppm MTBE 20 PPM Tetrahydrofuran 70 ppm |
| Bulk Density | 0.03-0.06 g/cc | 0.033 g/cc | | |
| Particle Size air disperant (D50 um) | 182-234 | 235 | | |
| Particle Size liquid disperant (um) | | D10: 8 D50: 22 D90: 37 | D10: 7 D50: 21 D90: 59 | |
| X-ray | Amorphous | | | |
| Sieve analysis (Percent retained) | | 600 um 3.6% 425 um 13.3% 250 um 8.7% 150 um 26.0% 106 um 33.2% | | |
| Water | | 5.4% | 7.3% | |

| | Preceipitation Process (lot 120210) WO 2012/118972 | Precipitation Process (lot 130117) | Solvent Exchange Process (lot 121026 IPA2) | Solvent Exchange Process (lot 121026 B) |
|---|---|---|---|---|
| Batch size | 10 g | 200 g | 50 g | 930 g |
| Acetamide | | <47 ppm | 35 ppm | <18 ppm |
| TFA | 0.09% | 0.10% | <0.04% | <0.04% |
| Acetate | | <0.01% | 0.08% | 0.21% |
| Ammonium | | 0.61% | 0.17% | 0.11% |
| Degradation product (RRT 1.33) | 0.31% | 0.89% | 0.10% | 0.11% |
| Chromatographic purity UPLC | | 97.0% | 97.8% | 97.1% |
| Total impurities | 2.51% | 2.89% | 2.17% | 2.92% |
| ROS (residual organic solvent) | IPA 90,000 ppm | IPA 1700 ppm | ACN 240 ppm | IPA 320 ppm |

TABLE XX-continued

| | | | | |
|---|---|---|---|---|
| Bulk Density | 0.486 g/cc | 0.64 g/cc | 0.03 g/cc | 0.056 g/cc |
| Particle Size air disperant (D50 um) | | 300 | 635 | 91 |
| Particle Size liquid disperant (um) | | | D10: 8<br>D50: 21<br>D90: 40 | D10: 4<br>D50: 17<br>D90: 34 |
| X-ray | | Amorphous | Amorphous | Amorphous |
| Sieve analysis<br>(Percent retained) | 600 um 7.1%<br>425 um 2.7%<br>250 um 10.5%<br>150 um 32.7%<br>106 um 19.2% | 600 um 11.0%<br>425 um 13.1%<br>250 um 24.7%<br>150 um 23.7%<br>106 um 11.0% | 600 um 42.1%<br>425 um 26.3%<br>250 um 21.1%<br>150 um 7.9%<br>106 um 2.6% | 600 um 3.6%<br>425 um 7.1%<br>250 um 17.9%<br>150 um 10.7%<br>106 um 25% |
| Water | | 4.9% | 5.3% | 2.7% |

TABLE XXI

Stability of Plecanatide Drug Substance Lot 121026B Stored at 25° C.
Lot No.: 121026B Container: 60 mL Clear Bottles

| Test | T = 0 | 3 Months | 6 Months |
|---|---|---|---|
| Appearance (visual) | White powder | White powder | White powder |
| UPLC Identity 1 | Conforms | Conforms | Conforms |
| Chromatographic Plecanatide Purity (UPLC) (% area) | 97.1% | 97.0% | 96.4% |
| Total impurities | 2.92% | 2.90% | 3.61% |
| Water Content (KF) | 2.7% | 8.7% | 8.3% |

We claim:

1. An oral formulation comprising a purified peptide comprising a Guanylate Cyclase-C(GCC) agonist of amino acid sequence of SEQ ID NO: 1, wherein the purified peptide has less than 0.25% alpha-Asp-9-plecanatide relative to the weight of the purified peptide.

2. The oral formulation of claim 1, wherein the formulation further comprises at least one pharmaceutically acceptable excipient, wherein the at least one pharmaceutically acceptable excipient comprises magnesium stearate.

3. The oral formulation of claim 1, comprising 0.01 mg to 10 mg of the purified peptide.

4. The oral formulation of claim 1, comprising 0.1 mg to 5 mg of the purified peptide.

5. The oral formulation of claim 1, comprising 3 mg of the purified peptide.

6. The oral formulation of claim 1, comprising 0.15% to 0.25% by weight of alpha-Asp-9-plecanatide relative to the weight of the purified peptide.

7. An oral formulation comprising:
   (i) a purified peptide comprising a Guanylate Cyclase-C (GCC) agonist of amino acid sequence of SEQ ID NO: 1, wherein the purified peptide has less than 0.25% alpha-Asp-9-plecanatide relative to the weight of the purified peptide; and
   (ii) at least one pharmaceutically acceptable excipient, wherein the at least one pharmaceutically acceptable excipient comprises microcrystalline cellulose.

8. The oral formulation of claim 7, comprising 0.01 mg to 10 mg of the purified peptide.

9. The oral formulation of claim 7, comprising 0.1 mg to 5 mg of the purified peptide.

10. The oral formulation of claim 7, comprising 3 mg of the purified peptide.

11. The oral formulation of claim 7, wherein the at least one pharmaceutically acceptable excipient further comprises magnesium stearate.

12. The oral formulation of claim 7, comprising 0.15 to 0.25% by weight of alpha-Asp-9-plecanatide relative to the weight of the purified peptide.

* * * * *

SEQUENCE LISTING

```
Sequence total quantity: 275
SEQ ID NO: 1              moltype = AA  length = 16
FEATURE                   Location/Qualifiers
REGION                    1..16
                          note = Chemically Synthesized
source                    1..16
                          mol_type = protein
                          organism = synthetic construct
REGION                    4..12
                          note = The peptide CELCVNVAC is circular.
SITE                      4..12
                          note = Cysteine cysteine disulfide
REGION                    7..15
                          note = The peptide CVNVACTGCL is circular.
SITE                      7..15
                          note = Cysteine cysteine disulfide
SEQUENCE: 1
NDECELCVNV ACTGCL                                                           16

SEQ ID NO: 2              moltype = AA  length = 15
FEATURE                   Location/Qualifiers
REGION                    1..15
                          note = Chemically Synthesized
source                    1..15
                          mol_type = protein
                          organism = synthetic construct
SEQUENCE: 2
DECELCVNVA CTGCL                                                            15

SEQ ID NO: 3              moltype = AA  length = 14
FEATURE                   Location/Qualifiers
REGION                    1..14
                          note = Chemically Synthesized
source                    1..14
                          mol_type = protein
                          organism = synthetic construct
SEQUENCE: 3
DECELCVNVA CTGC                                                             14
```

```
SEQ ID NO: 4              moltype = AA  length = 14
FEATURE                   Location/Qualifiers
REGION                    1..14
                          note = Chemcially Synthesized
source                    1..14
                          mol_type = protein
                          organism = synthetic construct
SEQUENCE: 4
ECELCVNVAC TGCL                                                           14

SEQ ID NO: 5              moltype = AA  length = 13
FEATURE                   Location/Qualifiers
REGION                    1..13
                          note = Chemically Synthesized
source                    1..13
                          mol_type = protein
                          organism = synthetic construct
SEQUENCE: 5
ECELCVNVAC TGC                                                            13

SEQ ID NO: 6              moltype = AA  length = 13
FEATURE                   Location/Qualifiers
REGION                    1..13
                          note = Chemically Synthesized
source                    1..13
                          mol_type = protein
                          organism = synthetic construct
SEQUENCE: 6
CELCVNVACT GCL                                                            13

SEQ ID NO: 7              moltype = AA  length = 12
FEATURE                   Location/Qualifiers
REGION                    1..12
                          note = Chemically Synthesized
source                    1..12
                          mol_type = protein
                          organism = synthetic construct
SEQUENCE: 7
CELCVNVACT GC                                                             12

SEQ ID NO: 8              moltype = AA  length = 16
FEATURE                   Location/Qualifiers
REGION                    1..16
                          note = Chemically Synthesized
SITE                      16
                          note = MISC_FEATURE - wherein LEU is a D amino acid
source                    1..16
                          mol_type = protein
                          organism = synthetic construct
SEQUENCE: 8
NDECELCVNV ACTGCL                                                         16

SEQ ID NO: 9              moltype = AA  length = 16
FEATURE                   Location/Qualifiers
REGION                    1..16
                          note = Chemically Synthesized
SITE                      1
                          note = D-asparagine
SITE                      16
                          note = d-leucine
source                    1..16
                          mol_type = protein
                          organism = synthetic construct
REGION                    4..12
                          note = The peptide CELCVNVAC is circular.
SITE                      4..12
                          note = Cysteine cysteine disulfide
REGION                    7..15
                          note = The peptide CVNVACTGC is circular.
SITE                      7..15
                          note = Cysteine cysteine disulfide
SEQUENCE: 9
NDECELCVNV ACTGCL                                                         16

SEQ ID NO: 10             moltype = AA  length = 16
FEATURE                   Location/Qualifiers
REGION                    1..16
                          note = Chemically Synthesized
```

| | | |
|---|---|---|
| SITE | 1 | |
| | note = D-asparagine | |
| SITE | 2 | |
| | note = D-aspartic acid | |
| SITE | 16 | |
| | note = D-leucine | |
| source | 1..16 | |
| | mol_type = protein | |
| | organism = synthetic construct | |
| SEQUENCE: 10 | | |
| NDECELCVNV ACTGCL | | 16 |
| | | |
| SEQ ID NO: 11 | moltype = AA   length = 16 | |
| FEATURE | Location/Qualifiers | |
| REGION | 1..16 | |
| | note = Chemically Synthesized | |
| SITE | 1 | |
| | note = D-asparagine | |
| SITE | 2 | |
| | note = D-aspartic acid | |
| SITE | 3 | |
| | note = D-glutamic acid | |
| SITE | 16 | |
| | note = D-leucine | |
| source | 1..16 | |
| | mol_type = protein | |
| | organism = synthetic construct | |
| SEQUENCE: 11 | | |
| NDECELCVNV ACTGCL | | 16 |
| | | |
| SEQ ID NO: 12 | moltype = AA   length = 16 | |
| FEATURE | Location/Qualifiers | |
| REGION | 1..16 | |
| | note = Chemically Synthesized | |
| SITE | 1 | |
| | note = D-asparagine | |
| source | 1..16 | |
| | mol_type = protein | |
| | organism = synthetic construct | |
| SEQUENCE: 12 | | |
| NDECELCVNV ACTGCL | | 16 |
| | | |
| SEQ ID NO: 13 | moltype = AA   length = 16 | |
| FEATURE | Location/Qualifiers | |
| REGION | 1..16 | |
| | note = Chemically Synthesized | |
| SITE | 1 | |
| | note = D-asparagine | |
| SITE | 6 | |
| | note = D-leucine | |
| SITE | 16 | |
| | note = D-leucine | |
| source | 1..16 | |
| | mol_type = protein | |
| | organism = synthetic construct | |
| SEQUENCE: 13 | | |
| NDECELCVNV ACTGCL | | 16 |
| | | |
| SEQ ID NO: 14 | moltype = AA   length = 15 | |
| FEATURE | Location/Qualifiers | |
| REGION | 1..15 | |
| | note = Chemically Synthesized | |
| source | 1..15 | |
| | mol_type = protein | |
| | organism = synthetic construct | |
| SEQUENCE: 14 | | |
| NDECELCVNV ACTGC | | 15 |
| | | |
| SEQ ID NO: 15 | moltype = AA   length = 16 | |
| FEATURE | Location/Qualifiers | |
| REGION | 1..16 | |
| | note = Chemically Synthesized | |
| SITE | 1 | |
| | note = MISC_FEATURE - wherein ASN at position 1 is attached to polyethylene glycol | |
| SITE | 16 | |
| | note = MISC_FEATURE - wherein LEU is a D amino acid | |

```
                          -continued

SITE              16
                  note = MISC_FEATURE - wherein LEU at position 16 is
                   attached to polyethylene glycol
source            1..16
                  mol_type = protein
                  organism = synthetic construct
SEQUENCE: 15
NDECELCVNV ACTGCL                                                       16

SEQ ID NO: 16     moltype = AA  length = 16
FEATURE           Location/Qualifiers
REGION            1..16
                  note = Chemically Synthesized
SITE              1
                  note = MISC_FEATURE - wherein ASN at position 1 is attached
                   to polyethylene glycol
SITE              1
                  note = D-asparagine
SITE              16
                  note = D-leucine
SITE              16
                  note = MISC_FEATURE - wherein LEU at position 16 is
                   attached to polyethylene glycol
source            1..16
                  mol_type = protein
                  organism = synthetic construct
SEQUENCE: 16
NDECELCVNV ACTGCL                                                       16

SEQ ID NO: 17     moltype = AA  length = 16
FEATURE           Location/Qualifiers
REGION            1..16
                  note = Chemically Synthesized
SITE              1
                  note = MISC_FEATURE - wherein ASN at position 1 is attached
                   to polyethylene glycol
SITE              1
                  note = MISC_FEATURE - wherein ASN is a D amino acid
SITE              2
                  note = MISC_FEATURE - wherein ASP is a D amino acid
SITE              16
                  note = MISC_FEATURE - wherein LEU is a D amino acid
SITE              16
                  note = MISC_FEATURE - wherein LEU at position 16 is
                   attached to polyethylene glycol
source            1..16
                  mol_type = protein
                  organism = synthetic construct
SEQUENCE: 17
NDECELCVNV ACTGCL                                                       16

SEQ ID NO: 18     moltype = AA  length = 16
FEATURE           Location/Qualifiers
REGION            1..16
                  note = Chemically Synthesized
SITE              1
                  note = MISC_FEATURE - wherein ASN is a D amino acid
SITE              16
                  note = MISC_FEATURE - wherein LEU at position 16 is
                   attached to polyethylene glycol
SITE              16
                  note = MISC_FEATURE - wherein LEU is a D amino acid
source            1..16
                  mol_type = protein
                  organism = synthetic construct
SEQUENCE: 18
NDECELCVNV ACTGCL                                                       16

SEQ ID NO: 19     moltype = AA  length = 16
FEATURE           Location/Qualifiers
REGION            1..16
                  note = Chemically Synthesized
SITE              1
                  note = MISC_FEATURE - wherein ASN at position 1 is attached
                   to polyethylene glycol
SITE              16
                  note = MISC_FEATURE - wherein LEU is a D amino acid
```

| | |
|---|---|
| source | 1..16<br>mol_type = protein<br>organism = synthetic construct |
| SEQUENCE: 19<br>NDECELCVNV ACTGCL | 16 |
| SEQ ID NO: 20<br>FEATURE<br>REGION | moltype = AA  length = 16<br>Location/Qualifiers<br>1..16<br>note = Chemically Synthesized |
| SITE | 1<br>note = MISC_FEATURE - wherein ASN at position 1 is attached to polyethylene glycol |
| SITE | 1<br>note = MISC_FEATURE - wherein ASN is a D amino acid |
| SITE | 16<br>note = MISC_FEATURE - wherein LEU is a D amino acid |
| source | 1..16<br>mol_type = protein<br>organism = synthetic construct |
| SEQUENCE: 20<br>NDECELCVNV ACTGCL | 16 |
| SEQ ID NO: 21<br>FEATURE<br>REGION | moltype = AA  length = 16<br>Location/Qualifiers<br>1..16<br>note = Chemically Synthesized |
| SITE | 16<br>note = MISC_FEATURE - wherein LEU at position 16 is attached to polyethylene glycol |
| SITE | 16<br>note = MISC_FEATURE - wherein LEU is a D amino acid |
| source | 1..16<br>mol_type = protein<br>organism = synthetic construct |
| SEQUENCE: 21<br>NDECELCVNV ACTGCL | 16 |
| SEQ ID NO: 22<br>FEATURE<br>REGION | moltype = AA  length = 16<br>Location/Qualifiers<br>1..16<br>note = Chemically Synthesized |
| SITE | 1<br>note = MISC_FEATURE - wherein ASN at position 1 is attached to polyethylene glycol |
| SITE | 1<br>note = MISC_FEATURE - wherein ASN is a D amino acid |
| SITE | 2<br>note = MISC_FEATURE - wherein ASP is a D amino acid |
| SITE | 3<br>note = MISC_FEATURE - wherein GLU is a D amino acid |
| SITE | 16<br>note = MISC_FEATURE - wherein LEU is a D amino acid |
| SITE | 16<br>note = MISC_FEATURE - wherein LEU at position 16 is attached to polyethylene glycol |
| source | 1..16<br>mol_type = protein<br>organism = synthetic construct |
| SEQUENCE: 22<br>NDECELCVNV ACTGCL | 16 |
| SEQ ID NO: 23<br>FEATURE<br>REGION | moltype = AA  length = 16<br>Location/Qualifiers<br>1..16<br>note = Chemically Synthesized |
| SITE | 1<br>note = MISC_FEATURE - wherein ASN at position 1 is attached to polyethylene glycol |
| SITE | 1<br>note = MISC_FEATURE - wherein ASN is a D amino acid |
| SITE | 2<br>note = MISC_FEATURE - wherein ASP is a D amino acid |
| SITE | 3<br>note = MISC_FEATURE - wherein GLU is a D amino acid |
| SITE | 16<br>note = MISC_FEATURE - wherein LEU is a D amino acid |

```
source                  1..16
                        mol_type = protein
                        organism = synthetic construct
SEQUENCE: 23
NDECELCVNV ACTGCL                                                           16

SEQ ID NO: 24           moltype = AA  length = 16
FEATURE                 Location/Qualifiers
REGION                  1..16
                        note = Chemically Synthesized
SITE                    1
                        note = MISC_FEATURE - wherein ASN is a D amino acid
SITE                    2
                        note = MISC_FEATURE - wherein ASP is a D amino acid
SITE                    3
                        note = MISC_FEATURE - wherein GLU is a D amino acid
SITE                    16
                        note = MISC_FEATURE - wherein LEU at position 16 is
                         attached to polyethylene glycol
SITE                    16
                        note = MISC_FEATURE - wherein LEU is a D amino acid
source                  1..16
                        mol_type = protein
                        organism = synthetic construct
SEQUENCE: 24
NDECELCVNV ACTGCL                                                           16

SEQ ID NO: 25           moltype = AA  length = 16
FEATURE                 Location/Qualifiers
REGION                  1..16
                        note = Chemically Synthesized
SITE                    1
                        note = MISC_FEATURE - wherein ASN is a D amino acid
SITE                    2
                        note = MISC_FEATURE - wherein ASP is a D amino acid
SITE                    16
                        note = MISC_FEATURE - wherein LEU at position 16 is
                         attached to polyethylene glycol
SITE                    16
                        note = MISC_FEATURE - wherein LEU is a D amino acid
source                  1..16
                        mol_type = protein
                        organism = synthetic construct
SEQUENCE: 25
NDECELCVNV ACTGCL                                                           16

SEQ ID NO: 26           moltype = AA  length = 16
FEATURE                 Location/Qualifiers
REGION                  1..16
                        note = Chemically Synthesized
SITE                    1
                        note = MISC_FEATURE - wherein ASN at position 1 is attached
                         to polyethylene glycol
SITE                    1
                        note = MISC_FEATURE - wherein ASN is a D amino acid
SITE                    2
                        note = MISC_FEATURE - wherein ASP is a D amino acid
SITE                    16
                        note = MISC_FEATURE - wherein LEU is a D amino acid
source                  1..16
                        mol_type = protein
                        organism = synthetic construct
SEQUENCE: 26
NDECELCVNV ACTGCL                                                           16

SEQ ID NO: 27           moltype = AA  length = 16
FEATURE                 Location/Qualifiers
REGION                  1..16
                        note = Chemically Synthesized
SITE                    1
                        note = MISC_FEATURE - wherein ASN is a D amino acid
SITE                    16
                        note = MISC_FEATURE - wherein x is 3-(2-naphthyl)alanine
SITE                    16
                        note = MISC_FEATURE - wherein x is a D amino acid
source                  1..16
                        mol_type = protein
                        organism = synthetic construct
```

```
SEQUENCE: 27
NDECELCVNV ACTGCX                                                               16

SEQ ID NO: 28              moltype = AA  length = 16
FEATURE                    Location/Qualifiers
REGION                     1..16
                           note = Chemically Synthesized
SITE                       1
                           note = MISC_FEATURE - wherein ASN is a D amino acid
SITE                       8
                           note = MISC_FEATURE - wherein x at position 8 is
                            alpha-amino isobutyric acid
SITE                       10
                           note = MISC_FEATURE - wherein x at position 10 is
                            alpha-amino isobutyric acid
SITE                       16
                           note = MISC_FEATURE - wherein LEU is a D amino acid
source                     1..16
                           mol_type = protein
                           organism = synthetic construct
SEQUENCE: 28
NDECELCXNX ACTGCL                                                               16

SEQ ID NO: 29              moltype = AA  length = 16
FEATURE                    Location/Qualifiers
REGION                     1..16
                           note = Chemically Synthesized
SITE                       1
                           note = MISC_FEATURE - wherein ASN is a D amino acid
SITE                       7
                           note = MISC_FEATURE - wherein ASP at position 7 is attached
                            to a Lactam bridge
SITE                       15
                           note = MISC_FEATURE - wherein x at position 15 is ornithine
SITE                       16
                           note = MISC_FEATURE - wherein LEU is a D amino acid
source                     1..16
                           mol_type = protein
                           organism = synthetic construct
SEQUENCE: 29
NDECELDVNV ACTGXL                                                               16

SEQ ID NO: 30              moltype = AA  length = 16
FEATURE                    Location/Qualifiers
REGION                     1..16
                           note = Chemically Synthesized
SITE                       1
                           note = MISC_FEATURE - wherein ASN is a D amino acid
SITE                       16
                           note = MISC_FEATURE - wherein LEU is a D amino acid
source                     1..16
                           mol_type = protein
                           organism = synthetic construct
SEQUENCE: 30
NDECEYCVNV ACTGCL                                                               16

SEQ ID NO: 31              moltype = AA  length = 16
FEATURE                    Location/Qualifiers
REGION                     1..16
                           note = Chemically Synthesized
SITE                       1
                           note = MISC_FEATURE - wherein ASN is a D amino acid
SITE                       16
                           note = MISC_FEATURE - wherein LEU is a D amino acid
source                     1..16
                           mol_type = protein
                           organism = synthetic construct
SEQUENCE: 31
NDECESCVNV ACTGCL                                                               16

SEQ ID NO: 32              moltype = AA  length = 16
FEATURE                    Location/Qualifiers
REGION                     1..16
                           note = Chemically Synthesized
SITE                       1
                           note = MISC_FEATURE - wherein ASN at position 1 is attached
                            to polyethylene glycol
SITE                       1
                           note = MISC_FEATURE - wherein ASN is a D amino acid
```

```
SITE              16
                  note = MISC_FEATURE - wherein LEU is a D amino acid
SITE              16
                  note = MISC_FEATURE - wherein LEU at position 16 is
                   attached to polyethylene glycol
source            1..16
                  mol_type = protein
                  organism = synthetic construct
SEQUENCE: 32
NDECEYCVNV ACTGCL                                                     16

SEQ ID NO: 33     moltype = AA  length = 16
FEATURE           Location/Qualifiers
REGION            1..16
                  note = Chemically Synthesized
SITE              1
                  note = MISC_FEATURE - wherein ASN at position 1 is attached
                   to polyethylene glycol
SITE              1
                  note = MISC_FEATURE - wherein ASN is a D amino acid
SITE              16
                  note = MISC_FEATURE - wherein LEU is a D amino acid
source            1..16
                  mol_type = protein
                  organism = synthetic construct
SEQUENCE: 33
NDECEYCVNV ACTGCL                                                     16

SEQ ID NO: 34     moltype = AA  length = 16
FEATURE           Location/Qualifiers
REGION            1..16
                  note = Chemically Synthesized
SITE              1
                  note = MISC_FEATURE - wherein ASN is a D amino acid
SITE              16
                  note = MISC_FEATURE - wherein LEU at position 16 is
                   attached to polyethylene glycol
SITE              16
                  note = MISC_FEATURE - wherein LEU is a D amino acid
source            1..16
                  mol_type = protein
                  organism = synthetic construct
SEQUENCE: 34
NDECEYCVNV ACTGCL                                                     16

SEQ ID NO: 35     moltype = AA  length = 16
FEATURE           Location/Qualifiers
REGION            1..16
                  note = Chemically Synthesized
SITE              1
                  note = MISC_FEATURE - wherein ASN at position 1 is attached
                   to polyethylene glycol
SITE              1
                  note = MISC_FEATURE - wherein ASN is a D amino acid
SITE              16
                  note = MISC_FEATURE - wherein LEU is a D amino acid
SITE              16
                  note = MISC_FEATURE - wherein LEU at position 16 is
                   attached to polyethylene glycol
source            1..16
                  mol_type = protein
                  organism = synthetic construct
SEQUENCE: 35
NDECESCVNV ACTGCL                                                     16

SEQ ID NO: 36     moltype = AA  length = 16
FEATURE           Location/Qualifiers
REGION            1..16
                  note = Chemically Synthesized
SITE              1
                  note = MISC_FEATURE - wherein ASN at position 1 is attached
                   to polyethylene glycol
SITE              1
                  note = MISC_FEATURE - wherein ASN is a D amino acid
SITE              16
                  note = MISC_FEATURE - wherein LEU is a D amino acid
source            1..16
                  mol_type = protein
                  organism = synthetic construct
```

```
SEQUENCE: 36
NDECESCVNV ACTGCL                                                                  16

SEQ ID NO: 37              moltype = AA  length = 16
FEATURE                    Location/Qualifiers
REGION                     1..16
                           note = Chemically Synthesized
SITE                       1
                           note = MISC_FEATURE - wherein ASN is a D amino acid
SITE                       16
                           note = MISC_FEATURE - wherein LEU at position 16 is
                            attached to polyethylene glycol
SITE                       16
                           note = MISC_FEATURE - wherein LEU is a D amino acid
source                     1..16
                           mol_type = protein
                           organism = synthetic construct
SEQUENCE: 37
NDECESCVNV ACTGCL                                                                  16

SEQ ID NO: 38              moltype = AA  length = 16
FEATURE                    Location/Qualifiers
REGION                     1..16
                           note = Chemically Synthesized
source                     1..16
                           mol_type = protein
                           organism = synthetic construct
SEQUENCE: 38
NDECELCVNV ACTGCS                                                                  16

SEQ ID NO: 39              moltype = AA  length = 16
FEATURE                    Location/Qualifiers
REGION                     1..16
                           note = Chemically Synthesized
SITE                       1
                           note = MISC_FEATURE - wherein ASN at position 1 is attached
                            to polyethylene glycol
SITE                       16
                           note = MISC_FEATURE - wherein SER at position 16 is
                            attached to polyethylene glycol
source                     1..16
                           mol_type = protein
                           organism = synthetic construct
SEQUENCE: 39
NDECELCVNV ACTGCS                                                                  16

SEQ ID NO: 40              moltype = AA  length = 16
FEATURE                    Location/Qualifiers
REGION                     1..16
                           note = Chemically Synthesized
SITE                       1
                           note = MISC_FEATURE - wherein ASN at position 1 is attached
                            to polyethylene glycol
source                     1..16
                           mol_type = protein
                           organism = synthetic construct
SEQUENCE: 40
NDECELCVNV ACTGCS                                                                  16

SEQ ID NO: 41              moltype = AA  length = 16
FEATURE                    Location/Qualifiers
REGION                     1..16
                           note = Chemically Synthesized
SITE                       16
                           note = MISC_FEATURE - wherein SER at position 16 is
                            attached to polyethylene glycol
source                     1..16
                           mol_type = protein
                           organism = synthetic construct
SEQUENCE: 41
NDECELCVNV ACTGCS                                                                  16

SEQ ID NO: 42              moltype = AA  length = 16
FEATURE                    Location/Qualifiers
REGION                     1..16
                           note = Chemically Synthesized
SITE                       1
                           note = MISC_FEATURE - wherein ASN at position 1 is attached
                            to polyethylene glycol
```

```
                                     -continued

SITE                  16
                      note = MISC_FEATURE - wherein SER is a D amino acid
SITE                  16
                      note = MISC_FEATURE - wherein SER at position 16 is
                       attached to polyethylene glycol
source                1..16
                      mol_type = protein
                      organism = synthetic construct
SEQUENCE: 42
NDECELCVNV ACTGCS                                                            16

SEQ ID NO: 43         moltype = AA  length = 16
FEATURE               Location/Qualifiers
REGION                1..16
                      note = Chemically Synthesized
SITE                  1
                      note = MISC_FEATURE - wherein ASN at position 1 is attached
                       to polyethylene glycol
SITE                  16
                      note = MISC_FEATURE - wherein SER is a D amino acid
source                1..16
                      mol_type = protein
                      organism = synthetic construct
SEQUENCE: 43
NDECELCVNV ACTGCS                                                            16

SEQ ID NO: 44         moltype = AA  length = 16
FEATURE               Location/Qualifiers
REGION                1..16
                      note = Chemically Synthesized
SITE                  16
                      note = MISC_FEATURE - wherein SER at position 16 is
                       attached to polyethylene glycol
SITE                  16
                      note = MISC_FEATURE - wherein SER is a D amino acid
source                1..16
                      mol_type = protein
                      organism = synthetic construct
SEQUENCE: 44
NDECELCVNV ACTGCS                                                            16

SEQ ID NO: 45         moltype = AA  length = 16
FEATURE               Location/Qualifiers
REGION                1..16
                      note = Chemically Synthesized
VARIANT               5..6
                      note = MISC_FEATURE - x is natural, unnatural, an analogue,
                       L, D, or methylated amino acid or any combination
VARIANT               8..11
                      note = MISC_FEATURE - x is natural, unnatural, an analogue,
                       L, D, or methylated amino acid or any combination
VARIANT               13..14
                      note = MISC_FEATURE - x is natural, unnatural, an analogue,
                       L, D, or methylated amino acid or any combination
VARIANT               16
                      note = MISC_FEATURE - x is natural, unnatural, an analogue,
                       L, D, or methylated amino acid or any combination
source                1..16
                      mol_type = protein
                      organism = synthetic construct
SEQUENCE: 45
NDECXXCXXX XCXXCX                                                            16

SEQ ID NO: 46         moltype = AA  length = 16
FEATURE               Location/Qualifiers
REGION                1..16
                      note = Chemically Synthesized
VARIANT               1
                      note = x is any natural, unnatural or an analogue amino
                       acid, may be L, D, or a methylated amino acid, or any
                       combination
VARIANT               2
                      note = x is any natural, unnatural or an analogue amino
                       acid, may be L, D, or a methylated amino acid, or any
                       combination
VARIANT               3
                      note = x is any natural, unnatural or an analogue amino
                       acid, may be L, D, or a methylated amino acid, or any
                       combination
```

```
VARIANT                 5..6
                        note = MISC_FEATURE - x is natural, unnatural, analogue, L,
                         D, or methylated amino acid or any combination
VARIANT                 8..11
                        note = MISC_FEATURE - x is natural, unnatural, analogue, L,
                         D, or methylated amino acid or any combination
VARIANT                 13..14
                        note = MISC_FEATURE - x is natural, unnatural, analogue, L,
                         D, or methylated amino acid or any combination
VARIANT                 16
                        note = x is any natural, unnatural or an analogue amino
                         acid, may be L, D, or a methylated amino acid, or any
                         combination
source                  1..16
                        mol_type = protein
                        organism = synthetic construct
SEQUENCE: 46
XXXCXXCXXX XCXXCX                                                            16

SEQ ID NO: 47           moltype = AA  length = 16
FEATURE                 Location/Qualifiers
REGION                  1..16
                        note = Chemically Synthesized
VARIANT                 1
                        note = MISC_FEATURE - x is none or a natural, unnatural or
                         an analogue amino acid, may be L, D, or a methylated amino
                         acid or any combination thereof
VARIANT                 2
                        note = MISC_FEATURE - x is none or a natural, unnatural or
                         an analogue amino acid, may be L, D, or a methylated amino
                         acid or any combination thereof
VARIANT                 3
                        note = MISC_FEATURE - x is none or a natural, unnatural or
                         an analogue amino acid, may be L, D, or a methylated amino
                         acid or any combination thereof
VARIANT                 4
                        note = MISC_FEATURE - wherein x is a cysteine,
                         penicillamine homocysteine, or 3-mercaptoproline
VARIANT                 6
                        note = MISC_FEATURE - x is none or a natural, unnatural or
                         an analogue amino acid, may be L, D, or a methylated amino
                         acid or any combination thereof
VARIANT                 7
                        note = MISC_FEATURE - wherein x is a cysteine,
                         penicillamine homocysteine, or 3-mercaptoproline
VARIANT                 12
                        note = MISC_FEATURE - wherein x is a cysteine,
                         penicillamine homocysteine, or 3-mercaptoproline
VARIANT                 15
                        note = MISC_FEATURE - wherein x is a cysteine,
                         penicillamine homocysteine, or 3-mercaptoproline
VARIANT                 16
                        note = MISC_FEATURE - x is none or a natural, unnatural or
                         an analogue amino acid, may be L, D, or a methylated amino
                         acid or any combination thereof
source                  1..16
                        mol_type = protein
                        organism = synthetic construct
SEQUENCE: 47
XXXXEXXVNV AXTGXX                                                            16

SEQ ID NO: 48           moltype =   length =
SEQUENCE: 48
000

SEQ ID NO: 49           moltype = AA  length = 16
FEATURE                 Location/Qualifiers
REGION                  1..16
                        note = Chemically Synthesized
VARIANT                 5..6
                        note = MISC_FEATURE - x is natural, unnatural, analogue, L,
                         D, or methylated amino acid or any combination
VARIANT                 8
                        note = MISC_FEATURE - x is natural, unnatural, analogue, L,
                         D, or methylated amino acid or any combination
VARIANT                 10..11
                        note = MISC_FEATURE - x is natural, unnatural, analogue, L,
                         D, or methylated amino acid or any combination
```

| | |
|---|---|
| VARIANT | 13..14<br>note = MISC_FEATURE - x is natural, unnatural, analogue, L, D, or methylated amino acid or any combination |
| VARIANT | 16<br>note = MISC_FEATURE - x is natural, unnatural, analogue, L, D, or methylated amino acid or any combination |
| source | 1..16<br>mol_type = protein<br>organism = synthetic construct |
| SEQUENCE: 49 | |
| NDDCXXCXNX XCXXCX | 16 |
| | |
| SEQ ID NO: 50 | moltype = AA length = 16 |
| FEATURE | Location/Qualifiers |
| REGION | 1..16<br>note = Chemically Synthesized |
| SITE | 1<br>note = MISC_FEATURE - wherein ASN is a D amino acid |
| VARIANT | 5..6<br>note = x is any natural, unnatural, analogue, L, D, or methylated amino acid or any combination |
| VARIANT | 8<br>note = x is any natural, unnatural, analogue, L, D, or methylated amino acid or any combination |
| VARIANT | 10..11<br>note = x is any natural, unnatural, analogue, L, D, or methylated amino acid or any combination |
| VARIANT | 13..14<br>note = x is any natural, unnatural, analogue, L, D, or methylated amino acid or any combination |
| VARIANT | 16<br>note = x is any natural, unnatural, analogue, L, D, or methylated amino acid or any combination |
| VARIANT | 16<br>note = MISC_FEATURE - wherein x is a D amino acid |
| source | 1..16<br>mol_type = protein<br>organism = synthetic construct |
| SEQUENCE: 50 | |
| NEECXXCXNX XCXXCX | 16 |
| | |
| SEQ ID NO: 51 | moltype = AA length = 16 |
| FEATURE | Location/Qualifiers |
| REGION | 1..16<br>note = Chemically Synthesized |
| SITE | 1<br>note = MISC_FEATURE - wherein ASN is a D amino acid |
| SITE | 2<br>note = MISC_FEATURE - wherein GLU is a D amino acid |
| VARIANT | 5..6<br>note = x is natural, unnatural, analogue, L, D, or methylated amino acid or any combination |
| VARIANT | 8<br>note = x is natural, unnatural, analogue, L, D, or methylated amino acid or any combination |
| VARIANT | 10..11<br>note = x is natural, unnatural, analogue, L, D, or methylated amino acid or any combination |
| VARIANT | 13..14<br>note = x is natural, unnatural, analogue, L, D, or methylated amino acid or any combination |
| VARIANT | 16<br>note = wherein x is a D amino acid |
| VARIANT | 16<br>note = x is natural, unnatural, analogue, L, D, or methylated amino acid or any combination |
| source | 1..16<br>mol_type = protein<br>organism = synthetic construct |
| SEQUENCE: 51 | |
| NEDCXXCXNX XCXXCX | 16 |
| | |
| SEQ ID NO: 52 | moltype = AA length = 16 |
| FEATURE | Location/Qualifiers |
| REGION | 1..16<br>note = Chemically Synthesized |
| SITE | 1<br>note = MISC_FEATURE - wherein ASN is a D amino acid |

```
SITE              2
                  note = MISC_FEATURE - wherein ASP is a D amino acid
VARIANT           5..6
                  note = x is natural, unnatural, analogue, L, D, or
                  methylated amino acid or any combination
VARIANT           8
                  note = x is natural, unnatural, analogue, L, D, or
                  methylated amino acid or any combination
VARIANT           10..11
                  note = x is natural, unnatural, analogue, L, D, or
                  methylated amino acid or any combination
VARIANT           13..14
                  note = x is natural, unnatural, analogue, L, D, or
                  methylated amino acid or any combination
VARIANT           16
                  note = wherein x is a D amino acid
VARIANT           16
                  note = x is natural, unnatural, analogue, L, D, or
                  methylated amino acid or any combination
source            1..16
                  mol_type = protein
                  organism = synthetic construct
SEQUENCE: 52
NDECXXCXNX XCXXCX                                                        16

SEQ ID NO: 53     moltype = AA  length = 16
FEATURE           Location/Qualifiers
REGION            1..16
                  note = Chemically Synthesized
SITE              1
                  note = MISC_FEATURE - wherein ASN is a D amino acid
SITE              2
                  note = MISC_FEATURE - wherein ASP is a D amino acid
SITE              3
                  note = MISC_FEATURE - wherein GLU is a D amino acid
VARIANT           5..6
                  note = x is natural, unnatural, analogue, L, D, or
                  methylated amino acid or any combination
VARIANT           8
                  note = x is natural, unnatural, analogue, L, D, or
                  methylated amino acid or any combination
VARIANT           10..11
                  note = x is natural, unnatural, analogue, L, D, or
                  methylated amino acid or any combination
VARIANT           13..14
                  note = x is natural, unnatural, analogue, L, D, or
                  methylated amino acid or any combination
VARIANT           16
                  note = wherein x is a D amino acid
VARIANT           16
                  note = wherein x is a D amino acid
source            1..16
                  mol_type = protein
                  organism = synthetic construct
SEQUENCE: 53
NDECXXCXYX XCXXCX                                                        16

SEQ ID NO: 54     moltype = AA  length = 16
FEATURE           Location/Qualifiers
REGION            1..16
                  note = Chemically Synthesized
SITE              1
                  note = MISC_FEATURE - wherein ASN is a D amino acid
SITE              2
                  note = MISC_FEATURE - wherein GLU is a D amino acid
SITE              3
                  note = MISC_FEATURE - wherein GLU is a D amino acid
VARIANT           5..6
                  note = x is natural, unnatural, analogue, L, D, or
                  methylated amino acid or any combination
VARIANT           8
                  note = x is natural, unnatural, analogue, L, D, or
                  methylated amino acid or any combination
VARIANT           10..11
                  note = x is natural, unnatural, analogue, L, D, or
                  methylated amino acid or any combination
VARIANT           13..14
                  note = x is natural, unnatural, analogue, L, D, or
                  methylated amino acid or any combination
```

```
VARIANT            16
                   note = wherein x is a D amino acid
source             1..16
                   mol_type = protein
                   organism = synthetic construct
SEQUENCE: 54
NEECXXCXYX XCXXCX                                                            16

SEQ ID NO: 55      moltype = AA  length = 14
FEATURE            Location/Qualifiers
REGION             1..14
                   note = Chemically Synthesized
source             1..14
                   mol_type = protein
                   organism = synthetic construct
SEQUENCE: 55
CCEYCCNPAC TGCY                                                              14

SEQ ID NO: 56      moltype = AA  length = 13
FEATURE            Location/Qualifiers
REGION             1..13
                   note = Chemically Synthesized
source             1..13
                   mol_type = protein
                   organism = synthetic construct
SEQUENCE: 56
CCEYCCNPAC TGC                                                               13

SEQ ID NO: 57      moltype = AA  length = 14
FEATURE            Location/Qualifiers
REGION             1..14
                   note = Chemically Synthesized
SITE               1
                   note = MISC_FEATURE - wherein CYS at position 1 is attached
                    to polyethylene glycol
SITE               14
                   note = MISC_FEATURE - wherein TYR at position 14 is
                    attached to polyethylene glycol
source             1..14
                   mol_type = protein
                   organism = synthetic construct
SEQUENCE: 57
CCEYCCNPAC TGCY                                                              14

SEQ ID NO: 58      moltype = AA  length = 16
FEATURE            Location/Qualifiers
REGION             1..16
                   note = Chemically Synthesized
source             1..16
                   mol_type = protein
                   organism = synthetic construct
REGION             3..8
                   note = The peptide CCESCC is circular.
SITE               3..8
                   note = Cysteine cysteine disulfide
SITE               4..12
                   note = The peptide CESCCNPAC is circular.
SITE               4..12
                   note = Cysteine cysteine disulfide
REGION             7..15
                   note = The peptide CCNPACTGC is circular.
SITE               7..15
                   note = Cysteine cysteine disulfide
SEQUENCE: 58
NFCCESCCNP ACTGCY                                                            16

SEQ ID NO: 59      moltype = AA  length = 16
FEATURE            Location/Qualifiers
REGION             1..16
                   note = Chemically Synthesized
source             1..16
                   mol_type = protein
                   organism = synthetic construct
SEQUENCE: 59
NFCCEFCCNP ACTGCY                                                            16
```

-continued

```
SEQ ID NO: 60              moltype = AA  length = 14
FEATURE                    Location/Qualifiers
REGION                     1..14
                           note = Chemically Synthesized
SITE                       14
                           note = MISC_FEATURE - wherein TYR is a D amino acid
source                     1..14
                           mol_type = protein
                           organism = synthetic construct
SEQUENCE: 60
CCEYCCNPAC TGCY                                                                14

SEQ ID NO: 61              moltype = AA  length = 14
FEATURE                    Location/Qualifiers
REGION                     1..14
                           note = Chemically Synthesized
SITE                       1
                           note = MISC_FEATURE - wherein CYS at position 1 is attached
                            to polyethylene glycol
source                     1..14
                           mol_type = protein
                           organism = synthetic construct
SEQUENCE: 61
CCEYCCNPAC TGCY                                                                14

SEQ ID NO: 62              moltype = AA  length = 16
FEATURE                    Location/Qualifiers
REGION                     1..16
                           note = Chemically Synthesized
source                     1..16
                           mol_type = protein
                           organism = synthetic construct
SEQUENCE: 62
NFCCETCCNP ACTGCY                                                              16

SEQ ID NO: 63              moltype = AA  length = 16
FEATURE                    Location/Qualifiers
REGION                     1..16
                           note = Chemically Synthesized
SITE                       16
                           note = MISC_FEATURE - wherein TYR is a D amino acid
source                     1..16
                           mol_type = protein
                           organism = synthetic construct
SEQUENCE: 63
NFCCESCCNP ACTGCY                                                              16

SEQ ID NO: 64              moltype = AA  length = 16
FEATURE                    Location/Qualifiers
REGION                     1..16
                           note = Chemically Synthesized
SITE                       1
                           note = MISC_FEATURE - wherein ASN is a D amino acid
source                     1..16
                           mol_type = protein
                           organism = synthetic construct
SEQUENCE: 64
NFCCESCCNP ACTGCY                                                              16

SEQ ID NO: 65              moltype = AA  length = 16
FEATURE                    Location/Qualifiers
REGION                     1..16
                           note = Chemically Synthesized
SITE                       1
                           note = MISC_FEATURE - wherein ASN is a D amino acid
SITE                       16
                           note = MISC_FEATURE - wherein TYR is a D amino acid
source                     1..16
                           mol_type = protein
                           organism = synthetic construct
SEQUENCE: 65
NFCCESCCNP ACTGCY                                                              16

SEQ ID NO: 66              moltype = AA  length = 16
FEATURE                    Location/Qualifiers
REGION                     1..16
                           note = Chemically Synthesized
SITE                       16
                           note = MISC_FEATURE - wherein TYR is a D amino acid
```

```
source                  1..16
                        mol_type = protein
                        organism = synthetic construct
SEQUENCE: 66
NFCCETCCNP ACTGCY                                                         16

SEQ ID NO: 67           moltype = AA  length = 16
FEATURE                 Location/Qualifiers
REGION                  1..16
                        note = Chemically Synthesized
SITE                    1
                        note = MISC_FEATURE - wherein ASN is a D amino acid
source                  1..16
                        mol_type = protein
                        organism = synthetic construct
SEQUENCE: 67
NFCCETCCNP ACTGCY                                                         16

SEQ ID NO: 68           moltype = AA  length = 16
FEATURE                 Location/Qualifiers
REGION                  1..16
                        note = Chemically Synthesized
SITE                    1
                        note = MISC_FEATURE - wherein ASN is a D amino acid
SITE                    16
                        note = MISC_FEATURE - wherein TYR is a D amino acid
source                  1..16
                        mol_type = protein
                        organism = synthetic construct
SEQUENCE: 68
NFCCETCCNP ACTGCY                                                         16

SEQ ID NO: 69           moltype = AA  length = 16
FEATURE                 Location/Qualifiers
REGION                  1..16
                        note = Chemically Synthesized
SITE                    16
                        note = MISC_FEATURE - wherein TYR is a D amino acid
source                  1..16
                        mol_type = protein
                        organism = synthetic construct
SEQUENCE: 69
NFCCEFCCNP ACTGCY                                                         16

SEQ ID NO: 70           moltype = AA  length = 16
FEATURE                 Location/Qualifiers
REGION                  1..16
                        note = Chemically Synthesized
SITE                    1
                        note = MISC_FEATURE - wherein ASN is a D amino acid
source                  1..16
                        mol_type = protein
                        organism = synthetic construct
SEQUENCE: 70
NFCCEFCCNP ACTGCY                                                         16

SEQ ID NO: 71           moltype = AA  length = 16
FEATURE                 Location/Qualifiers
REGION                  1..16
                        note = Chemically Synthesized
SITE                    1
                        note = MISC_FEATURE - wherein ASN is a D amino acid
SITE                    16
                        note = MISC_FEATURE - wherein TYR is a D amino acid
source                  1..16
                        mol_type = protein
                        organism = synthetic construct
SEQUENCE: 71
NFCCEFCCNP ACTGCY                                                         16

SEQ ID NO: 72           moltype = AA  length = 14
FEATURE                 Location/Qualifiers
REGION                  1..14
                        note = Chemically Synthesized
SITE                    14
                        note = MISC_FEATURE - wherein TYR at position 14 is
                        attached to polyethylene glycol
```

```
source                  1..14
                        mol_type = protein
                        organism = synthetic construct
SEQUENCE: 72
CCEYCCNPAC TGCY                                                          14

SEQ ID NO: 73           moltype = AA  length = 13
FEATURE                 Location/Qualifiers
REGION                  1..13
                        note = Chemically Synthesized
SITE                    1
                        note = MISC_FEATURE - wherein CYS at position 1 is attached
                         to polyethylene glycol
SITE                    13
                        note = MISC_FEATURE - wherein CYS at position 13 is
                         attached to polyethylene glycol
source                  1..13
                        mol_type = protein
                        organism = synthetic construct
SEQUENCE: 73
CCEYCCNPAC TGC                                                           13

SEQ ID NO: 74           moltype = AA  length = 13
FEATURE                 Location/Qualifiers
REGION                  1..13
                        note = Chemically Synthesized
SITE                    1
                        note = MISC_FEATURE - wherein CYS at position 1 is attached
                         to polyethylene glycol
source                  1..13
                        mol_type = protein
                        organism = synthetic construct
SEQUENCE: 74
CCEYCCNPAC TGC                                                           13

SEQ ID NO: 75           moltype = AA  length = 13
FEATURE                 Location/Qualifiers
REGION                  1..13
                        note = Chemically Synthesized
SITE                    13
                        note = MISC_FEATURE - wherein CYS at position 13 is
                         attached to polyethylene glycol
source                  1..13
                        mol_type = protein
                        organism = synthetic construct
SEQUENCE: 75
CCEYCCNPAC TGC                                                           13

SEQ ID NO: 76           moltype = AA  length = 16
FEATURE                 Location/Qualifiers
REGION                  1..16
                        note = Chemically Synthesized
SITE                    1
                        note = MISC_FEATURE - wherein ASN at position 1 is attached
                         to polyethylene glycol
SITE                    16
                        note = MISC_FEATURE - wherein TYR at position 16 is
                         attached to polyethylene glycol
source                  1..16
                        mol_type = protein
                        organism = synthetic construct
SEQUENCE: 76
NFCCESCCNP ACTGCY                                                        16

SEQ ID NO: 77           moltype = AA  length = 16
FEATURE                 Location/Qualifiers
REGION                  1..16
                        note = Chemically Synthesized
SITE                    1
                        note = MISC_FEATURE - wherein ASN at position 1 is attached
                         to polyethylene glycol
source                  1..16
                        mol_type = protein
                        organism = synthetic construct
SEQUENCE: 77
NFCCESCCNP ACTGCY                                                        16

SEQ ID NO: 78           moltype = AA  length = 16
FEATURE                 Location/Qualifiers
```

```
REGION                  1..16
                        note = Chemically Synthesized
SITE                    16
                        note = MISC_FEATURE - wherein TYR at position 16 is
                         attached to polyethylene glycol
source                  1..16
                        mol_type = protein
                        organism = synthetic construct
SEQUENCE: 78
NFCCESCCNP ACTGCY                                                            16

SEQ ID NO: 79           moltype = AA  length = 16
FEATURE                 Location/Qualifiers
REGION                  1..16
                        note = Chemically Synthesized
SITE                    1
                        note = MISC_FEATURE - wherein ASN at position 1 is attached
                         to polyethylene glycol
SITE                    16
                        note = MISC_FEATURE - wherein TYR at position 16 is
                         attached to polyethylene glycol
source                  1..16
                        mol_type = protein
                        organism = synthetic construct
SEQUENCE: 79
NFCCEFCCNP ACTGCY                                                            16

SEQ ID NO: 80           moltype = AA  length = 16
FEATURE                 Location/Qualifiers
REGION                  1..16
                        note = Chemically Synthesized
SITE                    1
                        note = MISC_FEATURE - wherein ASN at position 1 is attached
                         to polyethylene glycol
source                  1..16
                        mol_type = protein
                        organism = synthetic construct
SEQUENCE: 80
NFCCEFCCNP ACTGCY                                                            16

SEQ ID NO: 81           moltype = AA  length = 16
FEATURE                 Location/Qualifiers
REGION                  1..16
                        note = Chemically Synthesized
SITE                    16
                        note = MISC_FEATURE - wherein TYR at position 16 is
                         attached to polyethylene glycol
source                  1..16
                        mol_type = protein
                        organism = synthetic construct
SEQUENCE: 81
NFCCEFCCNP ACTGCY                                                            16

SEQ ID NO: 82           moltype = AA  length = 16
FEATURE                 Location/Qualifiers
REGION                  1..16
                        note = Chemically Synthesized
SITE                    1
                        note = MISC_FEATURE - wherein ASN at position 1 is attached
                         to polyethylene glycol
SITE                    16
                        note = MISC_FEATURE - wherein TYR at position 16 is
                         attached to polyethylene glycol
source                  1..16
                        mol_type = protein
                        organism = synthetic construct
SEQUENCE: 82
NFCCEYCCNP ACTGCY                                                            16

SEQ ID NO: 83           moltype = AA  length = 16
FEATURE                 Location/Qualifiers
REGION                  1..16
                        note = Chemically Synthesized
SITE                    1
                        note = MISC_FEATURE - wherein ASN at position 1 is attached
                         to polyethylene glycol
source                  1..16
                        mol_type = protein
                        organism = synthetic construct
```

```
SEQUENCE: 83
NFCCEYCCNP ACTGCY                                                    16

SEQ ID NO: 84           moltype = AA  length = 16
FEATURE                 Location/Qualifiers
REGION                  1..16
                        note = Chemically Synthesized
SITE                    16
                        note = MISC_FEATURE - wherein TYR at position 16 is
                         attached to polyethylene glycol
source                  1..16
                        mol_type = protein
                        organism = synthetic construct
SEQUENCE: 84
NFCCEYCCNP ACTGCY                                                    16

SEQ ID NO: 85           moltype = AA  length = 14
FEATURE                 Location/Qualifiers
REGION                  1..14
                        note = Chemically Synthesized
source                  1..14
                        mol_type = protein
                        organism = synthetic construct
SEQUENCE: 85
CCESCCNPAC TGCY                                                      14

SEQ ID NO: 86           moltype = AA  length = 14
FEATURE                 Location/Qualifiers
REGION                  1..14
                        note = Chemically Synthesized
source                  1..14
                        mol_type = protein
                        organism = synthetic construct
SEQUENCE: 86
CCEFCCNPAC TGCY                                                      14

SEQ ID NO: 87           moltype = AA  length = 13
FEATURE                 Location/Qualifiers
REGION                  1..13
                        note = Chemically Synthesized
source                  1..13
                        mol_type = protein
                        organism = synthetic construct
SEQUENCE: 87
CCESCCNPAC TGC                                                       13

SEQ ID NO: 88           moltype = AA  length = 13
FEATURE                 Location/Qualifiers
REGION                  1..13
                        note = Chemically Synthesized
source                  1..13
                        mol_type = protein
                        organism = synthetic construct
SEQUENCE: 88
CCEFCCNPAC TGC                                                       13

SEQ ID NO: 89           moltype = AA  length = 14
FEATURE                 Location/Qualifiers
REGION                  1..14
                        note = Chemically Synthesized
SITE                    1..2
                        note = MISC_FEATURE - wherein x is penicillamine
SITE                    5..6
                        note = MISC_FEATURE - wherein x is penicillamine
SITE                    10
                        note = MISC_FEATURE - wherein x is penicillamine
SITE                    13
                        note = MISC_FEATURE - wherein x is penicillamine
source                  1..14
                        mol_type = protein
                        organism = synthetic construct
SEQUENCE: 89
XXEYXXNPAX TGXY                                                      14

SEQ ID NO: 90           moltype = AA  length = 13
FEATURE                 Location/Qualifiers
REGION                  1..13
                        note = Chemically Synthesized
SITE                    1..2
```

-continued

| | | |
|---|---|---|
| SITE | 5..6 | note = MISC_FEATURE - wherein x is penicillamine |
| SITE | 10 | note = MISC_FEATURE - wherein x is penicillamine |
| SITE | 13 | note = MISC_FEATURE - wherein x is penicillamine |
| source | 1..13 | mol_type = protein<br>organism = synthetic construct |

SEQUENCE: 90
XXEYXXNPAX TGX                                                                13

| | | |
|---|---|---|
| SEQ ID NO: 91 | moltype = AA  length = 22 | |
| FEATURE | Location/Qualifiers | |
| REGION | 1..22 | note = Chemically Synthesized |
| VARIANT | 1..6 | note = MISC_FEATURE - x is natural, unnatural, analogue, L, D, or methylated amino acid or any combination |
| VARIANT | 11 | note = MISC_FEATURE - x is natural, unnatural, analogue, L, D, or methylated amino acid or any combination |
| VARIANT | 15..17 | note = MISC_FEATURE - x is natural, unnatural, analogue, L, D, or methylated amino acid or any combination |
| VARIANT | 19..20 | note = MISC_FEATURE - x is natural, unnatural, analogue, L, D, or methylated amino acid or any combination |
| VARIANT | 22 | note = MISC_FEATURE - x is natural, unnatural, analogue, L, D, or methylated amino acid or any combination |
| source | 1..22 | mol_type = protein<br>organism = synthetic construct |

SEQUENCE: 91
XXXXXXNYCC XYCCXXXCXX CX                                                      22

| | | |
|---|---|---|
| SEQ ID NO: 92 | moltype = AA  length = 22 | |
| FEATURE | Location/Qualifiers | |
| REGION | 1..22 | note = Chemically Synthesized |
| VARIANT | 1..6 | note = MISC_FEATURE - x is natural, unnatural, analogue, L, D, or methylated amino acid or any combination |
| VARIANT | 11 | note = MISC_FEATURE - x is natural, unnatural, analogue, L, D, or methylated amino acid or any combination |
| VARIANT | 15..17 | note = MISC_FEATURE - x is natural, unnatural, analogue, L, D, or methylated amino acid or any combination |
| VARIANT | 19..20 | note = MISC_FEATURE - x is natural, unnatural, analogue, L, D, or methylated amino acid or any combination |
| VARIANT | 22 | note = MISC_FEATURE - x is natural, unnatural, analogue, L, D, or methylated amino acid or any combination |
| source | 1..22 | mol_type = protein<br>organism = synthetic construct |

SEQUENCE: 92
XXXXXXNFCC XFCCXXXCXX CX                                                      22

| | | |
|---|---|---|
| SEQ ID NO: 93 | moltype = AA  length = 16 | |
| FEATURE | Location/Qualifiers | |
| REGION | 1..16 | note = Chemically Synthesized |
| VARIANT | 5 | note = MISC_FEATURE - x is natural, unnatural, analogue, L, D, or methylated amino acid or any combination |
| VARIANT | 9..11 | note = MISC_FEATURE - x is natural, unnatural, analogue, L, D, or methylated amino acid or any combination |
| VARIANT | 13..14 | note = MISC_FEATURE - x is natural, unnatural, analogue, L, D, or methylated amino acid or any combination |
| VARIANT | 16 | note = MISC_FEATURE - x is natural, unnatural, analogue, L, D, or methylated amino acid or any combination |

```
source                   1..16
                         mol_type = protein
                         organism = synthetic construct
SEQUENCE: 93
NFCCXFCCXX XCXXCX                                                    16

SEQ ID NO: 94            moltype = AA  length = 16
FEATURE                  Location/Qualifiers
REGION                   1..16
                         note = Chemically Synthesized
SITE                     3
                         note = MISC_FEATURE - wherein x is penicillamine
VARIANT                  5
                         note = MISC_FEATURE - x is natural, unnatural, analogue, L,
                         D, or methylated amino acid or any combination
SITE                     8
                         note = MISC_FEATURE - wherein x is penicillamine
VARIANT                  9..11
                         note = MISC_FEATURE - x is natural, unnatural, analogue, L,
                         D, or methylated amino acid or any combination
VARIANT                  13..14
                         note = MISC_FEATURE - x is natural, unnatural, analogue, L,
                         D, or methylated amino acid or any combination
VARIANT                  16
                         note = MISC_FEATURE - x is natural, unnatural, analogue, L,
                         D, or methylated amino acid or any combination
source                   1..16
                         mol_type = protein
                         organism = synthetic construct
SEQUENCE: 94
NFXCXFCXXX XCXXCX                                                    16

SEQ ID NO: 95            moltype =   length =
SEQUENCE: 95
000

SEQ ID NO: 96            moltype = AA  length = 14
FEATURE                  Location/Qualifiers
REGION                   1..14
                         note = Chemically Synthesized
VARIANT                  1..2
                         note = MISC_FEATURE - wherein x is a cysteine,
                         penicillamine homocysteine, or 3-mercaptoproline
VARIANT                  4
                         note = MISC_FEATURE - x is natural, unnatural, analogue, L,
                         D, or methylated amino acid or any combination
VARIANT                  5..6
                         note = MISC_FEATURE - wherein x is a cysteine,
                         penicillamine homocysteine, or 3-mercaptoproline
VARIANT                  10
                         note = MISC_FEATURE - wherein x is a cysteine,
                         penicillamine homocysteine, or 3-mercaptoproline
VARIANT                  13
                         note = MISC_FEATURE - wherein x is a cysteine,
                         penicillamine homocysteine, or 3-mercaptoproline
source                   1..14
                         mol_type = protein
                         organism = synthetic construct
SEQUENCE: 96
XXEXXXNPAX TGXY                                                      14

SEQ ID NO: 97            moltype = AA  length = 13
FEATURE                  Location/Qualifiers
REGION                   1..13
                         note = Chemically Synthesized
VARIANT                  1..2
                         note = MISC_FEATURE - wherein x is a cysteine,
                         penicillamine homocysteine, or 3-mercaptoproline
VARIANT                  4
                         note = MISC_FEATURE - x is natural, unnatural, analogue, L,
                         D, or methylated amino acid or any combination
VARIANT                  5..6
                         note = MISC_FEATURE - wherein x is a cysteine,
                         penicillamine homocysteine, or 3-mercaptoproline
VARIANT                  10
                         note = MISC_FEATURE - wherein x is a cysteine,
                         penicillamine homocysteine, or 3-mercaptoproline
```

```
VARIANT              13
                     note = MISC_FEATURE - wherein x is a cysteine,
                      penicillamine homocysteine, or 3-mercaptoproline
source               1..13
                     mol_type = protein
                     organism = synthetic construct
SEQUENCE: 97
XXEXXXNPAX TGX                                                              13

SEQ ID NO: 98        moltype =   length =
SEQUENCE: 98
000

SEQ ID NO: 99        moltype = AA   length = 16
FEATURE              Location/Qualifiers
REGION               1..16
                     note = Chemically Synthesized
SITE                 1
                     note = MISC_FEATURE - wherein ASN is a D amino acid
SITE                 16
                     note = MISC_FEATURE - wherein LEU is a D amino acid
SITE                 16
                     note = MISC_FEATURE - wherein LEU is conjugated to an AMIDE
source               1..16
                     mol_type = protein
                     organism = synthetic construct
SEQUENCE: 99
NDECELCVNV ACTGCL                                                           16

SEQ ID NO: 100       moltype = AA   length = 16
FEATURE              Location/Qualifiers
REGION               1..16
                     note = Chemically Synthesized
SITE                 1
                     note = MISC_FEATURE - wherein ASN is a D amino acid
SITE                 16
                     note = MISC_FEATURE - wherein SER is a D amino acid
source               1..16
                     mol_type = protein
                     organism = synthetic construct
SEQUENCE: 100
NDECELCVNV ACTGCS                                                           16

SEQ ID NO: 101       moltype = AA   length = 16
FEATURE              Location/Qualifiers
REGION               1..16
                     note = Chemically Synthesized
SITE                 1
                     note = MISC_FEATURE - wherein ASN is a D amino acid
SITE                 16
                     note = MISC_FEATURE - wherein SER is a D amino acid
SITE                 16
                     note = MISC_FEATURE - wherein SER is conjugated to an AMIDE
source               1..16
                     mol_type = protein
                     organism = synthetic construct
SEQUENCE: 101
NDECELCVNV ACTGCS                                                           16

SEQ ID NO: 102       moltype = AA   length = 16
FEATURE              Location/Qualifiers
REGION               1..16
                     note = Chemically Synthesized
SITE                 1
                     note = MISC_FEATURE - wherein ASN is a D amino acid
SITE                 16
                     note = MISC_FEATURE - wherein TYR is a D amino acid
source               1..16
                     mol_type = protein
                     organism = synthetic construct
SEQUENCE: 102
NDECELCVNV ACTGCY                                                           16

SEQ ID NO: 103       moltype = AA   length = 16
FEATURE              Location/Qualifiers
REGION               1..16
                     note = Chemically Synthesized
SITE                 1
                     note = MISC_FEATURE - wherein ASN is a D amino acid
```

```
SITE                    16
                        note = MISC_FEATURE - wherein TYR is a D amino acid
SITE                    16
                        note = MISC_FEATURE - wherein TYR is conjugated to an AMIDE
source                  1..16
                        mol_type = protein
                        organism = synthetic construct
SEQUENCE: 103
NDECELCVNV ACTGCY                                                             16

SEQ ID NO: 104          moltype = AA  length = 16
FEATURE                 Location/Qualifiers
REGION                  1..16
                        note = Chemically Synthesized
SITE                    1
                        note = MISC_FEATURE - wherein Xaa is a pyroglutamic acid
SITE                    16
                        note = MISC_FEATURE - wherein LEU is conjugated to an AMIDE
SITE                    16
                        note = MISC_FEATURE - wherein LEU is a D amino acid
source                  1..16
                        mol_type = protein
                        organism = synthetic construct
SEQUENCE: 104
XDECELCVNV ACTGCL                                                             16

SEQ ID NO: 105          moltype = AA  length = 16
FEATURE                 Location/Qualifiers
REGION                  1..16
                        note = Chemically Synthesized
SITE                    1
                        note = MISC_FEATURE - wherein ASN is attached to
                         polyethylene glycol
SITE                    16
                        note = MISC_FEATURE - wherein LEU is attached to
                         polyethylene glycol
source                  1..16
                        mol_type = protein
                        organism = synthetic construct
SEQUENCE: 105
NDECELCVNV ACTGCL                                                             16

SEQ ID NO: 106          moltype = AA  length = 16
FEATURE                 Location/Qualifiers
REGION                  1..16
                        note = Chemically Synthesized
SITE                    1
                        note = MISC_FEATURE - wherein ASN is attached to
                         polyethylene glycol
source                  1..16
                        mol_type = protein
                        organism = synthetic construct
SEQUENCE: 106
NDECELCVNV ACTGCL                                                             16

SEQ ID NO: 107          moltype = AA  length = 16
FEATURE                 Location/Qualifiers
REGION                  1..16
                        note = Chemically Synthesized
SITE                    16
                        note = MISC_FEATURE - wherein LEU is attached to
                         polyethylene glycol
source                  1..16
                        mol_type = protein
                        organism = synthetic construct
SEQUENCE: 107
NDECELCVNV ACTGCL                                                             16

SEQ ID NO: 108          moltype =   length =
SEQUENCE: 108
000

SEQ ID NO: 109          moltype = AA  length = 16
FEATURE                 Location/Qualifiers
REGION                  1..16
                        note = Chemically Synthesized
source                  1..16
                        mol_type = protein
                        organism = synthetic construct
```

```
SEQUENCE: 109
NDDCELCVNV ACTGCL                                                               16

SEQ ID NO: 110          moltype = AA  length = 16
FEATURE                 Location/Qualifiers
REGION                  1..16
                        note = Chemically Synthesized
source                  1..16
                        mol_type = protein
                        organism = synthetic construct
SEQUENCE: 110
EDDCELCVNV ACTGCL                                                               16

SEQ ID NO: 111          moltype = AA  length = 16
FEATURE                 Location/Qualifiers
REGION                  1..16
                        note = Chemically Synthesized
source                  1..16
                        mol_type = protein
                        organism = synthetic construct
SEQUENCE: 111
EDECELCVNV ACTGCL                                                               16

SEQ ID NO: 112          moltype = AA  length = 16
FEATURE                 Location/Qualifiers
REGION                  1..16
                        note = Chemically Synthesized
source                  1..16
                        mol_type = protein
                        organism = synthetic construct
SEQUENCE: 112
EEDCELCVNV ACTGCL                                                               16

SEQ ID NO: 113          moltype = AA  length = 16
FEATURE                 Location/Qualifiers
REGION                  1..16
                        note = Chemically Synthesized
source                  1..16
                        mol_type = protein
                        organism = synthetic construct
SEQUENCE: 113
EEECELCVNV ACTGCL                                                               16

SEQ ID NO: 114          moltype = AA  length = 16
FEATURE                 Location/Qualifiers
REGION                  1..16
                        note = Chemically Synthesized
source                  1..16
                        mol_type = protein
                        organism = synthetic construct
SEQUENCE: 114
DDDCELCVNV ACTGCL                                                               16

SEQ ID NO: 115          moltype = AA  length = 16
FEATURE                 Location/Qualifiers
REGION                  1..16
                        note = Chemically Synthesized
source                  1..16
                        mol_type = protein
                        organism = synthetic construct
SEQUENCE: 115
DDECELCVNV ACTGCL                                                               16

SEQ ID NO: 116          moltype = AA  length = 16
FEATURE                 Location/Qualifiers
REGION                  1..16
                        note = Chemically Synthesized
source                  1..16
                        mol_type = protein
                        organism = synthetic construct
SEQUENCE: 116
DEDCELCVNV ACTGCL                                                               16

SEQ ID NO: 117          moltype = AA  length = 16
FEATURE                 Location/Qualifiers
REGION                  1..16
                        note = Chemically Synthesized
```

```
source                        1..16
                              mol_type = protein
                              organism = synthetic construct
SEQUENCE: 117
DEECELCVNV ACTGCL                                                          16

SEQ ID NO: 118                moltype = AA  length = 16
FEATURE                       Location/Qualifiers
REGION                        1..16
                              note = Chemically Synthesized
source                        1..16
                              mol_type = protein
                              organism = synthetic construct
SEQUENCE: 118
QDDCELCVNV ACTGCL                                                          16

SEQ ID NO: 119                moltype = AA  length = 16
FEATURE                       Location/Qualifiers
REGION                        1..16
                              note = Chemically Synthesized
source                        1..16
                              mol_type = protein
                              organism = synthetic construct
SEQUENCE: 119
QDECELCVNV ACTGCL                                                          16

SEQ ID NO: 120                moltype = AA  length = 16
FEATURE                       Location/Qualifiers
REGION                        1..16
                              note = Chemically Synthesized
source                        1..16
                              mol_type = protein
                              organism = synthetic construct
SEQUENCE: 120
QEDCELCVNV ACTGCL                                                          16

SEQ ID NO: 121                moltype = AA  length = 16
FEATURE                       Location/Qualifiers
REGION                        1..16
                              note = Chemically Synthesized
source                        1..16
                              mol_type = protein
                              organism = synthetic construct
SEQUENCE: 121
QEECELCVNV ACTGCL                                                          16

SEQ ID NO: 122                moltype = AA  length = 16
FEATURE                       Location/Qualifiers
REGION                        1..16
                              note = Chemically Synthesized
source                        1..16
                              mol_type = protein
                              organism = synthetic construct
SEQUENCE: 122
KDDCELCVNV ACTGCL                                                          16

SEQ ID NO: 123                moltype = AA  length = 16
FEATURE                       Location/Qualifiers
REGION                        1..16
                              note = Chemically Synthesized
source                        1..16
                              mol_type = protein
                              organism = synthetic construct
SEQUENCE: 123
KDECELCVNV ACTGCL                                                          16

SEQ ID NO: 124                moltype = AA  length = 16
FEATURE                       Location/Qualifiers
REGION                        1..16
                              note = Chemically Synthesized
source                        1..16
                              mol_type = protein
                              organism = synthetic construct
SEQUENCE: 124
KEDCELCVNV ACTGCL                                                          16
```

```
SEQ ID NO: 125           moltype = AA  length = 16
FEATURE                  Location/Qualifiers
REGION                   1..16
                         note = Chemically Synthesized
source                   1..16
                         mol_type = protein
                         organism = synthetic construct
SEQUENCE: 125
KEECELCVNV ACTGCL                                                          16

SEQ ID NO: 126           moltype = AA  length = 16
FEATURE                  Location/Qualifiers
REGION                   1..16
                         note = Chemically Synthesized
source                   1..16
                         mol_type = protein
                         organism = synthetic construct
SEQUENCE: 126
EDDCELCVNV ACTGCS                                                          16

SEQ ID NO: 127           moltype = AA  length = 16
FEATURE                  Location/Qualifiers
REGION                   1..16
                         note = Chemically Synthesized
source                   1..16
                         mol_type = protein
                         organism = synthetic construct
SEQUENCE: 127
EDECELCVNV ACTGCS                                                          16

SEQ ID NO: 128           moltype = AA  length = 16
FEATURE                  Location/Qualifiers
REGION                   1..16
                         note = Chemically Synthesized
source                   1..16
                         mol_type = protein
                         organism = synthetic construct
SEQUENCE: 128
EEDCELCVNV ACTGCS                                                          16

SEQ ID NO: 129           moltype = AA  length = 16
FEATURE                  Location/Qualifiers
REGION                   1..16
                         note = Chemically Synthesized
source                   1..16
                         mol_type = protein
                         organism = synthetic construct
SEQUENCE: 129
EEECELCVNV ACTGCS                                                          16

SEQ ID NO: 130           moltype = AA  length = 16
FEATURE                  Location/Qualifiers
REGION                   1..16
                         note = Chemically Synthesized
source                   1..16
                         mol_type = protein
                         organism = synthetic construct
SEQUENCE: 130
DDDCELCVNV ACTGCS                                                          16

SEQ ID NO: 131           moltype = AA  length = 16
FEATURE                  Location/Qualifiers
REGION                   1..16
                         note = Chemically Synthesized
source                   1..16
                         mol_type = protein
                         organism = synthetic construct
SEQUENCE: 131
DDECELCVNV ACTGCS                                                          16

SEQ ID NO: 132           moltype = AA  length = 16
FEATURE                  Location/Qualifiers
REGION                   1..16
                         note = Chemically Synthesized
source                   1..16
                         mol_type = protein
                         organism = synthetic construct
```

```
SEQUENCE: 132
DEDCELCVNV ACTGCS                                                                           16

SEQ ID NO: 133              moltype = AA  length = 16
FEATURE                     Location/Qualifiers
REGION                      1..16
                            note = Chemically Synthesized
source                      1..16
                            mol_type = protein
                            organism = synthetic construct
SEQUENCE: 133
DEECELCVNV ACTGCS                                                                           16

SEQ ID NO: 134              moltype = AA  length = 16
FEATURE                     Location/Qualifiers
REGION                      1..16
                            note = Chemically Synthesized
source                      1..16
                            mol_type = protein
                            organism = synthetic construct
SEQUENCE: 134
QDDCELCVNV ACTGCS                                                                           16

SEQ ID NO: 135              moltype = AA  length = 16
FEATURE                     Location/Qualifiers
REGION                      1..16
                            note = Chemically Synthesized
source                      1..16
                            mol_type = protein
                            organism = synthetic construct
SEQUENCE: 135
QDECELCVNV ACTGCS                                                                           16

SEQ ID NO: 136              moltype = AA  length = 16
FEATURE                     Location/Qualifiers
REGION                      1..16
                            note = Chemically Synthesized
source                      1..16
                            mol_type = protein
                            organism = synthetic construct
SEQUENCE: 136
QEDCELCVNV ACTGCS                                                                           16

SEQ ID NO: 137              moltype = AA  length = 16
FEATURE                     Location/Qualifiers
REGION                      1..16
                            note = Chemically Synthesized
source                      1..16
                            mol_type = protein
                            organism = synthetic construct
SEQUENCE: 137
QEECELCVNV ACTGCS                                                                           16

SEQ ID NO: 138              moltype = AA  length = 16
FEATURE                     Location/Qualifiers
REGION                      1..16
                            note = Chemically Synthesized
source                      1..16
                            mol_type = protein
                            organism = synthetic construct
SEQUENCE: 138
KDDCELCVNV ACTGCS                                                                           16

SEQ ID NO: 139              moltype = AA  length = 16
FEATURE                     Location/Qualifiers
REGION                      1..16
                            note = Chemically Synthesized
source                      1..16
                            mol_type = protein
                            organism = synthetic construct
SEQUENCE: 139
KDECELCVNV ACTGCS                                                                           16

SEQ ID NO: 140              moltype = AA  length = 16
FEATURE                     Location/Qualifiers
REGION                      1..16
                            note = Chemically Synthesized
```

```
source                    1..16
                          mol_type = protein
                          organism = synthetic construct
SEQUENCE: 140
KEDCELCVNV ACTGCS                                                           16

SEQ ID NO: 141            moltype = AA   length = 16
FEATURE                   Location/Qualifiers
REGION                    1..16
                          note = Chemically Synthesized
source                    1..16
                          mol_type = protein
                          organism = synthetic construct
SEQUENCE: 141
KEECELCVNV ACTGCS                                                           16

SEQ ID NO: 142            moltype = AA   length = 16
FEATURE                   Location/Qualifiers
REGION                    1..16
                          note = Chemically Synthesized
source                    1..16
                          mol_type = protein
                          organism = synthetic construct
SEQUENCE: 142
EDDCELCINM ACTGCL                                                           16

SEQ ID NO: 143            moltype = AA   length = 16
FEATURE                   Location/Qualifiers
REGION                    1..16
                          note = Chemically Synthesized
source                    1..16
                          mol_type = protein
                          organism = synthetic construct
SEQUENCE: 143
EDECELCINM ACTGCL                                                           16

SEQ ID NO: 144            moltype = AA   length = 16
FEATURE                   Location/Qualifiers
REGION                    1..16
                          note = Chemically Synthesized
source                    1..16
                          mol_type = protein
                          organism = synthetic construct
SEQUENCE: 144
EEDCELCINM ACTGCL                                                           16

SEQ ID NO: 145            moltype = AA   length = 16
FEATURE                   Location/Qualifiers
REGION                    1..16
                          note = Chemically Synthesized
source                    1..16
                          mol_type = protein
                          organism = synthetic construct
SEQUENCE: 145
EEECELCINM ACTGCL                                                           16

SEQ ID NO: 146            moltype = AA   length = 16
FEATURE                   Location/Qualifiers
REGION                    1..16
                          note = Chemically Synthesized
source                    1..16
                          mol_type = protein
                          organism = synthetic construct
SEQUENCE: 146
DDDCELCINM ACTGCL                                                           16

SEQ ID NO: 147            moltype = AA   length = 16
FEATURE                   Location/Qualifiers
REGION                    1..16
                          note = Chemically Synthesized
source                    1..16
                          mol_type = protein
                          organism = synthetic construct
SEQUENCE: 147
DDECELCINM ACTGCL                                                           16
```

```
SEQ ID NO: 148            moltype = AA  length = 16
FEATURE                   Location/Qualifiers
REGION                    1..16
                          note = Chemically Synthesized
source                    1..16
                          mol_type = protein
                          organism = synthetic construct
SEQUENCE: 148
DEDCELCINM ACTGCL                                                             16

SEQ ID NO: 149            moltype = AA  length = 16
FEATURE                   Location/Qualifiers
REGION                    1..16
                          note = Chemically Synthesized
source                    1..16
                          mol_type = protein
                          organism = synthetic construct
SEQUENCE: 149
DEECELCINM ACTGCL                                                             16

SEQ ID NO: 150            moltype = AA  length = 16
FEATURE                   Location/Qualifiers
REGION                    1..16
                          note = Chemically Synthesized
source                    1..16
                          mol_type = protein
                          organism = synthetic construct
SEQUENCE: 150
QDDCELCINM ACTGCL                                                             16

SEQ ID NO: 151            moltype = AA  length = 16
FEATURE                   Location/Qualifiers
REGION                    1..16
                          note = Chemically Synthesized
source                    1..16
                          mol_type = protein
                          organism = synthetic construct
SEQUENCE: 151
QDECELCINM ACTGCL                                                             16

SEQ ID NO: 152            moltype = AA  length = 16
FEATURE                   Location/Qualifiers
REGION                    1..16
                          note = Chemically Synthesized
source                    1..16
                          mol_type = protein
                          organism = synthetic construct
SEQUENCE: 152
QEDCELCINM ACTGCL                                                             16

SEQ ID NO: 153            moltype = AA  length = 16
FEATURE                   Location/Qualifiers
REGION                    1..16
                          note = Chemically Synthesized
source                    1..16
                          mol_type = protein
                          organism = synthetic construct
SEQUENCE: 153
QEECELCINM ACTGCL                                                             16

SEQ ID NO: 154            moltype = AA  length = 16
FEATURE                   Location/Qualifiers
REGION                    1..16
                          note = Chemically Synthesized
source                    1..16
                          mol_type = protein
                          organism = synthetic construct
SEQUENCE: 154
KDDCELCINM ACTGCL                                                             16

SEQ ID NO: 155            moltype = AA  length = 16
FEATURE                   Location/Qualifiers
REGION                    1..16
                          note = Chemically Synthesized
source                    1..16
                          mol_type = protein
                          organism = synthetic construct
```

-continued

```
SEQUENCE: 155
KDECELCINM ACTGCL                                                           16

SEQ ID NO: 156          moltype = AA  length = 16
FEATURE                 Location/Qualifiers
REGION                  1..16
                        note = Chemically Synthesized
source                  1..16
                        mol_type = protein
                        organism = synthetic construct
SEQUENCE: 156
KEDCELCINM ACTGCL                                                           16

SEQ ID NO: 157          moltype = AA  length = 16
FEATURE                 Location/Qualifiers
REGION                  1..16
                        note = Chemically Synthesized
source                  1..16
                        mol_type = protein
                        organism = synthetic construct
SEQUENCE: 157
KEECELCINM ACTGCL                                                           16

SEQ ID NO: 158          moltype = AA  length = 16
FEATURE                 Location/Qualifiers
REGION                  1..16
                        note = Chemically Synthesized
source                  1..16
                        mol_type = protein
                        organism = synthetic construct
SEQUENCE: 158
EDDCELCINM ACTGCS                                                           16

SEQ ID NO: 159          moltype = AA  length = 16
FEATURE                 Location/Qualifiers
REGION                  1..16
                        note = Chemically Synthesized
source                  1..16
                        mol_type = protein
                        organism = synthetic construct
SEQUENCE: 159
EDECELCINM ACTGCS                                                           16

SEQ ID NO: 160          moltype = AA  length = 16
FEATURE                 Location/Qualifiers
REGION                  1..16
                        note = Chemically Synthesized
source                  1..16
                        mol_type = protein
                        organism = synthetic construct
SEQUENCE: 160
EEDCELCINM ACTGCS                                                           16

SEQ ID NO: 161          moltype = AA  length = 16
FEATURE                 Location/Qualifiers
REGION                  1..16
                        note = Chemically Synthesized
source                  1..16
                        mol_type = protein
                        organism = synthetic construct
SEQUENCE: 161
EEECELCINM ACTGCS                                                           16

SEQ ID NO: 162          moltype = AA  length = 16
FEATURE                 Location/Qualifiers
REGION                  1..16
                        note = Chemically Synthesized
source                  1..16
                        mol_type = protein
                        organism = synthetic construct
SEQUENCE: 162
DDDCELCINM ACTGCS                                                           16

SEQ ID NO: 163          moltype = AA  length = 16
FEATURE                 Location/Qualifiers
REGION                  1..16
                        note = Chemically Synthesized
```

```
                        -continued source                  1..16
                        mol_type = protein
                        organism = synthetic construct
SEQUENCE: 163
DDECELCINM ACTGCS                                                    16

SEQ ID NO: 164          moltype = AA   length = 16
FEATURE                 Location/Qualifiers
REGION                  1..16
                        note = Chemically Synthesized
source                  1..16
                        mol_type = protein
                        organism = synthetic construct
SEQUENCE: 164
DEDCELCINM ACTGCS                                                    16

SEQ ID NO: 165          moltype = AA   length = 16
FEATURE                 Location/Qualifiers
REGION                  1..16
                        note = Chemically Synthesized
source                  1..16
                        mol_type = protein
                        organism = synthetic construct
SEQUENCE: 165
DEECELCINM ACTGCS                                                    16

SEQ ID NO: 166          moltype = AA   length = 16
FEATURE                 Location/Qualifiers
REGION                  1..16
                        note = Chemically Synthesized
source                  1..16
                        mol_type = protein
                        organism = synthetic construct
SEQUENCE: 166
QDDCELCINM ACTGCS                                                    16

SEQ ID NO: 167          moltype = AA   length = 16
FEATURE                 Location/Qualifiers
REGION                  1..16
                        note = Chemically Synthesized
source                  1..16
                        mol_type = protein
                        organism = synthetic construct
SEQUENCE: 167
QDECELCINM ACTGCS                                                    16

SEQ ID NO: 168          moltype = AA   length = 16
FEATURE                 Location/Qualifiers
REGION                  1..16
                        note = Chemically Synthesized
source                  1..16
                        mol_type = protein
                        organism = synthetic construct
SEQUENCE: 168
QEDCELCINM ACTGCS                                                    16

SEQ ID NO: 169          moltype = AA   length = 16
FEATURE                 Location/Qualifiers
REGION                  1..16
                        note = Chemically Synthesized
source                  1..16
                        mol_type = protein
                        organism = synthetic construct
SEQUENCE: 169
QEECELCINM ACTGCS                                                    16

SEQ ID NO: 170          moltype = AA   length = 16
FEATURE                 Location/Qualifiers
REGION                  1..16
                        note = Chemically Synthesized
source                  1..16
                        mol_type = protein
                        organism = synthetic construct
SEQUENCE: 170
KDDCELCINM ACTGCS                                                    16
```

```
SEQ ID NO: 171            moltype = AA  length = 16
FEATURE                   Location/Qualifiers
REGION                    1..16
                          note = Chemically Synthesized
source                    1..16
                          mol_type = protein
                          organism = synthetic construct
SEQUENCE: 171
KDECELCINM ACTGCS                                                        16

SEQ ID NO: 172            moltype = AA  length = 16
FEATURE                   Location/Qualifiers
REGION                    1..16
                          note = Chemically Synthesized
source                    1..16
                          mol_type = protein
                          organism = synthetic construct
SEQUENCE: 172
KEDCELCINM ACTGCS                                                        16

SEQ ID NO: 173            moltype = AA  length = 16
FEATURE                   Location/Qualifiers
REGION                    1..16
                          note = Chemically Synthesized
source                    1..16
                          mol_type = protein
                          organism = synthetic construct
SEQUENCE: 173
KEECELCINM ACTGCS                                                        16

SEQ ID NO: 174            moltype =     length =
SEQUENCE: 174
000

SEQ ID NO: 175            moltype = AA  length = 15
FEATURE                   Location/Qualifiers
REGION                    1..15
                          note = Chemically Synthesized
source                    1..15
                          mol_type = protein
                          organism = synthetic construct
SEQUENCE: 175
SHTCEICAFA ACAGC                                                         15

SEQ ID NO: 176            moltype = AA  length = 15
FEATURE                   Location/Qualifiers
REGION                    1..15
                          note = Chemically Synthesized
source                    1..15
                          mol_type = protein
                          organism = synthetic construct
SEQUENCE: 176
SHTCEICANA ACAGC                                                         15

SEQ ID NO: 177            moltype = AA  length = 15
FEATURE                   Location/Qualifiers
REGION                    1..15
                          note = Chemically Synthesized
source                    1..15
                          mol_type = protein
                          organism = synthetic construct
SEQUENCE: 177
SHTCELCANA ACAGC                                                         15

SEQ ID NO: 178            moltype = AA  length = 15
FEATURE                   Location/Qualifiers
REGION                    1..15
                          note = Chemically Synthesized
source                    1..15
                          mol_type = protein
                          organism = synthetic construct
SEQUENCE: 178
SHTCEVCANA ACAGC                                                         15
```

```
SEQ ID NO: 179             moltype = AA   length = 15
FEATURE                    Location/Qualifiers
REGION                     1..15
                           note = Chemically Synthesized
source                     1..15
                           mol_type = protein
                           organism = synthetic construct
SEQUENCE: 179
SHTCEYCANA ACAGC                                                          15

SEQ ID NO: 180             moltype = AA   length = 15
FEATURE                    Location/Qualifiers
REGION                     1..15
                           note = Chemically Synthesized
source                     1..15
                           mol_type = protein
                           organism = synthetic construct
SEQUENCE: 180
SHTCEICANA ACAGC                                                          15

SEQ ID NO: 181             moltype = AA   length = 15
FEATURE                    Location/Qualifiers
REGION                     1..15
                           note = Chemically Synthesized
source                     1..15
                           mol_type = protein
                           organism = synthetic construct
SEQUENCE: 181
SHTCELCANA ACAGC                                                          15

SEQ ID NO: 182             moltype = AA   length = 15
FEATURE                    Location/Qualifiers
REGION                     1..15
                           note = Chemically Synthesized
source                     1..15
                           mol_type = protein
                           organism = synthetic construct
SEQUENCE: 182
SHTCEVCANA ACAGC                                                          15

SEQ ID NO: 183             moltype = AA   length = 15
FEATURE                    Location/Qualifiers
REGION                     1..15
                           note = Chemically Synthesized
source                     1..15
                           mol_type = protein
                           organism = synthetic construct
SEQUENCE: 183
SHTCEYCANA ACAGC                                                          15

SEQ ID NO: 184             moltype = AA   length = 15
FEATURE                    Location/Qualifiers
REGION                     1..15
                           note = Chemically Synthesized
source                     1..15
                           mol_type = protein
                           organism = synthetic construct
SEQUENCE: 184
SHTCEICANA ACAGC                                                          15

SEQ ID NO: 185             moltype = AA   length = 15
FEATURE                    Location/Qualifiers
REGION                     1..15
                           note = Chemically Synthesized
source                     1..15
                           mol_type = protein
                           organism = synthetic construct
SEQUENCE: 185
SHTCELCANA ACAGC                                                          15

SEQ ID NO: 186             moltype = AA   length = 15
FEATURE                    Location/Qualifiers
REGION                     1..15
                           note = Chemically Synthesized
source                     1..15
                           mol_type = protein
                           organism = synthetic construct
```

```
SEQUENCE: 186
SHTCEVCANA ACAGC                                                           15

SEQ ID NO: 187           moltype = AA  length = 15
FEATURE                  Location/Qualifiers
REGION                   1..15
                         note = Chemically Synthesized
source                   1..15
                         mol_type = protein
                         organism = synthetic construct
SEQUENCE: 187
SHTCEYCANA ACAGC                                                           15

SEQ ID NO: 188           moltype = AA  length = 15
FEATURE                  Location/Qualifiers
REGION                   1..15
                         note = Chemically Synthesized
source                   1..15
                         mol_type = protein
                         organism = synthetic construct
SEQUENCE: 188
SHTCEICANA ACAGC                                                           15

SEQ ID NO: 189           moltype = AA  length = 15
FEATURE                  Location/Qualifiers
REGION                   1..15
                         note = Chemically Synthesized
source                   1..15
                         mol_type = protein
                         organism = synthetic construct
SEQUENCE: 189
SHTCELCANA ACAGC                                                           15

SEQ ID NO: 190           moltype = AA  length = 15
FEATURE                  Location/Qualifiers
REGION                   1..15
                         note = Chemically Synthesized
source                   1..15
                         mol_type = protein
                         organism = synthetic construct
SEQUENCE: 190
SHTCEVCANA ACAGC                                                           15

SEQ ID NO: 191           moltype = AA  length = 15
FEATURE                  Location/Qualifiers
REGION                   1..15
                         note = Chemically Synthesized
source                   1..15
                         mol_type = protein
                         organism = synthetic construct
SEQUENCE: 191
SHTCEYCANA ACAGC                                                           15

SEQ ID NO: 192           moltype = AA  length = 15
FEATURE                  Location/Qualifiers
REGION                   1..15
                         note = Chemically Synthesized
source                   1..15
                         mol_type = protein
                         organism = synthetic construct
SEQUENCE: 192
NDECEICANA ACAGC                                                           15

SEQ ID NO: 193           moltype = AA  length = 15
FEATURE                  Location/Qualifiers
REGION                   1..15
                         note = Chemically Synthesized
source                   1..15
                         mol_type = protein
                         organism = synthetic construct
SEQUENCE: 193
NDECELCANA ACAGC                                                           15
```

```
SEQ ID NO: 194          moltype = AA   length = 15
FEATURE                 Location/Qualifiers
REGION                  1..15
                        note = Chemically Synthesized
source                  1..15
                        mol_type = protein
                        organism = synthetic construct
SEQUENCE: 194
NDECEVCANA ACAGC                                                        15

SEQ ID NO: 195          moltype = AA   length = 15
FEATURE                 Location/Qualifiers
REGION                  1..15
                        note = Chemically Synthesized
source                  1..15
                        mol_type = protein
                        organism = synthetic construct
SEQUENCE: 195
NDECEYCANA ACAGC                                                        15

SEQ ID NO: 196          moltype = AA   length = 15
FEATURE                 Location/Qualifiers
REGION                  1..15
                        note = Chemically Synthesized
source                  1..15
                        mol_type = protein
                        organism = synthetic construct
SEQUENCE: 196
NDECEICANA ACAGC                                                        15

SEQ ID NO: 197          moltype = AA   length = 15
FEATURE                 Location/Qualifiers
REGION                  1..15
                        note = Chemically Synthesized
source                  1..15
                        mol_type = protein
                        organism = synthetic construct
SEQUENCE: 197
NDECELCANA ACAGC                                                        15

SEQ ID NO: 198          moltype = AA   length = 15
FEATURE                 Location/Qualifiers
REGION                  1..15
                        note = Chemically Synthesized
source                  1..15
                        mol_type = protein
                        organism = synthetic construct
SEQUENCE: 198
NDECEVCANA ACAGC                                                        15

SEQ ID NO: 199          moltype = AA   length = 15
FEATURE                 Location/Qualifiers
REGION                  1..15
                        note = Chemically Synthesized
source                  1..15
                        mol_type = protein
                        organism = synthetic construct
SEQUENCE: 199
NDECEYCANA ACAGC                                                        15

SEQ ID NO: 200          moltype = AA   length = 15
FEATURE                 Location/Qualifiers
REGION                  1..15
                        note = Chemically Synthesized
source                  1..15
                        mol_type = protein
                        organism = synthetic construct
SEQUENCE: 200
NDECEICANA ACAGC                                                        15

SEQ ID NO: 201          moltype = AA   length = 15
FEATURE                 Location/Qualifiers
REGION                  1..15
                        note = Chemically Synthesized
source                  1..15
                        mol_type = protein
                        organism = synthetic construct
```

```
SEQUENCE: 201
NDECELCANA ACAGC                                                              15

SEQ ID NO: 202           moltype = AA  length = 15
FEATURE                  Location/Qualifiers
REGION                   1..15
                         note = Chemically Synthesized
source                   1..15
                         mol_type = protein
                         organism = synthetic construct
SEQUENCE: 202
NDECEVCANA ACAGC                                                              15

SEQ ID NO: 203           moltype = AA  length = 15
FEATURE                  Location/Qualifiers
REGION                   1..15
                         note = Chemically Synthesized
source                   1..15
                         mol_type = protein
                         organism = synthetic construct
SEQUENCE: 203
NDECEYCANA ACAGC                                                              15

SEQ ID NO: 204           moltype = AA  length = 15
FEATURE                  Location/Qualifiers
REGION                   1..15
                         note = Chemically Synthesized
source                   1..15
                         mol_type = protein
                         organism = synthetic construct
SEQUENCE: 204
NDECEICANA ACAGC                                                              15

SEQ ID NO: 205           moltype = AA  length = 15
FEATURE                  Location/Qualifiers
REGION                   1..15
                         note = Chemically Synthesized
source                   1..15
                         mol_type = protein
                         organism = synthetic construct
SEQUENCE: 205
NDECELCANA ACAGC                                                              15

SEQ ID NO: 206           moltype = AA  length = 15
FEATURE                  Location/Qualifiers
REGION                   1..15
                         note = Chemically Synthesized
source                   1..15
                         mol_type = protein
                         organism = synthetic construct
SEQUENCE: 206
NDECEVCANA ACAGC                                                              15

SEQ ID NO: 207           moltype = AA  length = 15
FEATURE                  Location/Qualifiers
REGION                   1..15
                         note = Chemically Synthesized
source                   1..15
                         mol_type = protein
                         organism = synthetic construct
SEQUENCE: 207
NDECEYCANA ACAGC                                                              15

SEQ ID NO: 208           moltype =     length =
SEQUENCE: 208
000

SEQ ID NO: 209           moltype = AA  length = 15
FEATURE                  Location/Qualifiers
REGION                   1..15
                         note = Chemically Synthesized
source                   1..15
                         mol_type = protein
                         organism = synthetic construct
SEQUENCE: 209
QEECELCINM ACTGY                                                              15

SEQ ID NO: 210           moltype = AA  length = 15
FEATURE                  Location/Qualifiers
```

```
REGION                      1..15
                            note = Chemically Synthesized
source                      1..15
                            mol_type = protein
                            organism = synthetic construct
SEQUENCE: 210
QEECETCINM ACTGY                                                              15

SEQ ID NO: 211              moltype = AA  length = 15
FEATURE                     Location/Qualifiers
REGION                      1..15
                            note = Chemically Synthesized
source                      1..15
                            mol_type = protein
                            organism = synthetic construct
SEQUENCE: 211
QDECETCINM ACTGY                                                              15

SEQ ID NO: 212              moltype = AA  length = 15
FEATURE                     Location/Qualifiers
REGION                      1..15
                            note = Chemically Synthesized
source                      1..15
                            mol_type = protein
                            organism = synthetic construct
SEQUENCE: 212
QDDCETCINM ACTGY                                                              15

SEQ ID NO: 213              moltype = AA  length = 15
FEATURE                     Location/Qualifiers
REGION                      1..15
                            note = Chemically Synthesized
source                      1..15
                            mol_type = protein
                            organism = synthetic construct
SEQUENCE: 213
QEDCETCINM ACTGY                                                              15

SEQ ID NO: 214              moltype = AA  length = 15
FEATURE                     Location/Qualifiers
REGION                      1..15
                            note = Chemically Synthesized
source                      1..15
                            mol_type = protein
                            organism = synthetic construct
SEQUENCE: 214
QEECEECINM ACTGY                                                              15

SEQ ID NO: 215              moltype = AA  length = 15
FEATURE                     Location/Qualifiers
REGION                      1..15
                            note = Chemically Synthesized
source                      1..15
                            mol_type = protein
                            organism = synthetic construct
SEQUENCE: 215
QDECEECINM ACTGY                                                              15

SEQ ID NO: 216              moltype = AA  length = 15
FEATURE                     Location/Qualifiers
REGION                      1..15
                            note = Chemically Synthesized
source                      1..15
                            mol_type = protein
                            organism = synthetic construct
SEQUENCE: 216
QDDCEECINM ACTGY                                                              15

SEQ ID NO: 217              moltype = AA  length = 15
FEATURE                     Location/Qualifiers
REGION                      1..15
                            note = Chemically Synthesized
source                      1..15
                            mol_type = protein
                            organism = synthetic construct
SEQUENCE: 217
QEDCEECINM ACTGY                                                              15

SEQ ID NO: 218              moltype = AA  length = 15
```

```
FEATURE              Location/Qualifiers
REGION               1..15
                     note = Chemically Synthesized
source               1..15
                     mol_type = protein
                     organism = synthetic construct
SEQUENCE: 218
QEECEYCINM ACTGY                                                         15

SEQ ID NO: 219       moltype = AA  length = 15
FEATURE              Location/Qualifiers
REGION               1..15
                     note = Chemically Synthesized
source               1..15
                     mol_type = protein
                     organism = synthetic construct
SEQUENCE: 219
QDECEYCINM ACTGY                                                         15

SEQ ID NO: 220       moltype = AA  length = 15
FEATURE              Location/Qualifiers
REGION               1..15
                     note = Chemically Synthesized
source               1..15
                     mol_type = protein
                     organism = synthetic construct
SEQUENCE: 220
QDDCEYCINM ACTGY                                                         15

SEQ ID NO: 221       moltype = AA  length = 15
FEATURE              Location/Qualifiers
REGION               1..15
                     note = Chemically Synthesized
source               1..15
                     mol_type = protein
                     organism = synthetic construct
SEQUENCE: 221
QEDCEYCINM ACTGY                                                         15

SEQ ID NO: 222       moltype = AA  length = 15
FEATURE              Location/Qualifiers
REGION               1..15
                     note = Chemically Synthesized
source               1..15
                     mol_type = protein
                     organism = synthetic construct
SEQUENCE: 222
QEECEICINM ACTGY                                                         15

SEQ ID NO: 223       moltype = AA  length = 15
FEATURE              Location/Qualifiers
REGION               1..15
                     note = Chemically Synthesized
source               1..15
                     mol_type = protein
                     organism = synthetic construct
SEQUENCE: 223
QDECEICINM ACTGY                                                         15

SEQ ID NO: 224       moltype = AA  length = 15
FEATURE              Location/Qualifiers
REGION               1..15
                     note = Chemically Synthesized
source               1..15
                     mol_type = protein
                     organism = synthetic construct
SEQUENCE: 224
QDDCEICINM ACTGY                                                         15

SEQ ID NO: 225       moltype = AA  length = 15
FEATURE              Location/Qualifiers
REGION               1..15
                     note = Chemically Synthesized
source               1..15
                     mol_type = protein
                     organism = synthetic construct
SEQUENCE: 225
QEDCEICINM ACTGY                                                         15
```

```
SEQ ID NO: 226            moltype = AA  length = 16
FEATURE                   Location/Qualifiers
REGION                    1..16
                          note = Chemically Synthesized
source                    1..16
                          mol_type = protein
                          organism = synthetic construct
SEQUENCE: 226
QEECETCINM ACTGCS                                                           16

SEQ ID NO: 227            moltype = AA  length = 16
FEATURE                   Location/Qualifiers
REGION                    1..16
                          note = Chemically Synthesized
source                    1..16
                          mol_type = protein
                          organism = synthetic construct
SEQUENCE: 227
QDECETCINM ACTGCS                                                           16

SEQ ID NO: 228            moltype = AA  length = 16
FEATURE                   Location/Qualifiers
REGION                    1..16
                          note = Chemically Synthesized
source                    1..16
                          mol_type = protein
                          organism = synthetic construct
SEQUENCE: 228
QDDCETCINM ACTGCS                                                           16

SEQ ID NO: 229            moltype = AA  length = 16
FEATURE                   Location/Qualifiers
REGION                    1..16
                          note = Chemically Synthesized
source                    1..16
                          mol_type = protein
                          organism = synthetic construct
SEQUENCE: 229
QEDCETCINM ACTGCS                                                           16

SEQ ID NO: 230            moltype = AA  length = 16
FEATURE                   Location/Qualifiers
REGION                    1..16
                          note = Chemically Synthesized
source                    1..16
                          mol_type = protein
                          organism = synthetic construct
SEQUENCE: 230
QEECEECINM ACTGCS                                                           16

SEQ ID NO: 231            moltype = AA  length = 16
FEATURE                   Location/Qualifiers
REGION                    1..16
                          note = Chemically Synthesized
source                    1..16
                          mol_type = protein
                          organism = synthetic construct
SEQUENCE: 231
QDECEECINM ACTGCS                                                           16

SEQ ID NO: 232            moltype = AA  length = 16
FEATURE                   Location/Qualifiers
REGION                    1..16
                          note = Chemically Synthesized
source                    1..16
                          mol_type = protein
                          organism = synthetic construct
SEQUENCE: 232
QDDCEECINM ACTGCS                                                           16

SEQ ID NO: 233            moltype = AA  length = 16
FEATURE                   Location/Qualifiers
REGION                    1..16
                          note = Chemically Synthesized
source                    1..16
                          mol_type = protein
                          organism = synthetic construct
SEQUENCE: 233
QEDCEECINM ACTGCS                                                           16
```

```
SEQ ID NO: 234          moltype = AA   length = 16
FEATURE                 Location/Qualifiers
REGION                  1..16
                        note = Chemically Synthesized
source                  1..16
                        mol_type = protein
                        organism = synthetic construct
SEQUENCE: 234
QEECEYCINM ACTGCS                                                          16

SEQ ID NO: 235          moltype = AA   length = 16
FEATURE                 Location/Qualifiers
REGION                  1..16
                        note = Chemically Synthesized
source                  1..16
                        mol_type = protein
                        organism = synthetic construct
SEQUENCE: 235
QDECEYCINM ACTGCS                                                          16

SEQ ID NO: 236          moltype = AA   length = 16
FEATURE                 Location/Qualifiers
REGION                  1..16
                        note = Chemically Synthesized
source                  1..16
                        mol_type = protein
                        organism = synthetic construct
SEQUENCE: 236
QDDCEYCINM ACTGCS                                                          16

SEQ ID NO: 237          moltype = AA   length = 16
FEATURE                 Location/Qualifiers
REGION                  1..16
                        note = Chemically Synthesized
source                  1..16
                        mol_type = protein
                        organism = synthetic construct
SEQUENCE: 237
QEDCEYCINM ACTGCS                                                          16

SEQ ID NO: 238          moltype = AA   length = 16
FEATURE                 Location/Qualifiers
REGION                  1..16
                        note = Chemically Synthesized
source                  1..16
                        mol_type = protein
                        organism = synthetic construct
SEQUENCE: 238
QEECEICINM ACTGCS                                                          16

SEQ ID NO: 239          moltype = AA   length = 16
FEATURE                 Location/Qualifiers
REGION                  1..16
                        note = Chemically Synthesized
source                  1..16
                        mol_type = protein
                        organism = synthetic construct
SEQUENCE: 239
QDECEICINM ACTGCS                                                          16

SEQ ID NO: 240          moltype = AA   length = 16
FEATURE                 Location/Qualifiers
REGION                  1..16
                        note = Chemically Synthesized
source                  1..16
                        mol_type = protein
                        organism = synthetic construct
SEQUENCE: 240
QDDCEICINM ACTGCS                                                          16

SEQ ID NO: 241          moltype = AA   length = 16
FEATURE                 Location/Qualifiers
REGION                  1..16
                        note = Chemically Synthesized
source                  1..16
                        mol_type = protein
                        organism = synthetic construct
```

-continued

```
SEQUENCE: 241
QEDCEICINM ACTGCS                                                        16

SEQ ID NO: 242          moltype = AA  length = 22
FEATURE                 Location/Qualifiers
REGION                  1..22
                        note = Chemically Synthesized
source                  1..22
                        mol_type = protein
                        organism = synthetic construct
SEQUENCE: 242
NSSNSSNYCC EKCCNPACTG CY                                                 22

SEQ ID NO: 243          moltype = AA  length = 16
FEATURE                 Location/Qualifiers
REGION                  1..16
                        note = Chemically Synthesized
SITE                    1
                        note = MISC_FEATURE - wherein ASN is attached to
                         polyethylene glycol
SITE                    16
                        note = MISC_FEATURE - wherein TYR is attached to
                         polyethylene glycol
source                  1..16
                        mol_type = protein
                        organism = synthetic construct
SEQUENCE: 243
NFCCETCCNP ACTGCY                                                        16

SEQ ID NO: 244          moltype = AA  length = 16
FEATURE                 Location/Qualifiers
REGION                  1..16
                        note = Chemically Synthesized
SITE                    1
                        note = MISC_FEATURE - wherein ASN is attached to
                         polyethylene glycol
source                  1..16
                        mol_type = protein
                        organism = synthetic construct
SEQUENCE: 244
NFCCETCCNP ACTGCY                                                        16

SEQ ID NO: 245          moltype = AA  length = 16
FEATURE                 Location/Qualifiers
REGION                  1..16
                        note = Chemically Synthesized
SITE                    16
                        note = MISC_FEATURE - wherein TYR is attached to
                         polyethylene glycol
source                  1..16
                        mol_type = protein
                        organism = synthetic construct
SEQUENCE: 245
NFCCETCCNP ACTGCY                                                        16

SEQ ID NO: 246          moltype = AA  length = 16
FEATURE                 Location/Qualifiers
REGION                  1..16
                        note = Chemically Synthesized
source                  1..16
                        mol_type = protein
                        organism = synthetic construct
SEQUENCE: 246
NFCCEYCCNP ACTGCY                                                        16

SEQ ID NO: 247          moltype = AA  length = 16
FEATURE                 Location/Qualifiers
REGION                  1..16
                        note = Chemically Synthesized
SITE                    1
                        note = MISC_FEATURE - wherein ASN is a D amino acid
SITE                    16
                        note = MISC_FEATURE - wherein TYR is a D amino acid
source                  1..16
                        mol_type = protein
                        organism = synthetic construct
SEQUENCE: 247
NFCCEYCCNP ACTGCY                                                        16
```

| | | |
|---|---|---|
| SEQ ID NO: 248 | moltype = AA length = 16 | |
| FEATURE | Location/Qualifiers | |
| REGION | 1..16 | |
| | note = Chemically Synthesized | |
| SITE | 16 | |
| | note = MISC_FEATURE - wherein TYR is a D amino acid | |
| source | 1..16 | |
| | mol_type = protein | |
| | organism = synthetic construct | |
| SEQUENCE: 248 | | |
| NFCCEYCCNP ACTGCY | | 16 |
| | | |
| SEQ ID NO: 249 | moltype = AA length = 16 | |
| FEATURE | Location/Qualifiers | |
| REGION | 1..16 | |
| | note = Chemically Synthesized | |
| SITE | 1 | |
| | note = MISC_FEATURE - wherein ASN is a D amino acid | |
| source | 1..16 | |
| | mol_type = protein | |
| | organism = synthetic construct | |
| SEQUENCE: 249 | | |
| NFCCEYCCNP ACTGCY | | 16 |
| | | |
| SEQ ID NO: 250 | moltype = length = | |
| SEQUENCE: 250 | | |
| 000 | | |
| | | |
| SEQ ID NO: 251 | moltype = AA length = 16 | |
| FEATURE | Location/Qualifiers | |
| REGION | 1..16 | |
| | note = Synthesized peptide | |
| SITE | 1 | |
| | note = MISC_FEATURE - wherein Xaa is a pyroglutamic acid | |
| source | 1..16 | |
| | mol_type = protein | |
| | organism = synthetic construct | |
| SEQUENCE: 251 | | |
| XDECELCVNV ACTGCL | | 16 |
| | | |
| SEQ ID NO: 252 | moltype = AA length = 15 | |
| FEATURE | Location/Qualifiers | |
| REGION | 1..15 | |
| | note = Synthesized peptide | |
| source | 1..15 | |
| | mol_type = protein | |
| | organism = synthetic construct | |
| SEQUENCE: 252 | | |
| PGTCEICAYA ACTGC | | 15 |
| | | |
| SEQ ID NO: 253 | moltype = AA length = 34 | |
| FEATURE | Location/Qualifiers | |
| REGION | 1..34 | |
| | note = Chemically synthesized peptide | |
| source | 1..34 | |
| | mol_type = protein | |
| | organism = synthetic construct | |
| SEQUENCE: 253 | | |
| IKPEAPGEDA SPEELNRYYA SLRHYLNLVT RQRY | | 34 |
| | | |
| SEQ ID NO: 254 | moltype = AA length = 27 | |
| FEATURE | Location/Qualifiers | |
| REGION | 1..27 | |
| | note = Chemically synthesized peptide | |
| SITE | 1 | |
| | note = MISC_FEATURE - wherein R is attached, R=H or an organic compound having from 1 to 10 carbon atoms | |
| source | 1..27 | |
| | mol_type = protein | |
| | organism = synthetic construct | |
| SEQUENCE: 254 | | |
| HAEGTFTSDV SYLEGQAAKE FIAWLVK | | 27 |
| | | |
| SEQ ID NO: 255 | moltype = AA length = 5 | |
| FEATURE | Location/Qualifiers | |
| REGION | 1..5 | |
| | note = Chemically Synthesized Sialorphin-related polypeptide | |

```
                          source              1..5
                                              mol_type = protein
                                              organism = synthetic construct
                          SEQUENCE: 255
                          QHNPR                                                              5

SEQ ID NO: 256      moltype = AA   length = 6
                          FEATURE             Location/Qualifiers
                          REGION              1..6
                                              note = Chemically Synthesized Sialorphin-related polypeptide
                          source              1..6
                                              mol_type = protein
                                              organism = synthetic construct
                          SEQUENCE: 256
                          VQHNPR                                                             6

SEQ ID NO: 257      moltype = AA   length = 7
                          FEATURE             Location/Qualifiers
                          REGION              1..7
                                              note = Chemically Synthesized Sialorphin-related polypeptide
                          source              1..7
                                              mol_type = protein
                                              organism = synthetic construct
                          SEQUENCE: 257
                          VRQHNPR                                                            7

SEQ ID NO: 258      moltype = AA   length = 8
                          FEATURE             Location/Qualifiers
                          REGION              1..8
                                              note = Chemically Synthesized Sialorphin-related polypeptide
                          source              1..8
                                              mol_type = protein
                                              organism = synthetic construct
                          SEQUENCE: 258
                          VRGQHNPR                                                           8

SEQ ID NO: 259      moltype = AA   length = 9
                          FEATURE             Location/Qualifiers
                          REGION              1..9
                                              note = Chemically Synthesized Sialorphin-related polypeptide
                          source              1..9
                                              mol_type = protein
                                              organism = synthetic construct
                          SEQUENCE: 259
                          VRGPQHNPR                                                          9

SEQ ID NO: 260      moltype = AA   length = 10
                          FEATURE             Location/Qualifiers
                          REGION              1..10
                                              note = Chemically Synthesized Sialorphin-related polypeptide
                          source              1..10
                                              mol_type = protein
                                              organism = synthetic construct
                          SEQUENCE: 260
                          VRGPRQHNPR                                                         10

SEQ ID NO: 261      moltype = AA   length = 11
                          FEATURE             Location/Qualifiers
                          REGION              1..11
                                              note = Chemically Synthesized Sialorphin-related polypeptide
                          source              1..11
                                              mol_type = protein
                                              organism = synthetic construct
                          SEQUENCE: 261
                          VRGPRRQHNP R                                                       11

SEQ ID NO: 262      moltype = AA   length = 6
                          FEATURE             Location/Qualifiers
                          REGION              1..6
                                              note = Chemically Synthesized Sialorphin-related polypeptide
                          source              1..6
                                              mol_type = protein
                                              organism = synthetic construct
                          SEQUENCE: 262
                          RQHNPR                                                             6

SEQ ID NO: 263      moltype = AA   length = 6
                          FEATURE             Location/Qualifiers
                          source              1..6
```

```
                        mol_type = protein
                        organism = synthetic construct
REGION                  1..6
                        note = Chemically synthesized
SEQUENCE: 263
NDECEL                                                                        6

SEQ ID NO: 264          moltype = AA  length = 8
FEATURE                 Location/Qualifiers
source                  1..8
                        mol_type = protein
                        organism = synthetic construct
REGION                  1..8
                        note = Chemically synthesized
SEQUENCE: 264
CVNVACTG                                                                      8

SEQ ID NO: 265          moltype = AA  length = 16
FEATURE                 Location/Qualifiers
source                  1..16
                        mol_type = protein
                        organism = synthetic construct
REGION                  1..16
                        note = Chemically synthesized
REGION                  4..12
                        note = The peptide CELCVNVAC is circular.
SITE                    4..12
                        note = Cysteine cysteine disulfide
SEQUENCE: 265
NDECELCVNV ACTGCL                                                            16

SEQ ID NO: 266          moltype = AA  length = 16
FEATURE                 Location/Qualifiers
source                  1..16
                        mol_type = protein
                        organism = synthetic construct
REGION                  1..16
                        note = Chemically synthesized
SEQUENCE: 266
NDECELCVNV ACTGCL                                                            16

SEQ ID NO: 267          moltype = AA  length = 10
FEATURE                 Location/Qualifiers
source                  1..10
                        mol_type = protein
                        organism = synthetic construct
REGION                  1..10
                        note = Chemically synthesized
SEQUENCE: 267
NFCCESCCNP                                                                   10

SEQ ID NO: 268          moltype = AA  length = 6
FEATURE                 Location/Qualifiers
source                  1..6
                        mol_type = protein
                        organism = synthetic construct
REGION                  1..6
                        note = Chemically synthesized
SEQUENCE: 268
ACTGCY                                                                        6

SEQ ID NO: 269          moltype =   length =
SEQUENCE: 269
000

SEQ ID NO: 270          moltype = AA  length = 6
FEATURE                 Location/Qualifiers
source                  1..6
                        mol_type = protein
                        organism = synthetic construct
REGION                  1..6
                        note = Chemically synthesized
SITE                    1
                        note = Asn is a D amino acid.
SEQUENCE: 270
NDECEL                                                                        6
```

```
SEQ ID NO: 271          moltype = AA   length = 16
FEATURE                 Location/Qualifiers
source                  1..16
                        mol_type = protein
                        organism = synthetic construct
REGION                  1..16
                        note = Chemically synthesized
SITE                    1
                        note = Asn is a D amino acid.
SITE                    16
                        note = Leu is a D amino acid.
REGION                  4..12
                        note = The peptide CELCVNVAC is circular.
SITE                    4..12
                        note = Cysteine cysteine disulfide
SEQUENCE: 271
NDECELCVNV ACTGCL                                                         16

SEQ ID NO: 272          moltype = AA   length = 16
FEATURE                 Location/Qualifiers
source                  1..16
                        mol_type = protein
                        organism = synthetic construct
REGION                  1..16
                        note = Chemically synthesized
SITE                    1
                        note = Asn is a D amino acid.
SITE                    16
                        note = Leu is a D amino acid.
SEQUENCE: 272
NDECELCVNV ACTGCL                                                         16

SEQ ID NO: 273          moltype = AA   length = 4
FEATURE                 Location/Qualifiers
source                  1..4
                        mol_type = protein
                        organism = synthetic construct
REGION                  1..4
                        note = Chemically synthesized
SEQUENCE: 273
ACTG                                                                       4

SEQ ID NO: 274          moltype = AA   length = 16
FEATURE                 Location/Qualifiers
source                  1..16
                        mol_type = protein
                        organism = synthetic construct
REGION                  1..16
                        note = Chemically synthesized
SITE                    1
                        note = Contains protecting group Trt
SITE                    3
                        note = Contains protecting group Trt
SITE                    4
                        note = Contains protecting group Trt
SITE                    5
                        note = Contains protecting group OtBu
SITE                    6
                        note = Contains protecting group tBu
SITE                    7
                        note = Contains protecting group Trt
SITE                    8
                        note = Contains protecting group Trt
SITE                    9
                        note = Contains protecting group Trt
SITE                    12
                        note = Contains protective group Trt
SITE                    13
                        note = Contains protecting group tBu
SITE                    15
                        note = Contains protecting group Trt
SITE                    16
                        note = Contains protective group tBu
SEQUENCE: 274
NFCCESCCNP ACTGCY                                                         16
```

```
SEQ ID NO: 275        moltype = AA  length = 16
FEATURE               Location/Qualifiers
source                1..16
                      mol_type = protein
                      organism = synthetic construct
SEQUENCE: 275
NFCCESCCNP ACTGCY                                                            16
```